United States Patent
Achab et al.

(10) Patent No.: US 10,544,147 B2
(45) Date of Patent: Jan. 28, 2020

(54) PURINE INHIBITORS OF HUMAN PHOSPHATIDYLINOSITOL 3-KINASE DELTA

(71) Applicant: MERCK SHARP & DOHME CORP., Rahway, NJ (US)

(72) Inventors: Abdelghani Abe Achab, Melrose, MA (US); Matthew P. Christopher, Brookline, MA (US); Francesc Xavier Fradera Llinas, Brookline, MA (US); Jason D. Katz, Newton Heights, MA (US); Joey L. Methot, Westwood, MA (US); Hua Zhou, Acton, MA (US); Shimin Xu, Beijing (CN); Jianmin Fu, Beijing (CN); Ning Fu, Beijing (CN); Yabin Li, Beijing (CN); Xichao Wang, Beijing (CN)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 16/089,509

(22) PCT Filed: Mar. 24, 2017

(86) PCT No.: PCT/US2017/023941
§ 371 (c)(1),
(2) Date: Sep. 28, 2018

(87) PCT Pub. No.: WO2017/172507
PCT Pub. Date: Oct. 5, 2017

(65) Prior Publication Data
US 2019/0119278 A1    Apr. 25, 2019

(30) Foreign Application Priority Data
Mar. 30, 2016 (WO) ............... PCT/CN2016/077824

(51) Int. Cl.
| | | |
|---|---|---|
| *C07D 403/00* | (2006.01) | |
| *C07D 473/00* | (2006.01) | |
| *A61P 37/02* | (2006.01) | |
| *A61P 11/06* | (2006.01) | |
| *A61P 19/02* | (2006.01) | |
| *A61P 35/00* | (2006.01) | |
| *C07D 519/00* | (2006.01) | |

(52) U.S. Cl.
CPC ............ *C07D 473/00* (2013.01); *A61P 11/06* (2018.01); *A61P 19/02* (2018.01); *A61P 35/00* (2018.01); *A61P 37/02* (2018.01); *C07D 519/00* (2013.01)

(58) Field of Classification Search
CPC .......................... C07D 473/00; C07D 473/40
See application file for complete search history.

(56) References Cited

U.S. PATENT DOCUMENTS

| | | | | |
|---|---|---|---|---|
| 9,540,377 B2* | 1/2017 | Cammarano | ........ | C07D 473/34 |
| 9,682,978 B2* | 6/2017 | Christopher | ......... | C07D 473/00 |
| 9,730,940 B2* | 8/2017 | Achab | .................... | A61K 31/52 |
| 2011/0009403 A1* | 1/2011 | Nagaraj | ............... | C07D 473/32 |
| | | | | 514/232.5 |
| 2011/0130395 A1 | 6/2011 | Liang et al. | | |
| 2014/0058103 A1* | 2/2014 | Kearney | .............. | C07D 471/10 |
| | | | | 544/277 |
| 2015/0353552 A1* | 12/2015 | Achab | .................... | A61K 31/52 |
| | | | | 514/210.18 |
| 2015/0353553 A1* | 12/2015 | Cammarano | ........ | C07D 473/34 |
| | | | | 514/210.21 |
| 2015/0368247 A1* | 12/2015 | Christopher | ......... | C07D 473/00 |
| | | | | 514/263.22 |
| 2016/0083401 A1* | 3/2016 | Fuchss | ................. | C07D 285/01 |
| | | | | 514/230.5 |

FOREIGN PATENT DOCUMENTS

| | | | | |
|---|---|---|---|---|
| WO | 2010114494 | 10/2010 | | |
| WO | WO-2012172043 A1 * | 12/2012 | ........... | C07D 473/32 |
| WO | 2014075393 | 5/2014 | | |
| WO | 2015188369 A1 | 12/2015 | | |

OTHER PUBLICATIONS

Q. Liu et al., 6 Drug Discovery Today: Therapeutic Strategies, 47-55 (2009) (Year: 2009).*
S.J. Shutteworth et al., 18 Current Medicinal Chemistry, 2686-2714 (2011) (Year: 2011).*
K. Hoegenauer et al., 8 ACS Medicinal Chemistry Letters, 975-980 (2017) (Year: 2017).*
A. Ghigo et al., 32 BioEssays, 185-196 (2010) (Year: 2010).*
R. Santos et al., 16 Nature Reviews—Drug Discovery (2017) (Year: 2017).*
J. Mullen et al., PLOS one (2016) (Year: 2016).*
K. Puri et al., 3 Frontiers in Immunology (2012) (Year: 2012).*
B. Bartok et al., 192 Journal of Immunology, 2063-2070 (2014) (Year: 2014).*

(Continued)

*Primary Examiner* — Alexander R Pagano
(74) *Attorney, Agent, or Firm* — Patricia A. Shatynski; John C. Todaro

(57) ABSTRACT

The instant invention provides compounds of formula (I) which are PI3K-delta inhibitors, and as such are useful for the treatment of PI3K-delta-mediated diseases such as inflammation, asthma, COPD and cancer.

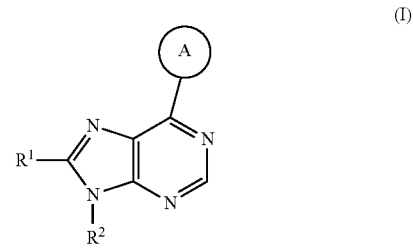

25 Claims, No Drawings

(56) References Cited

OTHER PUBLICATIONS

International Search Report and Written Opinion for PCT/CN2016/077824, dated Jan. 5, 2017, 13 pages.
International Search Report and Written Opinion for PCT/US2017/23941, dated Jun. 19, 2017, 8 pages.
Supplemental European Search Report EP 177763430-1116 dated Aug. 28, 2019, 7 pages.

* cited by examiner

PURINE INHIBITORS OF HUMAN PHOSPHATIDYLINOSITOL 3-KINASE DELTA

CROSS REFERENCE TO RELATED APPLICATIONS

This application is a U.S. National Phase application under 35 U.S.C. § 371 of PCT Application No. PCT/US2017/023941, filed Mar. 24, 2018 which claims priority from PCT Application No. PCT/CN2016/077824, filed on Mar. 30, 2016.

BACKGROUND OF THE INVENTION

Compounds are provided that inhibit phosphatidylinositol 3-kinase delta isoform (PI3K-delta) activity, including compounds that selectively inhibit PI3K-delta activity. The invention provides methods of using PI3K-delta inhibitory compounds to inhibit PI3K-delta mediated processes in vitro and in vivo.

Methods of inhibiting PI3K-delta activity, and methods of treating diseases, such as disorders of immunity and inflammation, in which PI3K-delta plays a role in leukocyte function are disclosed. Methods of using PI3K-delta inhibitory compounds to inhibit cancer cell growth or proliferation are also provided. Preferably, the methods employ active agents that selectively inhibit PI3K-delta, while not significantly inhibiting activity of other PI3K isoforms.

SUMMARY OF THE INVENTION

The present invention provides novel compounds which are inhibitors of phosphoinosititde 3-kinases delta (PI3K-delta). The invention also provides a method for the treatment and prevention of PI3K-delta-mediated diseases and disorders using the novel compounds, as well as pharmaceutical compositions containing the compounds.

DETAILED DESCRIPTION OF THE INVENTION

The present invention provides compounds of formula I or pharmaceutically acceptable salts thereof:

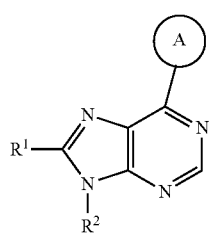

(I)

wherein:

A is selected from

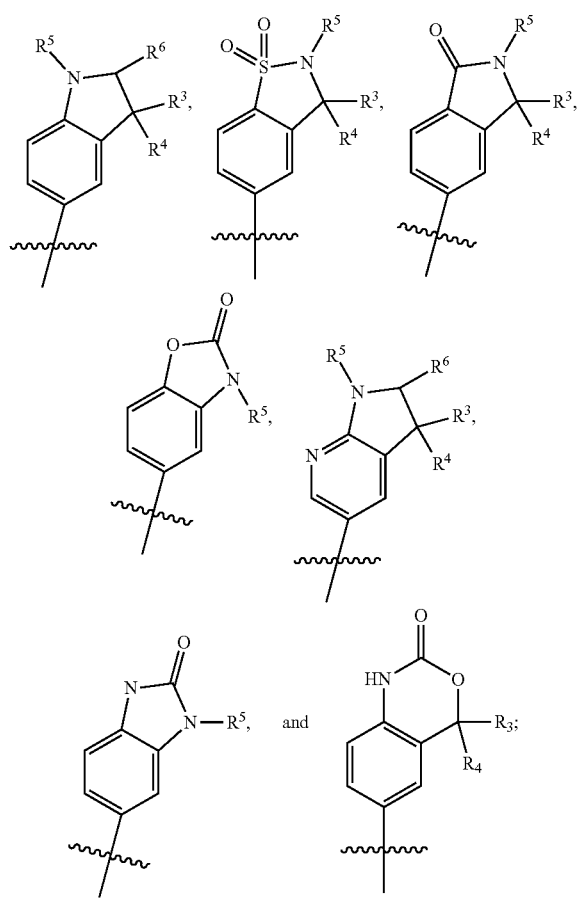

$R^1$ is selected from hydrogen, a 5- to 6-membered heteroaryl, $C_{1-6}$alkyl, and $C_{1-6}$haloalkyl, wherein said heteroaryl and alkyl is substituted with 0, 1, 2, or 3 moieties each independently selected from $C_{1-6}$alkyl, halogen, and OH.

$R^2$ is hydrogen or $C_{1-6}$ alkyl;

$R^3$ is selected from hydrogen, $C_{1-6}$alkyl, and cyano;

$R^4$ is selected from: hydrogen, cyano, $C_{1-6}$alkyl, $C_{1-6}$heteroalkyl, $C_{3-12}$heterocycloalkyl$C_{0-6}$alkyl, $C_{3-12}$cycloalkyl$C_{0-6}$alkyl, aryl$C_{0-6}$alkyl, heteroaryl$C_{0-6}$alkyl, spirocyclyl$C_{0-6}$alkyl, $C_{3-12}$cycloalkyl$C_{0-10}$alkyloxy, amino, -amino($C_{1-10}$ alkyl)$_{1-2}$, $C_{3-12}$cycloalkyl$C_{0-10}$alkylamino, heteroaryl$C_{0-10}$alkylamino, $C_{3-12}$heterocycloalkyl$C_{0-10}$alkylamino, aryl$C_{0-10}$alkylamino, hydroxy, —($C_{1-10}$ alkyl)OH, and $C_{1-10}$ alkoxy;

wherein $R^4$ is substituted with 0, 1, 2, or 3 groups selected from $C_{1-6}$alkyl, cyano, halogen, hydroxy, —O—$C_{1-6}$alkyl, and —($C_{1-10}$alkyl)OH;

further wherein, optionally, $R^3$ and $R^4$ along with the carbon to which they are attached may join together to form a 4 to 6 membered saturated ring system substituted with 0, 1, or 2 moieties selected from $C_{1-6}$alkyl, halogen, hydroxy, —O—$C_{1-6}$alkyl, —($C_{1-10}$ alkyl)OH, —SO$_2C_{1-6}$alkyl, —SO$_2$CF$_3$, —SO$_2$CF$_2$H, and $C_{3-12}$cycloalkyl$C_{0-10}$alkylcarbonyl;

$R^5$ is selected from: hydrogen, $C_{1-6}$ alkyl, $C_{1-10}$alkylcarbonyl, $C_{3-12}$cycloalkyl$C_{0-10}$alkyl, $C_{3-12}$heterocycloalkyl$C_{0-10}$alkyl, aryl$C_{0-10}$alkyl, and —($C_{1-10}$ alkyl)OH; and $R^6$ is hydrogen, oxo (=O), or $C_{1-3}$alkyl.

Representative compounds of the instant invention include, but are not limited to, the following compounds and their pharmaceutically acceptable salts thereof:

5-[9-ethyl-8-(2-methylpyrimidin-5-yl)-9H-purin-6-yl]-3-methyl-3-(2-methylpropyl)-1,3-dihydro-2H-indol-2-one;

(R)-5-[9-ethyl-8-(2-methylpyrimidin-5-yl)-9H-purin-6-yl]-3-methyl-3-(2-methylpropyl)-1,3-dihydro-2H-indol-2-one;

(S)-5-[9-ethyl-8-(2-methylpyrimidin-5-yl)-9H-purin-6-yl]-3-methyl-3-(2-methylpropyl)-1,3-dihydro-2H-indol-2-one;

5-[9-ethyl-8-(2-methylpyrimidin-5-yl)-9H-purin-6-yl]-3-methyl-3-(oxetan-3-ylmethyl)-1,3-dihydro-2H-indol-2-one;

(R)-5-[9-ethyl-8-(2-methylpyrimidin-5-yl)-9H-purin-6-yl]-3-methyl-3-(oxetan-3-ylmethyl)-1,3-dihydro-2H-indol-2-one;

(S)-5-[9-ethyl-8-(2-methylpyrimidin-5-yl)-9H-purin-6-yl]-3-methyl-3-(oxetan-3-ylmethyl)-1,3-dihydro-2H-indol-2-one;

5-[9-ethyl-8-(2-methylpyrimidin-5-yl)-9H-purin-6-yl]-3-methyl-3-[(3-methyloxetan-3-yl)methyl]-1,3-dihydro-2H-indol-2-one;

(R)-5-[9-ethyl-8-(2-methylpyrimidin-5-yl)-9H-purin-6-yl]-3-methyl-3-[(3-methyloxetan-3-yl)methyl]-1,3-dihydro-2H-indol-2-one;

(S)-5-[9-ethyl-8-(2-methylpyrimidin-5-yl)-9H-purin-6-yl]-3-methyl-3-[(3-methyloxetan-3-yl)methyl]-1,3-dihydro-2H-indol-2-one;

3-(cyclopropylmethyl)-5-(9-ethyl-8-(2-methylpyrimidin-5-yl)-9H-purin-6-yl)-3-methylindolin-2-one;

(R)-3-(cyclopropylmethyl)-5-(9-ethyl-8-(2-methylpyrimidin-5-yl)-9H-purin-6-yl)-3-methylindolin-2-one;

(S)-3-(cyclopropylmethyl)-5-(9-ethyl-8-(2-methylpyrimidin-5-yl)-9H-purin-6-yl)-3-methylindolin-2-one;

3-(cyclopropylmethyl)-5-(9-ethyl-8-(2-methylpyrimidin-5-yl)-9H-purin-6-yl)-1,3-dimethylindolin-2-one;

(R)-3-(cyclopropylmethyl)-5-(9-ethyl-8-(2-methylpyrimidin-5-yl)-9H-purin-6-yl)-1,3-dimethylindolin-2-one;

(S)-3-(cyclopropylmethyl)-5-(9-ethyl-8-(2-methylpyrimidin-5-yl)-9H-purin-6-yl)-1,3-dimethylindolin-2-one;

5-(9-ethyl-8-(2-methylpyrimidin-5-yl)-9H-purin-6-yl)-3-isobutyl-2-oxoindoline-3-carbonitrile;

5-(9-ethyl-8-(2-methylpyrimidin-5-yl)-9H-purin-6-yl)-3-isobutyl-3-methyl-1,3-dihydro-2H-pyrrolo[2,3-b]pyridin-2-one;

(R)-5-(9-ethyl-8-(2-methylpyrimidin-5-yl)-9H-purin-6-yl)-3-isobutyl-3-methyl-1,3-dihydro-2H-pyrrolo[2,3-b]pyridin-2-one;

(S)-5-(9-ethyl-8-(2-methylpyrimidin-5-yl)-9H-purin-6-yl)-3-isobutyl-3-methyl-1,3-dihydro-2H-pyrrolo[2,3-b]pyridin-2-one;

3-(cyclopropylmethyl)-5-(9-ethyl-8-(2-methylpyrimidin-5-yl)-9H-purin-6-yl)-3-methyl-1,3-dihydro-2H-pyrrolo[2,3-b]pyridin-2-one;

(R)-3-(cyclopropylmethyl)-5-(9-ethyl-8-(2-methylpyrimidin-5-yl)-9H-purin-6-yl)-3-methyl-1,3-dihydro-2H-pyrrolo[2,3-b]pyridin-2-one;

(S)-3-(cyclopropylmethyl)-5-(9-ethyl-8-(2-methylpyrimidin-5-yl)-9H-purin-6-yl)-3-methyl-1,3-dihydro-2H-pyrrolo[2,3-b]pyridin-2-one;

3-benzyl-5-(9-ethyl-8-(2-methylpyrimidin-5-yl)-9H-purin-6-yl)-3-methylindolin-2-one;

(R)-3-benzyl-5-(9-ethyl-8-(2-methylpyrimidin-5-yl)-9H-purin-6-yl)-3-methylindolin-2-one;

(S)-3-benzyl-5-(9-ethyl-8-(2-methylpyrimidin-5-yl)-9H-purin-6-yl)-3-methylindolin-2-one;

6-(3-benzyl-3-methylindolin-5-yl)-9-ethyl-8-(2-methylpyrimidin-5-yl)-9H-purine;

1-(3-benzyl-5-(9-ethyl-8-(2-methylpyrimidin-5-yl)-9H-purin-6-yl)-3-methylindolin-1-yl)ethan-1-one;

3-benzyl-5-(9-ethyl-8-(2-methylpyrimidin-5-yl)-9H-purin-6-yl)-1,3-dimethylindolin-2-one;

(R)-3-benzyl-5-(9-ethyl-8-(2-methylpyrimidin-5-yl)-9H-purin-6-yl)-1,3-dimethylindolin-2-one;

(S)-3-benzyl-5-(9-ethyl-8-(2-methylpyrimidin-5-yl)-9H-purin-6-yl)-1,3-dimethylindolin-2-one;

6-(3-benzyl-1,3-dimethylindolin-5-yl)-9-ethyl-8-(2-methylpyrimidin-5-yl)-9H-purine;

benzyl-5-(8-(difluoromethyl)-9-ethyl-9H-purin-6-yl)-3-methylindolin-2-one;

(R)-benzyl-5-(8-(difluoromethyl)-9-ethyl-9H-purin-6-yl)-3-methylindolin-2-one;

(S)-benzyl-5-(8-(difluoromethyl)-9-ethyl-9H-purin-6-yl)-3-methylindolin-2-one;

3-(cyclopropylmethyl)-5-(9-ethyl-8-(1-ethyl-5-methyl-1H-pyrazol-4-yl)-9H-purin-6-yl)-3-methylindolin-2-one;

(R)-3-(cyclopropylmethyl)-5-(9-ethyl-8-(1-ethyl-5-methyl-1H-pyrazol-4-yl)-9H-purin-6-yl)-3-methylindolin-2-one;

(S)-3-(cyclopropylmethyl)-5-(9-ethyl-8-(1-ethyl-5-methyl-1H-pyrazol-4-yl)-9H-purin-6-yl)-3-methylindolin-2-one;

3-isobutyl-3-methyl-5-(9-methyl-8-(2-methylpyrimidin-5-yl)-9H-purin-6-yl)-1,3-dihydro-2H-pyrrolo[2,3-b]pyridin-2-one;

(R)-3-isobutyl-3-methyl-5-(9-methyl-8-(2-methylpyrimidin-5-yl)-9H-purin-6-yl)-1,3-dihydro-2H-pyrrolo[2,3-b]pyridin-2-one;

(S)-3-isobutyl-3-methyl-5-(9-methyl-8-(2-methylpyrimidin-5-yl)-9H-purin-6-yl)-1,3-dihydro-2H-pyrrolo[2,3-b]pyridin-2-one;

3-benzyl-3-methyl-5-(9-methyl-9H-purin-6-yl)indolin-2-one;

(R)-3-benzyl-3-methyl-5-(9-methyl-9H-purin-6-yl)indolin-2-one;

(S)-3-benzyl-3-methyl-5-(9-methyl-9H-purin-6-yl)indolin-2-one;

5-(9-ethyl-8-(2-methylpyrimidin-5-yl)-9H-purin-6-yl)-3-methyl-3-(oxetan-2-ylmethyl)indolin-2-one;

(R,R)-5-(9-ethyl-8-(2-methylpyrimidin-5-yl)-9H-purin-6-yl)-3-methyl-3-(oxetan-2-ylmethyl)indolin-2-one;

(R,S)-5-(9-ethyl-8-(2-methylpyrimidin-5-yl)-9H-purin-6-yl)-3-methyl-3-(oxetan-2-ylmethyl)indolin-2-one;

(S,S)-5-(9-ethyl-8-(2-methylpyrimidin-5-yl)-9H-purin-6-yl)-3-methyl-3-(oxetan-2-ylmethyl)indolin-2-one;

(S,R)-5-(9-ethyl-8-(2-methylpyrimidin-5-yl)-9H-purin-6-yl)-3-methyl-3-(oxetan-2-ylmethyl)indolin-2-one;

5-(9-ethyl-8-(2-methylpyrimidin-5-yl)-9H-purin-6-yl)-3-methyl-3-(pyrimidin-5-ylmethyl)indolin-2-one;

5-(9-ethyl-8-(2-methylpyrimidin-5-yl)-9H-purin-6-yl)-3-methyl-3-(tetrahydro-2H-pyran-4-yl)indolin-2-one;

(R)-5-(9-ethyl-8-(2-methylpyrimidin-5-yl)-9H-purin-6-yl)-3-methyl-3-(tetrahydro-2H-pyran-4-yl)indolin-2-one;

(S)-5-(9-ethyl-8-(2-methylpyrimidin-5-yl)-9H-purin-6-yl)-3-methyl-3-(tetrahydro-2H-pyran-4-yl)indolin-2-one;

5-(9-ethyl-8-(2-methylpyrimidin-5-yl)-9H-purin-6-yl)-3-methyl-3-phenylindolin-2-one;

(R)-5-(9-ethyl-8-(2-methylpyrimidin-5-yl)-9H-purin-6-yl)-3-methyl-3-phenylindolin-2-one;

(S)-5-(9-ethyl-8-(2-methylpyrimidin-5-yl)-9H-purin-6-yl)-3-methyl-3-phenylindolin-2-one;

3-ethyl-5-(9-ethyl-8-(2-methylpyrimidin-5-yl)-9H-purin-6-yl)-3-methylindolin-2-one;

(R)-3-ethyl-5-(9-ethyl-8-(2-methylpyrimidin-5-yl)-9H-purin-6-yl)-3-methylindolin-2-one;

(S)-3-ethyl-5-(9-ethyl-8-(2-methylpyrimidin-5-yl)-9H-purin-6-yl)-3-methylindolin-2-one;
5-(9-ethyl-8-(2-methylpyrimidin-5-yl)-9H-purin-6-yl)-3-(2-hydroxy-2-methylpropyl)-3-methylindolin-2-one;
(R)-5-(9-ethyl-8-(2-methylpyrimidin-5-yl)-9H-purin-6-yl)-3-(2-hydroxy-2-methylpropyl)-3-methylindolin-2-one;
(S)-5-(9-ethyl-8-(2-methylpyrimidin-5-yl)-9H-purin-6-yl)-3-(2-hydroxy-2-methylpropyl)-3-methylindolin-2-one;
5-[9-ethyl-8-(2-methylpyrimidin-5-yl)-9H-purin-6-yl]-3-(3-methoxy-3-methylazetidin-1-yl)-3-methyl-1,3-dihydro-2H-indol-2-one;
(R)-5-[9-ethyl-8-(2-methylpyrimidin-5-yl)-9H-purin-6-yl]-3-(3-methoxy-3-methylazetidin-1-yl)-3-methyl-1,3-dihydro-2H-indol-2-one;
(S)-5-[9-ethyl-8-(2-methylpyrimidin-5-yl)-9H-purin-6-yl]-3-(3-methoxy-3-methylazetidin-1-yl)-3-methyl-1,3-dihydro-2H-indol-2-one;
3-[2,6-dimethylmorpholin-4-yl]-5-[9-ethyl-8-(2-methylpyrimidin-5-yl)-9H-purin-6-yl]-3-methyl-1,3-dihydro-2H-indol-2-one;
(R)-3-[(cis)-2,6-dimethylmorpholin-4-yl]-5-[9-ethyl-8-(2-methylpyrimidin-5-yl)-9H-purin-6-yl]-3-methyl-1,3-dihydro-2H-indol-2-one;
(S)-3-[(cis)-2,6-dimethylmorpholin-4-yl]-5-[9-ethyl-8-(2-methylpyrimidin-5-yl)-9H-purin-6-yl]-3-methyl-1,3-dihydro-2H-indol-2-one;
1-{5-[9-ethyl-8-(2-methylpyrimidin-5-yl)-9H-purin-6-yl]-3-methyl-2-oxo-2,3-dihydro-1H-indol-3-yl}-3-methylazetidine-3-carbonitrile;
(R)-1-{5-[9-ethyl-8-(2-methylpyrimidin-5-yl)-9H-purin-6-yl]-3-methyl-2-oxo-2,3-dihydro-1H-indol-3-yl}-3-methylazetidine-3-carbonitrile;
(S)-1-{5-[9-ethyl-8-(2-methylpyrimidin-5-yl)-9H-purin-6-yl]-3-methyl-2-oxo-2,3-dihydro-1H-indol-3-yl}-3-methylazetidine-3-carbonitrile;
5-[9-ethyl-8-(2-methylpyrimidin-5-yl)-9H-purin-6-yl]-3-methyl-3-(1-oxa-6-azaspiro[3.3]hept-6-yl)-1,3-dihydro-2H-indol-2-one;
(R)-5-[9-ethyl-8-(2-methylpyrimidin-5-yl)-9H-purin-6-yl]-3-methyl-3-(1-oxa-6-azaspiro[3.3]hept-6-yl)-1,3-dihydro-2H-indol-2-one;
(S)-5-[9-ethyl-8-(2-methylpyrimidin-5-yl)-9H-purin-6-yl]-3-methyl-3-(1-oxa-6-azaspiro[3.3]hept-6-yl)-1,3-dihydro-2H-indol-2-one;
5-[9-ethyl-8-(2-methylpyrimidin-5-yl)-9H-purin-6-yl]-3-methyl-3-(pyridin-4-ylamino)-1,3-dihydro-2H-indol-2-one;
(R)-5-[9-ethyl-8-(2-methylpyrimidin-5-yl)-9H-purin-6-yl]-3-methyl-3-(pyridin-4-ylamino)-1,3-dihydro-2H-indol-2-one;
(S)-5-[9-ethyl-8-(2-methylpyrimidin-5-yl)-9H-purin-6-yl]-3-methyl-3-(pyridin-4-ylamino)-1,3-dihydro-2H-indol-2-one;
5-[9-ethyl-8-(2-methylpyrimidin-5-yl)-9H-purin-6-yl]-3-(hexahydro-4H-furo[3,2-b]pyrrol-4-yl)-3-methyl-1,3-dihydro-2H-indol-2-one;
(R)-5-[9-ethyl-8-(2-methylpyrimidin-5-yl)-9H-purin-6-yl]-3-(hexahydro-4H-furo[3,2-b]pyrrol-4-yl)-3-methyl-1,3-dihydro-2H-indol-2-one;
(S)-5-[9-ethyl-8-(2-methylpyrimidin-5-yl)-9H-purin-6-yl]-3-(hexahydro-4H-furo[3,2-b]pyrrol-4-yl)-3-methyl-1,3-dihydro-2H-indol-2-one;
3-{[1-cyclopropylethyl]amino}-5-[9-ethyl-8-(2-methylpyrimidin-5-yl)-9H-purin-6-yl]-3-methyl-1,3-dihydro-2H-indol-2-one;
3-{[(1R)-1-cyclopropylethyl]amino}-5-[9-ethyl-8-(2-methylpyrimidin-5-yl)-9H-purin-6-yl]-3(R)-methyl-1,3-dihydro-2H-indol-2-one;
3-{[(1R)-1-cyclopropylethyl]amino}-5-[9-ethyl-8-(2-methylpyrimidin-5-yl)-9H-purin-6-yl]-3(S)-methyl-1,3-dihydro-2H-indol-2-one;
3-{[(1S)-1-cyclopropylethyl]amino}-5-[9-ethyl-8-(2-methylpyrimidin-5-yl)-9H-purin-6-yl]-3(R)-methyl-1,3-dihydro-2H-indol-2-one;
3-{[(1S)-1-cyclopropylethyl]amino}-5-[9-ethyl-8-(2-methylpyrimidin-5-yl)-9H-purin-6-yl]-3(S)-methyl-1,3-dihydro-2H-indol-2-one;
5-[9-ethyl-8-(2-methylpyrimidin-5-yl)-9H-purin-6-yl]-3-[(2-methoxyethyl)(methyl)amino]-3-methyl-1,3-dihydro-2H-indol-2-one;
(R)-5-[9-ethyl-8-(2-methylpyrimidin-5-yl)-9H-purin-6-yl]-3-[(2-methoxyethyl)(methyl)amino]-3-methyl-1,3-dihydro-2H-indol-2-one;
(S)-5-[9-ethyl-8-(2-methylpyrimidin-5-yl)-9H-purin-6-yl]-3-[(2-methoxyethyl)(methyl)amino]-3-methyl-1,3-dihydro-2H-indol-2-one;
5-[9-ethyl-8-(2-methylpyrimidin-5-yl)-9H-purin-6-yl]-3-methyl-3-[methyl(1-methylethyl)amino]-1,3-dihydro-2H-indol-2-one;
(R)-5-[9-ethyl-8-(2-methylpyrimidin-5-yl)-9H-purin-6-yl]-3-methyl-3-[methyl(1-methylethyl)amino]-1,3-dihydro-2H-indol-2-one;
(S)-5-[9-ethyl-8-(2-methylpyrimidin-5-yl)-9H-purin-6-yl]-3-methyl-3-[methyl(1-methylethyl)amino]-1,3-dihydro-2H-indol-2-one;
5-[9-ethyl-8-(2-methylpyrimidin-5-yl)-9H-purin-6-yl]-3-[(2-methoxyethyl)amino]-3-methyl-1,3-dihydro-2H-indol-2-one;
(R)-5-[9-ethyl-8-(2-methylpyrimidin-5-yl)-9H-purin-6-yl]-3-[(2-methoxyethyl)amino]-3-methyl-1,3-dihydro-2H-indol-2-one;
(S)-5-[9-ethyl-8-(2-methylpyrimidin-5-yl)-9H-purin-6-yl]-3-[(2-methoxyethyl)amino]-3-methyl-1,3-dihydro-2H-indol-2-one;
3-{[1-cyclobutylethyl]amino}-5-[9-ethyl-8-(2-methylpyrimidin-5-yl)-9H-purin-6-yl]-3-methyl-1,3-dihydro-2H-indol-2-one;
3-{[(1R)-1-cyclobutylethyl]amino}-5-[9-ethyl-8-(2-methylpyrimidin-5-yl)-9H-purin-6-yl]-3(R)-methyl-1,3-dihydro-2H-indol-2-one;
3-{[(1S)-1-cyclobutylethyl]amino}-5-[9-ethyl-8-(2-methylpyrimidin-5-yl)-9H-purin-6-yl]-3(S)-methyl-1,3-dihydro-2H-indol-2-one;
5-[9-ethyl-8-(2-methylpyrimidin-5-yl)-9H-purin-6-yl]-3-methyl-3-{[(1-methylcyclobutyl)methyl]amino}-1,3-dihydro-2H-indol-2-one;
(R)-5-[9-ethyl-8-(2-methylpyrimidin-5-yl)-9H-purin-6-yl]-3-methyl-3-{[(1-methylcyclobutyl)methyl]amino}-1,3-dihydro-2H-indol-2-one;
(S)-5-[9-ethyl-8-(2-methylpyrimidin-5-yl)-9H-purin-6-yl]-3-methyl-3-{[(1-methylcyclobutyl)methyl]amino}-1,3-dihydro-2H-indol-2-one;
1-[({5-[9-ethyl-8-(2-methylpyrimidin-5-yl)-9H-purin-6-yl]-3-methyl-2-oxo-2,3-dihydro-1H-indol-3-yl}-amino)methyl]cyclobutanecarbonitrile;
(R)-1-[({5-[9-ethyl-8-(2-methylpyrimidin-5-yl)-9H-purin-6-yl]-3-methyl-2-oxo-2,3-dihydro-1H-indol-3-yl}amino)methyl]cyclobutanecarbonitrile;
(S)-1-[({5-[9-ethyl-8-(2-methylpyrimidin-5-yl)-9H-purin-6-yl]-3-methyl-2-oxo-2,3-dihydro-1H-indol-3-yl}amino)methyl]cyclobutanecarbonitrile;

3-[(cyclobutylmethyl)amino]-5-[9-ethyl-8-(2-methylpyrimidin-5-yl)-9H-purin-6-yl]-3-methyl-1,3-dihydro-2H-indol-2-one;

(R)-3-[(cyclobutylmethyl)amino]-5-[9-ethyl-8-(2-methylpyrimidin-5-yl)-9H-purin-6-yl]-3-methyl-1,3-dihydro-2H-indol-2-one;

(S)-3-[(cyclobutylmethyl)amino]-5-[9-ethyl-8-(2-methylpyrimidin-5-yl)-9H-purin-6-yl]-3-methyl-1,3-dihydro-2H-indol-2-one;

5-[9-ethyl-8-(2-methylpyrimidin-5-yl)-9H-purin-6-yl]-3-methyl-3-{[tetrahydrofuran-2-ylmethyl]amino}-1,3-dihydro-2H-indol-2-one;

5-[9-ethyl-8-(2-methylpyrimidin-5-yl)-9H-purin-6-yl]-3(R)-methyl-3-{[(2R)-tetrahydrofuran-2-ylmethyl]amino}-1,3-dihydro-2H-indol-2-one;

5-[9-ethyl-8-(2-methylpyrimidin-5-yl)-9H-purin-6-yl]-3(S)-methyl-3-{[(2R)-tetrahydrofuran-2-ylmethyl]amino}-1,3-dihydro-2H-indol-2-one;

5-[9-ethyl-8-(2-methylpyrimidin-5-yl)-9H-purin-6-yl]-3-methyl-3-(8-oxa-5-azaspiro[3.5]non-5-yl)-1,3-dihydro-2H-indol-2-one;

(R)-5-[9-ethyl-8-(2-methylpyrimidin-5-yl)-9H-purin-6-yl]-3-methyl-3-(8-oxa-5-azaspiro[3.5]non-5-yl)-1,3-dihydro-2H-indol-2-one;

(S)-5-[9-ethyl-8-(2-methylpyrimidin-5-yl)-9H-purin-6-yl]-3-methyl-3-(8-oxa-5-azaspiro[3.5]non-5-yl)-1,3-dihydro-2H-indol-2-one;

3-(6,7-dihydropyrazolo[1,5-a]pyrazin-5(4H)-yl)-5-[9-ethyl-8-(2-methylpyrimidin-5-yl)-9H-purin-6-yl]-3-methyl-1,3-dihydro-2H-indol-2-one;

(R)-3-(6,7-dihydropyrazolo[1,5-a]pyrazin-5(4H)-yl)-5-[9-ethyl-8-(2-methylpyrimidin-5-yl)-9H-purin-6-yl]-3-methyl-1,3-dihydro-2H-indol-2-one;

(S)-3-(6,7-dihydropyrazolo[1,5-a]pyrazin-5(4H)-yl)-5-[9-ethyl-8-(2-methylpyrimidin-5-yl)-9H-purin-6-yl]-3-methyl-1,3-dihydro-2H-indol-2-one;

5-[9-ethyl-8-(2-methylpyrimidin-5-yl)-9H-purin-6-yl]-3-methyl-3-(tetrahydro-2H-pyran-4-ylamino)-1,3-dihydro-2H-indol-2-one;

(R)-5-[9-ethyl-8-(2-methylpyrimidin-5-yl)-9H-purin-6-yl]-3-methyl-3-(tetrahydro-2H-pyran-4-ylamino)-1,3-dihydro-2H-indol-2-one;

(S)-5-[9-ethyl-8-(2-methylpyrimidin-5-yl)-9H-purin-6-yl]-3-methyl-3-(tetrahydro-2H-pyran-4-ylamino)-1,3-dihydro-2H-indol-2-one;

5-[9-ethyl-8-(2-methylpyrimidin-5-yl)-9H-purin-6-yl]-3-methyl-3-[2-oxa-5-azabicyclo[2.2.1]hept-5-yl]-1,3-dihydro-2H-indol-2-one;

5-[9-ethyl-8-(2-methylpyrimidin-5-yl)-9H-purin-6-yl]-3(R)-methyl-3-[(1R,4R)-2-oxa-5-azabicyclo[2.2.1]hept-5-yl]-1,3-dihydro-2H-indol-2-one;

5-[9-ethyl-8-(2-methylpyrimidin-5-yl)-9H-purin-6-yl]-3(S)-methyl-3-[(1R,4R)-2-oxa-5-azabicyclo[2.2.1]hept-5-yl]-1,3-dihydro-2H-indol-2-one;

3-{[1-cyclobutylethyl]amino}-5-[9-ethyl-8-(2-methylpyrimidin-5-yl)-9H-purin-6-yl]-3-methyl-1,3-dihydro-2H-indol-2-one;

3-{[(1S)-1-cyclobutylethyl]amino}-5-[9-ethyl-8-(2-methylpyrimidin-5-yl)-9H-purin-6-yl]-3(R)-methyl-1,3-dihydro-2H-indol-2-one;

3-{[(1R)-1-cyclobutylethyl]amino}-5-[9-ethyl-8-(2-methylpyrimidin-5-yl)-9H-purin-6-yl]-3(S)-methyl-1,3-dihydro-2H-indol-2-one;

5-[9-ethyl-8-(2-methylpyrimidin-5-yl)-9H-purin-6-yl]-3-methyl-3-(6-oxa-2-azaspiro[3.4]oct-2-yl)-1,3-dihydro-2H-indol-2-one;

(R)-5-[9-ethyl-8-(2-methylpyrimidin-5-yl)-9H-purin-6-yl]-3-methyl-3-(6-oxa-2-azaspiro[3.4]oct-2-yl)-1,3-dihydro-2H-indol-2-one;

(S)-5-[9-ethyl-8-(2-methylpyrimidin-5-yl)-9H-purin-6-yl]-3-methyl-3-(6-oxa-2-azaspiro[3.4]oct-2-yl)-1,3-dihydro-2H-indol-2-one;

3-(cyclobutylamino)-5-[9-ethyl-8-(2-methylpyrimidin-5-yl)-9H-purin-6-yl]-3-methyl-1,3-dihydro-2H-indol-2-one;

(R)-3-(cyclobutylamino)-5-[9-ethyl-8-(2-methylpyrimidin-5-yl)-9H-purin-6-yl]-3-methyl-1,3-dihydro-2H-indol-2-one;

(S)-3-(cyclobutylamino)-5-[9-ethyl-8-(2-methylpyrimidin-5-yl)-9H-purin-6-yl]-3-methyl-1,3-dihydro-2H-indol-2-one;

5-[9-ethyl-8-(2-methylpyrimidin-5-yl)-9H-purin-6-yl]-3-methyl-3-[(1-methylethyl)amino]-1,3-dihydro-2H-indol-2-one;

(R)-5-[9-ethyl-8-(2-methylpyrimidin-5-yl)-9H-purin-6-yl]-3-methyl-3-[(1-methylethyl)amino]-1,3-dihydro-2H-indol-2-one;

(S)-5-[9-ethyl-8-(2-methylpyrimidin-5-yl)-9H-purin-6-yl]-3-methyl-3-[(1-methylethyl)amino]-1,3-dihydro-2H-indol-2-one;

3-[(cyclopropylmethyl)amino]-5-[9-ethyl-8-(2-methylpyrimidin-5-yl)-9H-purin-6-yl]-3-methyl-1,3-dihydro-2H-indol-2-one;

(R)-3-[(cyclopropylmethyl)amino]-5-[9-ethyl-8-(2-methylpyrimidin-5-yl)-9H-purin-6-yl]-3-methyl-1,3-dihydro-2H-indol-2-one;

(S)-3-[(cyclopropylmethyl)amino]-5-[9-ethyl-8-(2-methylpyrimidin-5-yl)-9H-purin-6-yl]-3-methyl-1,3-dihydro-2H-indol-2-one;

5-[9-ethyl-8-(2-methylpyrimidin-5-yl)-9H-purin-6-yl]-3-methyl-3-[tetrahydrofuran-3-ylamino]-1,3-dihydro-2H-indol-2-one;

5-[9-ethyl-8-(2-methylpyrimidin-5-yl)-9H-purin-6-yl]-3(R)-methyl-3-[(3S)-tetrahydrofuran-3-ylamino]-1,3-dihydro-2H-indol-2-one;

5-[9-ethyl-8-(2-methylpyrimidin-5-yl)-9H-purin-6-yl]-3(S)-methyl-3-[(3S)-tetrahydrofuran-3-ylamino]-1,3-dihydro-2H-indol-2-one;

5-(9-ethyl-8-(2-methylpyrimidin-5-yl)-9H-purin-6-yl)-3-((2-fluoro-2-methylpropyl)amino)-3-methylindolin-2-one;

(S)-5-(9-ethyl-8-(2-methylpyrimidin-5-yl)-9H-purin-6-yl)-3-((2-fluoro-2-methylpropyl)amino)-3-methylindolin-2-one;

(R)-5-(9-ethyl-8-(2-methylpyrimidin-5-yl)-9H-purin-6-yl)-3-((2-fluoro-2-methylpropyl)amino)-3-methylindolin-2-one;

3-((5-(9-ethyl-8-(2-methylpyrimidin-5-yl)-9H-purin-6-yl)-3-methyl-2-oxoindolin-3-yl)amino)-2,2-dimethylpropanenitrile;

(R)-3-((5-(9-ethyl-8-(2-methylpyrimidin-5-yl)-9H-purin-6-yl)-3-methyl-2-oxoindolin-3-yl)amino)-2,2-dimethylpropanenitrile;

(S)-3-((5-(9-ethyl-8-(2-methylpyrimidin-5-yl)-9H-purin-6-yl)-3-methyl-2-oxoindolin-3-yl)amino)-2,2-dimethylpropanenitrile;

3-((2,2-difluoropropyl)amino)-5-(9-ethyl-8-(2-methylpyrimidin-5-yl)-9H-purin-6-yl)-3-methylindolin-2-one;

(R)-3 ((2,2-difluoropropyl)amino)-5-(9-ethyl-8-(2-methylpyrimidin-5-yl)-9H-purin-6-yl)-3-methylindolin-2-one;

(S)-3-((2,2-difluoropropyl)amino)-5-(9-ethyl-8-(2-methylpyrimidin-5-yl)-9H-purin-6-yl)-3-methylindolin-2-one;

5-(9-ethyl-8-(2-methylpyrimidin-5-yl)-9H-purin-6-yl)-3-methyl-3-((tetrahydrofuran-3-yl)amino)-1,3-dihydro-2H-pyrrolo[2,3-b]pyridin-2-one;

(R)-5-(9-ethyl-8-(2-methylpyrimidin-5-yl)-9H-purin-6-yl)-3-methyl-3-(((S)-tetrahydrofuran-3-yl)amino)-1,3-dihydro-2H-pyrrolo[2,3-b]pyridin-2-one;

(S)-5-(9-ethyl-8-(2-methylpyrimidin-5-yl)-9H-purin-6-yl)-3-methyl-3-(((S)-tetrahydrofuran-3-yl)amino)-1,3-dihydro-2H-pyrrolo[2,3-b]pyridin-2-one;

3-methyl-5-(9-methyl-8-(2-methylpyrimidin-5-yl)-9H-purin-6-yl)-3-((tetrahydrofuran-3-yl)amino)-1H-pyrrolo[2,3-b]pyridin-2(3H)-one;

(R)-3-methyl-5-(9-methyl-8-(2-methylpyrimidin-5-yl)-9H-purin-6-yl)-3-(((S)-tetrahydrofuran-3-yl)amino)-1H-pyrrolo[2,3-b]pyridin-2(3H)-one;

(S)-3-methyl-5-(9-methyl-8-(2-methylpyrimidin-5-yl)-9H-purin-6-yl)-3-(((S)-tetrahydrofuran-3-yl)amino)-1H-pyrrolo[2,3-b]pyridin-2(3H)-one;

5-(9-ethyl-8-(2-methylpyrimidin-5-yl)-9H-purin-6-yl)-3-(3-methoxy-3-methylazetidin-1-yl)-3-methyl-1H-pyrrolo[2,3-b]pyridin-2(3H)-one;

(R)-5-(9-ethyl-8-(2-methylpyrimidin-5-yl)-9H-purin-6-yl)-3-methoxy-3-methylazetidin-1-yl)-3-methyl-1H-pyrrolo[2,3-b]pyridin-2(3H)-one;

(S)-5-(9-ethyl-8-(2-methylpyrimidin-5-yl)-9H-purin-6-yl)-3-(3-methoxy-3-methylazetidin-1-yl)-3-methyl-1H-pyrrolo[2,3-b]pyridin-2(3H)-one;

5-(9-ethyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one;

(S)-5-(9-ethyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one;

(R)-5-(9-ethyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one;

3-(cyclobutylamino)-5-(9-ethyl-8-(2-methylpyrimidin-5-yl)-9H-purin-6-yl)-3-methyl-1,3-dihydro-2H-pyrrolo[2,3-b]pyridin-2-one;

(S)-3-(cyclobutylamino)-5-(9-ethyl-8-(2-methylpyrimidin-5-yl)-9H-purin-6-yl)-3-methyl-1,3-dihydro-2H-pyrrolo[2,3-b]pyridin-2-one;

(R)-3-(cyclobutylamino)-5-(9-ethyl-8-(2-methylpyrimidin-5-yl)-9H-purin-6-yl)-3-methyl-1,3-dihydro-2H-pyrrolo[2,3-b]pyridin-2-one;

1-(5-(9-ethyl-8-(2-methylpyrimidin-5-yl)-9H-purin-6-yl)-3-methyl-2-oxo-2,3-dihydro-1H-pyrrolo[2,3-b]pyridin-3-yl)-3-methylazetidine-3-carbonitrile;

(S)-1-(5-(9-ethyl-8-(2-methylpyrimidin-5-yl)-9H-purin-6-yl)-3-methyl-2-oxo-2,3-dihydro-1H-pyrrolo[2,3-b]pyridin-3-yl)-3-methylazetidine-3-carbonitrile;

(R)-1-(5-(9-ethyl-8-(2-methylpyrimidin-5-yl)-9H-purin-6-yl)-3-methyl-2-oxo-2,3-dihydro-1H-pyrrolo[2,3-b]pyridin-3-yl)-3-methylazetidine-3-carbonitrile;

5-(9-ethyl-8-(2-methylpyrimidin-5-yl)-9H-purin-6-yl)-3-(2-fluoro-2-methylpropoxy)-3-methylindolin-2-one;

(R)-5-(9-ethyl-8-(2-methylpyrimidin-5-yl)-9H-purin-6-yl)-3-(2-fluoro-2-methylpropoxy)-3-methylindolin-2-one;

(S)-5-(9-ethyl-8-(2-methylpyrimidin-5-yl)-9H-purin-6-yl)-3-(2-fluoro-2-methylpropoxy)-3-methylindolin-2-one;

3-(cyclopropylmethoxy)-5-(9-ethyl-8-(2-methylpyrimidin-5-yl)-9H-purin-6-yl)-3-methylindolin-2-one;

(R)-3-(cyclopropylmethoxy)-5-(9-ethyl-8-(2-methylpyrimidin-5-yl)-9H-purin-6-yl)-3-methylindolin-2-one;

(S)-3-(cyclopropylmethoxy)-5-(9-ethyl-8-(2-methylpyrimidin-5-yl)-9H-purin-6-yl)-3-methylindolin-2-one;

5-(9-methyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one;

(S)-5-(9-methyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one;

(R)-5-(9-methyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one;

3-(3,4-difluoropyrrolidin-1-yl)-5-(9-ethyl-8-(2-methylpyrimidin-5-yl)-9H-purin-6-yl)-3-methylindolin-2-one;

3-(R)-((3R,4R)-3,4-difluoropyrrolidin-1-yl)-5-(9-ethyl-8-(2-methylpyrimidin-5-yl)-9H-purin-6-yl)-3-methylindolin-2-one;

3-(S)-((3R,4R)-3,4-difluoropyrrolidin-1-yl)-5-(9-ethyl-8-(2-methylpyrimidin-5-yl)-9H-purin-6-yl)-3-methylindolin-2-one;

5-(9-ethyl-8-(2-methylpyrimidin-5-yl)-9H-purin-6-yl)-3-(3-fluoro-3-methylazetidin-1-yl)-3-methylindolin-2-one;

(R)-5-(9-ethyl-8-(2-methylpyrimidin-5-yl)-9H-purin-6-yl)-3-(3-fluoro-3-methylazetidin-1-yl)-3-methylindolin-2-one;

(S)-5-(9-ethyl-8-(2-methylpyrimidin-5-yl)-9H-purin-6-yl)-3-(3-fluoro-3-methylazetidin-1-yl)-3-methylindolin-2-one;

5-(9-ethyl-8-(2-methylpyrimidin-5-yl)-9H-purin-6-yl)-3-(isobutylamino)-3-methylindolin-2-one;

(R)-5-(9-ethyl-8-(2-methylpyrimidin-5-yl)-9H-purin-6-yl)-3-(isobutylamino)-3-methylindolin-2-one;

(S)-5-(9-ethyl-8-(2-methylpyrimidin-5-yl)-9H-purin-6-yl)-3-(isobutylamino)-3-methylindolin-2-one;

3-((2-fluoro-2-methylpropyl)amino)-3-methyl-5-(9-methyl-8-(2-methylpyrimidin-5-yl)-9H-purin-6-yl)indolin-2-one;

(S)-3-((2-fluoro-2-methylpropyl)amino)-3-methyl-5-(9-methyl-8-(2-methylpyrimidin-5-yl)-9H-purin-6-yl)indolin-2-one;

(R)-3-((2-fluoro-2-methylpropyl)amino)-3-methyl-5-(9-methyl-8-(2-methylpyrimidin-5-yl)-9H-purin-6-yl)indolin-2-one;

3-((2,2-difluoropropyl)amino)-3-methyl-5-(9-methyl-8-(2-methylpyrimidin-5-yl)-9H-purin-6-yl)indolin-2-one;

(R)-3-((2,2-difluoropropyl)amino)-3-methyl-5-(9-methyl-8-(2-methylpyrimidin-5-yl)-9H-purin-6-yl)indolin-2-one;

(S)-3-((2,2-difluoropropyl)amino)-3-methyl-5-(9-methyl-8-(2-methylpyrimidin-5-yl)-9H-purin-6-yl)indolin-2-one;

5-(9-ethyl-8-(2-methylpyrimidin-5-yl)-9H-purin-6-yl)-3-(((3-fluorooxetan-3-yl)methyl)amino)-3-methylindolin-2-one;

(R)-5-(9-ethyl-8-(2-methylpyrimidin-5-yl)-9H-purin-6-yl)-3-(((3-fluorooxetan-3-yl)methyl)amino)-3-methylindolin-2-one;

(S)-5-(9-ethyl-8-(2-methylpyrimidin-5-yl)-9H-purin-6-yl)-3-(((3-fluorooxetan-3-yl)methyl)amino)-3-methylindolin-2-one;

5-(9-ethyl-8-(2-methylpyrimidin-5-yl)-9H-purin-6-yl)-3-isopropoxy-3-methylindolin-2-one;

3-cyclobutoxy-5-(9-ethyl-8-(2-methylpyrimidin-5-yl)-9H-purin-6-yl)-3-methylindolin-2-one;

3-(cyclopropylmethoxy)-3-methyl-5-(9-methyl-8-(2-methylpyrimidin-5-yl)-9H-purin-6-yl)indolin-2-one;

5-(9-ethyl-8-(2-methylpyrimidin-5-yl)-9H-purin-6-yl)-3-methyl-3-((tetrahydrofuran-3-yl)amino)indolin-2-one;

5-(9-ethyl-8-(2-methylpyrimidin-5-yl)-9H-purin-6-yl)-3-(R)-methyl-3-(((R)-tetrahydrofuran-3-yl)amino)indolin-2-one;

5-(9-ethyl-8-(2-methylpyrimidin-5-yl)-9H-purin-6-yl)-3-(S)-methyl-3-(((R)-tetrahydrofuran-3-yl)amino)indolin-2-one;

5-(9-ethyl-8-(2-methylpyrimidin-5-yl)-9H-purin-6-yl)-3-(3-methoxy-3-methylazetidin-1-yl)-2-oxoindoline-3-carbonitrile;

5-(9-ethyl-8-(2-methylpyrimidin-5-yl)-9H-purin-6-yl)-3-(3-methoxyazetidin-1-yl)-3-methylindolin-2-one;

(R)-5-(9-ethyl-8-(2-methylpyrimidin-5-yl)-9H-purin-6-yl)-3-(3-methoxyazetidin-1-yl)-3-methylindolin-2-one;

(S)-5-(9-ethyl-8-(2-methylpyrimidin-5-yl)-9H-purin-6-yl)-3-(3-methoxyazetidin-1-yl)-3-methylindolin-2-one;

5-(9-ethyl-8-(2-methylpyrimidin-5-yl)-9H-purin-6-yl)-3-(3-hydroxy-3-methylazetidin-1-yl)-3-methylindolin-2-one;

(R)-5-(9-ethyl-8-(2-methylpyrimidin-5-yl)-9H-purin-6-yl)-3-(3-hydroxy-3-methylazetidin-1-yl)-3-methylindolin-2-one;

(S)-5-(9-ethyl-8-(2-methylpyrimidin-5-yl)-9H-purin-6-yl)-3-(3-hydroxy-3-methylazetidin-1-yl)-3-methylindolin-2-one;

5-(9-ethyl-8-(2-methylpyrimidin-5-yl)-9H-purin-6-yl)-3-((3-methoxycyclobutyl)amino)-3-methylindolin-2-one;

5-(9-ethyl-8-(2-methylpyrimidin-5-yl)-9H-purin-6-yl)-3-(((1R,3R)-3-methoxycyclobutyl)amino)-3(R)-methylindolin-2-one;

5-(9-ethyl-8-(2-methylpyrimidin-5-yl)-9H-purin-6-yl)-3-(((1R,3R)-3-methoxycyclobutyl)amino)-3(S)-methylindolin-2-one;

1'-(cyclopropylcarbonyl)-5-[9-ethyl-8-(2-methylpyrimidin-5-yl)-9H-purin-6-yl]spiro[indole-3,2'-pyrrolidin]-2(1H)-one;

(R)-1'-(cyclopropylcarbonyl)-5-[9-ethyl-8-(2-methylpyrimidin-5-yl)-9H-purin-6-yl]spiro[indole-3,2'-pyrrolidin]-2(1H)-one;

(S)-1'-(cyclopropylcarbonyl)-5-[9-ethyl-8-(2-methylpyrimidin-5-yl)-9H-purin-6-yl]spiro[indole-3,2'-pyrrolidin]-2(1H)-one;

1'-(cyclopropylcarbonyl)-5-[9-ethyl-8-(2-methylpyrimidin-5-yl)-9H-purin-6-yl]-1-methylspiro[indole-3,2'-pyrrolidin]-2(1H)-one;

(R)-1'-(cyclopropylcarbonyl)-5-[9-ethyl-8-(2-methylpyrimidin-5-yl)-9H-purin-6-yl]-1-methylspiro[indole-3,2'-pyrrolidin]-2(1H)-one;

(S)-1'-(cyclopropylcarbonyl)-5-[9-ethyl-8-(2-methylpyrimidin-5-yl)-9H-purin-6-yl]-1-methylspiro[indole-3,2'-pyrrolidin]-2(1H)-one;

1'-(cyclopropanecarbonyl)-5-(9-ethyl-8-(2-methylpyrimidin-5-yl)-9H-purin-6-yl)spiro[indoline-3,3'-pyrrolidin]-2-one;

(R)-1'-(cyclopropanecarbonyl)-5-(9-ethyl-8-(2-methylpyrimidin-5-yl)-9H-purin-6-yl)spiro[indoline-3,3'-pyrrolidin]-2-one;

(S)-1'-(cyclopropanecarbonyl)-5-(9-ethyl-8-(2-methylpyrimidin-5-yl)-9H-purin-6-yl)spiro[indoline-3,3'-pyrrolidin]-2-one;

1'-(cyclopropanecarbonyl)-5-(9-methyl-8-(2-methylpyrimidin-5-yl)-9H-purin-6-yl)spiro[indoline-3,2'-pyrrolidin]-2-one;

(R)-1'-(cyclopropanecarbonyl)-5-(9-methyl-8-(2-methylpyrimidin-5-yl)-9H-purin-6-yl)spiro[indoline-3,2'-pyrrolidin]-2-one;

(S)-1'-(cyclopropanecarbonyl)-5-(9-methyl-8-(2-methylpyrimidin-5-yl)-9H-purin-6-yl)spiro[indoline-3,2'-pyrrolidin]-2-one;

1'-(cyclopropanecarbonyl)-1-methyl-5-(9-methyl-8-(2-methylpyrimidin-5-yl)-9H-purin-6-yl)spiro[indoline-3,2'-pyrrolidin]-2-one;

(R)-1'-(cyclopropanecarbonyl)-1-methyl-5-(9-methyl-8-(2-methylpyrimidin-5-yl)-9H-purin-6-yl)spiro[indoline-3,2'-pyrrolidin]-2-one;

(S)-1'-(cyclopropanecarbonyl)-1-methyl-5-(9-methyl-8-(2-methylpyrimidin-5-yl)-9H-purin-6-yl)spiro[indoline-3,2'-pyrrolidin]-2-one;

1'-(cyclopropanecarbonyl)-1-ethyl-5-(9-ethyl-8-(2-methylpyrimidin-5-yl)-9H-purin-6-yl)spiro[indoline-3,2'-pyrrolidin]-2-one, (R)-1'-(cyclopropanecarbonyl)-1-ethyl-5-(9-ethyl-8-(2-methylpyrimidin-5-yl)-9H-purin-6-yl)spiro[indoline-3,2'-pyrrolidin]-2-one;

(S)-1'-(cyclopropanecarbonyl)-1-ethyl-5-(9-ethyl-8-(2-methylpyrimidin-5-yl)-9H-purin-6-yl)spiro[indoline-3,2'-pyrrolidin]-2-one;

1'-(cyclopropanecarbonyl)-5-(9-ethyl-8-(2-methylpyrimidin-5-yl)-9H-purin-6-yl)-1-isopropylspiro[indoline-3,2'-pyrrolidin]-2-one;

(R)-1'-(cyclopropanecarbonyl)-5-(9-ethyl-8-(2-methylpyrimidin-5-yl)-9H-purin-6-yl)-1-isopropylspiro[indoline-3,2'-pyrrolidin]-2-one;

(S)-1'-(cyclopropanecarbonyl)-5-(9-ethyl-8-(2-methylpyrimidin-5-yl)-9H-purin-6-yl)-1-isopropylspiro[indoline-3,2'-pyrrolidin]-2-one;

5-(9-ethyl-8-(2-methylpyrimidin-5-yl)-9H-purin-6-yl)-1'-isopropylspiro[indoline-3,2'-pyrrolidin]-2-one;

(R)-5-(9-ethyl-8-(2-methylpyrimidin-5-yl)-9H-purin-6-yl)-1'-isopropylspiro[indoline-3,2'-pyrrolidin]-2-one;

(S)-5-(9-ethyl-8-(2-methylpyrimidin-5-yl)-9H-purin-6-yl)-1'-isopropylspiro[indoline-3,2'-pyrrolidin]-2-one;

1'-isopropyl-5-(9-methyl-8-(2-methylpyrimidin-5-yl)-9H-purin-6-yl)spiro[indoline-3,2'-pyrrolidin]-2-one;

(R)-1'-isopropyl-5-(9-methyl-8-(2-methylpyrimidin-5-yl)-9H-purin-6-yl)spiro[indoline-3,2'-pyrrolidin]-2-one;

(S)-1'-isopropyl-5-(9-methyl-8-(2-methylpyrimidin-5-yl)-9H-purin-6-yl)spiro[indoline-3,2'-pyrrolidin]-2-one;

1'-(cyclopropanecarbonyl)-5-(8-(difluoromethyl)-9-ethyl-9H-purin-6-yl)spiro[indoline-3,2'-pyrrolidin]-2-one;

(R)-1'-(cyclopropanecarbonyl)-5-(8-(difluoromethyl)-9-ethyl-9H-purin-6-yl)spiro[indoline-3,2'-pyrrolidin]-2-one;

(S)-1'-(cyclopropanecarbonyl)-5-(8-(difluoromethyl)-9-ethyl-9H-purin-6-yl)spiro[indoline-3,2'-pyrrolidin]-2-one;

1'-(cyclopropanecarbonyl)-5-(9-methyl-8-(2-methylpyrimidin-5-yl)-9H-purin-6-yl)-1-(2-morpholinoethyl)spiro[indoline-3,2'-pyrrolidin]-2-one;

(R)-1'-(cyclopropanecarbonyl)-5-(9-methyl-8-(2-methylpyrimidin-5-yl)-9H-purin-6-yl)-1-(2-morpholinoethyl)spiro[indoline-3,2'-pyrrolidin]-2-one;

(S)-1'-(cyclopropanecarbonyl)-5-(9-methyl-8-(2-methylpyrimidin-5-yl)-9H-purin-6-yl)-1-(2-morpholinoethyl)spiro[indoline-3,2'-pyrrolidin]-2-one;

1'-(cyclopropanecarbonyl)-1-(2-hydroxy-2-methylpropyl)-5-(9-methyl-8-(2-methylpyrimidin-5-yl)-9H-purin-6-yl)spiro[indoline-3,2'-pyrrolidin]-2-one;

(R)-1'-(cyclopropanecarbonyl)-1-(2-hydroxy-2-methylpropyl)-5-(9-methyl-8-(2-methylpyrimidin-5-yl)-9H-purin-6-yl)spiro[indoline-3,2'-pyrrolidin]-2-one;

(S)-1'-(cyclopropanecarbonyl)-1-(2-hydroxy-2-methylpropyl)-5-(9-methyl-8-(2-methylpyrimidin-5-yl)-9H-purin-6-yl)spiro[indoline-3,2'-pyrrolidin]-2-one;

1'-(cyclopropanecarbonyl)-1-(2-hydroxyethyl)-5-(9-methyl-8-(2-methylpyrimidin-5-yl)-9H-purin-6-yl)spiro[indoline-3,2'-pyrrolidin]-2-one;

(R)-1'-(cyclopropanecarbonyl)-1-(2-hydroxyethyl)-5-(9-methyl-8-(2-methylpyrimidin-5-yl)-9H-purin-6-yl)spiro[indoline-3,2'-pyrrolidin]-2-one;
(S)-1'-(cyclopropanecarbonyl)-1-(2-hydroxyethyl)-5-(9-methyl-8-(2-methylpyrimidin-5-yl)-9H-purin-6-yl)spiro[indoline-3,2'-pyrrolidin]-2-one;
5-(9-ethyl-8-(2-methylpyrimidin-5-yl)-9H-purin-6-yl)-1'-(methylsulfonyl)spiro[indoline-3,2'-pyrrolidin]-2-one;
(R)-5-(9-ethyl-8-(2-methylpyrimidin-5-yl)-9H-purin-6-yl)-1'-(methylsulfonyl)spiro[indoline-3,2'-pyrrolidin]-2-one;
(S)-5-(9-ethyl-8-(2-methylpyrimidin-5-yl)-9H-purin-6-yl)-1'-(methylsulfonyl)spiro[indoline-3,2'-pyrrolidin]-2-one;
5-(9-ethyl-8-(2-methylpyrimidin-5-yl)-9H-purin-6-yl)-1'-((trifluoromethyl)sulfonyl)spiro[indoline-3,2'-pyrrolidin]-2-one;
(R)-5-(9-ethyl-8-(2-methylpyrimidin-5-yl)-9H-purin-6-yl)-1'-((trifluoromethyl)sulfonyl)spiro[indoline-3,2'-pyrrolidin]-2-one;
(S)-5-(9-ethyl-8-(2-methylpyrimidin-5-yl)-9H-purin-6-yl)-1'-((trifluoromethyl)sulfonyl)spiro [indoline-3,2'-pyrrolidin]-2-one;
5-(9-ethyl-8-(2-methylpyrimidin-5-yl)-9H-purin-6-yl)-1-methyl-1'-(methylsulfonyl)spiro[indoline-3,2'-pyrrolidin]-2-one;
(R)-5-(9-ethyl-8-(2-methylpyrimidin-5-yl)-9H-purin-6-yl)-1-methyl-1'-(methylsulfonyl)spiro [indoline-3,2'-pyrrolidin]-2-one;
(S)-5-(9-ethyl-8-(2-methylpyrimidin-5-yl)-9H-purin-6-yl)-1-methyl-1'-(methylsulfonyl)spiro [indoline-3,2'-pyrrolidin]-2-one;
1'-(cyclopropanecarbonyl)-5-(9-methyl-8-(2-methylpyrimidin-5-yl)-9H-purin-6-yl)spiro[indoline-3,4'-piperidin]-2-one;
1'-ethyl-5-(9-ethyl-8-(2-methylpyrimidin-5-yl)-9H-purin-6-yl)spiro[indoline-3,2'-pyrrolidin]-2-one;
(R)-1'-ethyl-5-(9-ethyl-8-(2-methylpyrimidin-5-yl)-9H-purin-6-yl)spiro[indoline-3,2'-pyrrolidin]-2-one;
(S)-1'-ethyl-5-(9-ethyl-8-(2-methylpyrimidin-5-yl)-9H-purin-6-yl)spiro[indoline-3,2'-pyrrolidin]-2-one;
1'-ethyl-5-(9-methyl-8-(2-methylpyrimidin-5-yl)-9H-purin-6-yl)spiro[indoline-3,2'-pyrrolidin]-2-one;
(R)-1'-ethyl-5-(9-methyl-8-(2-methylpyrimidin-5-yl)-9H-purin-6-yl)spiro[indoline-3,2'-pyrrolidin]-2-one;
(S)-1'-ethyl-5-(9-methyl-8-(2-methylpyrimidin-5-yl)-9H-purin-6-yl)spiro[indoline-3,2'-pyrrolidin]-2-one;
5'-(9-ethyl-8-(2-methylpyrimidin-5-yl)-9H-purin-6-yl)-4,5-dihydro-3H-spiro[furan-2,3'-indolin]-2'-one;
(R)-5'-(9-ethyl-8-(2-methylpyrimidin-5-yl)-9H-purin-6-yl)-4,5-dihydro-3H-spiro[furan-2,3'-indolin]-2'-one;
(S)-5'-(9-ethyl-8-(2-methylpyrimidin-5-yl)-9H-purin-6-yl)-4,5-dihydro-3H-spiro[furan-2,3'-indolin]-2'-one;
5-(9-ethyl-8-(2-methylpyrimidin-5-yl)-9H-purin-6-yl)spiro[indoline-3,2'-pyrrolidin]-2-one;
(R)-5-(9-ethyl-8-(2-methylpyrimidin-5-yl)-9H-purin-6-yl)spiro[indoline-3,2'-pyrrolidin]-2-one;
(S)-5-(9-ethyl-8-(2-methylpyrimidin-5-yl)-9H-purin-6-yl)spiro[indoline-3,2'-pyrrolidin]-2-one;
5'-(9-ethyl-8-(2-methylpyrimidin-5-yl)-9H-purin-6-yl)spiro[cyclopentane-1,3'-indolin]-2'-one;
5-(9-ethyl-8-(2-methylpyrimidin-5-yl)-9H-purin-6-yl)-1'-isopropylspiro[indoline-3,3'-pyrrolidin]-2-one;
(R)-5-(9-ethyl-8-(2-methylpyrimidin-5-yl)-9H-purin-6-yl)-1'-isopropylspiro[indoline-3,3'-pyrrolidin]-2-one;
(S)-5-(9-ethyl-8-(2-methylpyrimidin-5-yl)-9H-purin-6-yl)-1'-isopropylspiro[indoline-3,3'-pyrrolidin]-2-one;
4-benzyl-6-[9-ethyl-8-(2-methylpyrimidin-5-yl)-9H-purin-6-yl]-1,4-dihydro-2H-3,1-benzoxazin-2-one;
(R)-4-benzyl-6-[9-ethyl-8-(2-methylpyrimidin-5-yl)-9H-purin-6-yl]-1,4-dihydro-2H-3,1-benzoxazin-2-one;
(S)-4-benzyl-6-[9-ethyl-8-(2-methylpyrimidin-5-yl)-9H-purin-6-yl]-1,4-dihydro-2H-3,1-benzoxazin-2-one;
6-[9-ethyl-8-(2-methylpyrimidin-5-yl)-9H-purin-6-yl]-4-methyl-4-(2-methylpropyl)-1,4-dihydro-2H-3,1-benzoxazin-2-one;
(R)-6-[9-ethyl-8-(2-methylpyrimidin-5-yl)-9H-purin-6-yl]-4-methyl-4-(2-methylpropyl)-1,4-dihydro-2H-3,1-benzoxazin-2-one;
(S)-6-[9-ethyl-8-(2-methylpyrimidin-5-yl)-9H-purin-6-yl]-4-methyl-4-(2-methylpropyl)-1,4-dihydro-2H-3,1-benzoxazin-2-one;
9-ethyl-6-[3-methyl-3-(2-methylpropyl)-1,1-dioxido-2,3-dihydro-1,2-benzisothiazol-5-yl]-8-(2-methylpyrimidin-5-yl)-9H-purine;
(R)-9-ethyl-6-[3-methyl-3-(2-methylpropyl)-1,1-dioxido-2,3-dihydro-1,2-benzisothiazol-5-yl]-8-(2-methylpyrimidin-5-yl)-9H-purine;
(S)-9-ethyl-6-[3-methyl-3-(2-methylpropyl)-1,1-dioxido-2,3-dihydro-1,2-benzisothiazol-5-yl]-8-(2-methylpyrimidin-5-yl)-9H-purine;
5-[9-ethyl-8-(2-methylpyrimidin-5-yl)-9H-purin-6-yl]-3-methyl-3-(2-methylpropyl)-2,3-dihydro-1H-isoindol-1-one;
(R)-5-[9-ethyl-8-(2-methylpyrimidin-5-yl)-9H-purin-6-yl]-3-methyl-3-(2-methylpropyl)-2,3-dihydro-1H-isoindol-1-one;
(S)-5-[9-ethyl-8-(2-methylpyrimidin-5-yl)-9H-purin-6-yl]-3-methyl-3-(2-methylpropyl)-2,3-dihydro-1H-isoindol-1-one;
3-benzyl-5-[9-ethyl-8-(2-methylpyrimidin-5-yl)-9H-purin-6-yl]-2,3-dihydro-1H-isoindol-1-one;
(R)-3-benzyl-5-[9-ethyl-8-(2-methylpyrimidin-5-yl)-9H-purin-6-yl]-2,3-dihydro-1H-isoindol-1-one;
(S)-3-benzyl-5-[9-ethyl-8-(2-methylpyrimidin-5-yl)-9H-purin-6-yl]-2,3-dihydro-1H-isoindol-1-one;
3-benzyl-5-[9-ethyl-8-(2-methylpyrimidin-5-yl)-9H-purin-6-yl]-3-methyl-2,3-dihydro-1H-isoindol-1-one;
(R)-3-benzyl-5-[9-ethyl-8-(2-methylpyrimidin-5-yl)-9H-purin-6-yl]-3-methyl-2,3-dihydro-1H-isoindol-1-one;
(S)-3-benzyl-5-[9-ethyl-8-(2-methylpyrimidin-5-yl)-9H-purin-6-yl]-3-methyl-2,3-dihydro-1H-isoindol-1-one;
3-benzyl-5-[9-ethyl-8-(2-methylpyrimidin-5-yl)-9H-purin-6-yl]-2,3-dimethyl-2,3-dihydro-1H-isoindol-1-one;
(R)-3-benzyl-5-[9-ethyl-8-(2-methylpyrimidin-5-yl)-9H-purin-6-yl]-2,3-dimethyl-2,3-dihydro-1H-isoindol-1-one;
(S)-3-benzyl-5-[9-ethyl-8-(2-methylpyrimidin-5-yl)-9H-purin-6-yl]-2,3-dimethyl-2,3-dihydro-1H-isoindol-1-one;
5-(9-ethyl-8-(2-methylpyrimidin-5-yl)-9H-purin-6-yl)-2,3-dihydrobenzo[d]isothiazole 1,1-dioxide;
5-(9-ethyl-8-(2-methylpyrimidin-5-yl)-9H-purin-6-yl)-2-methyl-2,3-dihydrobenzo[d]isothiazole 1,1-dioxide;
5-(9-ethyl-8-(2-methylpyrimidin-5-yl)-9H-purin-6-yl)isoindolin-1-one;
6-(9-ethyl-8-(2-methylpyrimidin-5-yl)-9H-purin-6-yl)-4-methyl-4-phenyl-1,4-dihydro-2H-benzo[d][1,3]oxazin-2-one;
5-[9-ethyl-8-(2-methylpyrimidin-5-yl)-9H-purin-6-yl]-3-(1-phenylethyl)-1,3-benzoxazol-2(3H)-one;
(R)-5-[9-ethyl-8-(2-methylpyrimidin-5-yl)-9H-purin-6-yl]-3-(1-phenylethyl)-1,3-benzoxazol-2(3H)-one;
(S)-5-[9-ethyl-8-(2-methylpyrimidin-5-yl)-9H-purin-6-yl]-3-(1-phenylethyl)-1,3-benzoxazol-2(3H)-one;
3-benzyl-5-[9-ethyl-8-(2-methylpyrimidin-5-yl)-9H-purin-6-yl]-1,3-benzoxazol-2(3H)-one;

5-[9-ethyl-8-(2-methylpyrimidin-5-yl)-9H-purin-6-yl]-3-(tetrahydro-2H-pyran-4-ylmethyl)-1,3-benzoxazol-2(3H)-one;

3-(1-cyclopropylethyl)-5-[9-ethyl-8-(2-methylpyrimidin-5-yl)-9H-purin-6-yl]-1,3-benzoxazol-2(3H)-one;

(R)-3-(1-cyclopropylethyl)-5-[9-ethyl-8-(2-methylpyrimidin-5-yl)-9H-purin-6-yl]-1,3-benzoxazol-2(3H)-one;

(S)-3-(1-cyclopropylethyl)-5-[9-ethyl-8-(2-methylpyrimidin-5-yl)-9H-purin-6-yl]-1,3-benzoxazol-2(3H)-one;

1-(1-cyclopropylethyl)-6-[9-ethyl-8-(2-methylpyrimidin-5-yl)-9H-purin-6-yl]-1,3-dihydro-2H-benzimidazol-2-one;

(R)-1-(1-cyclopropylethyl)-6-[9-ethyl-8-(2-methylpyrimidin-5-yl)-9H-purin-6-yl]-1,3-dihydro-2H-benzimidazol-2-one;

(S)-1-(1-cyclopropylethyl)-6-[9-ethyl-8-(2-methylpyrimidin-5-yl)-9H-purin-6-yl]-1,3-dihydro-2H-benzimidazol-2-one; and 5-(9-ethyl-8-(2-methylpyrimidin-5-yl)-9H-purin-6-yl)-3-(tetrahydro-2H-pyran-4-yl)benzo[d]oxazol-2(3H)-one.

The invention also encompasses pharmaceutical compositions containing a compound of formula I, and methods for treatment or prevention of PI3K-delta mediated diseases using compounds of formula I.

One aspect of the present invention is to provide compounds that can inhibit the biological activity of human PI3K-delta. Another aspect of the invention is to provide methods of selectively modulating human PI3K-delta activity and thereby promoting medical treatment of diseases mediated by PI3K-delta dysfunction.

In one embodiment of the invention, the compounds of formula I inhibit PI3K-delta activity in biochemical and cell-based assays and exhibit therapeutic activity in medical conditions in which PI3K-delta activity is excessive or undesirable.

The invention is described using the following definitions unless otherwise indicated.

When any variable (e.g. aryl, heteroaryl, $R^1$, $R^5$, etc.) occurs more than one time in any constituent, its definition on each occurrence is independent at every other occurrence. Also, combinations of substituents/or variables are permissible only if such combinations result in stable compounds.

The wavy line ∿∿ , as used herein, indicates a point of attachment to the rest of the compound.

The term "$C_{1-6}$" includes alkyls containing 6, 5, 4, 3, 2, or 1 carbon atoms.

Lines drawn into the ring systems, such as, for example:

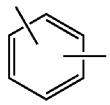

indicate that the indicated line (bond) may be attached to any of the substitutable ring carbon atoms. The term "alkyl," as used herein, refers to an aliphatic hydrocarbon group having one of its hydrogen atoms replaced with a bond. An alkyl group may be straight or branched and contain from about 1 to about 10 carbon atoms. In different embodiments, an alkyl group contains from 1 to 6 carbon atoms ($C_{1-6}$ alkyl) or from about 1 to about 3 carbon atoms ($C_{1-3}$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "alkoxy" represents a linear or branched alkyl group of indicated number of carbon atoms attached through an oxygen bridge.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkoxy" refers to an alkyl-O— group in which the alkyl group is as described above. $C_{1-6}$alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

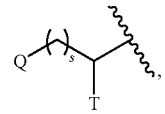

wherein s is an integer equal to zero, 1 or 2, the structure is

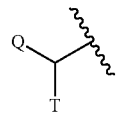

when s is zero.

The term "halogen" (or "halo") refers to fluorine, chlorine, bromine and iodine (alternatively referred to as fluoro (F), chloro (Cl), bromo (Br), and iodo (I)).

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl. In one embodiment, an aryl group contains from about 6 to about 10 carbon atoms. In one embodiment, an aryl group can be optionally fused to a cycloalkyl or cycloalkanoyl. Non-limiting examples of aryl groups include phenyl and naphthyl. In one embodiment, an aryl group is phenyl. Unless otherwise indicated, an aryl group is unsubstituted.

"Carboxy" refers to the functional group —C(O)OR, for example: ethylcarboxy is phenylcarboxy is

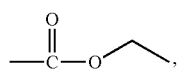

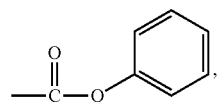

and cyclopropycarboxy is

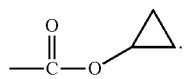

"Celite®" (Fluka) diatomite is diatomaceous earth, and can be referred to as "celite".

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound.

"Cycloalkyl" or "$C_{3-12}$ cycloalkyl" means any univalent radical derived from a monocyclic or bicyclic ring system having 3 to 12 ring carbons atoms; said ring system may be (a) a $C_3$ to a $C_8$ monocyclic, saturated ring, (b) a monocyclic saturated ring fused to a benzene or a partially unsaturated ring, or (c) a bicyclic saturated ring. Here, the point of attachment for a "cycloalkyl" to the rest of the molecule is on the saturated ring. For a bicyclic system, with either (b) or (c), the rings are fused across two adjacent ring carbon atoms (e.g., decalin), or are bridged groups (e.g., norbornane). Additional examples within the above meaning include, but are not limited to univalent radicals of cyclopropane, cyclobutane, cyclopentane, cyclohexane, decalin, bicyclo[2.2.2]octane and 3a,5,6,7-tetrahydro-4H-indene.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

"Heterocycloalkyl" or "$C_{3-12}$ heterocycloalkyl" refers to a "cycloalkyl" wherein one or more of the carbon atoms are replaced by at least one heteroatom, such as, for example, 1 to 4 heteroatoms selected from nitrogen, oxygen and sulfur. Additional examples within the above meaning include, but are not limited to, univalent radicals of 4,5,6,7-tetrahydropyrazolo[1,5-a]pyrazine, tetrahydro-2H-pyranyl, 2-oxa-5-azabicyclo[2.2.1]heptane, and thietane.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$ haloalkyl, for example, includes —$CF_3$, —$CF_2CF_3$, —$CHFCH_3$, and the like.

"Heteroalicyclic" group refers to a monocyclic or fused ring of 3 to 12 ring atoms containing one, or more heteroatoms in the ring.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

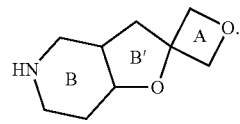

In one embodiment, all rings of the spirocyclyl system are saturated, such as spiro[2.5]octyl. In another embodiment, the individual rings of the spirocyclyl system are selected from both saturated and unsaturated rings.

Non-limiting examples of a carbocyclic spirocyclyl systems comprising include: spiro[2.2]pentane, spiro[cylclobutane-1,2'-indene], spiro[4.4]nonane, and spiro[4.5]decane.

For example a heteroalicyclic spirocyclyl or "spiroheterocyclic ring," as used herein, refers to a bicyclic heterocyclic ring as defined above wherein the two rings are joined through a common ring carbon atom. In one embodiment, a spiroheterocyclic ring is a 3- to 12-membered ring system containing one to three heteroatoms, e.g., one to two heteroatoms, selected from the group consisting of N and O. Non-limiting examples of spiroheterocyclic rings include 1-oxa-6-azaspiro[3.3]heptyl, 8-oxa-5-azaspiro[3.5]non-5-yl; 6-oxa-2-azaspiro[3.4]oct-2-yl; 2,8-diazaspiro[5.5]undecane; 1,7-diazaspiro[4.4]nonane; 1,7-diazaspiro[4.5]decane; 2,7-diazaspiro[4.5]decane, 1-oxa-7-azaspiro[4.5]decane; and 2-oxa-5-azabicylco[2.2.1]hept-5-yl.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

Structural representations of compounds having substituents terminating with a methyl group may display the terminal methyl group either using the characters "CH₃", e.g. "—CH₃" or using a straight line representing the presence of the methyl group, e.g. ——, i.e.,

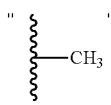

and

have equivalent meanings.

For variable definitions containing terms having repeated terms, e.g., $(CR_iR_j)_r$, where r is the integer 2, $R_i$ is a defined variable, and $R_j$ is a defined variable, the value of $R_i$ may differ in each instance in which it occurs, and the value of $R_j$ may differ in each instance in which it occurs. For example, if $R_i$ and $R_j$ are independently selected from the group consisting of methyl, ethyl, propyl and butyl, then $(CR_iR_j)_2$ can be

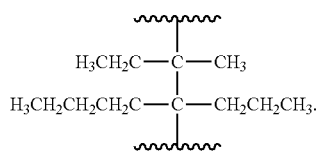

In one embodiment of the invention,

is selected from

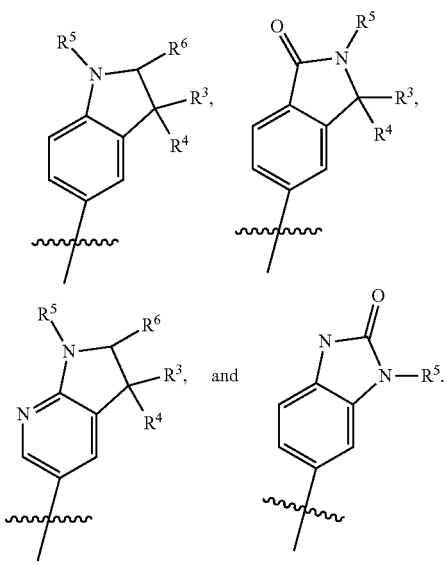

In another embodiment of the invention,

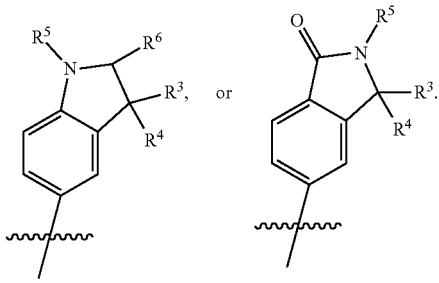

In a variant of this embodiment,

 is 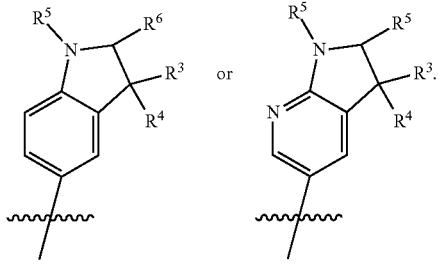

In another variant of this embodiment,

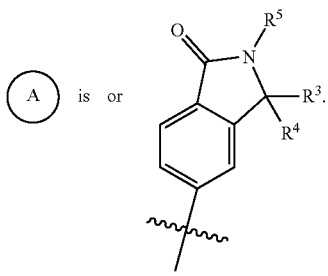

In one variant,

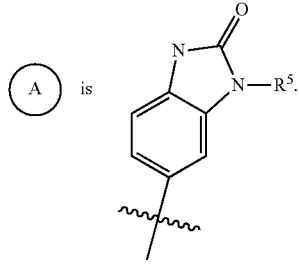

In yet another embodiment,

is selected from

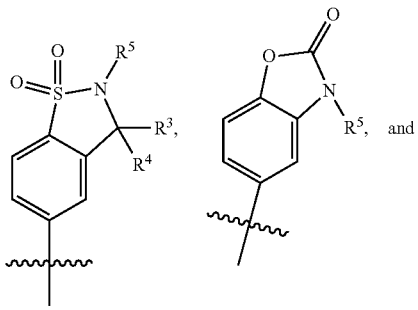

In yet another embodiment,

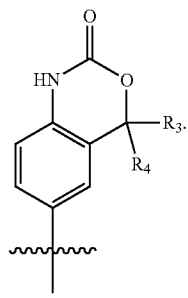

In another variant of this embodiment,

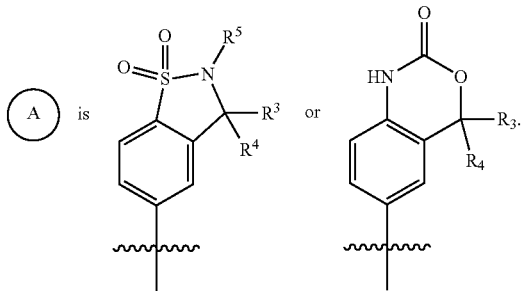

In one embodiment,

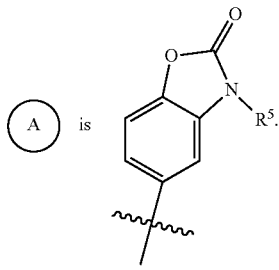

In yet another embodiment,

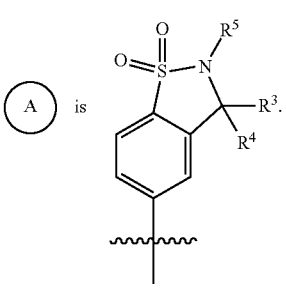

In yet another embodiment,

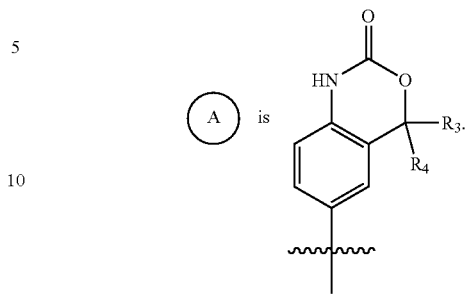

In one embodiment of the invention, $R^1$ is selected from hydrogen, a 5- to 6-membered heteroaryl, $C_{1-6}$alkyl, and $C_{1-6}$haloalkyl, wherein said heteroaryl is substituted with 0, 2, or 3 moeties each independently selected from $C_{1-6}$alkyl, halogen and OH.

In a variant of this embodiment, $R^1$ is selected from hydrogen, a 5- to 6-membered heteroaryl, $C_{1-4}$alkyl, and $C_{1-4}$haloalkyl, wherein said heteroaryl is substituted with 0, 1, 2, or 3 moeties each independently selected from $C_{1-6}$alkyl, halogen and OH.

In one embodiment, $R^1$ is selected from hydrogen, difluoromethyl, pyrimidinyl, pyrazolyl wherein said pyrimidinyl and said pyrazolyl are each substituted with 0, 1, 2, or 3 moeties each independently selected from $C_{1-6}$alkyl, halogen and OH.

In one embodiment of the invention, $R^2$ is hydrogen or $C_{1-6}$alkyl. In a variant of this embodiment, $R^2$ is selected from methyl, ethyl, propyl, butyl and tert-butyl. In another embodiment, $R^2$ is methyl or ethyl. In a variant of this embodiment, $R^2$ is ethyl.

In yet another embodiment, $R^2$ is hydrogen.

In one embodiment, $R^3$ is selected from hydrogen, $C_{1-6}$alkyl, and cyano.

In one embodiment, $R^3$ is selected from hydrogen, $C_{1-4}$alkyl, and cyano.

In yet another embodiment, $R^3$ is selected from hydrogen, methyl, and cyano.

In one embodiment of the invention, $R^4$ is selected from hydrogen, cyano, $C_{1-6}$alkyl, $C_{1-12}$heterocycloalkyl$C_{0-6}$alkyl, $C_{3-12}$cycloalkyl$C_{0-6}$alkyl, aryl$C_{0-6}$alkyl, heteroaryl $C_{0-6}$alkyl, spirocyclyl$C_{0-6}$alkyl, $C_{3-12}$cycloalkyl$C_{0-10}$alkyloxy, -amino($C_{1-10}$ alkyl)$_{1-2}$, $C_{3-12}$cycloalkyl-$C_{0-10}$alkylamino, heteroaryl$C_{0-10}$alkylamino, $C_{3-12}$heterocycloalkyl$C_{0-10}$alkylamino, and —($C_{1-10}$ alkyl)OH; wherein said aryl is a 6-membered aryl and said heteroaryl is a 5- to 6-membered heteroaryl and further wherein $R^4$ is substituted with 0, 1, 2, or 3 groups selected from $C_{1-6}$ alkyl, cyano, halogen, hydroxy, —O—($C_{1-6}$ alkyl, and —($C_{1-10}$ alkyl)OH.

In another embodiment of the invention, $R^4$ is selected from hydrogen, cyano, $C_{3-12}$heterocycloalkyl$C_{0-6}$alkyl, $C_{3-12}$cycloalkyl$C_{0-6}$alkyl, aryl$C_{0-6}$alkyl, heteroaryl $C_{0-6}$alkyl, spirocyclyl$C_{0-6}$alkyl, $C_{3-12}$cycloalkyl$C_{0-10}$alkyloxy, -amino($C_{1-10}$ alkyl)$_{1-2}$, $C_{3-12}$cycloalkyl-$C_{0-10}$alkylamino, heteroaryl$C_{0-10}$alkylamino, $C_{3-12}$heterocycloalkyl$C_{0-10}$alkylamino, and —($C_{1-10}$ alkyl)OH; wherein said aryl is a 6-membered aryl and said heteroaryl is a 5- to 6-membered heteroaryl and further wherein $R^4$ is substituted with 0, 1, 2, or 3 groups selected from $C_{1-6}$ alkyl, cyano, halogen, hydroxy, and methoxy.

In another embodiment, $R^4$ is selected from 2-methylpropyl (isobutyl), oxetanylmethyl, oxetan-3-ylmethyl, cyclopropylmethyl, benzyl, methylpyrimidinyl, methylpyrimidin-5-yl, tetrahydro-2H-pyranyl, phenyl, ethyl, 2-hydroxy-2-methylpropyl, azetidinyl, azetidin-1-yl, morpholinyl, oxa-6-azaspiro[3,3]heptyl, 1-oxa-6-azaspiro[3.3]hept-6-yl, pyridinylamino, hexahydro-4H-furo[3,2-b]pyrrol-4-yl, (1-cyclopropylethyl)amino, (methyl)(ethyl)amino, (methyl)(isopropyl)amino, (ethyl)amino, (1-cyclobutylethyl)amino, (cyclobutylmethyl)amino, (tetrahydrofuranylmethyl)amino, (tetrahydrofuran-2-ylmethyl)amino, 8-oxa-5-azaspiro[3.5]non-5-yl, 6,7-dihydropyrazolo[1.5-a]pyrazin-5(4H)-yl, tetrahydropyranylamino, tetrahydro-2H-pyra-4-ylamino, 2-oxa-5-azabicyclo[2.2.1]hept-5-yl, oxaazabicyclo[2.2.1]heptyl, 6-oxa-2-azaspiro-[3.4]oct-2-yl, cyclobutylamino, isopropylamino(cyclopropylmethyl)amino, tetrahydrofuranylamino, tetrahydrofuran-3-ylamino, isobutylamino, propylamino, azetidinyl, azetidin-1-yl, isobutoxy, cyclopropylmethoxy, pyrrolidinyl, (oxetanylmethyl)amino, (oxetan-3-ylmethyl)amino, isopropoxy, cyclobutoxy, hydrogen, and 1-phenylethyl; wherein $R^4$ is substituted with 0, 1, 2, or 3 groups selected from $C_{1-4}$ alkyl, cyano, halogen, hydroxy, and methoxy.

In one embodiment of the invention, $R^3$ and $R^4$ along with the carbon to which they are attached may join together to form a 4- to 6-membered saturated ring system substituted with 0, 1, or 2 moieties sected from $C_{1-6}$alkyl, halogen, —$SO_2C_{1-6}$alkyl, $C_{3-6}$cycloalkylcarbonyl, and —$SO_2CF_3$.

The saturated ring system may comprise all carbon ring members or may include a combination of carbon and 1 or 2 heteroatoms such as N, O, or S.

In another embodiment, $R^3$ and $R^4$ along with the carbon to which they are attached may join together to form a 4- to 6-membered saturated ring system selected from pyrrolidinyl, pyrrolidin-2-yl, piperidinyl, tetrahydrofuranyl, and cyclopentyl, said 4- to 6-membered saturated ring system is substituted with 0, 1, or 2 moieties sected from $C_{1-6}$alkyl, halogen, —$SO_2C_{1-6}$alkyl, $C_{3-6}$cycloalkylcarbonyl, and —$SO_2CF_3$.

In another embodiment, $R^3$ and $R^4$ along with the carbon to which they are attached may join together to form a 4- to 6-membered saturated ring system selected from pyrrolidinyl, pyrrolidin-2-yl, piperidinyl, tetrahydrofuranyl, and cyclopentyl, said 4- to 6-membered saturated ring system is substituted with 0, 1, or 2 moieties sected from isopropyl, ethyl, —$SO_2CH_3$, cyclopropylcarbonyl, and —$SO_2CF_3$.

In one embodiment of the invention, $R^5$ is selected from hydrogen, $C_{1-6}$ alkyl, $C_{1-10}$alkylcarbonyl, $C_{3-6}$cycloalkyl$C_{0-10}$alkyl, $C_{3-6}$heterocycloalkyl$C_{0-10}$alkyl, aryl$C_{0-10}$alkyl, and —($C_{1-10}$ alkyl)OH.

In a variant of this embodiment, $R^5$ is selected from hydrogen, methyl, methylcarbonyl, ethyl, isopropyl, morpholinoethyl, 2-hydroxy-2-methylpropyl, 2-hydroxyethyl, 1-phenylethyl, benzyl, tetrahydro-2H-pyranylmethyl, 1-cyclopropylethyl, and tetrahydro-2H-pyranyl.

In one embodiment, $R^6$ is hydrogen or oxo (=O).

One embodiment of the present invention is the compound of formula (I)

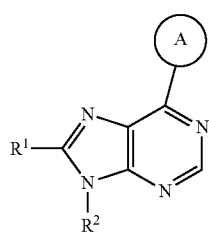

(I)

or a pharmaceutically acceptable salt thereof, wherein:

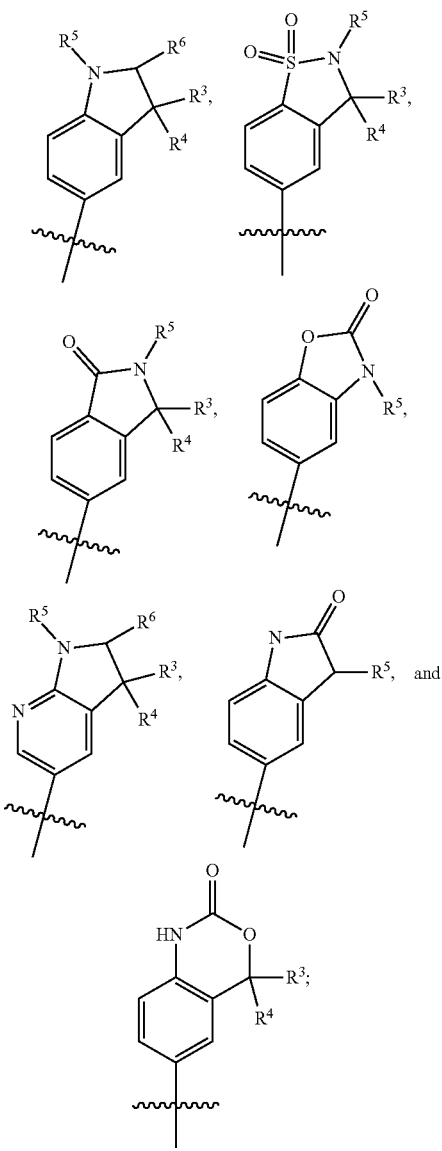

is selected from:

$R^1$ is selected from hydrogen, difluoromethyl, pyrimidinyl, pyrazolyl wherein said pyrimidinyl and said pyrazolyl are each substituted with 0, 1, 2, or 3 moeties each independently selected from $C_{1-6}$alkyl, halogen and OH;

$R^2$ is hydrogen, methyl or ethyl;

$R^3$ is selected from hydrogen, methyl, and cyano;

$R^4$ is selected from 2-methylpropyl (isobutyl), oxetanylmethyl, oxetan-3-ylmethyl, cyclopropylmethyl, benzyl, methylpyrimidinyl, methylpyrimidin-5-yl, tetrahydro-2H-pyranyl, phenyl, ethyl, 2-hydroxy-2-methylpropyl, azetidinyl, azetidin-1-yl, morpholinyl, oxa-6-azaspiro[3.3]heptyl, 1-oxa-6-azaspiro[3.3]hept-6-yl, pyridinylamino, hexahydro-4H-furo[3,2-b]pyrrol-4-yl, (1-cyclopropylethyl)amino, (methyl)(ethyl)amino, (methyl)(isopropyl)amino, (ethyl)amino, (1-cyclobutylethyl)amino, (cyclobutylmethyl)amino, (tetrahydrofuranylmethyl)amino, (tetrahydrofuran-2-ylmethyl)amino, 8-oxa-5-azaspiro[3.5]non-5-yl, 6,7-dihydropyrazolo[1.5-a]pyrazin-5(4H)-yl, tetrahydropyranylamino, tetrahydro-2H-pyra-4-ylamino, 2-oxa-5-azabicyclo[2.2.1]hept-5-yl, oxaazabicyclo[2.2.1]heptyl, 6-oxa-2-azaspiro[3.4]oct-2-yl, cyclobutylamino, isopropylamino, (cyclopropylmethyl)amino, tetrahydrofuranylamino, tetrahydrofuran-3-ylamino, isobutylamino, propylamino, azetidinyl, azetidin-1-yl, isobutoxy, cycloproylmethoxy, pyrrolidinyl, (oxetanylmethyl)amino, (oxetan-3-ylmethyl)amino, isopropoxy, cyclobutoxy, hydrogen, and 1-phenylethyl;

wherein $R^4$ is substituted with 0, 1, 2, or 3 groups selected from $C_{1-4}$ alkyl, cyano, halogen, hydroxy, and methoxy;

further wherein, optionally $R^3$ and $R^4$ along with the carbon to which they are attached may join together to form a 4- to 6-membered saturated ring system selected from pyrrolidinyl, pyrrolidin-2-yl, piperidinyl, tetrahydrofuranyl, and cyclopentyl, said 4- to 6-membered saturated ring system is substituted with 0, 1, or 2 moieties sected from isopropyl, ethyl, —$SO_2CH_3$, cyclopropylcarbonyl, and —$SO_2CF_3$;

$R^5$ is selected from hydrogen, methyl, methylcarbonyl, ethyl, isopropyl, morpholinoethyl, 2-hydroxy-2-methylpropyl, 2-hydroxyethyl, 1-phenylethyl, benzyl, tetrahydro-2H-pyranylmethyl, 1-cyclopropylethyl, and tetrahydro-2H-pyranyl; and $R^6$ is hydrogen or oxo (=O).

"Patient" for the purposes of the present invention includes humans and other animals, particularly mammals and other organisms. Thus the methods are applicable to both human therapy and veterinary applications.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —$(CR^3R^3)_2$—, each occurrence of the two $R^3$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

Optical Isomers—Diastereomers—Geometric Isomers—Tautomers

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, for example, (R and S)-5-[9-ethyl-8-(2-methylpyrimidin-5-yl)-9H-purin-6-yl]-3-[(2-methoxyethyl)amino]-3-methyl-1,3-dihydro-2H-indol-2-one, the "and" indicates a racemic mixture of the enantiomers. That is, the individual enantiomers were not individually isolated.

When the stereomeric nomenclature includes "or", for example, (R or S)-5-(9-ethyl-8-(2-methylpyrimidin-5-yl)-9H-purin-6-yl)-3-(2-hydroxy-2-methylpropyl)-3-methylindolin-2-one, the "or" indicates that chiral resolution of racemate into individual enantiomers was accomplished but the actual optical activity of the specific enantiomer was not determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

Diastereomeric mixtures can be separated into their individual diastereomers on the basis of their physical chemical differences by methods well known to those skilled in the art, such as, for example, by chromatography (e.g. chiral HPLC column) and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I, subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward. B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1$-$C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-(C1-C2)alkyl and piperidine-, pyrrolidino- or morpholino$(C_2-C_3)$alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$ alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_6)$ alkyl and Y$^3$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid.

"Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Labelled Compounds

In the compounds of genetic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Additionally, the present invention is meant to include in compounds of generic Formula I, all suitable replacements of sp3 orbital carbons to sp3 Si as can readily be envisioned by one of ordinary skill in the art.

Utilities

Compounds of the Invention have activity for PI3K-delta. Compounds of this invention have been tested using the assays described in the Biological Examples and have been determined to be inhibitors of PI3K-delta. Suitable in vitro assays for measuring PI3K-delta activity and the inhibition thereof by compounds are known in the art. For further details of an in vitro assay for measuring PI3K-delta, see the Biological Examples herein. Cell-based assays for measurement of in vitro efficacy in treatment of cancer are known in the art. In addition, assays are described in the Biological Examples provided herein.

Suitable in vivo models for cancer are known to those of ordinary skill in the art. See for example, international patent application published as WO 2012/037226 for further details of in vivo models for prostate adenocarcinoma, glioblastoma, lung carcinoma, and melanoma. Following the examples disclosed herein, as well as that disclosed in the art, a person of ordinary skill in the art can determine the activity of a compound of this invention.

Compounds of Formula I may be useful for treating diseases, including autoimmune disorders, inflammatory diseases, and cancers, which are listed below.

Cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartorna, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplasia syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

Autoimmune diseases: Hashimoto's thyroiditis, systemic lupus erythematosus (SLE), Goodpasture's syndrome, pemphigus, receptor autoimmune diseases, Basedow's disease (Graves' disease), myasthernia gravis, insulin resistant diseases, autoimmune hemolytic anemia, autoimmune thrombocytopenic purpura, autoimmune encephalomyelitis, rheumatism, rheumatoid arthritis, scleroderma, mixed connective tissue disease, polymyositis, pernicious anemia, idiopathic Addison's disease, some types of infertility, glomerulonephritis, bullous pemphigus, Sjogren's syndrome, some types of diabetes, adrenergic agent resistance, chronic active hepatitis, primary biliary cirrhosis, endocrine failure, vitiligo, angiitis, post-cardiac surgery syndrome, urticaria, atopic dermatiti and multiple sclerosis, autoimmune polyglandular disease (also known as autoimmune polyglandular syndrome), autoimmune alopecia; pernicious anemia; vitiligo; autoimmune hypopituatarism, and Guillain-Barre syndrome.

Inflammatory Diseases: asthma, allergic rhinitis, psoriasis, inflammatory arthritis, rheumatoid arthritis, psoriatic arthritis or osteoarthritis, irritable bowel syndrome, ulcerative colitis, Crohn's disease, respiratory allergies (asthma, hay fever, allergic rhinitis) or skin allergies, scleracierma, mycosis fungoides, acute inflammatory responses (such as acute respiratory distress syndrome and ishchemia/reperfusion injury), dermatomyositis, alopecia greata, chronic actinic dermatitis, eczema, Behcet's disease, Pustulosis palmoplanteris, Pyoderma gangrenum, Sezary's syndrome, atopic dermatitis, systemic sclerosis, and morphea.

Central Nervous System Disorders: multiple sclerosis, schizophrenia

Thus, in one embodiment, the invention provides a method of inhibiting PI3K-delta comprising contacting the PI3K-delta with an effective amount of a compound as disclosed herein.

In one embodiment, the compounds of the instant invention are selective PI3K-delta inhibitors relative to PI3K-alpha. The determination of relative selectivity for a given compound of PI3K-delta inhibition is defined as the relative ratio of the (PI3K-alpha $IC_{50}$ value/PI3K-delta $IC_{50}$ value) is at least 2. In yet another embodiment, for a given compound, the relative ratios of the (PI3K-alpha $IC_{50}$ value/PI3K-delta $IC_{50}$ value) is at least 4.

In another embodiment, the invention provides a method of treating a PI3K-delta modulated disease comprising administering to a mammal in need of such treatment a therapeutically effective amount of a compound as disclosed herein.

In another embodiment, the invention provides a method of treating cancer disease mediated by PI3K-delta comprising administering to a mammal in need of such treatment a therapeutically effective amount of a compound as disclosed herein.

Compounds of the invention are also useful as inhibitors of PI3K-delta in vivo for studying the in vivo role of PI3K-delta in biological processes, including the diseases described herein. Accordingly, the invention also comprises a method of inhibiting PI3K-delta in vivo comprising administering a compound or composition of the invention to a mammal.

Accordingly, another aspect of the present invention provides a method for the treatment or prevention of a PI3K-delta mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a PI3K-delta mediated diseases or disorders.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 milligram of active agent per kilogram body weight of a mammal (mg/kg) to about 100 mg/kg, typically, between 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.01 mg to 10 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, 400 mg, or 500 mg.

The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of the disease state. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be preferred for continuous infusion.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

In certain embodiments, a compound of Formula I is combined in a pharmaceutical combination formulation, or dosing regimen as combination therapy, with one or more other therapeutic agents that has anti-inflammatory or anti-hyperproliferative properties or that is useful for treating an inflammation, immune-response disorder, or hyperproliferative disorder (e.g., cancer). The other therapeutic agent of the pharmaceutical combination formulation or dosing regimen preferably has complementary activities to the compound of Formula I such that they do not adversely affect each other. Such agents are suitably present in combination in amounts that are effective for the purpose intended.

In one embodiment of the invention, the compound of Formula I, or a stereoisomer, tautomer, or pharmaceutically acceptable salt or prodrug thereof, may be co-administered with one or more other therapeutic agents for the treatment and prevention of PI3Kdelta mediated diseases. Thus in another aspect the present invention provides pharmaceutical compositions for treating PI3Kdelta mediated diseases comprising a therapeutically effective amount of a compound of formula I and one or more other therapeutic agents.

In one embodiment for example, for the treatment of the inflammatory diseases rheumatoid arthritis, psoriasis, inflammatory bowel disease, COPD, asthma and allergic rhinitis a compound of formula I may be combined with other therapeutic agents such as: (I) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide triamcinolone acetonide, beclomethasone dipropionate, budesonide, fluticasone propionate, ciclesonide and mometasone furoate.

In another embodiment of the invention, the compounds of Formula I, or a stereoisomer, tautomer, or pharmaceutically acceptable salt or prodrug thereof, may be employed alone or in combination with other therapeutic agents for the treatment of hyperproliferative disorders (e.g., cancer) including standard chemotherapy regimens, and anti-CD20 monoclonal antibodies, rituximab, bendamustine, ofatumumab, fludarabine, lenalidomide, and/or bortezomib.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active therapeutic agents simultaneously exert their biological activities.

SCHEMES AND EXAMPLES

The abbreviations used herein have the following tabulated meanings. Abbreviations not tabulated below have their meanings as commonly used unless specifically stated otherwise.

| | |
|---|---|
| ACN | acetonitrile |
| AcOH | acetic acid |
| BSA | N,O-bis(trimetihylsilyl)acetamide |
| B(iPrO)$_3$ | triisopropyl borate |
| B(Pin)$_2$ or (BPin)$_2$ | bis(pinacolato)diboron |
| Boc | tert-butoxycarbamate |
| tBu—OH | tert-butyl alcohol |
| BuLi (n-BuLi) | n-butyllithium |
| CELITE | A trademarked version of diatomaceous earth |
| CDI | carbonyl diimidazole |
| DCE | dichloroethane |
| DCM | dichloromethane |
| DIPEA | diisopropylethylamine |
| DMA | dimethylacetamide |
| DMAP | dimethylaminopyridine |
| DME | dimethoxyetane |
| DMEA | dimethylethylamine |
| DMF | dimethylformamide |
| DMSO | dimethyl sulfoxide |
| EI | electron ionization |
| EtI | ethyl iodide |
| EtOAc | ethyl acetate |
| EtOH | ethanol |
| Et$_3$N | triethylamine |
| EtNiPr$_2$ | ethyldiisopropylamine |
| HATU | 1-[bis(dimethylamino)methylene]-1H-1,2,3-triazolo[4,5-b]pyridinium 3-oxid hexafluorophosphate |
| HPLC | high performance liquid chromatography |
| KOAc | potassium acetate |
| K$_3$PO$_4$ | tripotassium phosphate |
| LC/MS | liquid chromatography coupled to mass spectrometer |
| LDA | |
| MeCN | acetonitrile |
| MeI | Methyl iodine |
| MeOH | methanol |
| MS | mass spectrum (data) |
| MsCl | methanesulfonyl chloride |
| NBS | N-bromosuccinimide |
| Na$_2$SO$_4$ | sodium sulfate |
| NaBH(OAc)$_3$ | sodium triacetoxyborohydride |
| NaHMDS | sodium bis(trimethylsilyl)amide |
| NCCH$_2$CO$_2$H | 2-cyanoacetic acid |
| NEt$_3$ | triethylamine |
| NMR | nuclear magnetic resonance (data) |
| OsO$_4$ | Osmium tetrachloride (osmium(VIII) oxide) |
| PdCl$_2$(dppf) | 1,1'-bis(diphenylphosphino)ferrocene-palladium(II)dichloride |
| Pd$_2$(dba)$_3$ | tris(dibenzylideneacetone)dipalladium(0) |
| PdCl$_2$(dtbpf) | [1,1'-bis(di-tert-butylphosphino)ferrocene]dichloropalladium(II) |
| PCl$_2$(dppf)-CH$_2$Cl$_2$ | 1,1'-bis(diphenyiphosphino)ferrocene]palladium(II) dichloride dichloromethane complex |
| Pd(PPh$_3$)$_4$ | tetrakis(triphenylphosphine) palladium(0) |
| PMP-CHO | 4-methoxybenzaldehyde |
| PG | Protecting Group |
| RT | room temperature |
| SPhos Precatalyst (SPhos Biphenyl precatalyst), (SPhos PreCat) | (2-dicyclohexylphosphino-2',6'-dimethoxy-1,1'-biphenyl)[2-(2-aminoethylphenyl)]palladium(II) chloride |

| | |
|---|---|
| TBAF | tetrabutylammonium fluoride |
| TfOH | Trifluoromethanesulfonic acid |
| NaO$^t$Bu (t-BuONa) | sodium tert-butoxide (t-BuONa) |
| TEA | triethylamine |
| TFA | trifluoroacetic acid |
| THF | tetrahydrofuran |
| TMEDA | $N^1,N^1,N^2,N^2$-tetramethylethane-1,2-diamine |
| TMSCN | (pg 112) |
| XPhos | 2-dicyclohexylphosphino-2',4',6'-triisopropylbiphenyl |
| G2-XPhos Precatalyst | chloro(2-dicyclohexylphosphino-2',4',6'-triisopropyl-1,1'-biphenyl)[2-(2'-amino-1,1'-biphenyl)]palladium(II) |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated.

All reactions were stirred (mechanically, stir bar/stir plate, or shaken) and conducted under an inert atmosphere of nitrogen or argon unless specifically stated otherwise.

All temperatures are degrees Celsius (° C.) unless otherwise noted. Ambient temperature is 15-25° C.

Most compounds were purified by reverse-phase preparative HPLC, MPLC on silica gel, recrystallization and/or trituration (suspension in a solvent followed by filtration of the solid). The course of the reactions was followed by thin layer chromatography (TLC) and/or LCMS and/or NMR and reaction times are given for illustration only.

All end products were analyzed by NMR and LCMS. Intermediates were analyzed by NMR and/or TLC and/or LCMS.

General Synthetic Schemes

Several synthetic schemes were employed to access the diverse compounds described herein. Final compounds were screened in kinase activity assays as either the racemate or as resolved enantiomers and diastereomers. The chiral separations were conducted on either the final compounds or on a synthetic intermediate. Chiral separation conditions are noted where appropriate.

One common synthetic approach was to begin with indolin-2-one or 7-aza-indolin-2-one (Gen-1), alkylating sequentially with base and two electrophiles; denoted $R^3$ and $R^4$. Bromination at the C(5) position of Gen-2 followed by borylation and Suzuki coupling to a substituted chloropurine provided example inhibitors Gen-3. In some cases, intermediate Gen-2 was protected on the oxindole nitrogen prior to the borylation-Suzuki steps, and the protective group removed at the end of the synthesis. Compounds such as Gen-3 may be further elaborated by treatment with base and an electrophile to arrive at compounds Gen-4 bearing an $R^5$ group. The groups $R^3$ and $R^4$ may be further elaborated after incorporation into the indolin-2-one or 7-aza-indolin-2-one. The carbonyl at the 2-position of Gen-2 may be optionally reduced to afford the indoline. Examples of this are included throughout the text.

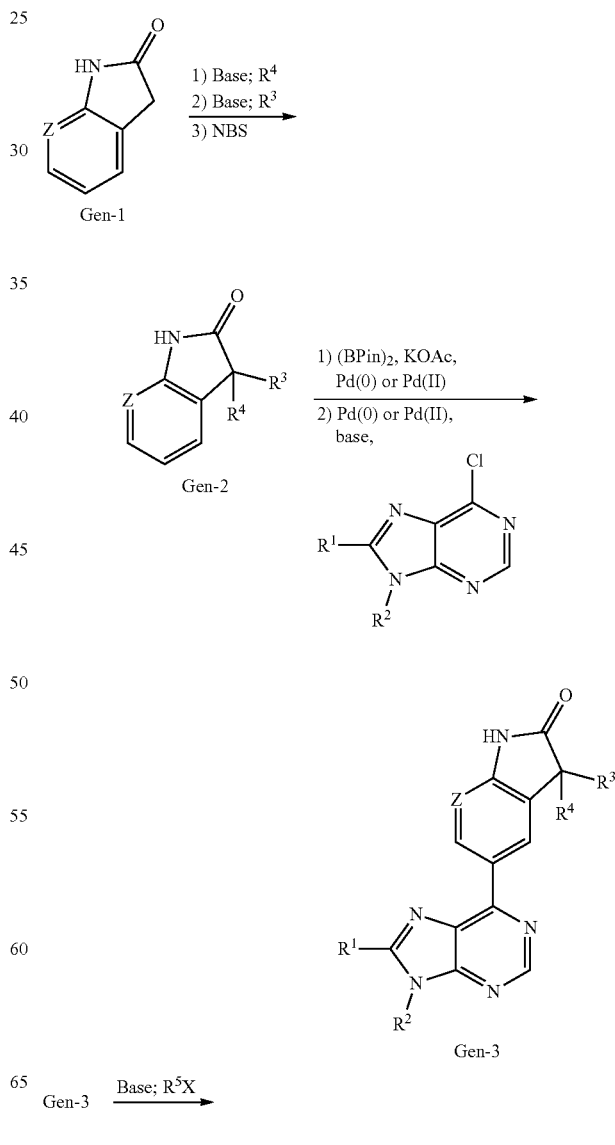

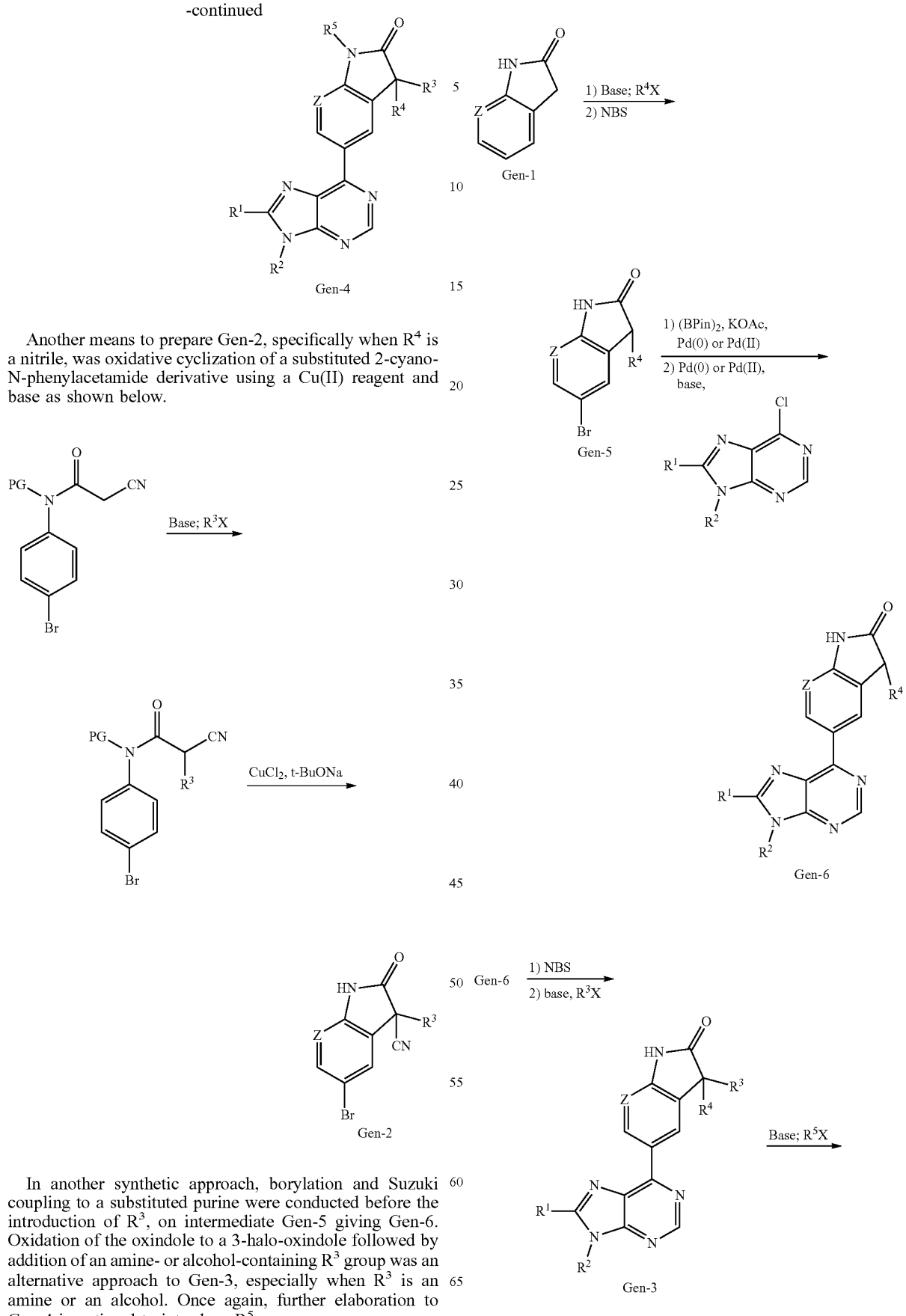

Another means to prepare Gen-2, specifically when $R^4$ is a nitrile, was oxidative cyclization of a substituted 2-cyano-N-phenylacetamide derivative using a Cu(II) reagent and base as shown below.

In another synthetic approach, borylation and Suzuki coupling to a substituted purine were conducted before the introduction of $R^3$, on intermediate Gen-5 giving Gen-6. Oxidation of the oxindole to a 3-halo-oxindole followed by addition of an amine- or alcohol-containing $R^3$ group was an alternative approach to Gen-3, especially when $R^3$ is an amine or an alcohol. Once again, further elaboration to Gen-4 is optional to introduce $R^5$.

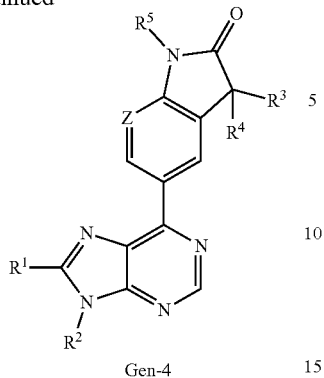

Gen-4

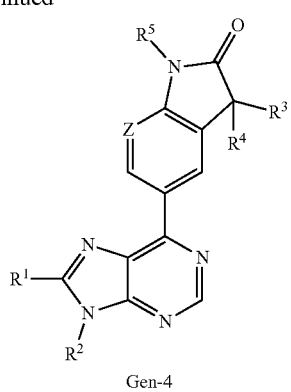

Gen-4

Rather than oxidize at a later stage in the synthesis, an alternative was to begin with hydroxy-oxindole Gen-7. Gen-7 was prepared by the addition of $R^4$ to 3-keto-oxindole. Gen-7 can be further elaborated to purine Gen-8 via a Suzuki coupling. Conversion of the 3-hydroxy-oxindole to a 3-halo-oxindole followed by addition of nucleophilic $R^3$ substituents (e.g. amines, alcohols) gave Gen-3.

In another synthetic approach, indole Gen-9 can be coupled to the chloropurine giving Gen-10. Oxidation with HBr and bromine converted the indole to a 3-bromo-2-oxindole intermediate. This is then treated with a nucleophilic $R^3$ group (e.g. amines, alcohols) to provided Gen-3.

To access the spirocyclic compounds, a suitably substituted 3-aminopropyl-indole derivative Gen-11 (bearing diverse $R^3$ groups) was oxidized to the 3-bromo-3-aminopropyl-oxindole with NBS and then cyclized with base to provide the spirocyclic oxindoles, denoted Gen-12. Borylation and Suzuki coupling to a chloropurine derivative provided Gen-13 which may optionally be further elaborated at the oxindole nitrogen giving Gen-14.

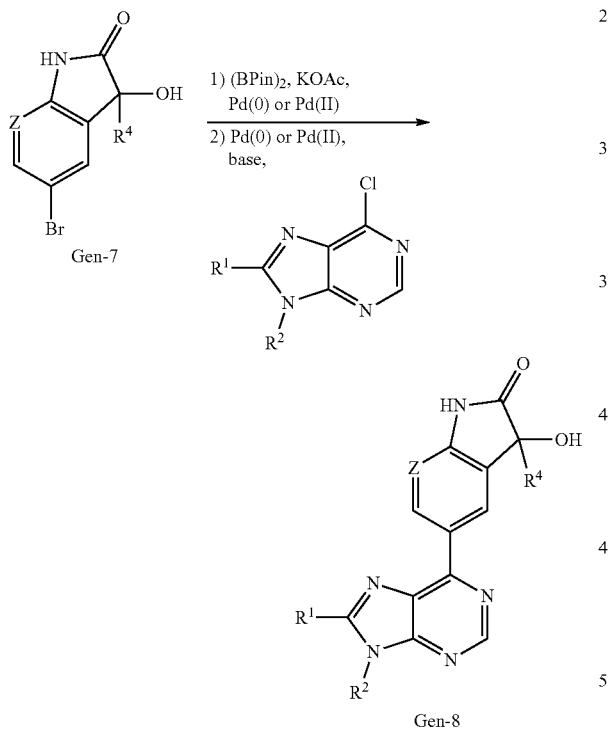

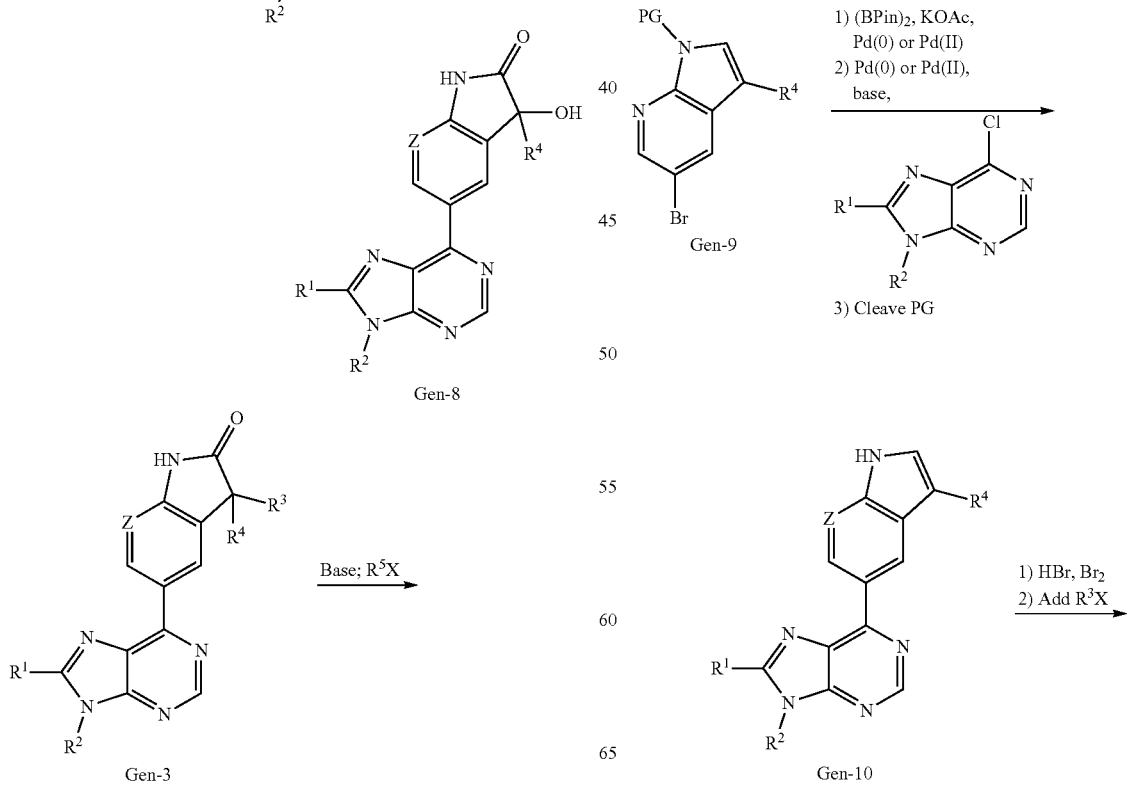

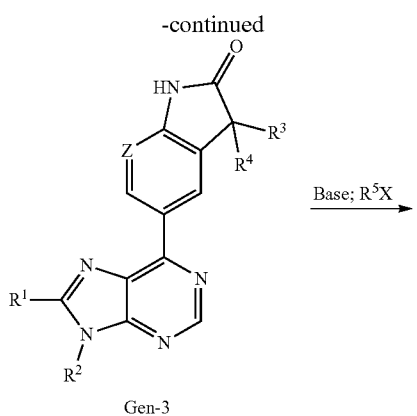
Gen-3
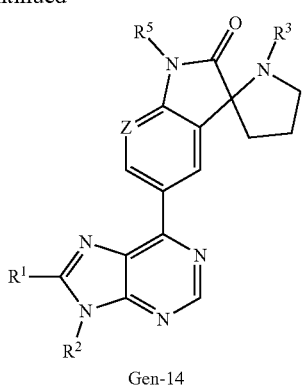
Gen-14
The synthetic route to a different design began with aniline Gen-15 bearing the $R^4$ group, by the addition of $R^3$ followed by cyclization with triphosgene. Borylation and Suzuki coupling gave Gen-17 which can be optionally derivatized to give Gen-48.
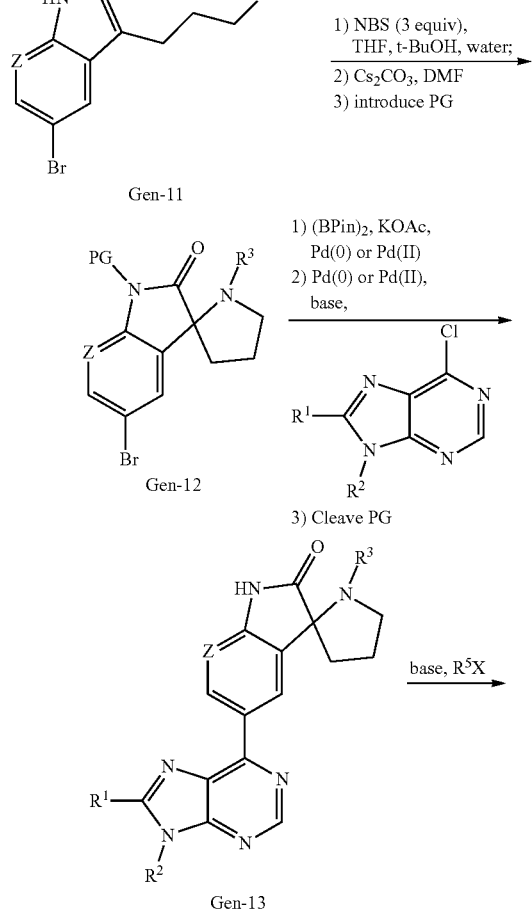
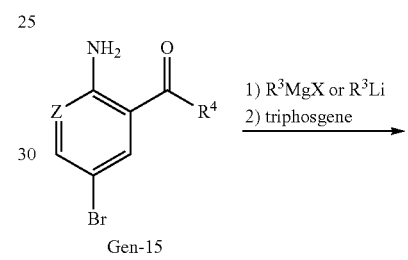
Gen-15
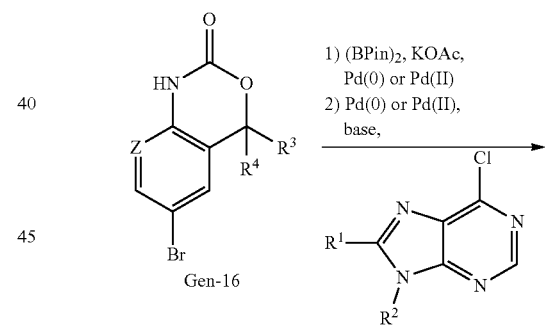
Gen-16
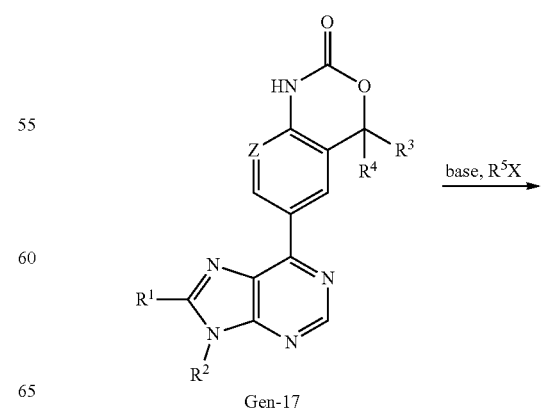
Gen-17

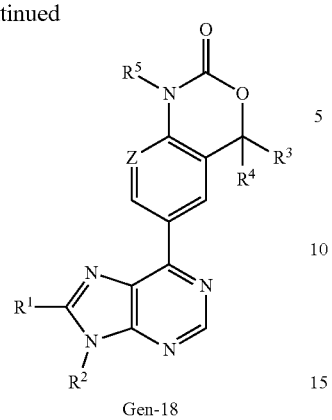

Gen-18

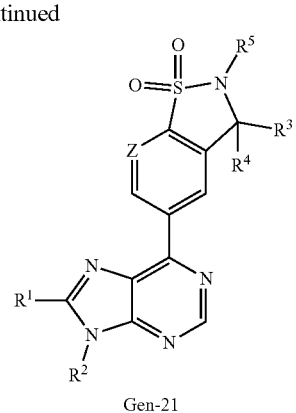

Gen-21

Another approach began with 5-bromobenzo[d]isothiazol-3(2H)-one 1,1-dioxide, in which the $R^3$ and $R^4$ groups were introduced as successive organomagnesium halide or organolithium additions, giving Gen-19. Borylation and Suzuki coupling to Gen-19 with a suitably substituted chloropurine provided Gen-20, which may be optionally substituted on nitrogen with an $R^5$ group giving Gen-21.

In a related sequence, Boc-protected 5-bromoisoindolin-1-one was successively alkylated by treatment with base and $R^3$ and $R^4$ halides, giving Gen-22. Borylation and Suzuki coupling to Gen-22 with a suitably substituted chloropurine provided Gen-23, which may be optionally substituted on nitrogen with an $R^5$ group giving Gen-24.

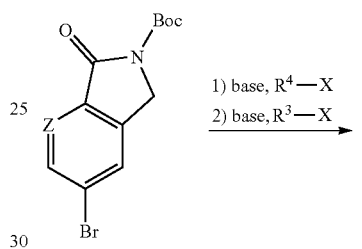

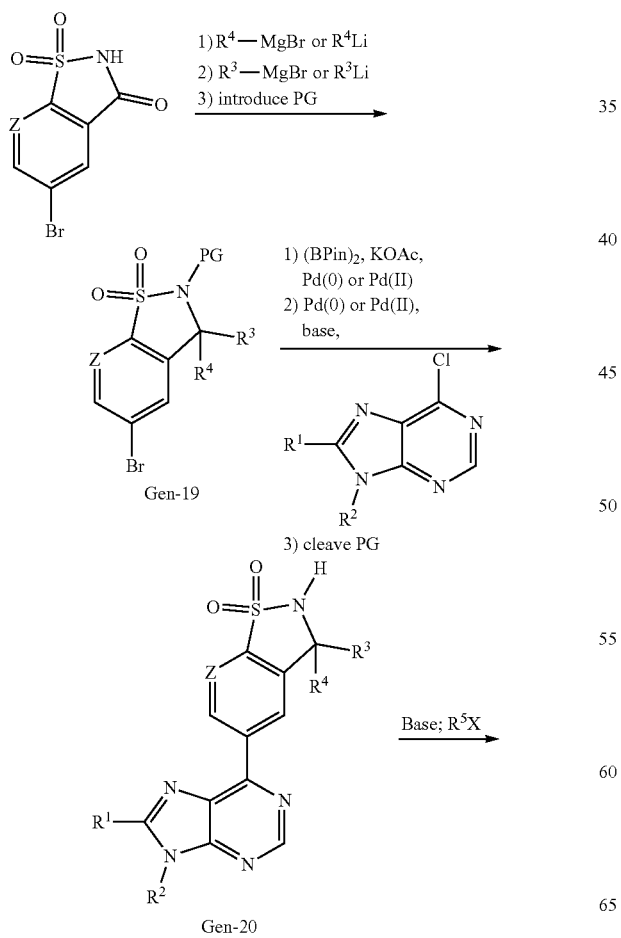

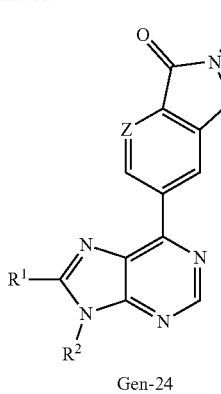

Gen-24

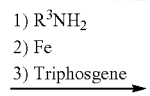

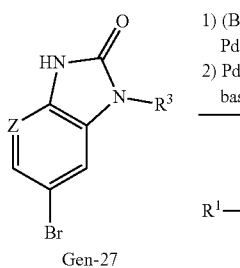

Gen-27

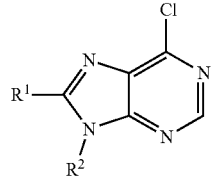

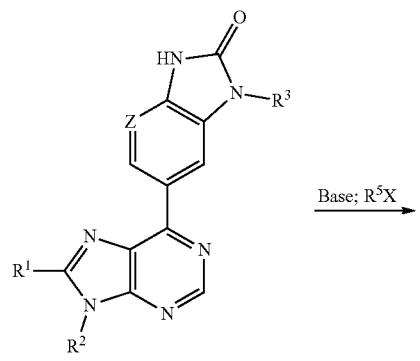

Gen-28

An alternative design began with 2-aminophenol derivatives, in which $R^3$ was introduced by a reductive amination reaction with a suitable carbonyl-bearing reagent. Cyclization with CDI or phosgene gave Gen-25. Borylation and Suzuki coupling to Gen-25 with a suitably substituted chloropurine provided Gen-26. Related to this approach, 2-fluoronitroaryls were treated with an amine bearing the $R^3$ substituent. Reduction of the nitro group followed by cyclization with CDI or phosgene gave Gen-27, Borylation and Suzuki coupling to Gen-27 with a suitably substituted chloropurine provided Gen-28, which may be optionally substituted on nitrogen with an $R^5$ group to give Gen-29.

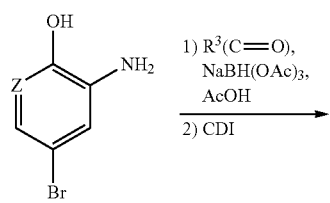

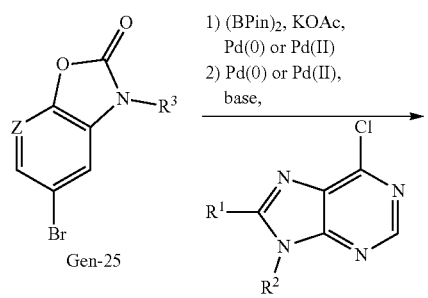

Gen-25

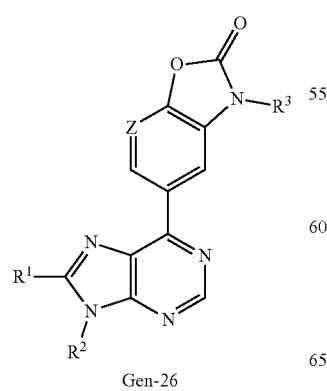

Gen-26

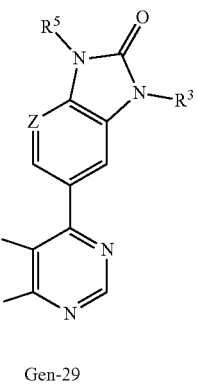

Gen-29

Synthesis of Common Intermediates

Preparation of Intermediate I

Intermediate I was prepared via two routes, one convergent approach and the other approach linear. Both approaches are described in the figures and associated procedures below.

Convergent Approach to Intermediate I

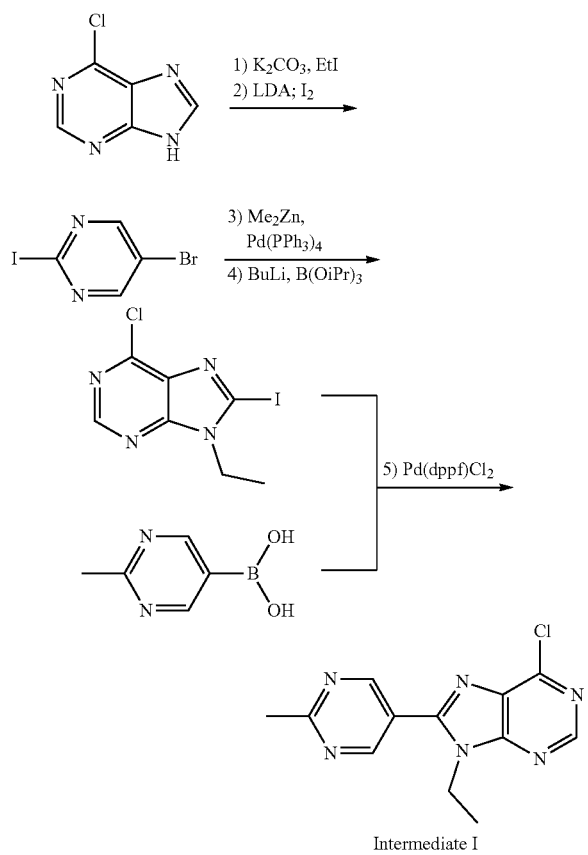

Steps 1 and 2 6-chloro-9-ethyl-8-iodo-9H-purine

Into a 10-L 4-neck round-bottom flask was placed a solution of 6-chloro-9H-purine (500 g, 3.24 mol), iodoethane (1009 g, 6.47 mol) and potassium carbonate (447 g, 3.23 mol) in DMSO (5 L). The resulting solution was stirred overnight at room temperature. It was then diluted with brine and extracted with 3×1.5 L of ethyl acetate. The organic extracts were combined, dried over anhydrous magnesium sulfate and concentrated under vacuum. The residue was purified by chromatography on SiO₂ (1:2 EtOAc/petroleum ether) providing 6-chloro-9-ethyl-9H-purine.

Into a 10-L 4-neck round-bottom flask purged and maintained with an inert atmosphere of nitrogen was placed a solution of diisopropylamine (200 g, 1.98 mol) in THF (1.2 L). This was followed by addition of a 2.5 M solution of n-BuLi (736 mL, 1.40 equiv) at −78° C. After stirring for 30 min, a solution of 6-chloro-9-ethyl-9H-purine (240 g, 1.31 mol) in THF (1.2 L) was added dropwise with stirring at −78° C. The resulting solution was stirred for 5 min at −78° C., followed by addition of a solution of I₂ (467 g, 1.84 mol) in THF (1.2 L) at −78° C. The resulting solution was stirred for an additional 10 min at −78° C., then quenched by the addition of 200 mL of aqueous NH₄Cl. The organic layer was washed with 2×1.5 L of aqueous Na₂S₂O₃, dried (MgSO₄) and concentrated under vacuum. The obtained solid was washed with 2×200 mL of ethyl ether to give 6-chloro-9-ethyl-8-iodo-9H-purine.

Steps 3 and 4 (2-methylpyrimidin-5-yl)boronic acid

Into a 10-L 4-neck round-bottom flask purged and maintained with an inert atmosphere of nitrogen was placed a solution of 5-bromo-2-iodopyrimidine (590 g, 2.07 mol) in THF (3 L). This was followed by dropwise addition of 1 M solution of dimethyl zinc (3.11 L, 3.11 mol) with stirring at 0° C. To this was added Pd(PPh₃)₄ (120 g, 104 mmol). The resulting solution was stirred for 3 h at 0° C., then quenched by the addition of 600 mL of aqueous NH₄Cl. The resulting solution was extracted with 2×1.5 L of EtOAc. The organic extracts were combined, dried (MgSO₄) and concentrated under vacuum. The residue was purified by chromatography on SiO₂ (1:50 EtOAc/petroleum ether) to provide 5-bromo-2-methylpyrimidine.

Into a 10-L 4-neck round-bottom flask purged and maintained with an inert atmosphere of nitrogen was placed a solution of 5-bromo-2-methylpyrimidine (184 g, 1.06 mol) and B(i-PrO)₃ (240 g, 1.28 mol) in THF/toluene (3/3 L). This was followed by the dropwise addition of a 2.5 M solution of n-BuLi (510 mL, 1.28 mol) with stirring at −78° C. The resulting solution was stirred for 1 h at −78° C., then quenched by the addition of 200 mL of aqueous NH₄Cl. The organic phase was dried and concentrated under vacuum. The aqueous phase was adjusted to pH 4 with AcOH. The solid was collected by filtration and dried in an oven under reduced pressure providing (2-methylpyrimidin-5-yl)boronic acid.

Step 5 6-chloro-9-ethyl-8-(2-methylpyrimidin-5-yl)-9H-purine

Into a 5-L 4-neck round-bottom flask purged and maintained with an inert atmosphere of nitrogen was placed a solution of 6-chloro-9-ethyl-8-iodo-9H-purine (242 g, 784 mmol), (2-methylpyrimidin-5-yl)boronic acid (108 g, 783 mmol), potassium carbonate (162 g, 1.17 mol) and Pd(dppf)Cl₂-DCM (32 g, 39 mmol) in dioxane (2.4 L) and water (480 mL). The resulting solution was stirred overnight at 90° C. The reaction mixture was cooled to room temperature, then extracted with 2×1.5 L of EtOAc. The organic extracts were combined, dried (MgSO₄) and concentrated under vacuum. The residue was purified by chromatography on SiO₂ (5:1:1 petroleum ether/DCM/EtOAc) providing 6-chloro-9-ethyl-8-(2-methylpyrimidin-5-yl)-9H-purine (Intermediate I). ¹H NMR (300 MHz, CDCl₃) δ 9.12 (s, 2H), 8.80 (s, 1H), 4.46 (q, J=7.2 Hz, 2H), 2.89 (s, 3H), 1.57-1.51 (t, J=7.2 Hz, 3H). MS (EI) calc'd for C₁₂H₁₂N₆Cl [M+H]⁺, 275; found, 275.

Linear Approach to Intermediate I

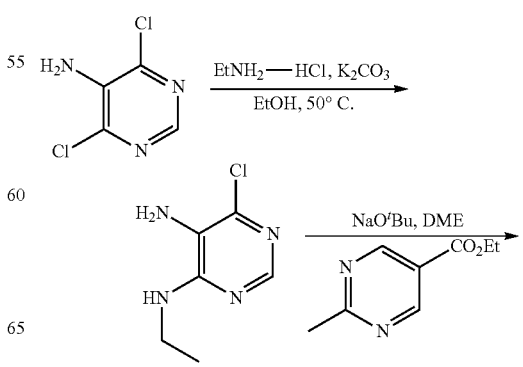

-continued

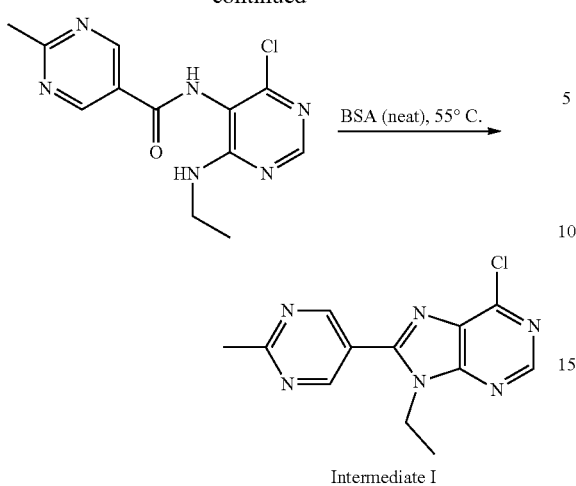

Intermediate I

A mixture of 4,6-dichloropyrimidin-5-amine (20.0 g, 122 mmol), ethanamine hydrochloride (19.9 g, 243 mmol), $K_2CO_3$ (50.7 g, 367 mmol) in ethanol (100 mL) was heated to 50° C. for 39 hr. After cooling to room temperature, the reaction mixture was diluted with DCM (750 mL) and then filtered. The cake was washed with DCM (250 mL). The combined filtrate was concentrated to dryness to provide 6-chloro-N4-ethylpyrimidine-4,5-diamine. MS (EI) calc'd for $C_6H_{10}ClN_4$ [M+H]$^+$, 173; found, 173.

To a mixture of 6-chloro-N4-ethylpyrimidine-4,5-diamine (16.4 g, 91 mmol) and ethyl-2-methylpyrimidine-5-carboxylate (15 g, 90 mmol) in 50 mL of DMF, a slurry of sodium tert-butoxide (9.1 g, 92 mmol) in DMF (25 mL) was added. The reaction mixture was stirred at 40° C. for 2 hr and then quenched by adding 75 mL of water and 75 mL of EtOAc. The reaction mixture was extracted with EtOAc (75 mL×2). The aqueous layer was charged with acetic acid (5.3 mL, 92 mmol) and a slurry was formed. The solid was collected by filtration and washed with 75 mL of 1:1 DMF/water and dried in a vacuum at 35° C. overnight to provide N-(4-chloro-6-(ethylamino)pyrimidin-5-yl)-2-methylpyrimidine-5-carboxamide. MS (EI) calc'd for $C_{12}H_{14}ClN_6O$ [M+H]$^+$, 293; found, 293.

To trimethylsilyl N-(trimethylsilyl)acetimidate (BSA, 22 mL, 91 mmol), N-(4-chloro-6-(ethylamino)pyrimidin-5-yl)-2-methylpyrimidine-5-carboxamide (5.0 g, 17 mmol) was added in portions. The reaction solution was heated to 55° C. for 1 hr and then cooled to room temperature. The formed solid was collected by filtration and washed with heptane (15 mL). The solid was dried in a vacuum at 50° C. overnight to provide 6-chloro-9-ethyl-8-(2-methylpyrimidin-5-yl)-9H-purine. MS (EI) calc'd for $C_{12}H_{12}ClN_6$ [M+H]$^+$, 275; found, 275.

Preparation of Intermediate II.

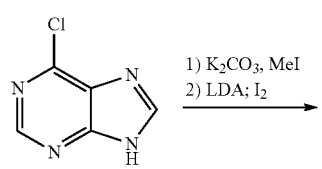

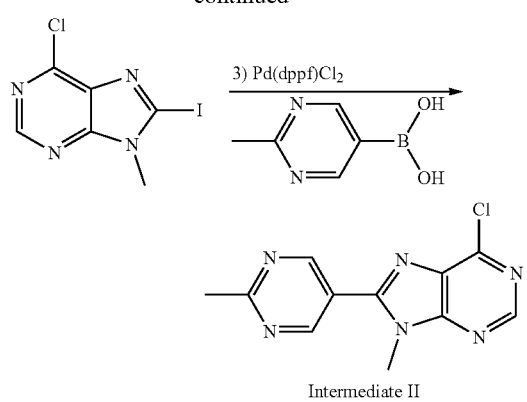

Intermediate II

As shown in the scheme, Intermediate II was prepared in a fashion analogous to intermediate I, substituting ethyl iodide for methyl iodide. MS (EI) calc'd for $C_{11}H_{10}ClN_6$ [M+H]$^+$, 261; found, 261.

Preparation of Intermediate III.

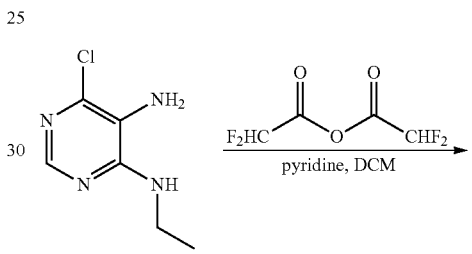

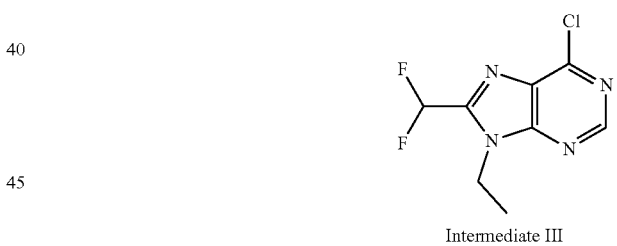

Intermediate III

Intermediate III, shown above, was prepared via the route described in the international patent application publication, WO 2014/075392 titled "Preparation of purines as selective inhibitors of human phosphatidylinositol 3-kinase delta"; by Achab, A. et al.

Preparation of Intermediate IV

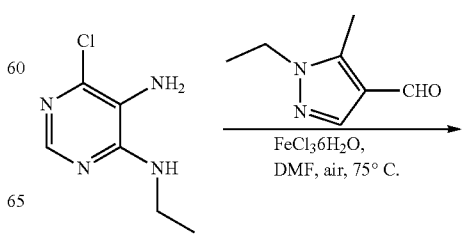

-continued

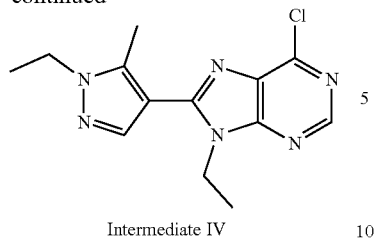

Intermediate IV

A mixture of 6-chloro-N$^4$-ethylpyrimidine-4,5-diamine (200 mg, 1.1 mmol) and FeCl$_3$-6H$_2$O (80 mg, 0.30 mmol) in DMF (1 ml) was treated with 1-ethyl-5-methyl-1H-pyrazole-4-carbaldehyde (200 mg, 1.45 mmol). The mixture was heated at 75° C. in an open vessel for 24 h. The reaction mixture was then concentrated and the residue was purified by chromatography on SiO$_2$ (0-10% MeOH in DCM) to afford 6-chloro-9-ethyl-8-(1-ethyl-5-methyl-1H-pyrazol-4-yl)-9H-purine. MS (EI) calc'd for C$_{13}$H$_{16}$ClN$_6$ [M+H]$^+$, 291; found, 291.

Compound Examples of Table 1

Example 1A Compounds 1-1 and 1-2

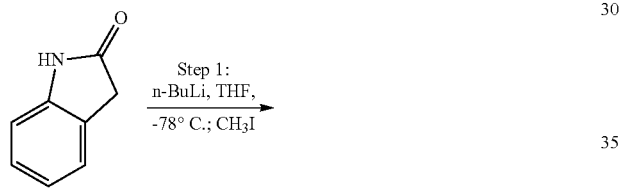

Step 1:
n-BuLi, THF,
-78° C.; CH$_3$I

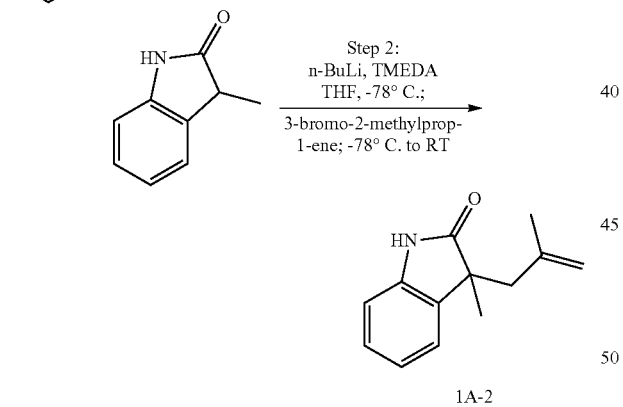

Step 2:
n-BuLi, TMEDA
THF, -78° C.;
3-bromo-2-methylprop-1-ene; -78° C. to RT 1A-2

Step 3:
1A-2 → H$_2$, Pd/C, EtOH
Step 4:
NBS, DMF

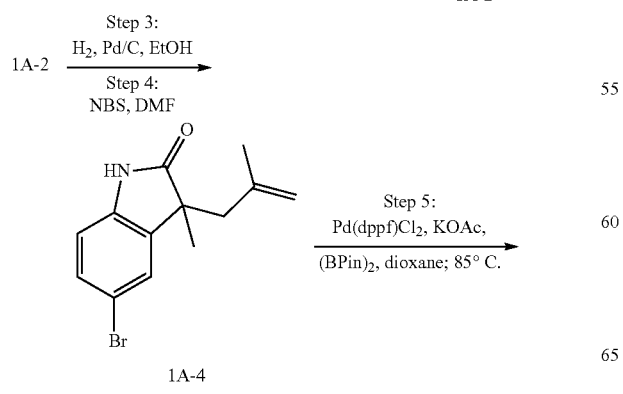

Step 5:
Pd(dppf)Cl$_2$, KOAc,
(BPin)$_2$, dioxane; 85° C.

1A-4

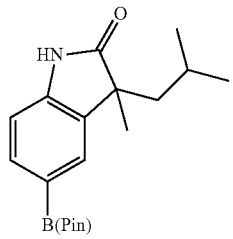

1A-5

Step 5:
Pd(dppf)Cl$_2$, K$_2$CO$_3$,
1A-5 → Intermediate I, dioxane, 90° C.

Step 7:
Chiral separation

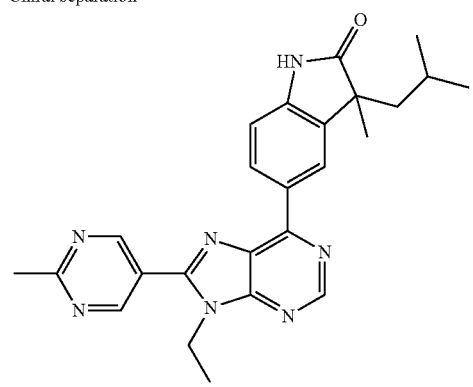

1-1
(R or S)

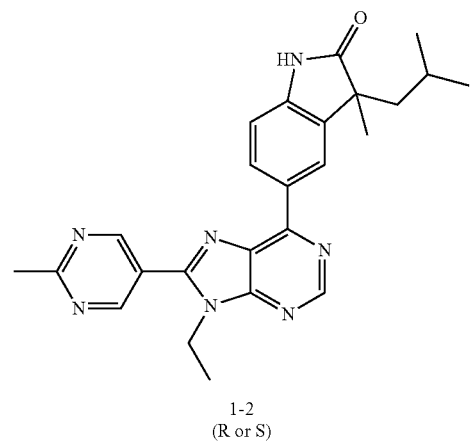 [SMILES: CCn1c(-c2cnc(C)nc2)nc2c(-c3ccc4c(c3)C(C)(CC(C)C)C(=O)N4)ncnc21]

1-2
(R or S)

Steps 1 and 2 3-Methyl-3-(2-methylallyl)indolin-2-one (1A-2)

An oven-dried 250 mL round-bottom flask containing indolin-2-one (5.00 g, 36.7 mmol) was fitted with a stirbar and septa, then flushed with nitrogen. Tetrahydrofuran (50 mL) was added and the mixture cooled to -78° C. A solution of n-butyllithium in hexane (32.3 mL, 80.7 mmol, 2.5 M solution) was added, and the resulting solution was stirred at -78° C. for 30 minutes. Next, iodomethane (13.0 g, 91.8 mmol) was added and the mixture stirred at -78° C. for 10 minutes. The reaction solution was quenched with saturated aqueous ammonia hydrochloride solution. The resulting mixture was extracted with EtOAc (3×30 mL) and the combined organic layers were washed with brine (50 mL), dried (MgSO$_4$) and filtered. The filtrate was concentrated under reduced pressure. The residue was purified by chromatography on SiO$_2$ (0% to 50% EtOAc/petroleum ether) to afford 3-methylindolin-2-one. MS (EI) calc'd for C$_9$H$_{10}$NO [M+H]$^+$, 148; found, 148.

To a solution of N$^1$,N$^1$,N$^2$,N$^2$-tetramethylethane-1,2-diamine (2.77 mL, 18.4 mmol) in THF (30 mL) was added 3-methylindolin-2-one (2.70 g, 18.4 mmol) at −78° C. A solution of n-butyllithium in hexane (16.2 mL, 36.8 mmol, 2.5 M) was added, and the resulting solution was stirred at −78° C. for 30 minutes. 3-Bromo-2-methylprop-1-ene (2.71 g, 20.2 mmol) was then added to the reaction solution at −78° C. The reaction solution then was transferred to a 0° C. bath and stirred with slow warming to room temperature for 16 h. The resulting solution was quenched with saturated aqueous ammonia hydrochloride solution. The mixture was extracted with EtOAc (3×30 mL). The combined organic layers were dried (MgSO$_4$) and filtered. The filtrate was concentrated under reduced pressure and purified by chromatography on SiO$_2$ (10% to 60% EtOAc/hexane) to afford 3-methyl-3-(2-methylallyl)indolin-2-one (1A-2). MS (EI) calc'd for C$_{13}$H$_{16}$NO [M+H]$^+$, 202; found, 202.

Steps 3 and 4
5-Bromo-3-isobutyl-3-methylindolin-2-one (1A-4)

To a solution of 3-methyl-3-(2-methylallyl)indolin-2-one (1A-2) (1.50 g, 7.46 mmol) in ethanol (15.0 mL) was added Pd/C (0.30 g, 2.8 mmol, 10% wt.) at room temperature. The reaction mixture was deoxygenated with hydrogen gas three times and stirred under a hydrogen balloon at room temperature for 12 h. The mixture was filtered and the filter cake was washed with EtOAc (3×30 mL). The filtrate was washed with water (3×30 mL) and brine (30 mL). The resulting organic layer was dried (MgSO$_4$) and filtered. The filtrate was concentrated under reduced pressure. The residue was purified by chromatography on SiO$_2$ (10% to 50% EtOAc/petroleum ether) to afford 3-isobutyl-3-methylindolin-2-one. MS (EI) calc'd for C$_{13}$H$_{18}$NO [M+H]$^+$, 204; found, 204.

To a solution of 3-isobutyl-3-methylindolin-2-one (1.00 g, 4.91 mmol) in DMF (1 mL) was added N-bromosuccinimide (4.15 g, 4.91 mmol) at 0° C. The resulting solution was stirred for 18 h at RT, then diluted with EtOAc and washed with brine. The combined organic layers were dried (Na$_2$SO$_4$), filtered, then concentrated. The residue was purified by chromatography on SiO$_2$ (EtOAc/petroleum ether) to afford 5-bromo-3-isobutyl-3-methylindolin-2-one (1A-4). MS (EI) calc'd for C$_{13}$H$_{17}$BrNO [M+H]$^+$, 282; found, 282.

Steps 5 and 6 Racemic 5-(9-Ethyl-8-(2-methylpyrimidin-5-yl)-9H-purin-6-yl)-3-isobutyl-3-methylindolin-2-one To a solution of 5-bromo-3-isobutyl-3-methylindolin-2-one (1A-4) (0.58 g, 2.1 mmol) in dioxane (20 mL) under argon, were added potassium acetate (400 mg, 4.20 mmol), (BPin)$_2$ (625 mg, 2.5 mmol) and PdCl$_2$(dppf) (150 mg, 0.2 mmol) at room temperature. The resulting mixture was stirred for 2 h at 85° C. After cooling to room temperature, the reaction mixture was diluted with water (2 mL) and extracted with EtOAc (3×5 mL). The combined organic layers was washed with brine (5 mL), dried over anhydrous sodium sulfate and filtered. The filtrate was concentrated under reduced pressure. The residue was purified by chromatography on SiO$_2$ (0% to 50% EtOAc/petroleum ether) to afford 3-isobutyl-3-methyl-5-(4,4,5,5-tetramethyl-1,3,2-dioxaborolan-2-yl)indolin-2-one (1A-5). MS (EI) calc'd for C$_{19}$H$_{29}$BNO$_3$ [M+H]$^+$, 330; found, 330.

To a solution of 3-isobutyl-3-methyl-5-(4,4,5,5-tetramethyl-1,3,2-dioxaborolan-2-yl)-indolin-2-one (330 mg, 1.0 mmol) in dioxane/water (5/1 mL), were added Intermediate I (275 mg, 1.0 mmol), K$_2$CO$_3$ (276 mg, 2.0 mmol) and PdCl$_2$(dppf)-CH$_2$Cl$_2$ (69 mg, 0.1 mmol) at room temperature. The resulting mixture was stirred for 4 h at 90° C. After cooling to room temperature, the reaction mixture was diluted with water and extracted with EtOAc. The combined organic layers were washed with brine, dried (Na$_2$SO$_4$) and filtered. The filtrate was concentrated under reduced pressure. The residue was purified by reverse phase Prep-HPLC [Column: XBridge RP C18, 19×150 mm; 30-50% MeCN/water with 10 mM NH$_4$HCO$_3$; Flow rate: 20 mL/min] to give the racemic title compound. MS (EI) calc'd for C$_{25}$H$_{28}$N$_7$O [M+H]$^+$, 442; found, 442.

Step 7 (R or S)- and (S or R)-5-(9-Ethyl-8-(2-methylpyrimidin-5-yl)-9H-purin-6-yl)-3-isobutyl-3-methylindolin-2-one (1-1 and 1-2)

The racemate material was separated by Prep-Chiral HPLC [Column: ChiralPak™ AD-H 2×25 cm; 30% EtOH/hexane; Flow rate: 20 mL/min; Retention Time 1: 9.50 min; Retention Time 2: 13.0 min). The faster-eluting enantiomer of the title compound (1-1) was obtained at 9.50 min: $^1$H NMR (400 MHz, DMSO-d$_6$) δ 10.72 (s, 1H), 9.26 (s, 2H), 8.99 (s, 1H), 8.92-8.90 (d, J=4.2 Hz, 1H), 8.65 (s, 1H), 7.10-7.08 (d, J=4.1 Hz, 1H), 4.47-4.45 (m, J=3.6 Hz, 2H), 2.79 (s, 3H), 1.87-1.76 (m, 2H), 1.41-1.38 (m, 3H),1.29-1.30 (m, 4H), 0.69-0.61 (m, 6H). MS (EI) calc'd for C$_{25}$H$_{28}$N$_7$O [M+H]$^+$, 442; found, 442. The slower-eluting enantiomer of the title compound (1-2) was obtained at 13.0 min: $^1$H NMR (400 MHz, DMSO-d$_6$) δ 10.72 (s, 1H), 9.26 (s, 2H), 8.99 (s, 1H), 8.91-8.90 (d, J=4.2 Hz, 1H), 8.65 (s, 1H), 7.10-7.08 (d, J=4.1 Hz, 1H), 4.47-4.45 (m, J=3.6 Hz, 2H), 2.79 (s, 3H), 1.87-1.80 (m, 2H), 1.41-1.38 (m, 3H), 1.29-1.30 (m, 4H), 0.69-0.61 (m, 6H). MS (EI) calc'd for C$_{25}$H$_{28}$N$_7$O [M+H]$^+$, 442; found, 442.

Example 1B Compounds 1-3 and 1-4

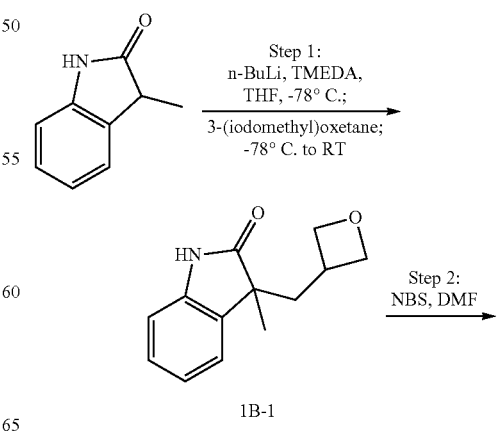

1B-1

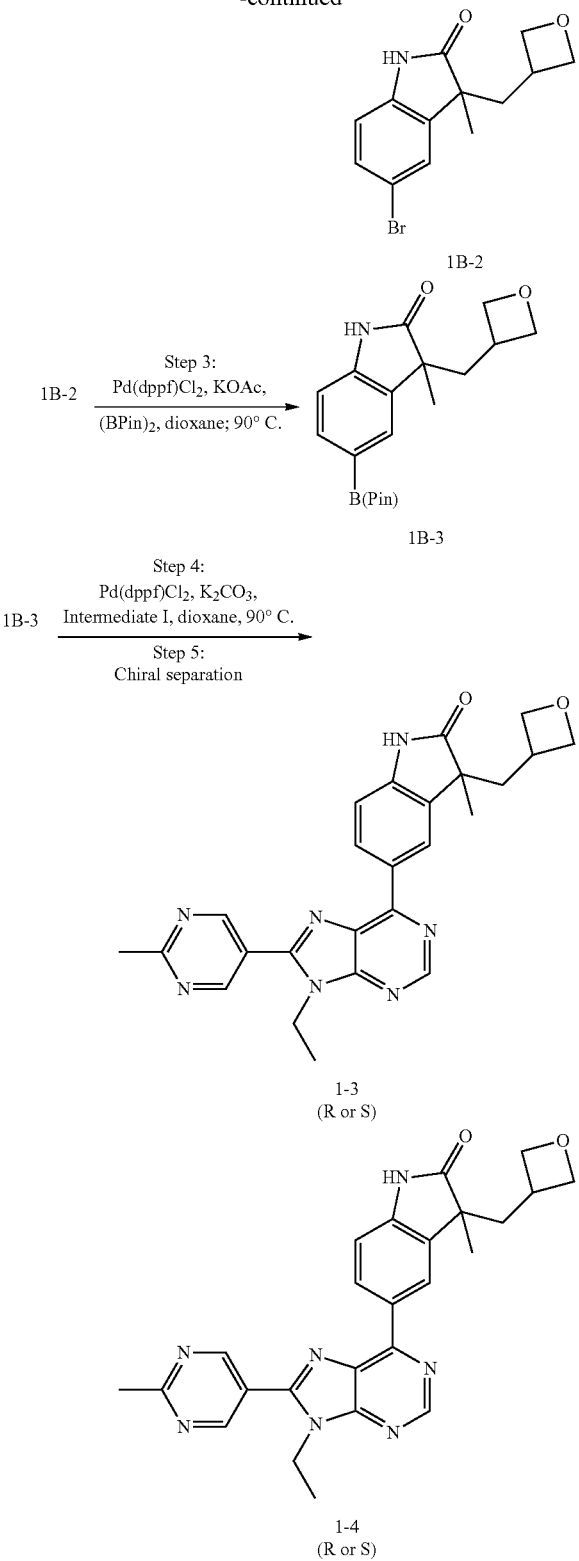

3-methylindolin-2-one (200 mg, 1.36 mmol) at −78° C. A solution of n-butyllithium in hexane (1.2 mL, 3.0 mmol, 2.50 M) was added, and the resulting solution was stirred at −78° C. for 30 minutes. 3-(Iodomethyl)oxetane (404 mg, 2.038 mmol) was then added to the reaction solution at −78° C. The reaction solution then was then slowly warmed to room temperature overnight. The resulting solution was quenched with saturated aqueous ammonia hydrochloride solution. The mixture was extracted with EtOAc (3×30 mL). The combined organic layers were dried (Na$_2$SO$_4$) and filtered. The filtrate was concentrated under reduced pressure and purified by chromatography on SiO$_2$ (10% to 60% EtOAc/petroleum ether) to afford 3-methyl-3-(oxetan-3-yl-methyl)indolin-2-one (1B-1). MS (EI) calc'd for C$_{13}$H$_{16}$NO$_2$ [M+H]$^+$, 218; found, 218.

Step 2 5-Bromo-3-methyl-3-(oxetan-3-ylmethyl)indolin-2-one (1B-2)

To a solution of 3-methyl-3-(oxetan-3-ylmethyl)indolin-2-one (1B-1) (150 mg, 0.69 mmol) in DMF (5 mL), was added NBS (135 mg, 0.759 mmol) at 0° C. The resulting solution was warmed to 25° C. and stirred for 2 h. The reaction mixture was quenched with saturated sodium bicarbonate (10 mL) and the resulting mixture was extracted with EtOAc (3×15 mL). The combined organic layers was washed with brine (3×10 mL), dried (Na$_2$SO$_4$) and filtered. The filtrate was concentrated under reduced pressure. The residue was purified by chromatography on SiO$_2$ (0 to 3% MeOH/DCM) to afford 5-bromo-3-methyl-3-(oxetan-3-yl-methyl)indolin-2-one (1B-2). MS (EI) calc'd for C$_{13}$H$_{15}$BrNO$_2$ [M+H]$^+$, 296; found, 296.

Steps 3-5 (R or S)- and (S or R)-5-(9-Ethyl-8-(2-methylpyrimidin-5-yl)-9H-purin-6-yl)-3-methyl-3-(oxetan-3-ylmethyl)indolin-2-one (1-3 and 1-4)

A mixture of 5-bromo-3-methyl-3-(oxetan-3-ylmethyl)indolin-2-one (1B-2) (170 mg, 0.574 mmol), (BPin)$_2$ (160 mg, 0.631 mmol), potassium acetate (141 mg, 1.44 mmol) and PdCl$_2$(dppf) (84 mg, 0.12 mmol) in 1,4-dioxane (2 mL) was deoxygenated with nitrogen, then stirred for 3 h at 90° C. After cooling to room temperature, Intermediate I (173 mg, 0.631 mmol), K$_2$CO$_3$ (159 mg, 1.15 mmol) and water (0.4 mL) were added to the above mixture, the resulting mixture warmed to 90° C. and stirred for 16 h. After cooling to room temperature, the reaction mixture was diluted water (10 mL). The resulting mixture was extracted with EtOAc (3×15 mL). The combined organic layers was washed with brine (2×10 mL), dried over anhydrous sodium sulfate and filtered. The filtrate was concentrated under reduced pressure, and the crude product was purified by Prep-TLC with 30:1 DCM/MeOH to afford 5-(9-ethyl-8-(2-methylpyrimidin-5-yl)-9H-purin-6-yl)-3-methyl-3-(oxetan-3-ylmethyl)indolin-2-one.

The racemate was separated by Prep-Chiral HPLC [Column: ChiralPak™ IC-3, 2×25 cm; 60% EtOH/hexane; Flow rate: 18 mL/min; Retention Time 1: 15.9 min; Retention Time 2: 21.7 min]. The faster-eluting enantiomer of the title compound (1-3) was obtained at 15.9 min: $^1$H NMR (400 MHz, DMSO-d$_6$) δ 10.76 (s, 1H), 9.26 (s, 2H), 8.99 (s, 1H), 8.93 (dd, J=8.4 Hz & 1.6 Hz, 1H), 8.65 (d, J=1.6 Hz, 1H), 7.07 (d, J=8.0 Hz, 1H), 4.44-4.47 (m, 3H), 4.23 (t, J=6.4 Hz, 1H), 4.10-4.04 (m, 2H), 2.79 (s, 3H), 2.77-2.75 (m, 1H), 2.27-2.15 (m, 2H), 1.39 (t, J=9.2 Hz, 3H), 1.33 (s, 3H). MS (EI) calc'd for C$_{25}$H$_{26}$N$_7$O$_2$ [M+H]$^+$, 456; found, 456. The slower-eluting enantiomer of the title compound (1-4) was Step 1 3-Methyl-3-(oxetan-3-ylmethyl)indolin-2-one (1B-1)

To a solution of N$^1$,N$^1$,N$^2$,N$^2$-tetramethylethane-1,2-diamine (160 mg, 1.4 mmol) in THF (8 mL) was added obtained at 21.7 min: $^1$H NMR (400 MHz, DMSO-d$_6$) δ 10.76 (s, 1H), 9.26 (s, 2H), 8.99 (s, 1H), 8.93 (dd, J=8.4 Hz & 1.6 Hz, 1H), 8.65 (d, J=1.6 Hz, 1H), 7.07 (d, J=8.0 Hz, 1H), 4.44-4.47 (m, 3H), 4.23 (t, J=6.4 Hz, 1H), 4.10-4.04 (m, 2H), 2.79 (s, 3H), 2.77-2.75 (m, 1H), 2.27-2.15 (m, 2H), 1.39 (t, J=9.2 Hz, 3H), 1.33 (s, 3H). MS (EI) calc'd for $C_{25}H_{26}N_7O_2$ [M+H]$^+$, 456; found, 456.

Example 1C Compounds 1-7 and 1-8

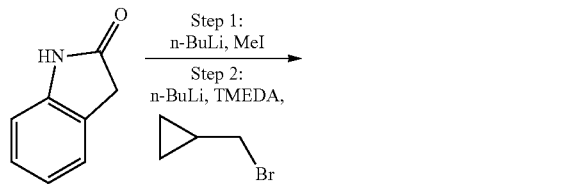

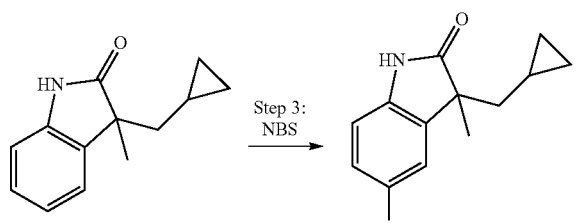

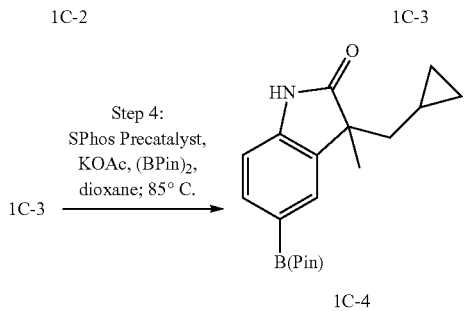

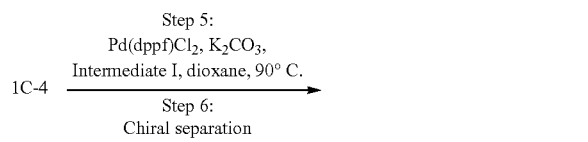

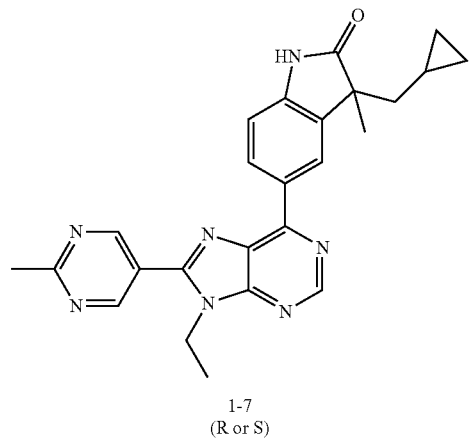 [SMILES: CCn1c(-c2cnc(C)nc2)nc2c(-c3ccc4c(c3)C(C)(CC3COC3)C(=O)N4)ncnc21]

1-7
(R or S)

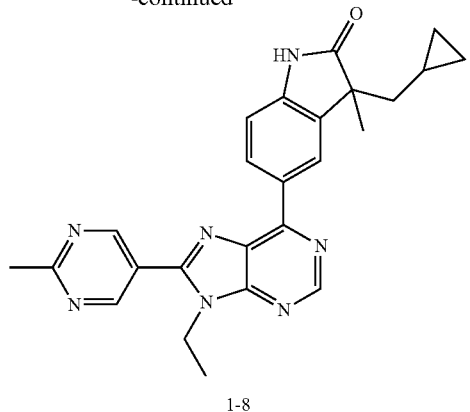

1-8
(R or S)

Step 1 3-Methylindolin-2-one

A 3-L round-bottom flask purged and maintained with an atmosphere of nitrogen was charged with a solution of 2,3-dihydro-1H-indol-2-one (100 g, 751 mmol) in 1 L of THF. A 2.5 M solution of n-BuLi (661 mL) was then added dropwise at −78° C. and the mixture stirred for 30 min. Next, iodomethane (267 g, 1.88 mol) was added dropwise at −78° C., and the resulting solution stirred for 10 min at 20-25° C. The reaction was then quenched by the addition of sat. NH$_4$Cl and extracted with EtOAc. The combined organic layers were washed with brine, dried (Na$_2$SO$_4$) and concentrated. The residue was purified by chromatography on SiO$_2$ (1% to 90% EtOAc/petroleum ether) to give the desired product.

Step 2
3-(Cyclopropylmethyl)-3-methylindolin-2-one
(1C-2)

A 100-mL round-bottom flask was charged with a solution of 3-methyl-2,3-dihydro-1H-indol-2-one (150 mg, 1.02 mmol) in 5 mL of THF and TMEDA (0.15 mL, 1.0 mmol). The mixture was cooled to −78° C. and treated with a 2.5 M solution of n-BuLi (0.90 mL), then stirred for 30 min. Next, (bromomethyl)cyclopropane (0.11 mL, 1.1 mmol) was added dropwise with stirring at −78° C. The resulting solution was stirred overnight at 25° C., and then quenched by the addition of sat. NH$_4$Cl. The resulting solution was extracted with EtOAc and the combined organic layers dried (MgSO$_4$) and concentrated. The residue was purified by chromatography on SiO$_2$ (10% to 60% EtOAc/hexane) to give the desired product (1C-2). MS (EI) calc'd for $C_{13}H_{16}NO$ [M+H]$^+$, 202; found, 202.

Step 3 5-Bromo-3-(cyclopropylmethyl)-3-methylindolin-2-one (1C-3)

A solution of 3-(cyclopropylmethyl)-3-methylindolin-2-one (1C-2) (145 mg, 0.720 mmol) in 3 mL of DMF was cooled to 0° C. N-Bromosuccinimide (133 mg, 0.749 mmol) was then added, and the resulting solution stirred with slow warming to room temperature overnight. The reaction was diluted with EtOAc and washed with brine. The organic layer was dried (MgSO$_4$), filtered and concentrated. The residue was purified by chromatography on SiO$_2$ (10% to 60% EtOAc/hexane) to give the desired product (1C-3). MS (EI) calc'd for $C_{13}H_{15}BrNO$ [M+H]$^+$, 282; found, 282.

Step 4 3-(Cyclopropylmethyl)-3-methyl-5-(4,4,5,5-tetramethyl-1,3,2-dioxaborolan-2-yl)indolin-2-one (1C-4)

A vial containing 5-bromo-3-(cyclopropylmethyl)-3-methylindolin-2-one (1C-3) (270 mg, 0.97 mmol), (BPin)$_2$ (296 mg, 1.17 mmol), KOAc (238 mg, 2.43 mmol), SPhos precatalyst (76 mg, 0.097 mmol) in 4 mL of dioxane was purged with nitrogen and stirred at 85° C. for 2 h. The mixture was filtered through a pad of CELITE and concentrated to afford a residue which was purified by chromatography on $SiO_2$ (2% to 20% EtOAc/hexane) to give the desired product (1C-4). MS (EI) calc'd for $C_{19}H_{27}BNO_3$ [M+H]$^+$, 328; found, 328.

Step 5 3-(Cyclopropylmethyl)-5-(9-ethyl-8-(2-methylpyrimidin-5-yl)-9H-purin-6-yl)-3-methylindolin-2-one A mixture of 3-(cyclopropylmethyl)-3-methyl-5-(4,4,5,5-tetramethyl-1,3,2-dioxaborolan-2-yl)indolin-2-one (70 mg, 0.21 mmol), Intermediate I (59 mg, 0.21 mmol) and $PdCl_2$(dtbpf) (19 mg, 0.021 mmol) in 1.5 mL of 1,4-dioxane and 2 M aqueous sodium carbonate (0.2 ml, 0.4 mmol) was stirred at reflux under argon for overnight. The reaction mixture was partitioned between DCM and water. The organic layer was dried ($Na_2SO_4$), filtered and concentrated. The residue was purified by reverse phase chromatography (MeCN/water gradient with 0.1% TFA modifier) to provide the racemic product. MS (EI) calc'd for $C_{25}H_{26}N_7O$ [M+H]$^+$, 440; found, 440.

Step 6 (R or S)- and (S or R)-3-(Cyclopropylmethyl)-5-(9-ethyl-8-(2-methylpyrimidin-5-yl)-9H-purin-6-yl)-3-methylindolin-2-one (1-7 and 1-8)

The racemic material prepared in step 5 was then dissolved in MeOH/MeCN and resolved using chiral column chromatography [Column: ChiralPak™ AS-H, 21×250 mm; 220 nm detection; 70 mL/min flow rate; 30% MeOH and 0.25% $Me_2NEt$ in $CO_2$]. The faster eluting enantiomer came at a retention time of 3.49 min (1-7): $^1$H NMR (600 MHz, DMSO-d$_6$) δ 10.71 (s, 1H), 9.23 (s, 2H), 8.96 (s, 1H), 8.90 (d, J=7.9 Hz, 1H), 8.70 (s, 1H), 7.06 (d, J=8.2 Hz, 1H), 4.43 (q, J=6.7 Hz, 2H), 2.77 (s, 3H), 1.91 (dd, J=12.9, 4.7 Hz, 1H), 1.55 (dd, J=13.2, 5.9 Hz, 1H), 1.37 (t, J=5.9 Hz, 3H), 1.31 (s, 3H), 0.34-0.00 (m, 5H). MS (EI) calc'd for $C_{25}H_{26}N_7O$ [M+H]$^+$, 440; found, 440. The slower eluting enantiomer came at a retention time of 4.45 min (1-8): $^1$H NMR (600 MHz, DMSO-d$_6$) δ 10.72 (s, 1H), 9.24 (s, 2H), 8.97 (s, 1H), 8.92 (d, J=8.3 Hz, 1H), 8.72 (s, 1H), 7.07 (d, J=8.2 Hz, 1H), 4.44 (q, J=7.3 Hz, 2H), 2.78 (s, 3H), 1.92 (dd, J=13.9, 6.0 Hz, 1H), 1.56 (dd, J=13.9, 7.7 Hz, 1H), 1.38 (t, J=7.2 Hz, 3H), 1.32 (s, 3H), 1.15 (dt, J=18.8, 7.3 Hz, 1H), 0.35 (d, 8.6 Hz, 1H), −0.1-0.23 (m, 3H). MS (EI) calc'd for $C_{25}H_{26}N_7O$ [M+H]$^+$, 440; found, 440.

Example 1D Compounds 1-9 and 1-10

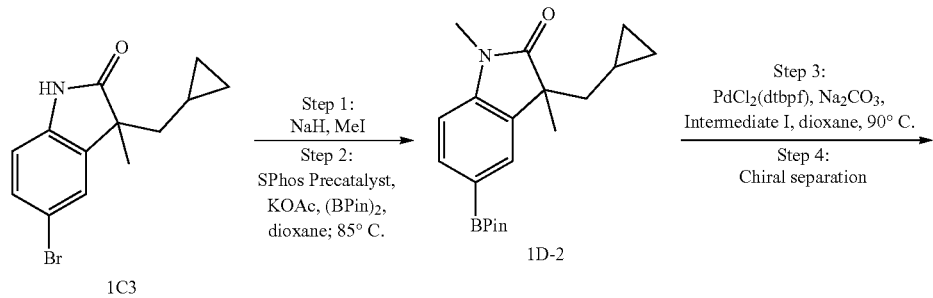

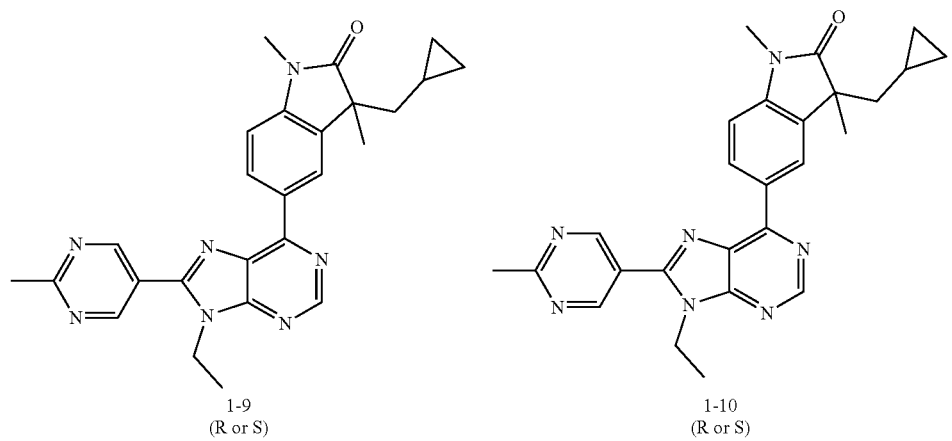

1-9 (R or S)

1-10 (R or S)

Steps 1-2 3-(Cyclopropylmethyl)-1,3-dimethyl-5-(4,4,5,5-tetramethyl-1,3,2-dioxaborolan-2-yl)indolin-2-one (1D-2)

A mixture of 5-bromo-3-(cyclopropylmethyl)-3-methylindolin-2-one (1C-3) (100 mg, 0.357 mmol) in 3 mL of DMF was treated at 0° C. with 60% NaH in mineral oil (21 mg, 0.54 mmol), followed by MeI (0.027 mL, 0.43 mmol), and then stirred for 3 h. The reaction was partitioned between EtOAc and water, the combined organic layers were then concentrated under reduced pressure, and the resulting residue purified by chromatography on $SiO_2$ (10-100% EtOAc/hexanes) to afford 5-bromo-3-(cyclopropylmethyl)-1,3-dimethylindolin-2-one. MS (EI) calc'd for $C_{14}H_{17}BrNO$ $[M+H]^+$, 296; found, 296.

A reaction vial was charged with 5-bromo-3-(cyclopropylmethyl)-1,3-dimethylindolin-2-one (115 mg, 0.389 mmol), $(BPin)_2$ (119 mg, 0.467 mmol), KOAc (95 mg, 0.97 mmol), SPHOS biphenyl precatalyst (31 mg, 0.039 mmol) and dioxane (3.0 mL). The mixture was deoxygenated by repeated exposure to vacuum and backfilling with nitrogen, then heated at 85° C. for 2 h. The mixture was filtered through CELITE and concentrated. The resulting residue was purified by chromatography on $SiO_2$ (2-20% MeOH/DCM) to give 3-(cyclopropylmethyl)-1,3-dimethyl-5-(4,4,5,5-tetramethyl-1,3,2-dioxaborolan-2-yl)indolin-2-one (1D-3). MS (EI) calc'd for $C_{20}H_{29}BNO_3$ $[M+H]^+$, 342; found, 342.

Steps 3-4 (R or S)- and (S or R)-3-(Cyclopropylmethyl)-5-(9-ethyl-8-(2-methyl pyrimidin-5-yl)-9H-purin-6-yl)-1,3-dimethylindolin-2-one (1-9 and 1-10)

A 10 mL round bottom flask was charged with 3-(cyclopropylmethyl)-1,3-dimethyl-5-(4,4,5,5-tetramethyl-1,3,2-dioxaborolan-2-yl)indolin-2-one (1D-2) (75 mg, 0.22 mmol), Intermediate I (60 mg, 0.22 mmol), Pd(dtbpf)(OAc)$_2$ (20 mg, 0.022 mmol) and 2 mL of dioxane. Aqueous $Na_2CO_3$ (2 M solution, 0.2 mL, 0.4 mmol) was added and the mixture deoxygenated by exchanging vacuum and nitrogen (3×). The mixture was stirred at 80° C. overnight, then partitioned between DCM and water. The organic layer was dried ($Na_2SO_4$), filtered and concentrated. The residue was purified by mass-directed reverse phase chromatography (MeCN/water gradient with 0.1% TFA modifier) to give 3-(cyclopropylmethyl)-5-(9-ethyl-8-(2-methylpyrimidin-5-yl)-9H-purin-6-yl)-1,3-dimethylindolin-2-one. MS (EI) calc'd for $C_{26}H_{28}N_7O$ $[M+H]^+$, 454; found, 454.

The racemic material was then dissolved in MeOH/MeCN and resolved using chiral column chromatography [Column: ChiralPak™ OJ-H, 21×250 mm; 220 nm detection; 70 mL/min flow rate; 15% MeOH and 0.25% Me$_2$NEt in CO$_2$]. The faster eluting enantiomer came at a retention time of 4.11 min (1-9), while the slower eluting enantiomer came at a retention time of 4.80 min (1-10). Characterization data for compound 1-9: $^1$H NMR (600 MHz, DMSO-d$_6$) δ 9.40 (s, 2H), 9.15 (d, J=8.3 Hz, 1H), 9.14 (s, 1H), 8.92 (s, 1H), 7.41 (d, J=8.5 Hz, 1H), 4.60 (q, J=7.0 Hz, 2H), 3.37 (s, 3H), 2.93 (s, 3H), 2.12 (m, 1H), 1.71 (m, 1H), 1.54 (t, J=Hz, 3H), 1.49 (s, 3H), 0.42 (m, 1H), 0.31 (m, 1H), 0.28 (m, 1H), 0.11 (m, 1H), 0.02 (m, 1H); MS (EI) calc'd for $C_{26}H_{28}N_7O$ $[M+H]^+$, 454; found, 454. Characterization data for compound 1-10: $^1$H NMR (600 MHz, DMSO-d$_6$) δ 9.40 (s, 2H), 9.15 (d, J=8.2 Hz, 1H), 9.14 (s, 1H), 8.91 (s, 1H), 7.41 (d, J=8.2 Hz, 1H), 4.60 (q, J=7.0 Hz, 2H), 3.37 (s, 3H), 2.93 (s, 3H), 2.12 (m, 1H), 1.71 (m, 1H), 1.54 (t, J=Hz, 3H), 1.49 (s, 3H), 0.42 (m, 1H), 0.30 (m, 1H), 0.28 (m, 1H), 0.11 (m, 1H), 0.02 (m, 1H); MS (EI) calc'd for $C_{26}H_{28}N_7O$ $[M+H]^+$, 454; found, 454.

Example 1E Compound 1-11

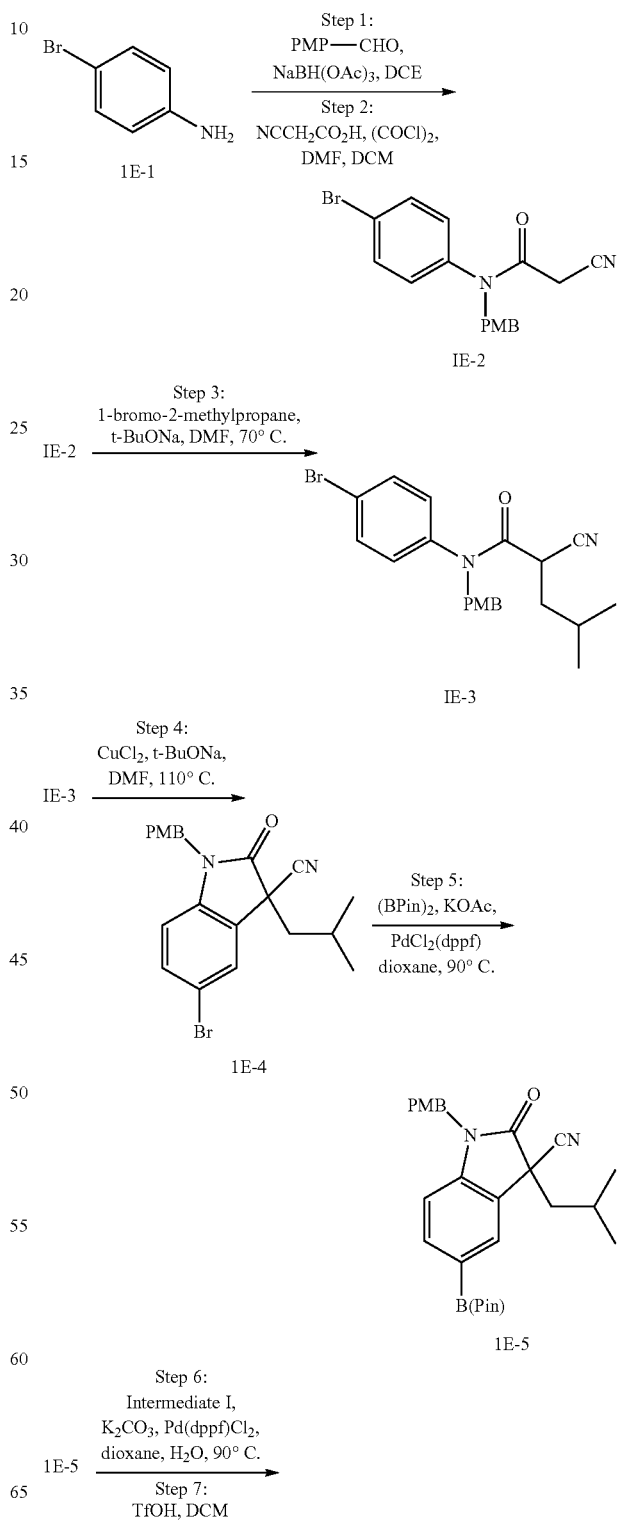

-continued

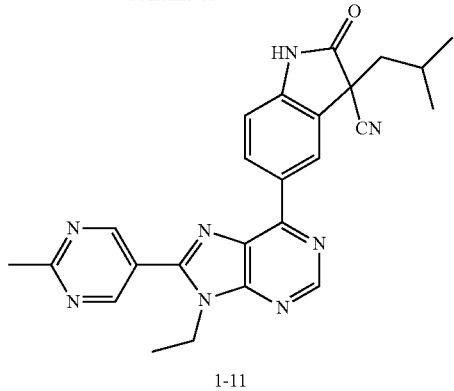 [SMILES: CCn1c(-c2cnc(C)nc2)nc2c(-c3ccc4c(c3)C(C#N)(CC(C)C)C(=O)N4)ncnc21]

1-11

Steps 1-2 N-(4-Bromophenyl)-2-cyano-N-(4-methoxybenzyl)acetamide (1E-2)

A solution of 4-bromoaniline (1E-1) (5.0 g, 29 mmol) in 100 mL of DCE was treated with 4-methoxybenzaldehyde (4.4 g, 32 mmol) and sodium triacetoxyborohydride (31 g, 150 mmol). The resulting mixture was stirred for 25 h and quenched with water. The resulting mixture was extracted with DCM and the combined organic layers washed with brine, dried ($Na_2SO_4$) and concentrated. The residue was purified by chromatography on $SiO_2$ (0%-10% EtOAc/hexane) to afford 4-bromo-2-((1-phenylethyl)amino)phenol. MS (EI) calc'd for $C_{14}H_{15}BrNO$ $[M+H]^+$, 292; found, 292.

A solution of 2-cyanoacetic acid (2.62 g, 30.8 mmol) in 50 mL of DCM was treated at 0° C. with DMF (0.5 mL) and oxalyl chloride (3.91 g, 30.8 mmol). The resulting solution was stirred for 1 h at room temperature, then added to a solution of 4-bromo-N-(4-methoxybenzyl)aniline (6.00 g, 20.5 mmol) and $NEt_3$ (2.9 mL, 21 mmol) in 50 mL of DCM. The resulting mixture was stirred for 1 h, quenched with water, then extracted with DCM. The combined organic layers were washed with brine, dried ($Na_2SO_4$), and concentrated. The residue was purified by chromatography on $SiO_2$ (0%-30% EtOAc/hexanes) to afford N-(4-bromophenyl)-2-cyano-N-(4-methoxybenzyl)acetamide (1E-2). MS (EI) calc'd for $C_{17}H_{16}BrN_2O_2$ $[M+H]^-$, 359; found, 359.

Step 3 N-(4-Bromophenyl)-2-cyano-N-(4-methoxybenzyl)-4-methylpentanamide (1E-3)

A solution of N-(4-bromophenyl)-2-cyano-N-(4-methoxybenzyl)acetamide (1E-2) (5.00 g, 13.9 mmol) in 50 mL of DMF was treated at 0° C. with sodium tert-butoxide (1.47 g, 15.3 mmol) and 1-bromo-2-methylpropane (2.10 g, 15.3 mmol). The mixture was stirred for 2 h at 70° C., then quenched with water and extracted with EtOAc. The combined organic layers was washed with brine, dried ($Na_2SO_4$) and concentrated. The residue was purified by chromatography on $SiO_2$ (0%-20% EtOAc/hexane) to afford N-(4-bromophenyl)-2-cyano-N-(4-methoxybenzyl)-4-methylpentanamide (1E-3). MS (EI) calc'd for $C_{21}H_{24}BrN_2O_2$ $[M+H]^+$, 415; found, 415.

Step 4 5-Bromo-3-isobutyl-1-(4-methoxybenzyl)-2-oxoindoline-3-carbonitrile (1E-4)

A solution of N-(4-bromophenyl)-2-cyano-N-(4-methoxybenzyl)-4-methylpentanamide (1E-3) (0.30 g, 0.72 mmol) in 5 mL of DMF was treated with sodium tert-butoxide (139 mg, 1.45 mmol) and copper(II) chloride (19 mg, 0.14 mmol). The resulting mixture was stirred for 1 h at 110° C., then quenched with saturated aqueous ammonium chloride. The resulting mixture was extracted with EtOAc, the combined organic layers was washed with brine, dried ($Na_2SO_4$) and concentrated. The residue was purified by chromatography on $SiO_2$ (0%400% EtOAc/hexanes) to afford 5-bromo-3-isobutyl-1-(4-methoxybenzyl)-2-oxoindoline-3-carbonitrile (1E-4). MS (EI) calc'd for $C_{21}H_{22}BrN_2O_2$ $[M+H]^+$, 413; found, 413.

Step 5 3-Isobutyl-1-(4-methoxybenzyl)-2-oxo-5-(4,4,5,5-tetramethyl-1,3,2-dioxaborolan-2-yl)indoline-3-carbonitrile (1E-5)

A solution of 5-bromo-3-isobutyl-1-(4-methoxybenzyl)-2-oxoindoline-3-carbonitrile (1E-4) (220 mg, 0.532 mmol) in 5 mL of dioxane was treated with KOAc (104 mg, 1.07 mmol), $(BPin)_2$ (160 mg, 0.64 mmol) and $PdCl_2(dppf)$ (39 mg, 0.053 mmol) at 20° C. The mixture was stirred at 90° C. for 1 h and quenched with sat. aq. $NH_4Cl$. The mixture was extracted with EtOAc, the combined organic layers washed with brine, dried ($Na_2SO_4$) and concentrated. The residue was used without further purification. MS (EI) calc'd for $C_{27}H_{34}BN_2O_4$ $[M+H]^+$, 461; found, 461.

Step 6 5-(9-Ethyl-8-(2-methylpyrimidin-5-yl)-9H-purin-6-yl)-3-isobutyl-1-(4-methoxybenzyl)-2-oxoindoline-3-carbonitrile A solution of 3-isobutyl-1-(4-methoxybenzyl)-2-oxo-5-(4,4,5,5-tetramethyl-1,3,2-dioxaborolan-2-yl)indoline-3-carbonitrile (220 mg, 0.478 mmol) in 5 mL of dioxane was treated with Intermediate I (131 mg, 0.478 mmol), $K_2CO_3$ (198 mg, 1.43 mmol), water (1 mL) and $PdCl_2(dppf)$ (35 mg, 0.048 mmol). The mixture was stirred at 90° C. for 1 h and quenched with sat. aq. $NH_4Cl$. The resulting mixture was extracted with EtOAc, washed with brine, dried ($Na_2SO_4$) and concentrated. The residue was purified by a chromatography on $SiO_2$ (0-100% EtOAc/hexane) to afford 5-(9-ethyl-8-(2-methylpyrimidin-5-yl)-9H-purin-6-yl)-3-isobutyl-1-(4-methoxybenzyl)-2-oxoindoline-3-carbonitrile. MS (EI) calc'd for $C_{33}H_{33}N_8O_2$ $[M+H]^+$, 573; found, 573.

Step 7 5-(9-Ethyl-8-(2-methylpyrimidin-5-yl)-9H-purin-6-yl)-3-isobutyl-2-oxoindoline-3-carbonitrile (1-yl)

A solution of 5-(9-ethyl-8-(2-methylpyrimidin-5-yl)-9H-purin-6-yl)-3-isobutyl-1-(4-methoxybenzyl)-2-oxoindoline-3-carbonitrile (100 mg, 0.18 mmol) in 0.5 mL of DCM was treated with trifluoromethanesulfonic acid (0.5 mL). The mixture was stirred for 3 h and quenched with saturated aqueous sodium bicarbonate. The resulting mixture was extracted with EtOAc, the combined organic layers washed with brine, dried ($Na_2SO_4$) and concentrated. The residue was purified by chromatography on $SiO_2$ (0%-100% EtOAc/hexanes) to afford 5-(9-ethyl-8-(2-methylpyrimidin-5-yl)-9H-purin-6-yl)-3-isobutyl-2-oxoindoline-3-carbonitrile (1-yl). $^1H$ NMR (300 MHz, $CD_3OD$) δ 9.21 (s, 2H), 8.99-8.95 (m, 3H), 7.18 (d, J=8.1 Hz, 1H), 4.53 (q, J=7.2 Hz, 2H), 2.82 (s, 3H), 2.28-2.08 (m, 2H), 1.87-1.78 (m, 1H), 1.49 (t, J=7.2 Hz, 3H), 0.98-0.82 (m, 6H). MS (EI) calc'd for $C_{25}H_{25}N_8O$ [M+H]$^+$, 453; found, 453.

Example 1F Compounds 1-12 and 1-13

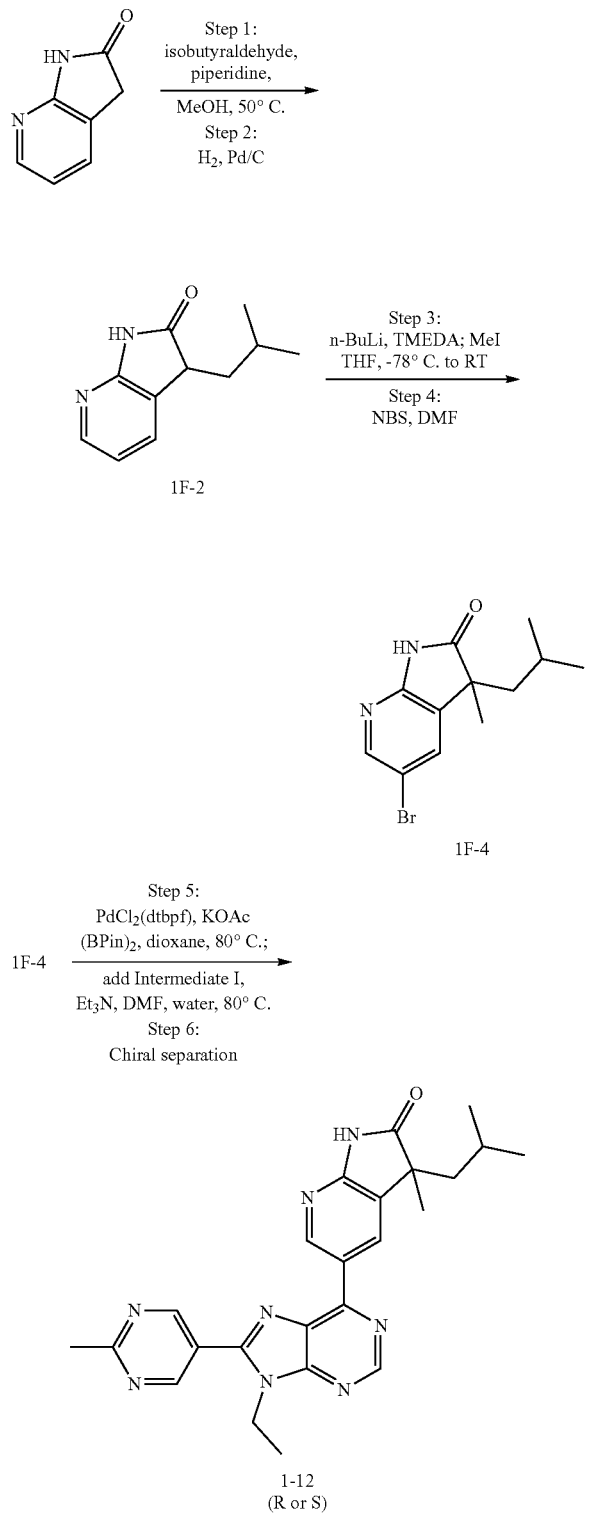

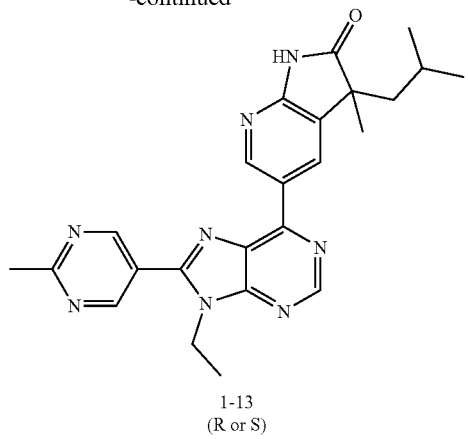

1-13
(R or S)

Steps 1-2 3-Isobutyl-1,3-dihydro-2H-pyrrolo[2,3-b]pyridin-2-one (1F-2)

A suspension of 1H-pyrrolo[2,3-b]pyridin-2(3H)-one (1.00 g, 7.46 mmol) in 15 mL of MeOH was treated dropwise with isobutyraldehyde (810 mg 11 mmol) and dropwise with piperidine (1.3 g, 15 mmol). After stirring for several minutes, the reaction mixture was heated at 50° C. for 3 h. Upon cooling, a precipitate had formed and was collected. The precipitate was washed with cold MeOH and dried under vacuum. Chromatography on SiO$_2$ (2-20% MeOH/DCM) gave 3-(2-methylpropylidene)-1,3-dihydro-2H-pyrrolo[2,3-b]pyridin-2-one. MS (EI) calc'd for $C_{11}H_{13}N_2O$ [M+H]$^+$, 189; found, 189.

A solution of 3-(2-methylpropylidene)-1H-pyrrolo[2,3-b]pyridin-2(3H)-one (772 mg, 4.10 mmol) in 10 mL of ethanol was treated with 5% Pd/C (220 mg, 2.1 mmol). The heterogeneous mixture was stirred under an atmosphere of hydrogen for 12 hours, filtered through a pad of CELITE and concentrated. The residue was purified by chromatography on SiO$_2$ (10-100% EtOAc/hexanes) to give 3-isobutyl-1,3-dihydro-2H-pyrrolo[2,3-b]pyridin-2-one (1F-2). MS (EI) calc'd for $C_{11}H_{15}N_7O$ [M+H]$^+$, 191; found, 191.

Steps 3-4 5-Bromo-3-isobutyl-3-methyl-1,3-dihydro-2H-pyrrolo[2,3-b]pyridin-2-one (1F-4)

An oven-dried 100 mL round-bottom flask containing 3-isobutyl-1H-pyrrolo[2,3-b]pyridin-2(3H)-one (1F-2) (470 mg, 2.47 mmol) was fitted with a stir bar and rubber septum, and flushed with nitrogen. Next, THF (5 mL) and TMEDA (0.37 ml, 2.4 mmol) were added and the solution cooled to −78° C. A 2.5 M solution of n-BuLi (2.2 mL, 5.5 mmol) was added dropwise and the resulting solution stirred for 30 min. Iodomethane (700 mg, 4.94 mmol) was then added dropwise, and the reaction was transferred to a 0° C. bath and stirred overnight. The reaction was quenched with EtOAc and concentrated. The residue was purified by chromatography on SiO$_2$ (2-20% MeOH/DCM) to provide 3-isobutyl-3-methyl-1,3-dihydro-2H-pyrrolo[2,3-b]pyridin-2-one. MS (EI) calc'd for $C_{12}H_{17}N_2O$ [M+H]$^+$, 205; found, 205.

A solution of 3-isobutyl-3-methyl-1H-pyrrolo[2,3-b]pyridin-2(3H)-one (410 mg, 2.01 mmol) in 3 mL of DMF was cooled to 0° C. and treated with N-bromosuccinimide (410 mg, 2.3 mmol). The mixture was stirred overnight at room temperature, diluted with EtOAc and washed with brine. The organic layer was dried (MgSO$_4$) and concentrated. The residue was purified by chromatography on SiO$_2$ (10-60% EtOAc/hexanes) to provide 5-bromo-3-isobutyl-3-methyl-1,3-dihydro-2H-pyrrolo[2,3-b]pyridin-2-one (1F-4). MS (EI) calc'd for C$_{12}$H$_{16}$BrNO [M+H]$^+$, 283; found, 283.

Steps 5-6 (R or S)- and (S or R)-5-(9-ethyl-8-(2-methylpyrimidin-5-yl)-9H-purin-6-yl)-3-isobutyl-3-methyl-1,3-dihydro-2H-pyrrolo[2,3-b]pyridin-2-one (1-12 and 1-13)

A mixture of 5-bromo-3-isobutyl-3-methyl-1H-pyrrolo[2,3-b]pyridin-2(3H)-one (0.260 g, 0.918 mmol), (BPin)$_2$ (0.280 g, 1.10 mmol), PdCl$_2$(dtbpf) (0.054 g, 0.083 mmol) and KOAc (0.279 g, 2.75 mmol) in 4 mL of dioxane was deoxygenated by exchanging vacuum and nitrogen, then heated to 85° C. for 3 h. To the reaction mixture, Intermediate I (100 mg, 0.364 mmol), PdCl$_2$(dtbpf) (0.054 g, 0.083 mmol), NEt$_3$ (0.15 mL, 1.1 mmol), DMF (2 mL), and water (2 mL) were added. The mixture was again deoxygenated by exchanging vacuum and nitrogen, then heated to 85° C. for 2 h. The mixture was then filtered through a pad of CELITE and concentrated. The residue was purified by reverse phase chromatography (MeCN/water with 0.1% TFA modifier) to provide racemic 5-(9-ethyl-8-(2-methylpyrimidin-5-yl)-9H-purin-6-yl)-3-isobutyl-3-methyl-1,3-dihydro-2H-pyrrolo[2,3-b]pyridin-2-one. MS (EI) calc'd for C$_{24}$H$_{27}$N$_8$O [M+H]$^+$, 443; found, 443.

The racemic material was then dissolved in MeOH/MeCN and resolved using chiral column chromatography [Column: ChiralPak™ AS-H, 21×250 mm; 220 nm detection; 70 mL/min flow rate; 20% MeOH and 0.25% DMEA in CO$_2$]. The faster eluting enantiomer came at a retention time of 2.39 min (1-12), while the slower eluting enantiomer came at a retention time of 3.16 min (1-13). Characterization Data for 1-12: $^1$H NMR (600 MHz, DMSO-d$_6$) δ 11.42 (s, 1H), 9.71 (d, J=2.0 Hz, 1H), 9.26 (s, 2H), 9.03 (s, 1H), 8.80 (s, 1H), 4.46 (q, J=7.3 Hz, 2H), 2.78 (s, 3H), 1.94 (dd, J=14.0, 5.6 Hz, 1H), 1.80 (dd, J=14.0, 7.4 Hz, 1H), 1.39 (t, J=7.2 Hz, 3H), 1.34 (s, 3H), 1.13-1.18 (m, 1H), 0.69 (d, J=6.6 Hz, 3H), 0.63 (d, J=6.6 Hz, 3H). MS (EI) calc'd for C$_{24}$H$_{27}$N$_8$O [M+H]$^+$, 443; found, 443. Characterization Data for 1-13: $^1$H NMR (600 MHz, DMSO-d$_6$) δ 11.41 (s, 1H), 9.70 (d, J=2.0 Hz, 1H), 9.25 (s, 2H), 9.02 (s, 1H), 8.79 (s, 1H), 4.45 (q, J=7 Hz, 2H), 2.77 (s, 3H), 1.93 (dd, J=14, 5.6 Hz, 1H), 1.79 (dd, J=14, 7.6 Hz, 1H), 1.38 (t, J=7.3 Hz, 3H), 1.33 (s, 3H), 1.15-1.18 (m, 1H), 0.68 (d, J=6.7 Hz, 3H), 0.62 (d, J=6.5 Hz, 3H). MS (EI) calc'd for C$_{24}$H$_{27}$N$_8$O [M+H]$^+$, 443; found. 443.

Example 1G Compounds 1-16 and 1-17

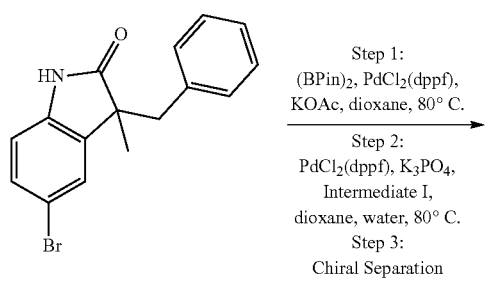

Step 1: (BPin)$_2$, PdCl$_2$(dppf), KOAc, dioxane, 80° C.
Step 2: PdCl$_2$(dppf), K$_3$PO$_4$, Intermediate I, dioxane, water, 80° C.
Step 3: Chiral Separation

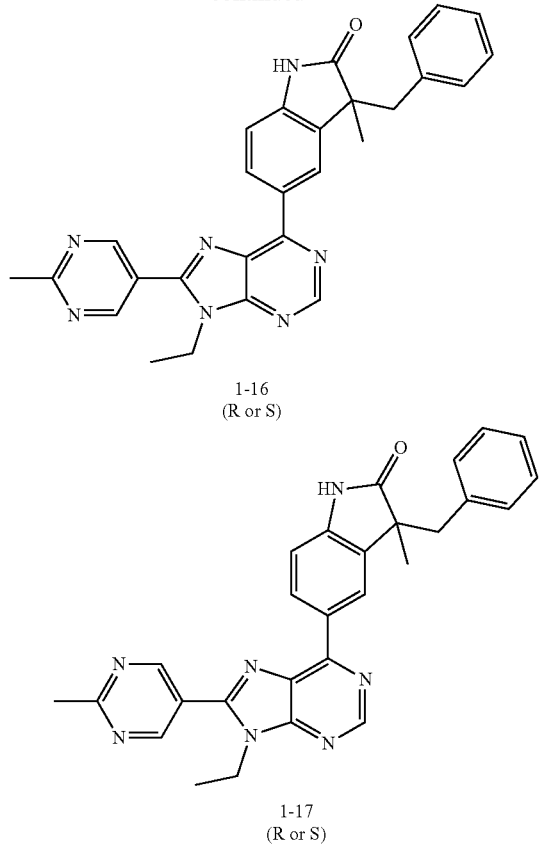

1-16 (R or S)

1-17 (R or S)

Steps 1-3 (R or S)- and (S or R)-3-Benzyl-5-(9-ethyl-8-(2-methylpyrimidin-5-yl)-9H-purin-6-yl)-3-methylindolin-2-one (1-16 and 1-17)

Oxindole 3-benzyl-5-bromo-3-methylindolin-2-one was prepared in a fashion analogous to 5-bromo-3-(cyclopropylmethyl)-3-methylindolin-2-one in Example 1C for the preparation of 1-7 and 1-8. In this case, (bromomethyl)cyclopropane was replaced by benzyl bromide.

A mixture of 3-benzyl-5-bromo-3-methylindolin-2-one (100 mg, 0.316 mmol) in dioxane (1 mL) was treated with (BPin)$_2$ (120 mg, 0.47 mmol), KOAc (100 mg, 1.0 mmol) and PdCl$_2$(dppf) (20 mg, 0.027 mmol). The mixture was stirred at 100° C. for 3 hours, cooled, diluted with DCM, washed with water, dried (Na$_2$SO$_4$) and concentrated. Chromatography on SiO$_2$ (0-100% EtOAc/DCM) gave 3-benzyl-3-methyl-5-(4,4,5,5-tetramethyl-1,3,2-dioxaborolan-2-yl)indolin-2-one. MS (EI) calc'd for C$_{22}$H$_{27}$BNO$_3$ [M+H]$^+$, 364; found, 364.

A solution of 3-benzyl-3-methyl-5-(4,4,5,5-tetramethyl-1,3,2-dioxaborolan-2-yl)indolin-2-one (50 mg, 0.14 mmol), intermediate I (75 mg, 0.2.7 mmol) in 1 mL of dioxane and 0.2 mL of water was treated with PdCl$_2$(dppf) (10 mg, 0.012 mmol) and K$_3$PO$_4$ (50 mg, 0.24 mmol). The reaction mixture was stirred for 2 hours at 80° C., cooled, filtered and concentrated. The residue was purified by reverse phase chromatography (MeCN/water with 0.1% TFA) to provide racemic 3-benzyl-5-(9-ethyl-8-(2-methylpyrimidin-5-yl)-9H-purin-6-yl)-3-methylindolin-2-one, MS (EI) calc'd for C$_{28}$H$_{26}$N$_7$O [M+H]$^+$, 476; found, 476.

The racemic material was then dissolved in 2 mL of DMF and resolved using chiral column chromatography [Column:

ChiralPak™ IB, 21×250 mm; 220 nm detection; 70 mL/min flow rate; 25% MeOH and 0.25% $Me_2NEt$ in $CO_2$]. The faster eluting enantiomer came at a retention time of 5.46 min (1-16), while the slower eluting enantiomer came at a retention time of 6.09 min (1-17). Characterization data for compound 1-16: $^1H$ NMR (600 MHz, DMSO-$d_6$) δ 10.52 (s, 1H), 9.26 (s, 2H), 9.00 (s, 1H), 8.82 (m, 1H), 8.78 (m, 1H), 7.01-7.03 (m, 3H), 6.84-6.90 (m, 3H), 4.46 (m, 2H), 3.18 (d, J=13 Hz, 1H), 3.08 (d, J=13 Hz, 1H), 2.79 (s, 3H), 1.46 (s, 3H), 1.40 (t, J=5.0 Hz, 3H). MS (EI) calc'd for $C_{25}H_{26}N_7O$ [M+H]$^+$, 476; found, 476. Characterization data for compound 1-17: $^1H$ NMR (600 MHz, DMSO-$d_6$) δ 10.51 (s, 1H), 9.22 (s, 2H), 8.96 (s, 1H), 8.78 (d, J=7.9 Hz, 1H), 8.74 (m, 1H), 6.98 (m, 3H), 6.80-6.85 (m, 3H), 4.43 (m, 2H), 3.13 (d, J=13 Hz, 1H), 3.03 (d, J=13 Hz. 1H), 2.74 (s, 3H), 1.41 (s, 3H), 1.36 (t, J=7.0 Hz, 3H). MS (EI) calc'd for $C_{28}H_{26}N_7O$ [M+H]$^+$, 476; found, 476.

Example 1H Compounds 1-18 and 1-19

Step 2 6-(3-Benzyl-3-methylindolin-5-yl)-9-ethyl-8-(2-methylpyrimidin-5-yl)-9H-purine (1-18)

A mixture containing 3-benzyl-5-bromo-3-methylindoline (1H-1) (50 mg, 0.17 mmol), KOAc (35 mg, 0.36 mmol), (BPin)$_2$ (60 mg, 0.24 mmol) and PdCl$_2$(dppf) (15 mg, 0.018 mmol) in dioxane (0.8 ml) was stirred for 4 hours at 90° C. To this mixture were added additional PdCl$_2$(dppf) (15 mg, 0.018 mmol), K$_3$PO$_4$ (100 mg, 0.48 mmol), Intermediate I (50 mg, 0.18 mmol) and water (0.2 mL). The reaction mixture was stirred for 2 h, filtered and concentrated. The residue was purified by reverse phase chromatography (MeCN/water with 0.1% TFA) to provide 6-(3-benzyl-3-methylindolin-5-yl)-9-ethyl-8-(2-methylpyrimidin-5-yl)-9H-purine (1-18) as a TFA salt. $^1H$ NMR (600 MHz, DMSO-$d_6$) δ 9.19 (s, 2H), 8.85 (s, 1H), 8.74 (dd, J=8.5, 1.8 Hz, 1H), 8.44 (m, 1H), 7.17 (m, 2H), 7.12 (d, J=7.3 Hz, 1H), 7.08 (m, 2H), 6.60 (d, J=8.5 Hz, 1H), 4.40 (m, 2H), 3.56 (d,

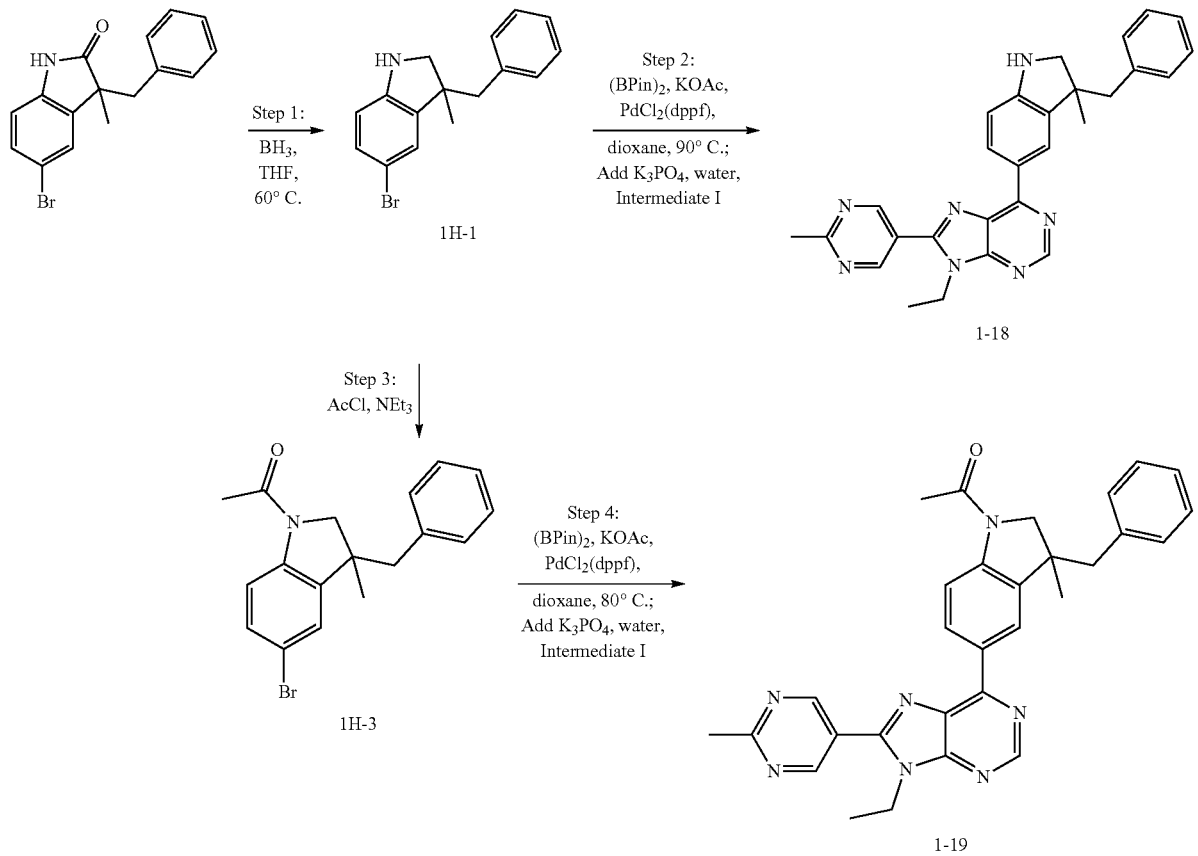

J=10 Hz, 1H), 3.13 (d, J=10 Hz, 1H), 2.88 (m, 2H), 2.75 (s, 3H), 1.35 (t, J=7.3 Hz, 3H), 1.28 (s, 3H). MS (EI) calc'd for $C_{28}H_{28}N_7$ [M+H]$^+$, 462; found, 462.

Step 3 1-(3-Benzyl-5-bromo-3-methylindolin-1-yl)ethan-1-one (1H-3)

Step 1 3-Benzyl-5-bromo-3-methylindoline (1H-1)

A solution of 3-benzyl-5-bromo-3-methylindolin-2-one (500 mg, 1.58 mmol) in THF (5 mL) was treated with a 1 M THF solution of BH$_3$-THF complex (5.0 mL, 5.0 mmol) and stirred at 60° C. for 3 hours. The mixture was quenched at RT by dropwise addition to MeOH and concentrated. Chromatography on SiO$_2$ (0-50% MeOH/DCM) gave the desired intermediate (1H-1). MS (EI) calc'd for $C_{16}H_{17}BrN$ [M+H]$^+$, 302; found, 302.

A solution of 3-benzyl-5-bromo-3-methylindoline (1H-1) (50 mg, 0.17 mmol) in DCM (1 mL) was treated with TEA (0.050 mL, 0.36 mmol) followed by acetyl chloride (0.025 mL, 0.35 mmol). The reaction mixture was stirred for 1 h and then concentrated to dryness to provide the desired product (1H-3).

Step 4 1-(3-Benzyl-5-(9-ethyl-8-(2-methylpyrimidin-5-yl)-9H-purin-6-yl)-3-methylindolin-1-yl)ethan-1-one (1-19)

The residue from Step 3 (1H-3) was dissolved in dioxane (1 mL) and treated with KOAc (50 mg, 0.51 mmol), (BPin)$_2$ (60 mg, 0.24 mmol) and PdCl$_2$(dppf) (15 mg, 0.018 mmol). The reaction mixture was warmed to 100° C. and stirred for 3 hours. The mixture was then treated with K$_3$PO$_4$ (100 mg, 0.47 mmol) and Intermediate I (50 mg, 0.18 mmol) followed by water (0.2 mL). The mixture was stirred overnight at 80° C., cooled and filtered. The residue was purified by reverse phase chromatography to provide the TFA salt. $^1$H NMR (600 MHz, DMSO-d$_6$) δ 9.23 (s, 2H), 8.97 (s, 1H), 8.83 (d, J=8.3 Hz, 1H), 8.69 (m, 1H), 8.04 (d, J=8.5 Hz, 1H), 7.45-7.53 (m, 2H), 7.08-7.13 (m, 3H), 7.02 (m, 2H), 4.43 (m, 2H), 4.15 (d, J=10 Hz, 1H), 3.75 (d, J=10 Hz, 1H), 2.92 (m, 2H), 2.75 (s, 3H), 2.07 (s, 3H), 1.41 (s, 3H), 1.36 (t, J=6.7 Hz, 3H). MS (EI) calc'd for C$_{30}$H$_{30}$N$_7$O [M+H]$^+$, 504; found, 504.

Example 1I Compounds 1-20, 1-21, 2-22

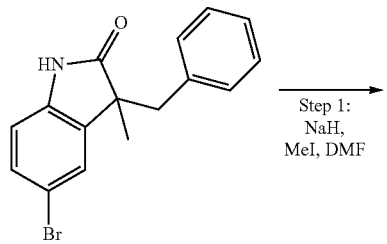

Step 1:
NaH,
MeI, DMF

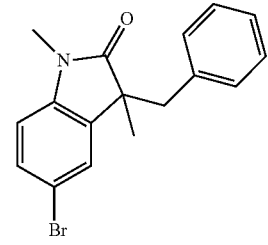

1I-1

Step 4:
BH$_3$, THF,
60° C.

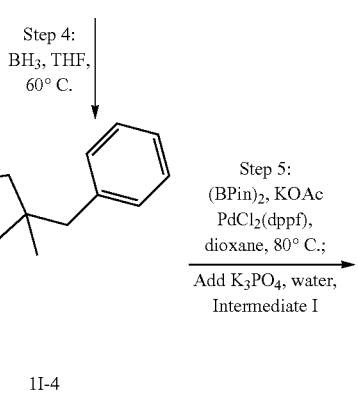

1I-4

Step 5:
(BPin)$_2$, KOAc
PdCl$_2$(dppf),
dioxane, 80° C.;
Add K$_3$PO$_4$, water,
Intermediate I

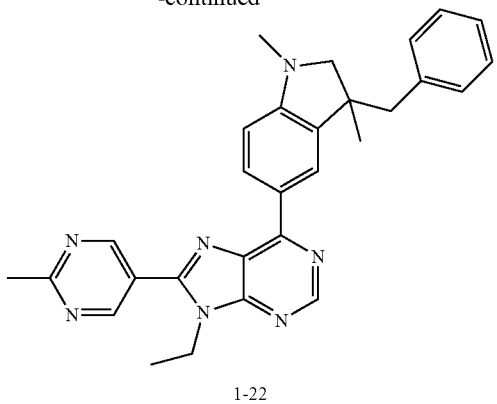

1-22

Step 2:
(BPin)$_2$, KOAc
PdCl$_2$(dppf),
dioxane, 80° C.;
Add K$_3$PO$_4$, water,
Intermediate I 1I-1 ⟶

Step 3:
Chiral Separation

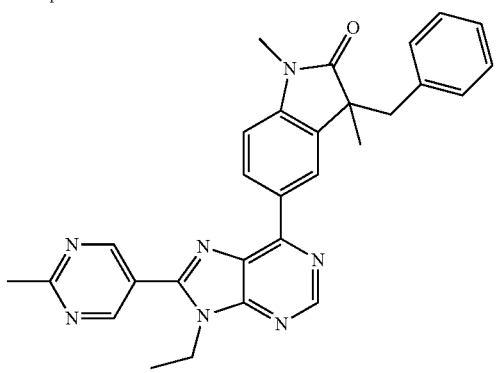

1-20
(R or S)

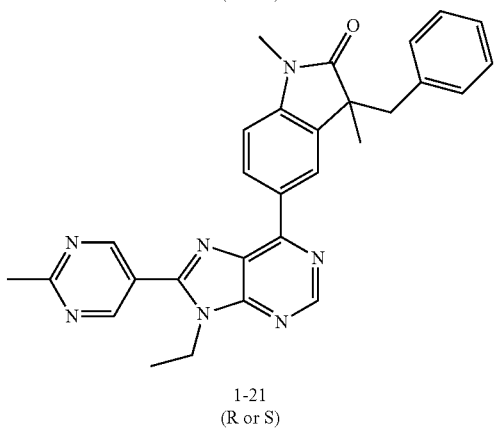

1-21
(R or S)

Step 1 3-Benzyl-5-bromo-1,3-dimethylindolin-2-one (1I-1)

A mixture containing 3-benzyl-5-bromo-3-methylindolin-2-one (250 mg, 0.79 mmol) in THF (2 ml) was treated with a 60% suspension of NaH in mineral oil (50 mg, 1.3 mmol) followed by iodomethane (0.070 ml, 1.1 mmol). The mixture was stirred overnight, then diluted with DCM, washed with water, dried (Na$_2$SO$_4$) and concentrated to provide the desired product (1I-1). MS (EI) calc'd for C$_{17}$H$_{17}$BrNO [M+H]$^-$, 332; found, 332.

Step 2 3-Benzyl-5-(9-ethyl-8-(2-methylpyrimidin-5-yl)-9H-purin-6-yl)-1,3-dimethylindolin-2-one A solution of 3-benzyl-5-bromo-1,3-dimethylindolin-2-one (1I-1) (50 mg 0.15 mmol) in dioxane (1 mL) was treated with KOAc (30 mg, 0.31 mmol), (BPin)$_2$ (50 mg, 0.20 mmol) and PdCl$_2$(dppf) (12 mg, 0.015 mmol). The reaction mixture was warmed to 90° C. and stirred for 2 hours. The mixture was then treated with K$_3$PO$_4$ (100 mg, 0.47 mmol) and intermediate I (40 mg, 0.15 mmol) followed by water (0.2 mL). The mixture was stirred overnight at 80° C., cooled and filtered. The residue was purified by reverse phase chromatography to provide the TFA salt of the desired product. MS (EI) calc'd for C$_{29}$H$_{28}$N$_7$O [M+H]$^-$, 490; found, 490.

Step 3 (R or S)- and (S or R)-3-Benzyl-5-(9-ethyl-8-(2-methylpyrimidin-5-yl)-9H-purin-6-yl)-1,3-dimethylindolin-2-one (1-20 and 1-21)

The racemic material from Step 2 was then dissolved in MeOH/MeCN and resolved using chiral column chromatography [Column: ChiralPak™ AD-H, 21×250 mm; 220 nm detection; 70 mL/min flow rate; 40% MeOH and 0.25% Me$_2$NEt in CO$_2$]. The faster eluting enantiomer came at a retention time of 2.86 min (1-20), while the slower eluting enantiomer came at a retention time of 4.58 min (1-21). Characterization data for compound 1-20: $^1$H NMR (600 MHz, DMSO-d$_6$) δ 9.22 (s, 2H), 8.97 (s, 1H), 8.86 (d, J=8.2 Hz, 1H), 8.77 (s, 1H), 6.96-6.99 (m, 4H), 6.78-6.80 (m, 2H), 4.43 (m, 2H), 3.13 (d, J=14 Hz, 1H), 3.06 (d, J=14 Hz, 1H), 2.95 (s, 3H), 2.75 (s, 3H), 1.44 (s, 3H), 1.37 (t, f=7.0 Hz, 3H). MS (EI) calc'd for C$_{29}$H$_{28}$N$_7$O [M+H]$^+$, 490; found, 490. Characterization data for compound 1-21: $^1$H NMR (600 MHz, DMSO-d$_6$) δ 9.2 (s, 2H), 8.97 (s, 1H), 8.86 (d, J=8.2 Hz, 1H), 8.77 (s, 1H), 6.96-6.97 (m, 4H), 6.78-6.80 (m, 2H), 4.43 (m, 2H), 3.13 (d, J=13 Hz, 1H), 3.06 (d, J=13 Hz, 1H), 2.95 (s, 3H), 2.75 (s, 3H), 1.46 (s, 3H), 1.37 (t, J=7.3 Hz, 3H). MS (EI) calc'd for C$_{29}$H$_{28}$N$_7$O [M+H]$^+$, 490; found, 490.

Step 4 3-Benzyl-5-bromo-1,3-dimethylindoline (1I-4)

A solution of 3-benzyl-5-bromo-1,3-dimethylindolin-2-one (1I-1) (200 mg, 0.61 mmol) in THF (2 mL) was treated with a 1 M THF solution of BH$_3$-THF complex (1.2 mL, 1.2 mmol) and stirred at reflux for one hour. The solution was cooled to RT, quenched dropwise with 1 mL of methanol and stirred one hour. The mixture was concentrated to dryness to provide the title compound (1I-4). MS (EI) calc'd for C$_{17}$H$_{19}$BrN [M+H]$^+$, 316; found, 316.

Step 5 6-(3-Benzyl-1,3-dimethylindolin-5-yl)-9-ethyl-8-(2-methylpyrimidin-5-yl)-9H-purine (1-22)

A mixture containing 3-benzyl-5-bromo-1,3-dimethylindoline (1I-4) (75 mg, 0.24 mmol) in dioxane (1 mL) was treated with PdCl$_2$(dppf) (20 mg, 0.024 mmol), KOAc (50 mg, 0.51 mmol) and (BPin)$_2$ (100 mg, 0.39 mmol). The reaction mixture was stirred for 3 hours at 100° C. Once cool, Intermediate I (70 mg, 0.26 mmol), K$_3$PO$_4$ (100 mg, 0.48 mmol) and water (0.2 mL) were added. The reaction mixture was stirred overnight at 80 filtered, concentrated and the residue purified by reverse phase chromatography (MeCN/water with 0.1% TFA) to provide the TFA salt of the title compound. $^1$H NMR (600 MHz, DMSO-d$_6$) δ 9.19 (s, 2H), 8.84 (s, 1H), 8.82 (d, J=8.2 Hz, 1H), 8.42 (s, 1H), 8.38 (m, 1H), 7.17-7.20 (m, 2H), 7.13 (m, 1H), 7.08 (m, 2H), 4.40 (m, 2H), 3.49 (d, J=9 Hz, 1H), 3.01 (d, J=9 Hz, 1H), 2.87 (m, 2H), 2.76 (s, 3H), 2.75 (s, 3H), 1.35 (t, J=7.3 Hz, 3H), 1.27 (s, 3H). MS (EI) calc'd for C$_{29}$H$_{30}$N$_7$ [M+H]$^-$, 476; found, 476.

Example 1J Compound 1-25

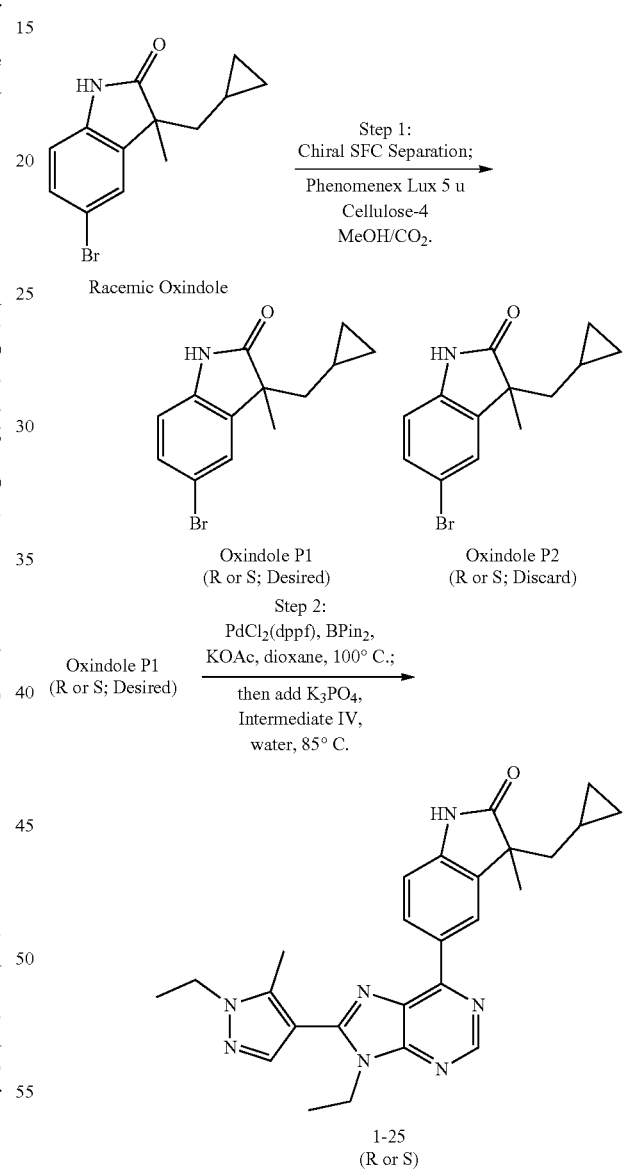

Step 1 Chiral separation of 5-Bromo-3-(cyclopropylmethyl)-3-methylindolin-2-one The synthesis of racemic 5-bromo-3-(cyclopropylmethyl)-3-methylindolin-2-one is described in Example 1C (towards compounds 1-7 and 1-8). The racemic material was then resolved using chiral column chromatography [Column: Phenomenex Lux® 5u Cellulose-4 (Phenomenex, Torrance, Calif. USA), 50×250 mm; 220 nm detection; 30% MeOH in $CO_2$]. The faster eluting enantiomer came at a retention time of 2.72 min (Desired Oxindole P1); while the slower eluting enantiomer came at a retention time of 3.20 min (Discard P2). Characterization data for desired P1: $^1$H NMR (400 MHz, $CDCl_3$) δ 8.63 (s, 1H), 7.31-7.35 (m, 2H), 6.81-6.83 (d, 1H), 1.90-1.95 (m, 1H), 1.59-1.64 (m, 1H), 1.37 (s, 3H), −0.1-0.4 (m, 5H). MS (EI) calc'd for $C_{13}H_{15}BrNO$ [M+H]$^+$, 280; found, 480.

Step 2 3-(Cyclopropylmethyl)-5-(9-ethyl-8-(1-ethyl-5-methyl-1H-pyrazol-4-yl)-9H-purin-6-yl)-3-methyl-indolin-2-one (1-25)

A suspension of (BPin)$_2$ (70 mg, 0.28 mmol), 5-bromo-3-(cyclopropylmethyl)-3-methylindolin-2-one (desired P1) (50 mg, 0.18 mmol), KOAc (35 mg, 0.36 mmol) in dioxane (1 mL) was treated with $PdCl_2$(dppf) (15 mg, 0.018 mmol) and stirred for 2 hours at 100° C. Cooled to RT, added Intermediate IV (60 mg, 0.21 mmol), added more $PdCl_2$ (dppf) (15 mg, 0.018 mmol), $K_3PO_4$ (120 mg, 0.57 mmol) and water (0.2 mL). The reaction mixture was stirred overnight at 85° C. Cooled, filtered and then purified by reverse phase chromatography (MeCN/water with 0.1% TFA) to provide the title compound. $^1$H NMR (600 MHz, DMSO-$d_6$) δ 10.85 (s, 1H), 9.04 (s, 1H), 9.00 (s, 1H), 8.89 (d, J=8.2 Hz, 1H), 8.20 (s, 1H), 7.19 (d, J=8.2 Hz, 1H), 4.60 (m, 2H), 4.38 (m, 2H), 2.87 (s, 3H), 2.04 (dd, J=14, 5.9 Hz, 1H), 1.72 (dd, J=14, 7.6 Hz, 1H), 1.50-1.54 (m, 6H), 1.46 (s, 3H), 0.49 (m, 1H), 0.35 (m, 1H), 0.28 (m, 1H), 0.16 (m, 1H), 0.01 (m, 1H). MS (EI) calc'd for $C_{26}H_{30}N_7O$ [M+H]$^+$, 456; found, 456.

Example 1K Compounds 1-34 and 1-35

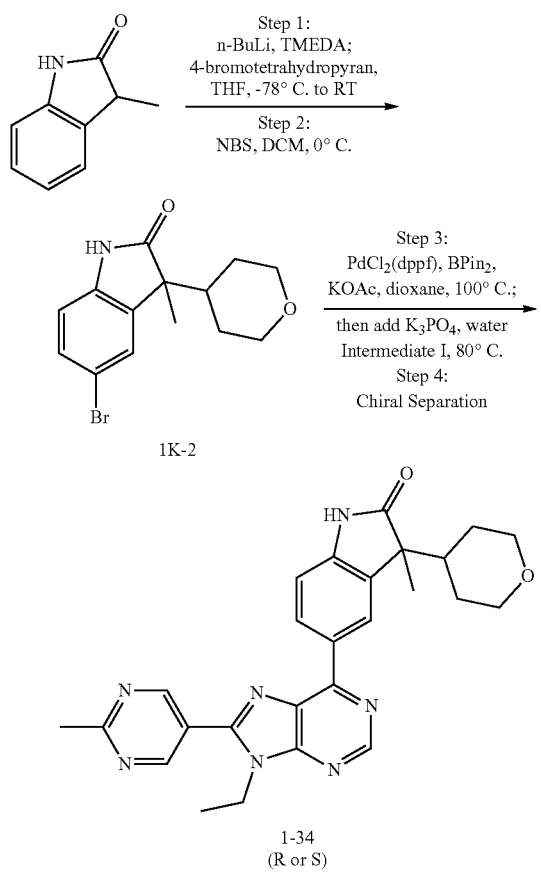

1K-2

1-34
(R or S)

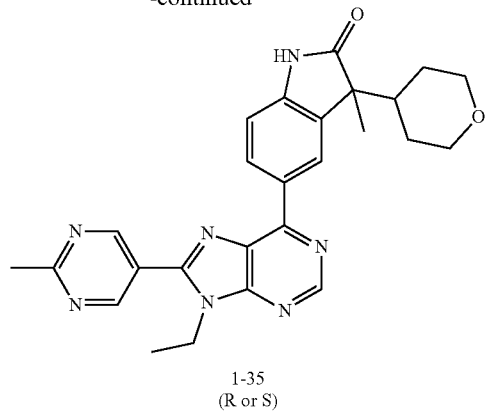

1-35
(R or S)

Steps 1-2 5-Bromo-3-methyl-3-(tetrahydro-2H-pyran-4-yl)indolin-2-one (1K-2)

A mixture containing 3-methylindolin-2-one (1.0 g, 6.79 mmol) in 10 mL of THF was treated with TMEDA (1.1 mL, 7.3 mmol) and cooled to −78° C. A 2.5 M solution of n-BuLi in THF (6.5 mL, 16 mmol) was added dropwise, followed by 4-bromotetrahydro-2H-pyran (1.3 g, 8.2 mmol). The reaction mixture was allowed to warm to RT over a 2 hour period, then stirred at that temperature overnight. The reaction mixture was concentrated to dryness, then dissolved in 10 mL of DCM and treated at 0° C. with NBS (1.33 g, 7.47 mmol). The mixture was then stirred for 1 hour and concentrated to dryness. Chromatography on $SiO_2$ (0-50% EtOAc/DCM) gave the title product (1K-2). MS (EI) calc'd for $C_{14}H_{17}BrNO_2$ [M+H]$^+$, 310; found, 310.

Steps 3-4 (R or S)- and (S or R)-5-(9-Ethyl-8-(2-methylpyrimidin-5-yl)-9H-purin-6-yl)-3-methyl-3-(tetrahydro-2H-pyran-4-yl)indolin-2-one (1-34 and 1-35)

A solution on 5-bromo-3-methyl-3-(tetrahydro-2H-pyran-4-yl)indolin-2-one (1K-2) (80 mg, 0.26 mmol) in 1 mL of dioxane (1 mL) was treated with KOAc (50 mg, 0.51 mmol), (BPin)$_2$ (100 mg, 0.394 mmol) and $PdCl_2$(dppl) (20 mg, 0.024 mmol), then stirred at 100° C. for 3 hours. Cooled to RT, then added 1 M aqueous solution of $K_3PO_4$ (0.50 mL, 0.50 mmol) and more $PdCl_2$(dppf) (20 mg, 0.024 mmol) along with Intermediate I (80 mg, 0.29 mmol). The mixture was stirred overnight at 80° C. Cooled to RT, filtered and purified by reverse phase chromatography (MeCN/water with 0.1% TFA modifier) to provide racemic product. The residue was then dissolved in 2 mL of 1:1 MeOH/MeCN and resolved using chiral column chromatography [Column: Chiralcel® OJ-H (Chiral Technologies. Inc., West Chester, Pa. USA), 21×250 mm; 220 nm detection; 70 mL/min flow rate; 25% MeOH and 0.25% $Me_2NEt$ in $CO_2$; Retention Time 1=2.6 min; Retention Time 2=4.4 min]. The faster eluting enantiomer came at a retention time of 2.6 min (1-34), while the slower eluting enantiomer came at a retention time of 4.4 min (1-35). Characterization data for 1-34: $^1$H NMR (600 MHz, DMSO-$d_6$) δ 10.73 (s, 1H), 9.22 (s, 2H), 8.95 (s, 1H), 8.82 (d, J=8.2 Hz, 1H), 8.75 (s, 1H), 7.04 (d, J=8.2 Hz, 1H), 4.43 (q, J=7.0 Hz, 2H), 3.84 (m, 1H), 3.72 (m, 1H), 3.26-3.17 (m, 2H), 2.75 (s, 3H), 1.95 (m, 1H), 1.65 (m, 1H), 1.54 (m, 1H), 1.36 (t, J=7.0 Hz, 3H), 1.33 (m, 1H), 1.30 (s, 3H), 1.05 (m, 1H). MS (EI) calc'd for $C_{26}H_{28}N_7O_2$ [M+H]$^+$, 470; found, 470. Characterization data for 1-35: $^1$H NMR (600 MHz, DMSO-d$_6$) δ 10.73 (s, 1H), 9.22 (s, 2H), 8.95 (s, 1H), 8.82 (d, J=6.7 Hz, 1H), 8.75 (s, 1H), 7.04 (d, J=8.2 Hz, 1H), 4.43 (q, J=7.0 Hz, 2H), 3.85 (m, 1H), 3.72 (m, 1H), 3.26-3.17 (m, 2H), 2.75 (s, 3H), 1.95 (m, 1H), 1.66 (m, 1H), 1.55 (m, 1H), 1.36 (t, J=7.0 Hz, 3H), 1.32 (m, 1H), 1.30 (s, 3H), 1.06 (m, 1H). MS (EI) calc'd for $C_{26}H_{28}N_7O_2$ [M+H]$^+$, 470; found, 470.

Example 1L Compounds 1-36 and 1-37

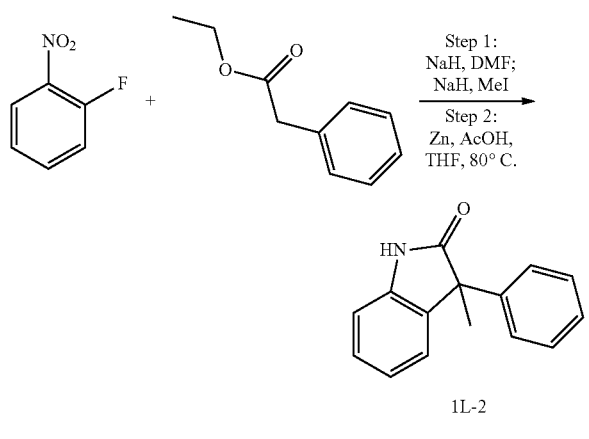

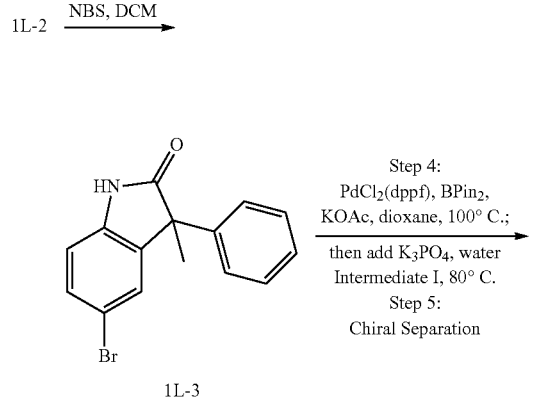

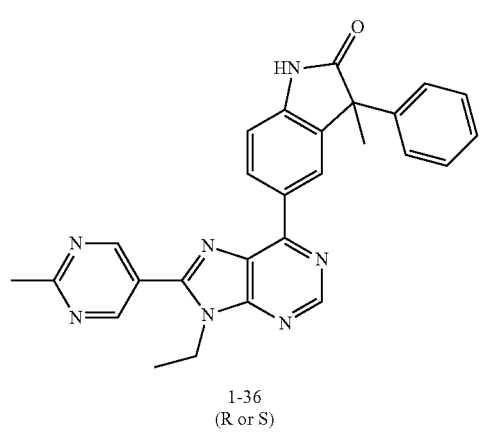

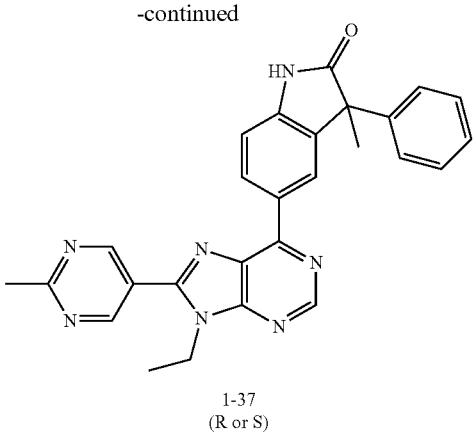

Steps 1-2 3-Methyl-3-phenylindolin-2-one (1L-2)

A solution of ethyl 2-phenylacetate (2.0 g, 12 mmol) in 10 mL of DMF was treated with a 60% suspension of NaH in mineral oil (0.70 g, 18 mmol). After stirring for 10 min, the mixture was treated with 1-fluoro-2-nitrobenzene (2.0 g, 14 mmol) and stirred for 6 h. The mixture was then treated with more 60% suspension of NaH in mineral oil (0.70 g, 18 mmol), followed by iodomethane (1.0 mL, 16 mmol), and stirred overnight. The mixture was diluted with DCM, washed with water, dried (Na$_2$SO$_4$), and concentrated. The residue was dissolved in 10 mL of THF and 10 mL of AcOH, treated with zinc dust (4.0 g, 61 mmol) and warmed to 80° C. After stirring for 3 h, the mixture was cooled, filtered through a pad of CELITE and concentrated. Chromatography on SiO$_2$ (0-40% EtOAc/DCM) gave the title intermediate (1L-2). MS (EI) calc'd for $C_{15}H_{14}NO$ [M+H]$^+$, 224; found, 224.

Step 3 5-Bromo-3-methyl-3-phenylindolin-2-one (1L-3)

A mixture containing 3-methyl-3-phenylindolin-2-one (1L-2) (1.12 g, 3.31 mmol) in 10 mL of DCM was treated with NBS (0.70 g, 3.9 mmol) and stirred for 1 hour. The mixture was concentrated to dryness and purified by chromatography on SiO$_2$ (0-40% EtOAc/DCM) to give the title product (1L-3). MS (EI) calc'd for $C_{15}H_{13}BrNO$ [M+H]$^+$, 304; found, 304.

Steps 4-5 (R or S)- and (S or R)-5-(9-ethyl-8-(2-methylpyrimidin-5-yl)-9H-purin-6-yl)-3-methyl-3-phenylindolin-2-one (1-36 and 1-37)

A solution of 5-bromo-3-methyl-3-phenylindolin-2-one (75 mg, 0.25 mmol) in 1 mL of dioxane was treated with (BPin)$_2$ (100 mg, 0.39 mmol), KOAc (50 mg, 0.51 mmol) and PdCl$_2$(dppl) (20 mg, 0.024 mmol). The reaction mixture was stirred for 2 hours at 100° C., then cooled to RT and treated with Intermediate I (70 mg, 0.26 mmol), K$_3$PO$_4$ (100 mg, 0.48 mmol), PdCl$_2$(dppf) (20 mg, 0.024 mmol) and water (0.2 mL). The reaction mixture was stirred overnight at 80° C. Cooled to RT, filtered and purified by reverse phase chromatography (MeCN/water with 0.1% TFA) to provide the racemate. The racemate was then dissolved in 3.5 mL of 1:1 MeOH/MeCN and resolved using chiral column chromatography [Column: ChiralPak™ AS-H, 21×250 mm; 220 nm detection; 70 mL/min flow rate; 25% MeOH and 0.25% Me$_2$NEt in CO$_2$]. The faster eluting enantiomer came at a retention time of 7.3 min (1-36), while the slower eluting enantiomer came at a retention time of 10.2 min (1-37). Characterization data for compound 1-36: $^1$H NMR (600 MHz, DMSO-d$_6$) δ 10.89 (s, 1H), 9.19 (s, 2H), 8.94 (d, J=8.2. Hz, 1H), 8.90 (s, 1H), 8.55 (s, 1H), 7.32-7.28 (m, 4H), 7.24 (m, 1H), 7.14 (d, J=8.2 Hz, 1H), 4.40 (q, J=7.0 Hz, 2H), 2.74 (s, 3H), 1.73 (s, 3H), 1.33 (t, J=7.0 Hz, 3H). MS (EI) calc'd for C$_{27}$H$_{24}$N$_7$O [M+H]$^+$, 461; found, 461. Characterization data for compound 1-37: $^1$H NMR (600 MHz, DMSO-d$_6$) δ 10.89 (s, 1H), 9.19 (s, 2H), 8.94 (d, J=8.2 Hz, 1H), 8.90 (s, 1H), 8.55 (s, 1H), 7.32-7.28 (m, 4H), 7.24 (m, 1H), 7.14 (d, J=8.2 Hz, 1H), 4.40 (q, J=7.4 Hz, 2H), 2.74 (s, 3H), 1.73 (s, 3H), 1.33 (t, J=7.0 Hz, 3H). MS (EI) calc'd for C$_{27}$H$_{24}$N$_7$O [M+H]$^+$, 461; found, 461.

Example 1M Compounds 1-40 and 1-41

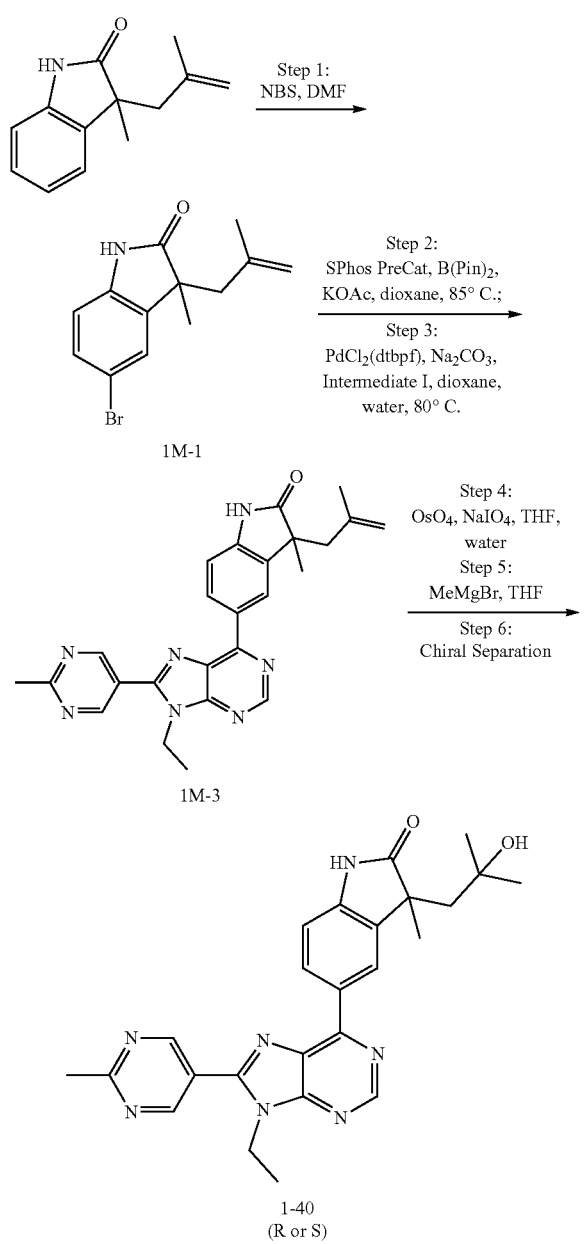

1-40
(R or S)

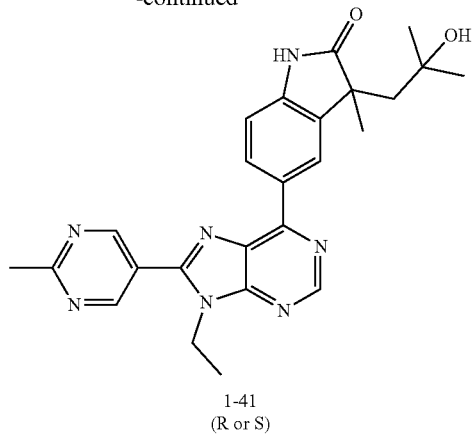

1-41
(R or S)

Step 1 5-Bromo-3-methyl-3(2-methylallyl)indolin-2-one (1M-1)

A solution of 3-methyl-3-(2-methylallyl)indolin-2-one described in Example 1A (155 mg, 0.770 mmol) in 3 of DMF was treated at 0° C. with NBS (140 mg, 0.786 mmol) and stirred with slow warming to room temperature overnight. The mixture was diluted with ethyl acetate and washed with brine. The organic layer was dried (MgSO$_4$), concentrated, and purified by chromatography on SiO$_2$ (10-60% EtOAc/hexanes) to provide the title compound (1M-1). MS (EI) calc'd for C$_{13}$H$_{15}$BrNO [M+H]$^+$, 282; found, 282.

Steps 2-3 5-(9-Ethyl-8-(2-methylpyrimidin-5-yl)-9H-purin-6-yl)-3-methyl-3-(2-methylallyl)indolin-2-one (1M-3)

A solution of 5-bromo-3-methyl-3-(2-methylallyl)indolin-2-one (1M-1) (898 mg, 3.21 mmol), (BPin)$_2$ (977 mg, 3.85 mmol), KOAc (786 mg, 8.01 mmol) and S-Phos Precatalyst (252 mg, 0.321 mmol) in 8 mL of dioxane was deoxygenated with vacuum and backfilling with nitrogen. The mixture was warmed to 85° C. and stirred for 2 h. The mixture was filtered through CELITE, concentrated, then purified by chromatography on SiO$_2$ (2-20% MeOH/DCM) to give 3-methyl-3-(2-methylallyl)-5-(4,4,5,5-tetramethyl-1,3,2-dioxaborolan-2-yl)indolin-2-one.

A solution of Intermediate I (420 mg, 1.53 mmol), 3-methyl-3-(2-methylallyl)-5-(4,4,5,5-tetramethyl-1,3,2-dioxaborolan-2-yl)indolin-2-one (500 mg, 1.53 mmol) and PdCl$_2$(dtbpf) (139 mg, 0.153 mmol) in 2 mL of dioxane was treated with a 2 M solution of Na$_2$SO$_4$ (1.53 ml, 3.06 mmol). The mixture was stirred overnight at 80° C., poured into DCM and washed with water. The organic layer was dried (Na$_2$SO$_4$), concentrated and purified by chromatography on SiO$_2$ (10-60% EtOAc/hexane followed by 10-90% MeOH/DCM) to afford the title compound (1M-3). MS (EI) calc'd for C$_{25}$H$_{26}$N$_7$O [M+H]$^+$, 440; found, 440.

Steps 4-6 (R or S)- and (S or R)-5-(9-Ethyl-8-(2-methylpyrimidin-5-yl)-9H-purin-6-yl)-3-(2-hydroxy-2-methylpropyl)-3-methylindolin-2-one (1-40 and 1-41)

A solution of 5-(9-ethyl-8-(2-methylpyrimidin-5-yl)-9H-purin-6-yl)-3-methyl-3-(2-methylallyl)indolin-2-one (1M-3) (370 mg, 0.842 mmol) in 4 mL of THF and 4 mL of water was treated with a 2.5% solution of $OsO_4$ (0.53 mL, 0.042 mmol) and $NaIO_4$ (540 mg, 2.53 mmol). The mixture was stirred for 1 h, then quenched with sat'd $NaHCO_3$ and extracted with DCM. The organic layer was dried ($MgSO_4$), concentrated and the residue purified by chromatography on $SiO_2$ (2-20% MeOH/DCM) to provide 5-(9-ethyl-8-(2-methylpyrimidin-5-yl)-9H-purin-6-yl)-3-methyl-3-(2-oxopropyl)indolin-2-one. MS (EI) calc'd for $C_{24}H_{24}N_7O_2$ [M+H]$^+$, 442; found, 442.

A solution of 5-(9-ethyl-8-(2-methylpyrimidin-5-yl)-9H-purin-6-yl)-3-methyl-3-(2-oxopropyl)indolin-2-one (205 mg, 0.464 mmol) in 3 mL of THF was treated with a solution of MeMgBr in THF (111 mg, 0.929 mmol). The mixture was stirred for 1 h, then concentrated to dryness. Reverse phase chromatography (MeCN/water with 0.1% TFA) gave racemic 5-(9-ethyl-8-(2-methylpyrimidin-5-yl)-9H-purin-6-yl)-3-(2-hydroxy-2-methylpropyl)-3-methylindolin-2-one. The racemic product was dissolved in 4 mL of MeOH and resolved using chiral column chromatography [Column: ChiralPak™ AD-H, 21×250 mm; 220 nm detection; 70 mL/min flow rate; 30% MeOH and 0.25% DMEA in $CO_2$; Retention Time 1: 4.27 min; Retention Time 2: 5.06 min]. The faster eluting enantiomer at 4.27 min was denoted 1-40, while the slower eluting enantiomer at 5.06 min was denoted 1-41. Characterization data for 1-40: $^1$H NMR (600 MHz, DMSO-$d_6$) δ 10.59 (s, 1H), 9.21 (s, 2H), 8.93 (s, 1H), 8.86 (d, J=8.2 Hz, 1H), 8.66 (s, 1H), 7.02 (d, J=8.3 Hz, 1H), 4.41 (q, J=7.4 Hz, 2H), 3.99 (s, 1H), 2.75 (s, 3H), 2.12 (m, 2H), 1.35 (t, J=7.0 Hz, 3H), 1.22 (s, 3H), 0.82 (s, 3H), 0.77 (s, 3H); MS (EI) calc'd for $C_{25}H_{28}N_7O_2$ [M+H]$^+$, 458; found, 458. Characterization data for 1-41: $^1$H NMR (600 MHz, DMSO-$d_6$) δ10.59 (s, 1H), 9.21 (s, 2H), 8.93 (s, 1H), 8.86 (dd, J=8.2, 1.8 Hz, 1H), 8.65 (d, J=1.5 Hz, 1H), 7.02 (d, J=8.2 Hz, 1H), 4.41 (q, J=7.3 Hz, 2H), 3.98 (s, 1H), 2.75 (s, 3H), 2.12 (m, 2H), 1.35 (t, J=7.3 Hz, 3H), 1.22 (s, 3H), 0.80 (s, 3H), 0.75 (s, 3H); MS (EI) calc'd for $C_{25}H_{28}N_7O_2$ [M+H]$^+$, 458; found, 458.

Compounds 1-5, 1-6, 1-14, 1-15, 1-23, 1-24, 1-26 to 1-33, 1-38 and 1-39

Compounds 1-5 and 1-6 were prepared in a fashion analogous to compounds 1-3 and 1-4, substituting 3-iodomethyloxetane for 3-methyl-3-iodomethyloxetane. The racemic material was then resolved using chiral column chromatography [Column: ChiralPak™ IC, 20×250 mm; 220 nm detection; 20 mL/min flow rate; 10% EtOH in MTBE]. The faster eluting enantiomer came at a retention time of 6.55 min (1-5); while the slower eluting enantiomer came at a retention time of 7.48 min (1-6).

Compounds 1-14 and 1-15 were prepared in a fashion analogous to compounds 1-12 and 1-13, substituting isobutyraldehyde for cyclopropanecarbaldehyde. The racemic material was then resolved using chiral column chromatography [Column: ChiralPak™ AS-H, 21×250 mm; 220 nm detection; 70 mL/min flow rate; 25% MeOH and 0.25% DMEA in $CO_2$]. The faster eluting enantiomer came at a retention time of 3.76 min (1-14); while the slower eluting enantiomer came at a retention time of 4.80 min (1-15).

Compounds 1-23 and 1-24 were prepared in a fashion analogous to compounds 1-16 and 1-17, substituting Intermediate I for Intermediate III. The racemic material was then resolved using chiral column chromatography [Column: ChiralPak™ 21×250 mm; 220 nm detection; 70 mL/min flow rate; 15% MeOH and 0.25% DMEA in $CO_2$]. The faster eluting enantiomer came at a retention time of 6.35 min (1-23); while the slower eluting enantiomer came at a retention time of 7.27 min (1-24).

Compounds 1-26 and 1-27 were prepared in a fashion analogous to compounds 1-12 and 1-13, substituting Intermediate I for Intermediate II. The racemic material was then resolved using chiral column chromatography [Column: ChiralPak™ OD-H, 21×250 mm; 220 nm detection; 70 mL/min flow rate; 30% MeOH and 0.25% DMEA in $CO_2$]. The faster eluting enantiomer came at a retention time of 6.45 min (1-26); while the slower eluting enantiomer came at a retention time of 7.25 min (1-27).

Compounds 1-28 and 1-29 were prepared in a fashion analogous to compounds 1-16 and 1-17, substituting Intermediate I for 6-chloro-9-methyl-9H-purine. The racemic material was then resolved using chiral column chromatography [Column: Phenomenex Lux-4, 21×250 mm; 220 nm detection; 70 mL/min flow rate; 35% MeOH and 0.25% DMEA in $CO_2$]. The faster eluting enantiomer came at a retention time of 4.95 min (1-28); while the slower eluting enantiomer came at a retention time of 5.85 min (1-29).

Compounds 1-30, 1-31 and 1-32 were prepared in a fashion analogous to compounds 1-3 and 1-4, substituting 3-(bromomethyl)oxetane for 2-(bromomethyl)oxetane. The mixture of four diastereomers were separated using chiral column chromatography [Column: ChiralPak™ IA, 20×250 mm; 220 nm detection; 40% MeOH and 0.1% diethylamine in hexane]. Three fractions were collected at 4.8, 5.6 and 8.6 min. The faster eluting fraction (4.8 min; denoted as 1-30), the middle fraction (5.6 min; denoted as 1-31), and the last fraction (8.6 min; denoted as 1-32).

Compound 1-33 was prepared in racemic form in a fashion analogous to the preparation of 1-16 and 1-17, replacing benzyl bromide for 5-(bromomethyl)pyrimidine.

Compounds 1-38 and 1-39 were prepared in a fashion analogous to compounds 1-7 and 1-8, substituting bromomethylcyclopropane for the ethyl halide. The racemic material was then dissolved in 12 mL of 1:3 MeOH/MeCN and resolved using chiral column chromatography [Column: ChiralPak™ AS-H, 21×250 mm; 220 nm detection; 70 mL/min flow rate; 35% MeOH and 0.25% DMEA in $CO_2$]. The faster eluting enantiomer came at a retention time of 3.2 min (1-38); while the slower eluting enantiomer came at a retention time of 4.7 min (1-39).

Table 1 provides structures for compounds 1-1 through 1-41 which were synthesized directly by the methods described above or by analogous methods to those described above.

TABLE 1

| Compound | Structure | Name | Exact Mass [M + H]+ |
|---|---|---|---|
| 1-1 | 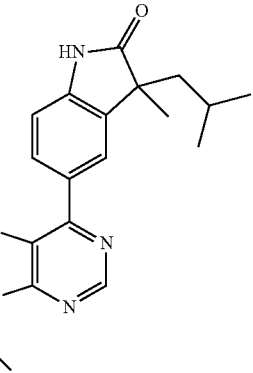 | (R or S)-5-[9-ethyl-8-(2-methylpyrimidin-5-yl)-9H-purin-6-yl]-3-methyl-3-(2-methylpropyl)-1,3-dihydro-2H-indol-2-one | Calc'd 442, found 442 |
| 1-2 | 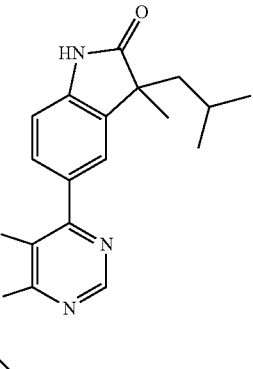 | (R or S)-5-[9-ethyl-8-(2-methylpyrimidin-5-yl)-9H-purin-6-yl]-3-methyl-3-(2-methylpropyl)-1,3-dihydro-2H-indol-2-one | Calc'd 442, found 442 |
| 1-3 | 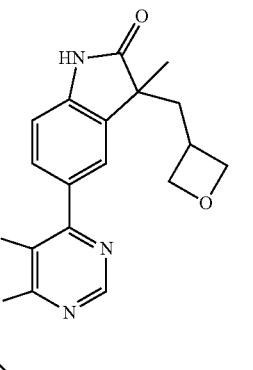 | (R or S)-5-[9-ethyl-8-(2-methylpyrimidin-5-yl)-9H-purin-6-yl]-3-methyl-3-(oxetan-3-ylmethyl)-1,3-dihydro-2H-indol-2-one | Calc'd 456, found 456 |
| 1-4 | 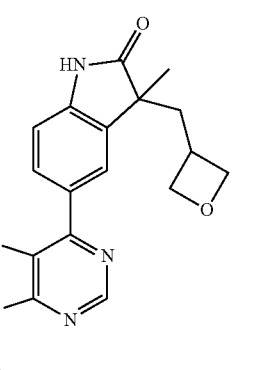 | (R or S)-5-[9-ethyl-8-(2-methylpyrimidin-5-yl)-9H-purin-6-yl]-3-methyl-3-(oxetan-3-ylmethyl)-1,3-dihydro-2H-indol-2-one | Calc'd 456, found 456 |

TABLE 1-continued

| Compound | Structure | Name | Exact Mass [M + H]+ |
|---|---|---|---|
| 1-5 | 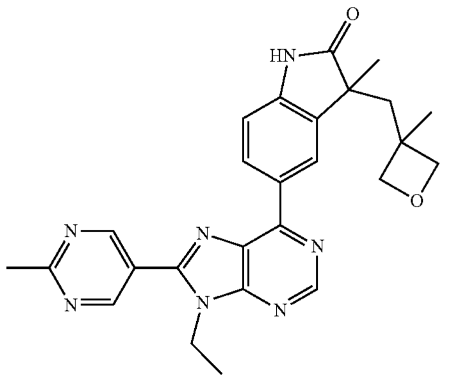 [SMILES: CCn1c(-c2cnc(C)nc2)nc2c(-c3ccc4c(c3)C(C)(CC3(C)COC3)C(=O)N4)ncnc21] | (R or S)-5-[9-ethyl-8-(2-methylpyrimidin-5-yl)-9H-purin-6-yl]-3-methyl-3-[(3-methyloxetan-3-yl)methyl]-1,3-dihydro-2H-indol-2-one | Calc'd 470, found 470 |
| 1-6 | 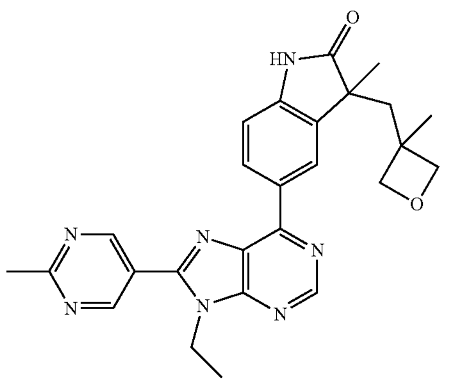 [SMILES: CCn1c(-c2cnc(C)nc2)nc2c(-c3ccc4c(c3)C(C)(CC3(C)COC3)C(=O)N4)ncnc21] | (R or S)-5-[9-ethyl-8-(2-methylpyrimidin-5-yl)-9H-purin-6-yl]-3-methyl-3-[(3-methyloxetan-3-yl)methyl]-1,3-dihydro-2H-indol-2-one | Calc'd 470, found 470 |
| 1-7 | 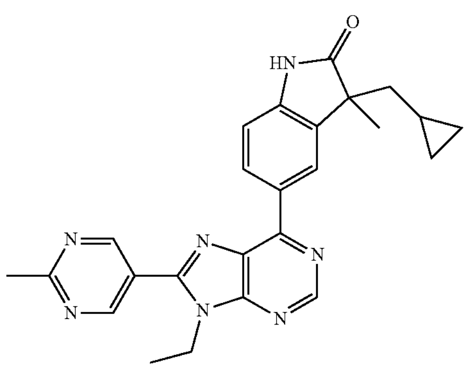 [SMILES: CCn1c(-c2cnc(C)nc2)nc2c(-c3ccc4c(c3)C(C)(CC3CC3)C(=O)N4)ncnc21] | (R or S)-3-(cyclopropylmethyl)-5-(9-ethyl-8-(2-methylpyrimidin-5-yl)-9H-purin-6-yl)-3-methylindolin-2-one | Calc'd 440, found 440 |
| 1-8 | 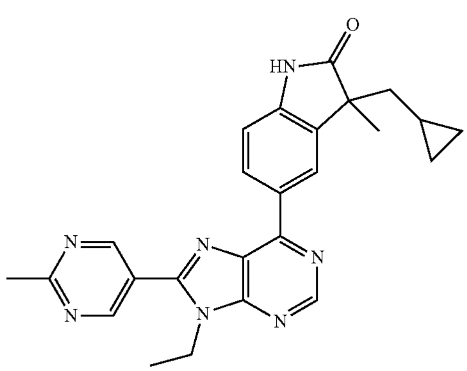 [SMILES: CCn1c(-c2cnc(C)nc2)nc2c(-c3ccc4c(c3)C(C)(CC3CC3)C(=O)N4)ncnc21] | (R or S)-3-(cyclopropylmethyl)-5-(9-ethyl-8-(2-methylpyrimidin-5-yl)-9H-purin-6-yl)-3-methylindolin-2-one | Calc'd 440, found 440 |

TABLE 1-continued

| Compound | Structure | Name | Exact Mass [M + H]+ |
|---|---|---|---|
| 1-9 | 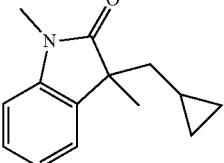 | (R or S)-3-(cyclopropylmethyl)-5-[9-ethyl-8-(2-methylpyrimidin-5-yl)-9H-purin-6-yl)-1,3-dimethylindolin-2-one | Calc'd 454, found 454 |
| 1-10 | 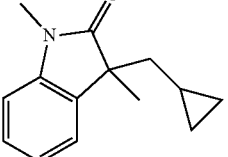 | (R or S)-3-(cyclopropylmethyl)-5-(9-ethyl-8-(2-methylpyrimidin-5-yl)-9H-purin-6-yl)-1,3-dimethylindolin-2-one | Calc'd 454, found 454 |
| 1-11 | 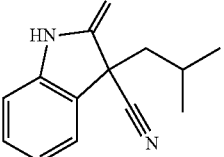 | 5-(9-ethyl-8-(2-methylpyrimidin-5-yl)-9H-purin-6-yl)-3-isobutyl-2-oxoindoline-3-carbonitrile | Calc'd 453, found 453 |
| 1-12 | 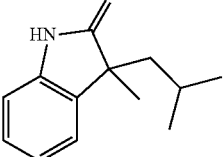 | (R or S)-5-(9-ethyl-8-(2-methylpyrimidin-5-yl)-9H-purin-6-yl)-3-isobutyl-3-methyl-1,3-dihydro-2H-pyrrolo[2,3-b]pyridin-2-one | Calc'd 443, found 443 |

TABLE 1-continued

| Compound | Structure | Name | Exact Mass [M + H]+ |
|---|---|---|---|
| 1-13 | 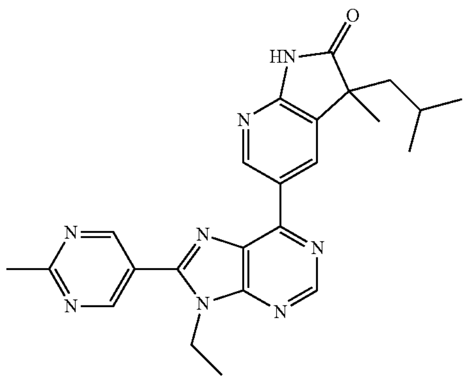 [SMILES: CCn1c(-c2cnc(C)nc2)nc2c(-c3ccc4c(c3)C(C)(CC(C)C)C(=O)N4)ncnc21] | (R or S)-5-(9-ethyl-8-(2-methylpyrimidin-5-yl)-9H-purin-6-yl)-3-isobutyl-3-methyl-1,3-dihydro-2H-pyrrolo[2,3-b]pyridin-2-one | Calc'd 443, found 443 |
| 1-14 | 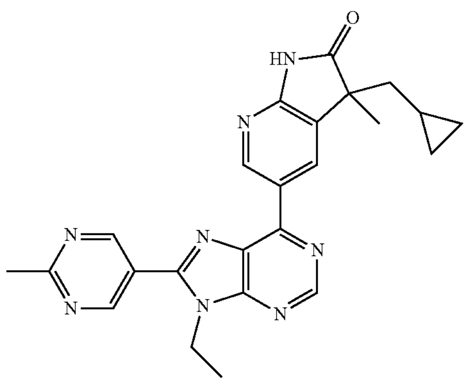 [SMILES: CCn1c(-c2cnc(C)nc2)nc2c(-c3cnc4c(c3)C(C)(CC3CC3)C(=O)N4)ncnc21] | (R or S)-3-(cyclopropylmethyl)-5-(9-ethyl-8-(2-methylpyrimidin-5-yl)-9H-purin-6-yl)-3-methyl-1,3-dihydro-2H-pyrrolo[2,3-b]pyridin-2-one | Calc'd 441, found 441 |
| 1-15 | 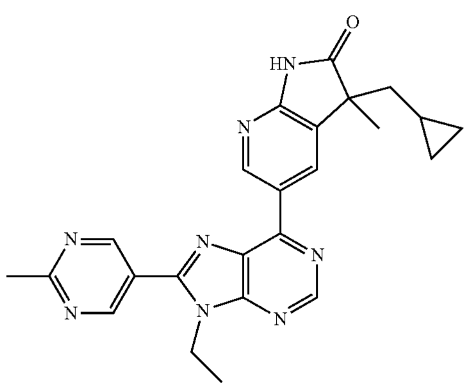 [SMILES: CCn1c(-c2cnc(C)nc2)nc2c(-c3cnc4c(c3)C(C)(CC3CC3)C(=O)N4)ncnc21] | (R or S)-3-(cyclopropylmethyl)-5-(9-ethyl-8-(2-methylpyrimidin-5-yl)-9H-purin-6-yl)-3-methyl-1,3-dihydro-2H-pyrrolo[2,3-b]pyridin-2-one | Calc'd 441 found 441 |
| 1-16 | 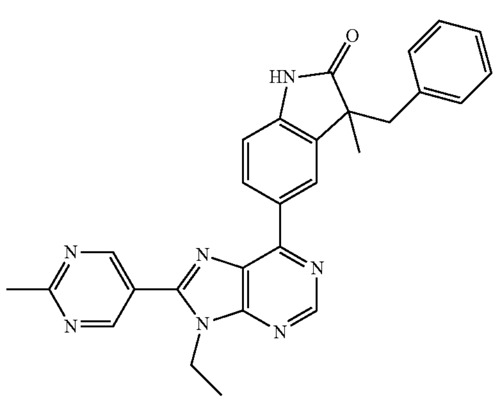 [SMILES: CCn1c(-c2cnc(C)nc2)nc2c(-c3ccc4c(c3)C(C)(Cc3ccccc3)C(=O)N4)ncnc21] | (R or S)-3-benzyl-5-(9-ethyl-8-(2-methylpyrimidin-5-yl)-9H-purin-6-yl)-3-methylindolin-2-one | Calc'd 476, found 476 |

TABLE 1-continued

| Compound | Structure | Name | Exact Mass [M + H]+ |
|---|---|---|---|
| 1-17 | 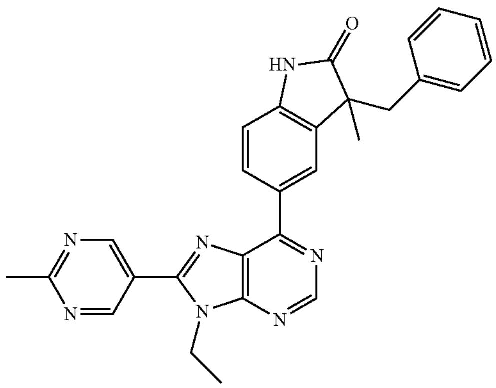 [SMILES: CCn1c(-c2cnc(C)nc2)nc2c(-c3ccc4c(c3)C(C)(Cc3ccccc3)C(=O)N4)ncnc21] | (R or S)-3-benzyl-5-(9-ethyl-8-(2-methylpyrimidin-5-yl)-9H-purin-6-yl)-3-methylindolin-2-one | Calc'd 476, found 476 |
| 1-18 | 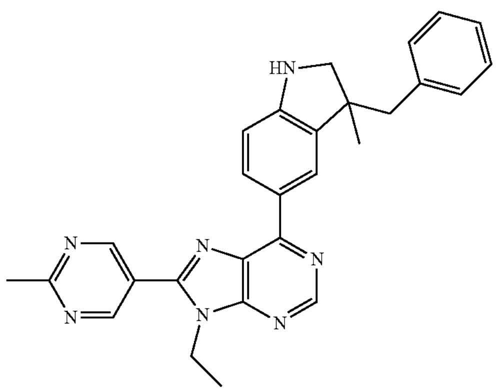 [SMILES: CCn1c(-c2cnc(C)nc2)nc2c(-c3ccc4c(c3)C(C)(Cc3ccccc3)CN4)ncnc21] | 6-(3-benzyl-3-methylindol-5-yl)-9-ethyl-8-(2-methylpyrimidin-5-yl)-9H-purine | Calc'd 462, found 462 |
| 1-19 | 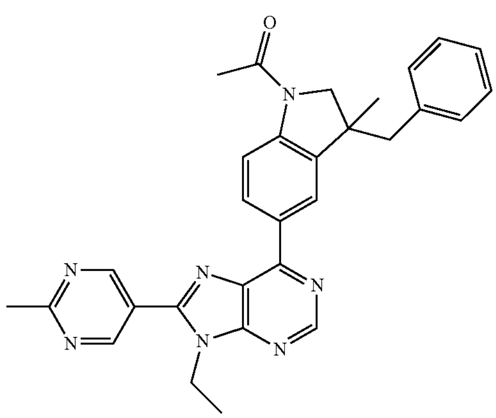 [SMILES: CCn1c(-c2cnc(C)nc2)nc2c(-c3ccc4c(c3)C(C)(Cc3ccccc3)CN4C(C)=O)ncnc21] | 1-(3-benzyl-5-(9-ethyl-8-(2-methylpyrimidin-5-yl)-9H-purin-6-yl)-3-methylindolin-1-yl)ethan-1-one | Calc'd 504, found 504 |
| 1-20 | 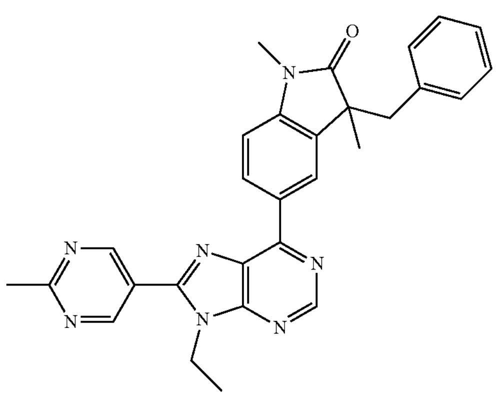 [SMILES: CCn1c(-c2cnc(C)nc2)nc2c(-c3ccc4c(c3)C(C)(Cc3ccccc3)C(=O)N4C)ncnc21] | (R or S)-3-benzyl-5-(9-ethyl-8-(2-methylpyrimidin-5-yl)-9H-purin-6-yl)-1,3-dimethylindolin-2-one | Calc'd 490, found 490 |

TABLE 1-continued

| Compound | Structure | Name | Exact Mass [M + H]+ |
|---|---|---|---|
| 1-21 | 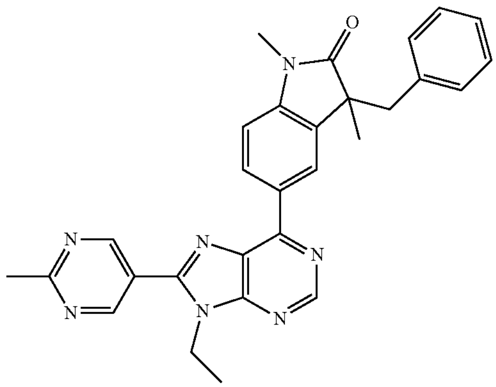 [SMILES: CCn1c(-c2cnc(C)nc2)nc2c(-c3ccc4c(c3)C(C)(Cc3ccccc3)C(=O)N4C)ncnc21] | (R or S)-3-benzyl-5-(9-ethyl-8-(2-methylpyrimidin-5-yl)-9H-purin-6-yl)-1,3-dimethylindolin-2-one | Calc'd 490, found 490 |
| 1-22 | 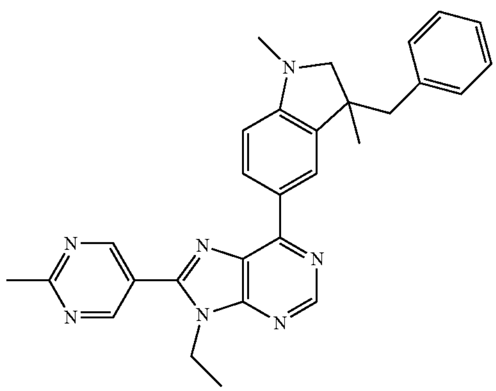 [SMILES: CCn1c(-c2cnc(C)nc2)nc2c(-c3ccc4c(c3)C(C)(Cc3ccccc3)CN4C)ncnc21] | 6-(3-benzyl-1,3-dimethylindolin-5-yl)-9-ethyl-8-(2-methylpyrimidin-5-yl)-9H-purine | Calc'd 476, found 476 |
| 1-23 | 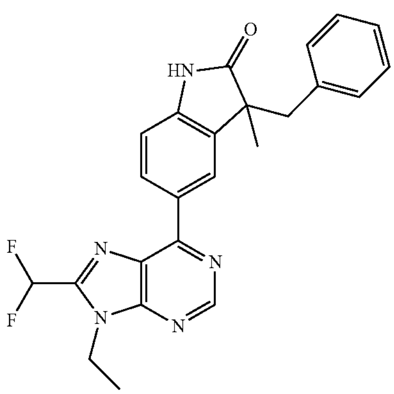 [SMILES: CCn1c(C(F)F)nc2c(-c3ccc4c(c3)C(C)(Cc3ccccc3)C(=O)N4)ncnc21] | (R or S)-benzyl-5-(8-(difluoromethyl)-9-ethyl-9H-purin-6-yl)-3-methylindolin-2-one | Calc'd 434, found 434 |
| 1-24 | 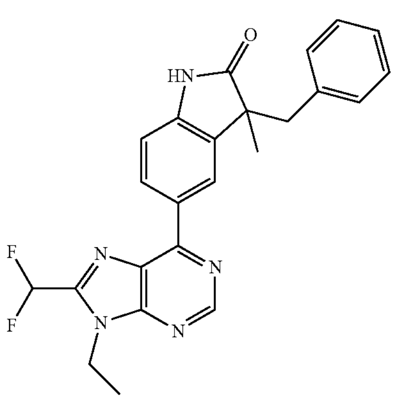 [SMILES: CCn1c(C(F)F)nc2c(-c3ccc4c(c3)C(C)(Cc3ccccc3)C(=O)N4)ncnc21] | (R or S)-benzyl-5-(8-(difluoromethyl)-9-ethyl-9H-purin-6-yl)-3-methylindolin-2-one | Calc'd 434, found 434 |

TABLE 1-continued

| Compound | Structure | Name | Exact Mass [M + H]+ |
|---|---|---|---|
| 1-25 | 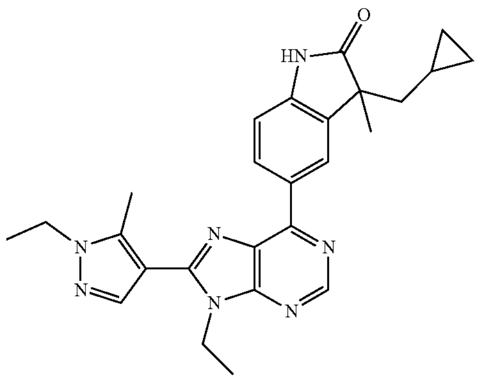 [SMILES: CCn1ncc(-c2nc3c(-c4ccc5c(c4)C(C)(CC4CC4)C(=O)N5)ncnc3n2CC)c1C] | (R or S)-3-(cyclopropylmethyl)-5-(9-ethyl-8-(1-ethyl-5-methyl-1H-pyrazol-4-yl)-9H-purin-6-yl)-3-methylindolin-2-one | Calc'd 456, found 456 |
| 1-26 | 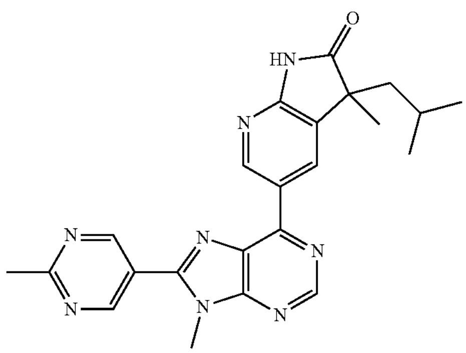 [SMILES: Cc1ncc(-c2nc3c(-c4cnc5c(c4)C(C)(CC(C)C)C(=O)N5)ncnc3n2C)cn1] | (R or S)-3-isobutyl-3-methyl-5-(9-methyl-8-(2-methylpyrimidin-5-yl)-9H-purin-6-yl)-1,3-dihydro-2H-pyrrolo[2,3-b]pyridin-2-one | Calc'd 429, found 429 |
| 1-27 | 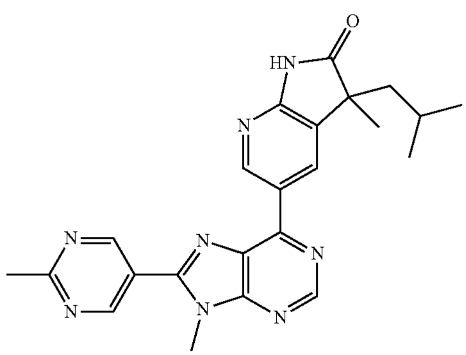 [SMILES: Cc1ncc(-c2nc3c(-c4cnc5c(c4)C(C)(CC(C)C)C(=O)N5)ncnc3n2C)cn1] | (R or S)-3-isobutyl-3-methyl-5-(9-methyl-8-(2-methylpyrimidin-5-yl)-9H-purin-6-yl)-1,3-dihydro-2H-pyrrolo[2,3-b]pyridin-2-one | Calc'd 429, found 429 |
| 1-28 | 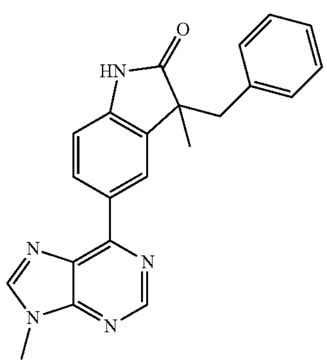 [SMILES: Cn1cnc2c(-c3ccc4c(c3)C(C)(Cc3ccccc3)C(=O)N4)ncnc21] | (R or S)-3-benzyl-3-methyl-5-(9-methyl-9H-purin-6-yl)indolin-2-one | Calc'd 370, found 370 |

TABLE 1-continued

| Compound | Structure | Name | Exact Mass [M + H]+ |
|---|---|---|---|
| 1-29 | 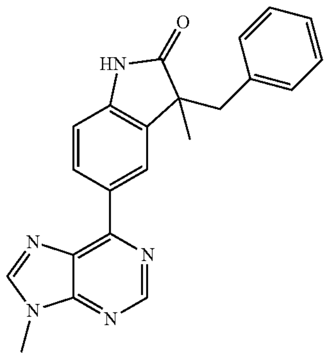 [SMILES: Cn1cnc2c(-c3ccc4c(c3)C(C)(Cc3ccccc3)C(=O)N4)ncnc21] | (R or S)-3-benzyl-3-methyl-5-(9-methyl-9H-purin-6-yl)indolin-2-one | Calc'd 370, found 370 |
| 1-30 | 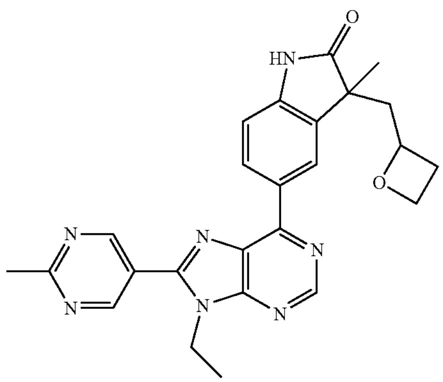 [SMILES: CCn1c(-c2cnc(C)nc2)nc2c(-c3ccc4c(c3)C(C)(CC3CCO3)C(=O)N4)ncnc21] | [(R,R) or (R,S) or (S,S) or (S,R)]-5-(9-ethyl-8-(2-methylpyrimidin-5-yl)-9H-purin-6-yl)-3-methyl-3-(oxetan-2-ylmethyl)indolin-2-one | Calc'd 456, found 456 |
| 1-31 | 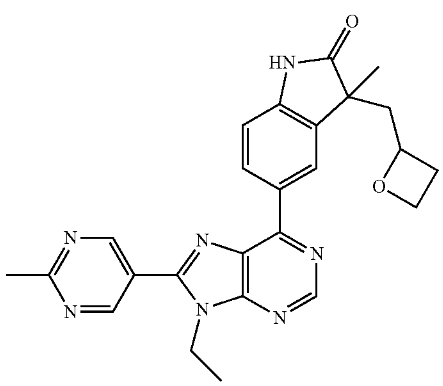 [SMILES: CCn1c(-c2cnc(C)nc2)nc2c(-c3ccc4c(c3)C(C)(CC3CCO3)C(=O)N4)ncnc21] | [(R,R) or (R,S) or (S,S) or (S,R)]-5-(9-ethyl-8-(2-methylpyrimidin-5-yl)-9H-purin-6-yl)-3-methyl-3-(oxetan-2-ylmethyl)indolin-2-one | Calc'd 456, found 456 |
| 1-32 | 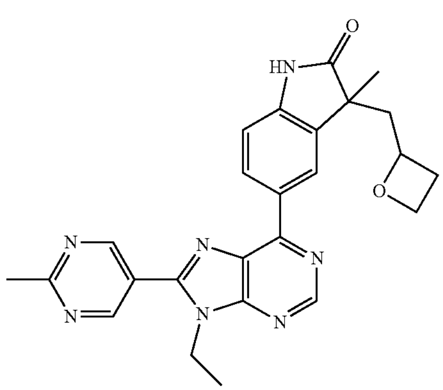 [SMILES: CCn1c(-c2cnc(C)nc2)nc2c(-c3ccc4c(c3)C(C)(CC3CCO3)C(=O)N4)ncnc21] | [(R,R) or (R,S) or (S,S) or (S,R)]-5-(9-ethyl-8-(2-methylpyrimidin-5-yl)-9H-purin-6-yl)-3-methyl-3-(oxetan-2-ylmethyl)indolin-2-one | Calc'd 456, found 456 |

TABLE 1-continued

| Compound | Structure | Name | Exact Mass [M + H]+ |
|---|---|---|---|
| 1-33 | 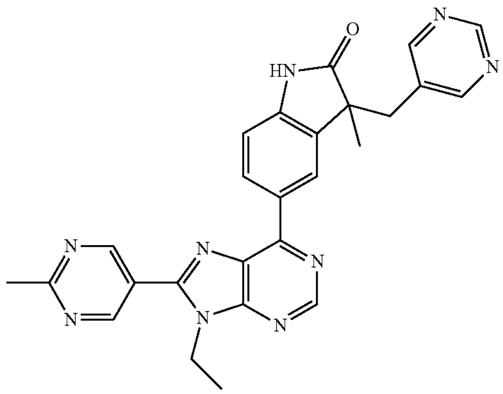 [SMILES: CCn1c(-c2cnc(C)nc2)nc2c(-c3ccc4c(c3)C(C)(Cc3cncnc3)C(=O)N4)ncnc21] | 5-(9-ethyl-8-(2-methylpyrimidin-5-yl)-9H-purin-6-yl)-3-methyl-3-(pyrimidin-5-ylmethyl)indolin-2-one | Calc'd 478, found 478 |
| 1-34 | 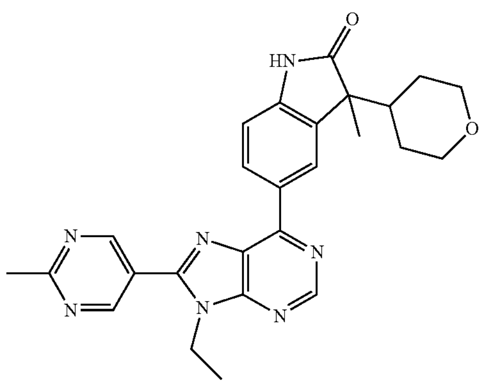 [SMILES: CCn1c(-c2cnc(C)nc2)nc2c(-c3ccc4c(c3)C(C)(C3CCOCC3)C(=O)N4)ncnc21] | (R or S)-5-(9-ethyl-8-(2-methylpyrimidin-5-yl)-9H-purin-6-yl)-3-methyl-3-(tetrahydro-2H-pyran-4-yl)indolin-2-one | Calc'd 470, found 470 |
| 1-35 | 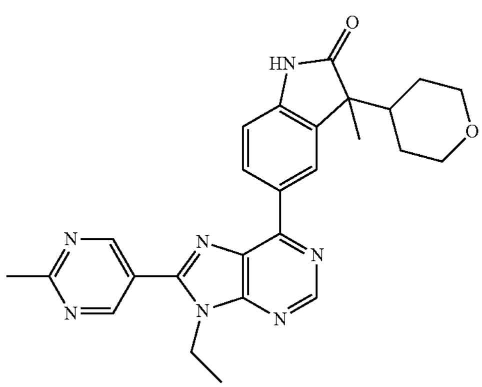 [SMILES: CCn1c(-c2cnc(C)nc2)nc2c(-c3ccc4c(c3)C(C)(C3CCOCC3)C(=O)N4)ncnc21] | (R or S)-5-(9-ethyl-8-(2-methylpyrimidin-5-yl)-9H-purin-6-yl)-3-methyl-3-(tetrahydro-2H-pyran-4-yl)indolin-2-one | Calc'd 470, found 470 |
| 1-36 | 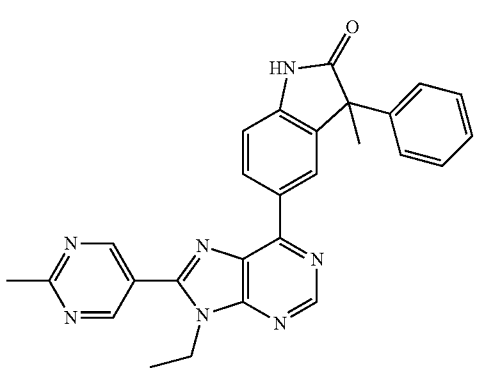 [SMILES: CCn1c(-c2cnc(C)nc2)nc2c(-c3ccc4c(c3)C(C)(c3ccccc3)C(=O)N4)ncnc21] | (R or S)-5-(9-ethyl-8-(2-methylpyrimidin-5-yl)-9H-purin-6-yl)-3-methyl-3-phenylindolin-2-one | Calc'd 461, found 461 |

TABLE 1-continued

| Compound | Structure | Name | Exact Mass [M + H]+ |
|---|---|---|---|
| 1-37 | 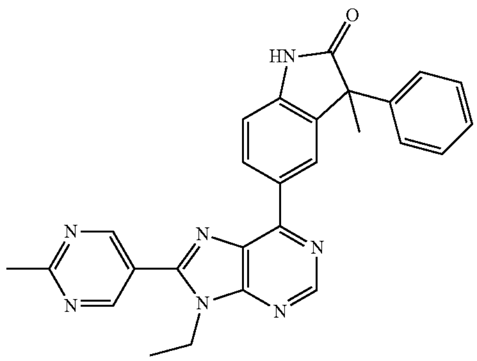 [SMILES: CCn1c(-c2cnc(C)nc2)nc2c(-c3ccc4c(c3)C(C)(c3ccccc3)C(=O)N4)ncnc21] | (R or S)-5-(9-ethyl-8-(2-methylpyrimidin-5-yl)-9H-purin-6-yl)-3-methyl-3-phenylindolin-2-one | Calc'd 461, found 461 |
| 1-38 | 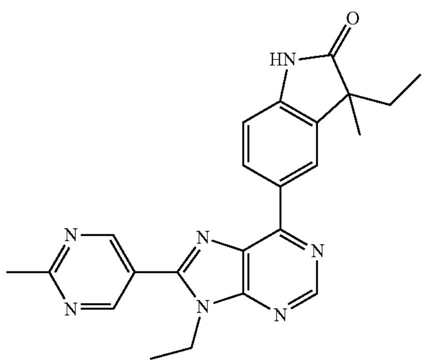 [SMILES: CCn1c(-c2cnc(C)nc2)nc2c(-c3ccc4c(c3)C(C)(CC)C(=O)N4)ncnc21] | (R or S)-3-ethyl-5-(9-ethyl-8-(2-methylpyrimidin-5-yl)-9H-purin-6-yl)-3-methylindolin-2-one | Calc'd 414, found 414 |
| 1-39 | 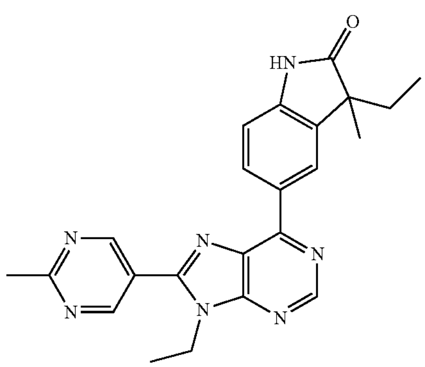 [SMILES: CCn1c(-c2cnc(C)nc2)nc2c(-c3ccc4c(c3)C(C)(CC)C(=O)N4)ncnc21] | (R or S)-3-ethyl-5-(9-ethyl-8-(2-methylpyrimidin-5-yl)-9H-purin-6-yl)-3-methylindolin-2-one | Calc'd 414, found 414 |
| 1-40 | 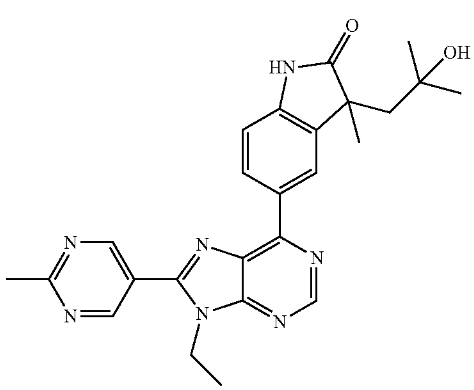 [SMILES: CCn1c(-c2cnc(C)nc2)nc2c(-c3ccc4c(c3)C(C)(CC(C)(C)O)C(=O)N4)ncnc21] | (R or S)-5-(9-ethyl-8-(2-methylpyrimidin-5-yl)-9H-purin-6-yl)-3-(2-hydroxy-2-methylpropyl)-3-methylindolin-2-one | Calc'd 458, found 458 |

TABLE 1-continued

| Compound | Structure | Name | Exact Mass [M + H]+ |
|---|---|---|---|
| 1-41 | 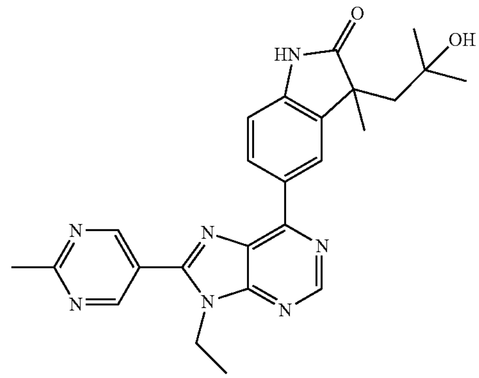 [SMILES: CCn1c(-c2cnc(C)nc2)nc2c(-c3ccc4c(c3)C(C)(CC(C)(C)O)C(=O)N4)ncnc21] | (R or S)-5-(9-ethyl-8-(2-methylpyrimidin-5-yl)-9H-purin-6-yl)-3-(2-hydroxy-2-methylpropyl)-3-methylindolin-2-one | Calc'd 458, found 458 |

Compound Examples of Table 2

Example 2A Compounds 2-1 and 2-2

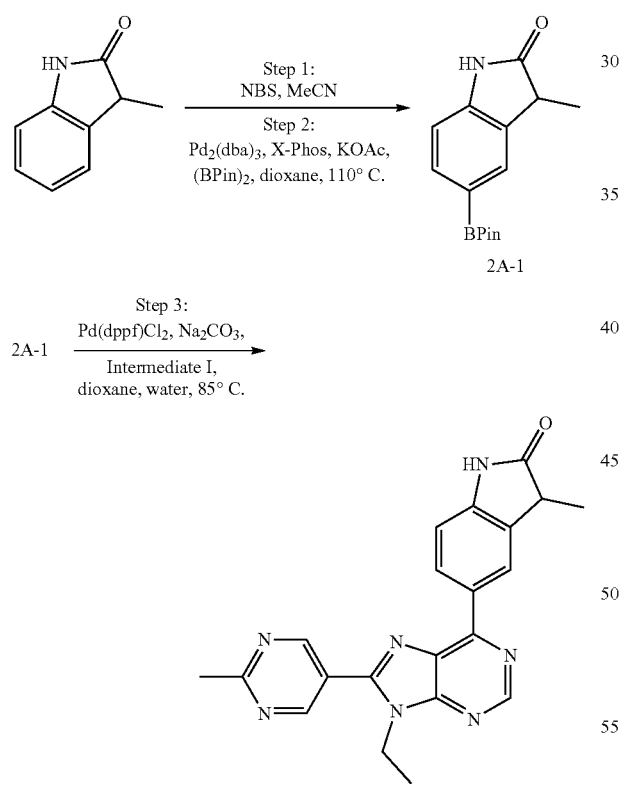

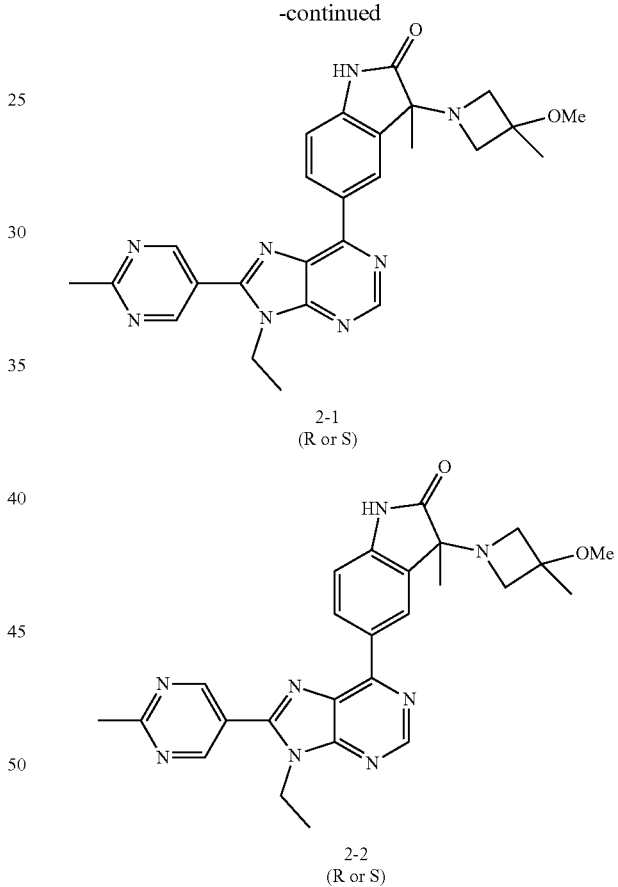

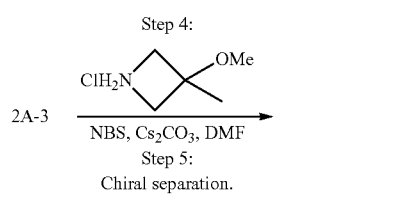

Steps 1-2 3-Methyl-5-(4,4,5,5-tetramethyl-1,3,2-dioxaborolan-2-yl)indolin-2-one (2A-2)

A solution of 3-methylindolin-2-one (50.0 g, 340 mmol) in MeCN (500 mL) was charged with NBS (66.0 g. 374 mmol) portionwise over 30 min at −20° C. The resulting reaction mixture was stirred for 30 min, then poured into ice (2 L) and extracted with EtOAc (3×1 L). The combined organic layers were dried (Na₂SO₄) and concentrated to afford 5-bromo-3-methylindolin-2-one. ¹H NMR (300 MHz, CDCl₃) δ 8.78 (s, 1H), 7.36-7.32 (m, 2H), 6.79 (d, J=8.7 Hz, 1H), 3.51-3.43 (m, 1H), 1.49 (d, J=7.8 Hz, 3H).

A solution of 5-bromo-3-methylindolin-2-one (58.7 g, 260 mmol) in 1,4-dioxane (500 mL) was charged with (BPin)₂ (79.3 g, 312 mmol) and KOAc (76.5 g, 780 mmol) at room temperature. The reaction mixture was purged with argon for 30 min and XPhos (6.20 g, 13.0 mmol) and Pd₂(dba)₃ (4.76 g, 5.20 mmol) were added. The reaction mixture was heated to reflux for 6 h, then filtered through CELITE. The organic layer was poured into water (2 L) and extracted with EtOAc (3×1 L), the combined organic layers were dried (Na₂SO₄) and concentrated. The obtained crude was washed with n-hexane to afford 3-methyl-5-(4,4,5,5-tetramethyl-1,3,2-dioxaborolan-2-yl)indolin-2-one (2A-2). ¹H NMR (400 MHz, CDCl₃) δ 8.55 (s, 1H), 7.70 (d, J=7.6 Hz, 1H), 7.66 (s, 1H), 6.91 (d, J=8.0 Hz, 1H), 3.49-3.43 (m, 1H), 1.51 (d, J=7.6 Hz, 3H), 1.35 (s, 12H). MS (EI) calc'd for C₁₅H₂₁BNO₃ [M+H]⁺, 274; found, 274.

Step 3 5-(9-Ethyl-8-(2-methylpyrimidin-5-yl)-9H-purin-6-yl)-3-methylindolin-2-one (2A-3)

A solution of Intermediate I (1.00 g, 3.66 mmol), 3-methyl-5-(4,4,5,5-tetramethyl-1,3,2-dioxaborolan-2-yl)indolin-2-one (2A-2) (1.00 g, 3.66 mmol), and PdCl₂(dppf) (240 mg, 0.37 mmol) in 1,4-dioxane (15 mL) was deoxygenated via evacuation followed by back-filling with nitrogen gas. A 2 M aqueous solution of Na₂CO₃ (3.7 mL, 7.4 mmol) was then added and the reaction mixture stirred for 2 days at 85° C. The reaction mixture was diluted with DCM and washed with water. The combined organic layers were dried (Na₂SO₄), filtered and concentrated to dryness. The residue was purified by chromatography on SiO₂ (2% to 20% MeOH/DCM gradient) to afford 5-(9-ethyl-8-(2-methylpyrimidin-5-yl)-9H-purin-6-yl)-3-methylindolin-2-one (2A-3). MS (EI) calc'd for C₂₁H₂₀N₇O [M+H]⁺, 386; found, 386.

Steps 4-5 (R or S)- and (S or R)-5-(9-ethyl-8-(2-methylpyrimidin-5-yl)-9H-purin-6-yl)-3-(3-methoxy-3-methylazetidin-1-yl)-3-methylindolin-2-one (2-1 and 2-2)

A solution of 5-(9-ethyl-8-(2-methylpyrimidin-5-yl)-9H-purin-6-yl)-3-methylindolin-2-one (2A-3) (100 mg, 0.259 mmol) in DMF (2 mL) was treated with Cs₂CO₃ (250 mg, 0.767 mmol), 3-methoxy-3-methylazetidine, HCl salt (80 mg, 0.58 mmol) and NBS (50 mg, 0.28 mmol). The suspension was stirred for 30 min, filtered and the filtrate purified by mass-directed reverse phase chromatography (MeCN/water gradient with 0.1% TFA modifier). MS (EI) calc'd for C₂₆H₂₉N₈O₂ [M+H]⁺, 485; found, 485.

The racemic material was then dissolved in MeOH/MeCN and resolved using chiral column chromatography [Column: ChiralPak™ AD-H, 21×250 mm; 220 nm detection; 70 mL/min flow rate; 25% MeOH and 0.25% Me₂NEt in CO₂]. The faster eluting enantiomer came at a retention time of 3.95 min (2-1); while the slower eluting enantiomer came at a retention time of 4.87 min (2-2). Characterization data for 2-1: ¹H NMR (600 MHz, DMSO-d₆) δ 10.70 (s, 1H), 9.21 (s, 2H), 8.95 (s, 1H), 8.88 (dd, J=8.2, 1.8 Hz, 1H), 8.69 (d, J=1.2 Hz, 1H), 7.02 (d, J=8.2 Hz, 1H), 4.41 (q, J=7.3 Hz, 2H), 3.66 (d, J=6.7 Hz, 1H), 3.01-2.97 (m, 6H), 2.75 (s, 3H), 1.35 (t, J=7.0 Hz, 3H), 1.31 (s, 3H), 1.29 (s, 3H); MS (ESI) calc'd for C₂₆H₂₉N₈O₂ [M+H]⁺, 485; found, 485. Characterization data for 2-2: ¹H NMR (600 MHz, DMSO-d₆) δ 10.70 (s, 1H), 9.21 (s, 2H), 8.95 (d, J=2.3 Hz, 1H), 8.88 (d, J=7.9 Hz, 1H), 8.69 (s, 1H), 7.03 (dd, J=8.2, 2.9 Hz, 1H), 4.41 (q, J=5.0 Hz, 2H), 3.66 (d, J=5.0 Hz, 1H), 3.00-2.97 (m, 6H), 2.75 (s, 3H), 1.35 (t, J=7.3 Hz, 3H), 1.31 (s, 3H), 1.29 (s, 3H); MS (ESI) calc'd for C₂₆H₂₉N₈O₂ [M+H]⁺, 485; found, 485.

Example 2B Compounds 2-37 and 2-38

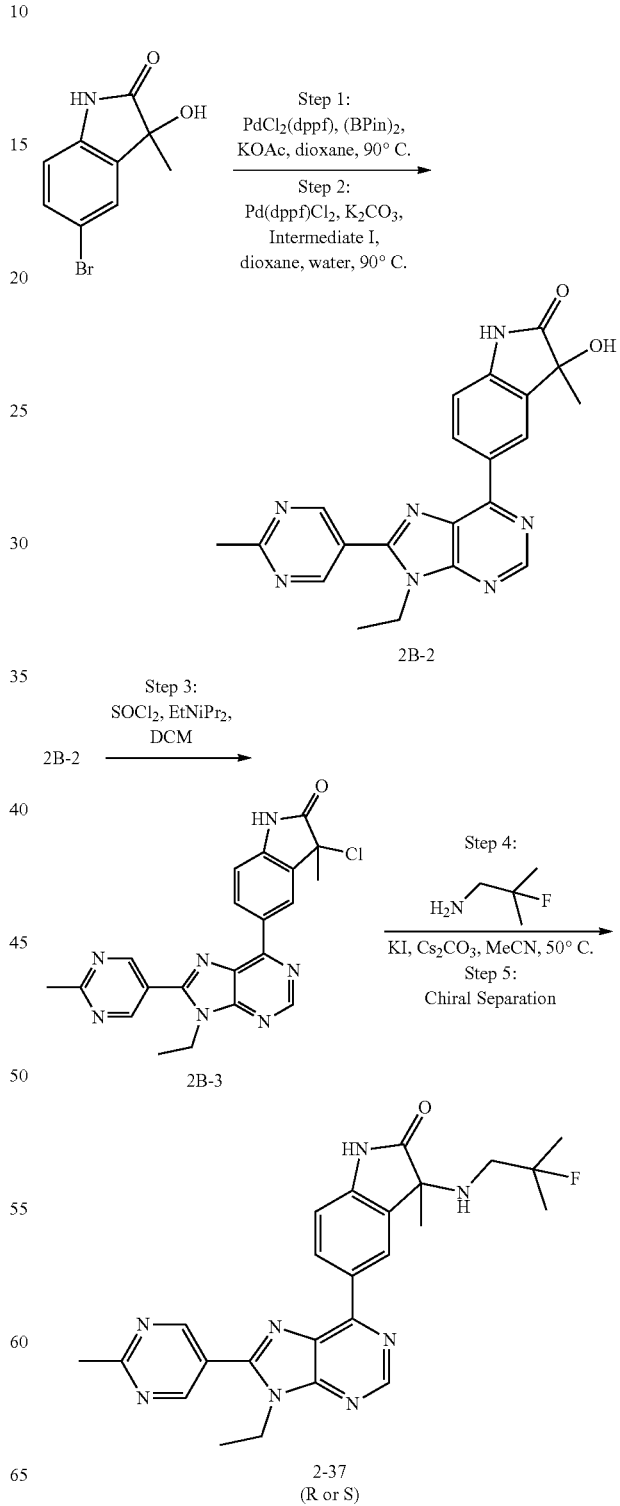

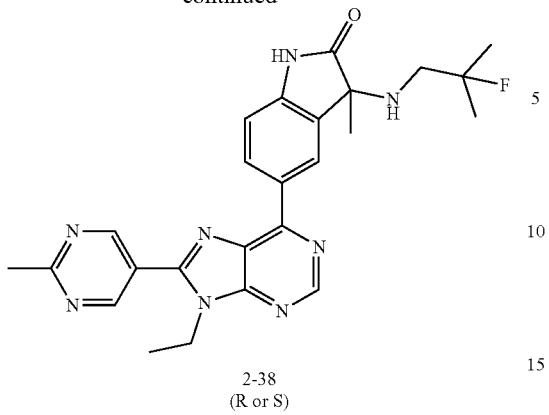

2-38
(R or S)

Steps 1-2 5-(9-Ethyl-8-(2-methylpyrimidin-5-yl)-9H-purin-6-yl)-3-hydroxy-3-methylindolin-2-one (2B-2)

A solution of 5-bromo-3-hydroxy-3-methylindolin-2-one (8.0 g, 33 mmol) in 150 mL of dioxane was treated with (BPin)$_2$ (10 g, 40 mmol), KOAc (6.5 g, 66 mmol) and PdCl$_2$(dppf) (2.4 g, 3.3 mmol). The reaction was warmed to 90° C. and stirred for 3 hours. Upon cooling to ambient temperature, the reaction mixture was quenched with water (100 mL) and extracted with DCM (3×100 mL). The combined organic layers were dried (Na$_2$SO$_4$), filtered and concentrated to dryness. The residue was purified by chromatography on SiO$_2$ (0-30% EtOAc/hexanes) to afford 3-hydroxy-3-methyl-5-(4,4,5,5-tetramethyl-1,3,2-dioxaborolan-2-yl)indolin-2-one. MS (EI) calc'd for C$_{15}$H$_{19}$BNO$_3$ [M−H$_2$O+H]$^+$, 272; found, 272.

A mixture containing 3-hydroxy-3-methyl-5-(4,4,5,5-tetramethyl-1,3,2-dioxaborolan-2-yl)indolin-2-one (3.0 g, 10 mmol) in 50 mL of dioxane was treated with Intermediate I (2.9 g, 10 mmol), K$_2$CO$_3$ (4.3 g, 31 mmol), water (5 mL) and PdCl$_2$(dppf) (0.76 g, 1.0 mmol). The mixture was stirred at 90° C. for 3 hours and quenched with 30 mL of water. The mixture was extracted into EtOAc (3×100 mL), the combined organic layers were washed with brine and dried (Na$_2$SO$_4$). The solution was concentrated and the residue was purified by chromatography on SiO$_2$ (0-10% MeOH/DCM) to afford 5-(9-ethyl-8-(2-methylpyrimidin-5-yl)-9H-purin-6-yl)-3-hydroxy-3-methylindolin-2-one (2B-2). $^1$H NMR (300 MHz, DMSO-d$_6$) δ 10.60 (s, 1H), 9.26 (s, 2H), 8.99 (s, 1H), 8.95 (d, J=8.4 Hz, 1H), 8.82 (s, 1H), 7.05 (d, J=8.4 Hz, 1H), 6.06 (s, 1H), 4.45 (q, J=7.2 Hz, 2H), 2.80 (s, 3H), 1.49-1.32 (m, 6H). MS (EI) calc'd for C$_{21}$H$_{20}$N$_7$O$_2$ [M+H]$^+$, 402; found, 402.

Step 3 3-Chloro-5-(9-ethyl-8-(2-methylpyrimidin-5-yl)-9H-purin-6-yl)-3-methylindoline-2-one (2B-3)

A solution of 5-(9-ethyl-8-(2-methylpyrimidin-5-yl)-9H-purin-6-yl)-3-hydroxy-3-methylindolin-2-one (2B-2) (300 mg, 0.747 mmol) in 10 mL of DCM was treated with EtNiPr$_2$ (0.26 ml, 1.5 mmol) and SOCl$_2$ (0.11 ml, 1.5 mmol) at 0° C. The mixture was stirred at 0° C. for 3 h and then quenched with water (30 mL). The resulting mixture was extracted with EtOAc (3×20 mL). The combined organic layers were washed with brine (10 mL), dried (Na$_2$SO$_4$) and concentrated. The residue was purified by chromatography on SiO$_2$ (0-5% MeOH/DCM) to afford 3-chloro-5-(9-ethyl-8-(2-methylpyrimidin-5-yl)-9H-purin-6-yl)-3-methylindolin-2-one (2B-3). MS (EI) calc'd for C$_{21}$H$_{19}$ClN$_7$O [M+H]$^+$, 420; found, 420.

Steps 4-5 (R or S)- and (S or R)-5-(9-Ethyl-8-(2-methylpyrimidin-5-yl)-9H-purin-6-yl)-3-((2-fluoro-2-methylpropyl)amino)-3-methylindolin-2-one (2-37 and 2-38)

To a solution of 3-chloro-5-(9-ethyl-8-(2-methylpyrimidin-5-yl)-9H-purin-6-yl)-3-methylindolin-2-one (2B-3) (50 mg, 0.12 mmol) in 2 mL of MeCN were added 2-fluoro-2-methylpropan-1-amine-2,2,2-trifluoroacetate (37 mg, 0.18 mmol), cesium carbonate (190 mg, 0.60 mmol) and potassium iodide (20 mg, 0.12 mmol). The reaction mixture was stirred for 3 h at 50° C., then quenched with water (10 mL) and extracted with EtOAc (3×10 mL). The combined organic layers were washed with brine (10 mL), dried (Na$_2$SO$_4$) and concentrated. The crude product was purified by reverse phase chromatography [Column: XSelect™ CSH Prep C18 OBD (Waters Corporation, Milford Mass., USA), 19×150 mm; 254/220 nm detection; 20 mL/min flow rate; 20% to 39% MeCN/water with 0.05% TFA].

The racemic material was then resolved using chiral column chromatography [Column: ChiralPak™ IC; 20×250 mm, 254 nm detection; 20 mL/min flow rate; 30% IPA/hexane with 0.2% Et$_2$NH]. The faster eluting enantiomer came at a retention time of 13 min (2-37), while the slower eluting enantiomer came at a retention time of 18 min (2-38). Characterization data for 2-37: $^1$H NMR (300 MHz, CD$_3$OD) δ 9.19 (s, 2H), 8.90 (s, 1H), 8.80 (s, 1H), 8.78 (d, J=9.0 Hz, 1H), 7.07 (d, J=9.0 Hz, 1H), 4.52-4.45 (m, 2H), 2.81 (s, 3H), 2.55-2.46 (m, 1H), 2.11-2.00 (m, 1H), 1.50-1.44 (m, 6H), 1.33-1.16 (m, 6H). MS (ESI) calc'd for C$_{25}$H$_{28}$FN$_8$O [M+H]$^+$, 475; found, 475. Characterization for 2-38: $^1$H NMR (300 MHz, CD$_3$OD) δ 9.18 (s, 2H), 8.89 (s, 1H), 8.82 (s, 1H), 8.80 (d, J=9.0 Hz, 1H), 7.06 (d, J=9.0 Hz, 1H), 4.51-4.44 (m, 2H), 2.81 (s, 3H), 2.55-2.46 (m, 1H), 2.11-2.00 (m, 1H), 1.48-1.44 (m, 6H), 1.33-1.16 (m, 6H). MS (ESI) calc'd for C$_{25}$H$_{28}$FN$_8$O [M+H]$^+$, 475; found, 475.

Example 2C Compounds 2-43 and 2-44

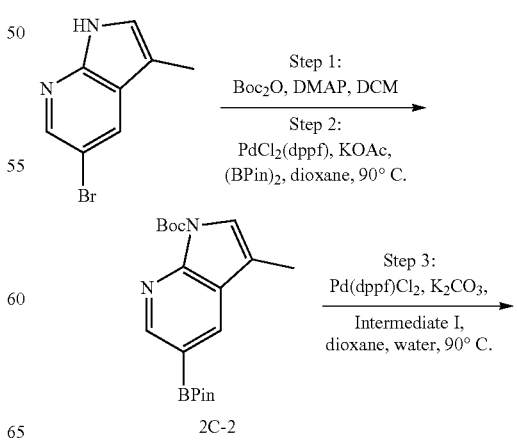

2C-2

113
-continued

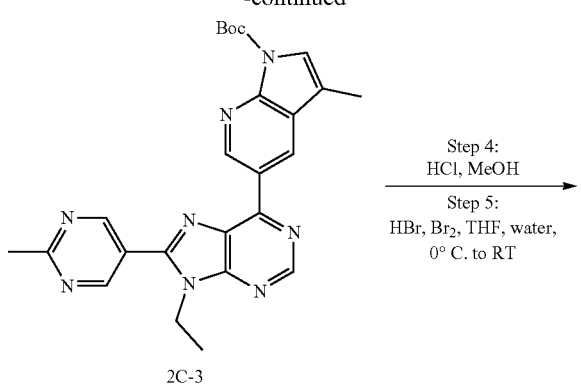

2C-3

Step 4:
HCl, MeOH

Step 5:
HBr, Br₂, THF, water,
0° C. to RT

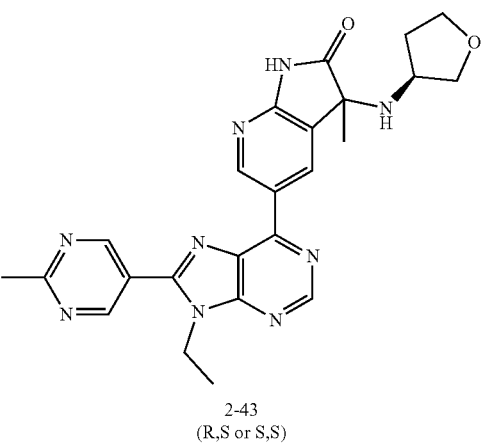 [SMILES: CCn1c(-c2cnc(C)nc2)nc2c(-c3cnc4c(c3)C(C)(N[C@H]3CCOC3)C(=O)N4)ncnc21]

2C-5

Step 6:
(S)-tetrahydrofuran-3-amine,
Cs₂CO₃, KI, DMF

Step 7:
Chiral separation.

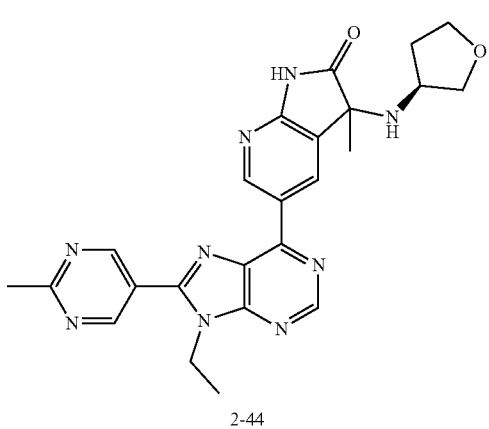

2-43
(R,S or S,S)

2-44
(R,S or S,S)

114

Steps 1-2 tert-Butyl 3-Methyl-5-(4,4,5,5-tetramethyl-1,3,2-dioxaborolan-2-yl)-1H-pyrrolo[2,3-b]pyridine-1-carboxylate (2C-2)

To a solution of 5-bromo-3-methyl-1H-pyrrolo[2,3-b]pyridine (1.50 g, 7.11 mmol) in 5 mL of DCM were added DMAP (0.080 g, 0.71 mmol) and di-tert-butyl dicarbonate (1.55 g, 7.11 mmol). The resulting solution was stirred for 1 h at room temperature and then concentrated under reduced pressure to afford tert-butyl 5-bromo-3-methyl-1H-pyrrolo[2,3-b]pyridine-1-carboxylate as a white solid which was used in the subsequent step without further purification. MS (EI) calc'd for $C_{13}H_{16}BrN_2O_2$ [M+H]⁺, 311; found, 311.

To a solution of tert-butyl 5-bromo-3-methyl-1H-pyrrolo[2,3-b]pyridine-1-carboxylate (2.0 g, 6.4 mmol) in 20 mL of dioxane were added KOAc (1.26 g, 12.9 mmol), (PinB)₂ (1.63 g, 6.43 mmol) and PdCl₂(dppf)-CH₂Cl₂ (0.53 g, 0.64 mmol). The resulting mixture was stirred for 1 h at 90° C. After cooling to room temperature, the reaction mixture was diluted with water (10 mL). The resulting solution was extracted with EtOAc (2×10 mL), then the combined organic layers was concentrated under reduced pressure. The residue was purified by chromatography on SiO₂ (0 to 20% EtOAc/hexane) to afford tert-butyl 3-methyl-5-(4,4,5,5-tetramethyl-1,3,2-dioxaborolan-2-yl)-1H-pyrrolo[2,3-b]pyridine-1-carboxylate (2C-2). MS (EI) calc'd for $C_{19}H_{28}BN_2O_4$ [M+H]⁺, 359; found, 359.

Step 3 tert-Butyl 5-(9-Ethyl-8-(2-methylpyrimidin-5-yl)-9H-purin-6-yl)-3-methyl-1H-pyrrolo[2,3-b]pyridine-1-carboxylate (2C-3)

To a solution of tert-butyl-3-methyl-5-(4,4,5,5-tetramethyl-1,3,2-dioxaborolan-2-yl)-1H-pyrrolo[2,3-b]pyridine-1-carboxylate (2C-2) (2.00 g, 5.58 mmol) in 16 mL of dioxane and 4 mL of water were added intermediate I (1.53 g, 5.58 mmol), potassium carbonate (1.54 g, 11.1 mmol) and PdCl₂(dppf)-CH₂Cl₂ (460 mg, 0.56 mmol). The resulting mixture was stirred for 1 h at 90° C. After cooling to room temperature, the reaction mixture was diluted with water (10 mL) and extracted with ethyl acetate (2×20 mL). The combined organic layers was washed with brine (5 mL), dried over Na₂SO₄ and filtered. The filtrate was concentrated under reduced pressure and the residue purified by chromatography on SiO₂ (0% to 30% EtOAc/hexane) to afford tert-butyl 3-methyl-5-(9-methyl-8-(2-methylpyrimidin-5-yl)-9H-purin-6-yl)-1H-pyrrolo[2,3-b]pyridine-1-carboxylate (2C-3). MS (EI) calc'd for $C_{25}H_{27}N_8O_2$ [M+H]⁺, 471; found, 471.

Steps 4-5 3-Bromo-5-(9-ethyl-8-(2-methylpyrimidin-5-yl)-9H-purin-6-yl)-3-methyl-1,3-dihydro-2H-pyrrolo[2,3-b]pyridin-2-one HBr Salt (2C-5)

Hydrogen chloride gas was bubbled through a solution of tert-butyl 5-(9-ethyl-8-(2-methylpyrimidin-5-yl)-9H-purin-6-yl)-3-methyl-1H-pyrrolo[2,3-b]pyridine-1-carboxylate (2C-3) (0.29 g, 0.62 mmol) in 15 mL of MeOH. The resulting solution was stirred for 4 h at room temperature. The reaction mixture was neutralized with triethylamine (2 mL) and then concentrated under reduced pressure. The residue was purified by chromatography on SiO₂ (0% to 10% MeOH/DCM) to afford 9-ethyl-6-(3-methyl-1H-pyrrolo[2,3-b]pyridin-5-yl)-8-(2-methylpyrimidin-5-yl)-9H-purine. MS (EI) calc'd for $C_{20}H_{19}N_8$ [M+H]⁺, 371; found, 371.

To a solution of 9-ethyl-6-(3-methyl-1H-pyrrolo[2,3-b]pyridin-5-yl)-8-(2-methylpyrimidin-5-yl)-9H-purine (0.30 g, 0.81 mmol) in 4 mL of THF/water were added at 0° C. 48% aqueous hydrogen bromide (68 mg, 0.34 mmol) and bromine (0.090 mL, 1.7 mmol). The resulting mixture was stirred for 2 h at room temperature, then filtered. The solid residue was collected to afford 3-bromo-3-ethyl-5-(9-methyl-8-(2-methylpyrimidin-5-yl)-9H-purin-6-yl)-1H-pyrrolo[2,3-b]pyridin-2(3H)-one hydrobromide salt (2C-5). MS (EI) calc'd for $C_{20}H_{18}BrN_8O$ [M+H]$^+$, 465; found, 465.

Steps 6-7 5-(9-ethyl-8-(2-methylpyrimidin-5-yl)-9H-purin-6-yl)-3-(R or S)-methyl-3-(((S)-tetrahydrofuran-3-yl)amino)-1,3-dihydro-2H-pyrrolo[2,3-b]pyridin-2-one and 5-(9-ethyl-8-(2-methylpyrimidin-5-yl)-9H-purin-6-yl)-3-(R or S)-methyl-3-(((S)-tetrahydrofuran-3-yl)amino)-1,3-dihydro-2H-pyrrolo[2,3-b]pyridin-2-one (2-43 and 2-44)

To a solution of 3-bromo-5-(9-ethyl-8-(2-methylpyrimidin-5-yl)-9H-purin-6-yl)-3-methyl-1H-pyrrolo[2,3-b]pyridin-2(3H)-one hydrobromide salt (2C-5) (0.55 g, 1.0 mmol) in 5 mL of DMF were added KI (84 mg, 0.50 mmol), cesium carbonate (1.64 g, 5.03 mmol) and (S)-tetrahydrofuran-3-amine (175 mg, 2.01 mmol). The resulting mixture was stirred for 2 h at room temperature. The reaction mixture was filtered and the filter cake was washed with DMF (10 mL). The filtrate was concentrated under reduced pressure and the residue purified by reverse phase chromatography [Column: XBridge BEH130; 19×150 mm, 254 nm detection; 20 mL/min flow rate; 15% to 26% MeCN/water with $NH_4HCO_3$ modifier] to afford 5-(9-ethyl-8-(2-methylpyrimidin-5-yl)-9H-purin-6-yl)-3-methyl-3-(((S)-tetrahydrofuran-3-yl)amino)-1H-pyrrolo[2,3-b]pyridin-2(3H)-one as a mixture of two diastereomers.

The diastereomeric mixture was separated using chiral column chromatography [Column: ChiralPak™ IA; 21×150 mm, 254/220 nm detection; 25 mL/min flow rate; MeOH with 0.1% diethylamine modifier]. The faster eluting enantiomer came at a retention time of 9.31 min (2-43), while the slower eluting enantiomer came at a retention time of 20.25 min (2-44). Characterization data for 2-43: $^1$H NMR (400 MHz, DMSO-d$_6$) δ 11.37 (s, 1H), 9.69 (s, 1H), 9.25 (s, 2H), 9.03 (s, 1H), 8.90 (s, 1H), 4.47-4.45 (m, 2H), 3.61-3.58 (m, 2H), 3.44-3.41 (m, 1H), 3.21-3.20 (m, 1H), 3.01-2.98 (m, 1H), 2.78 (s, 3H), 1.54-1.50 (m, 1H), 1.40-1.37 (m, 7H). MS (EI) calc'd for $C_{24}H_{26}N_9O_2$ [M+H]$^+$, 472; found, 472. Characterization data for 2-44: $^1$H NMR (400 MHz, CD$_3$OD) δ 9.69 (s, 1H), 9.26 (s, 2H), 9.04 (s, 1H), 8.99 (s, 1H), 4.58-4.52 (m, 2H), 3.80-3.79 (m, 1H), 3.65-3.61 (m, 1H), 3.41-3.39 (m, 1H), 3.32-3.24 (m, 1H), 3.10-3.08 (m, 1H), 2.85 (s, 3H), 2.07-1.98 (m, 1H), 1.82-1.75 (m, 1H), 1.54-1.49 (m, 6H). MS (EI) calc'd for $C_{24}H_{26}N_9O_2$ [M+H]$^+$, 472; found, 472.

Example 2D Compounds 2-55 and 2-56

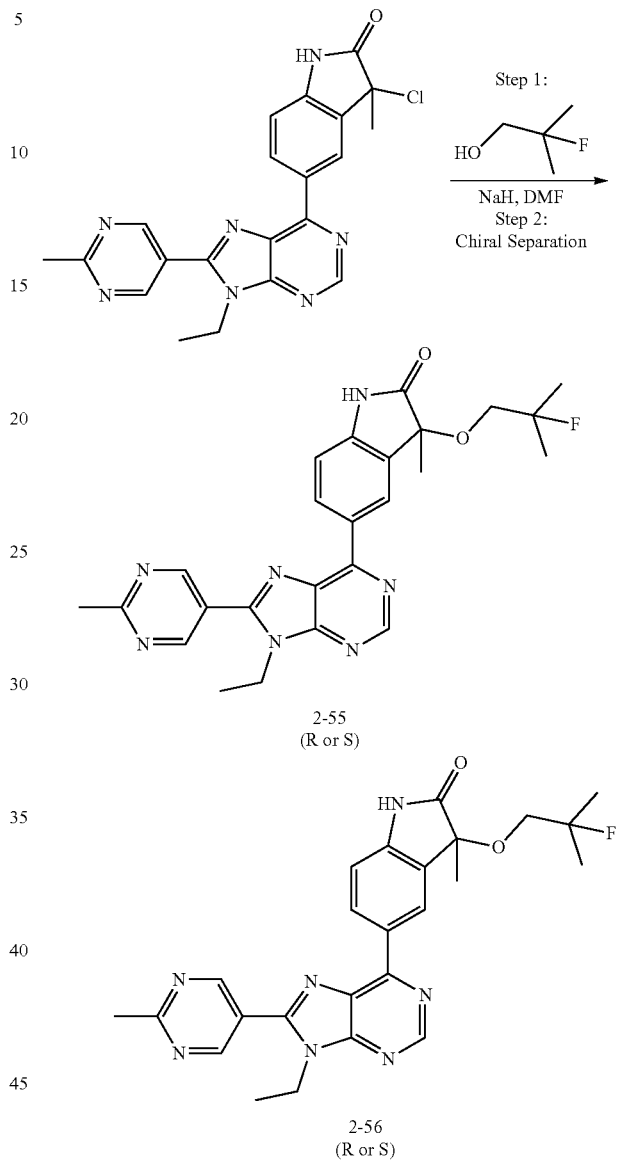

2-55
(R or S)

2-56
(R or S)

Step 1 5-(9-Ethyl-8-(2-methylpyrimidin-5-yl)-9H-purin-6-yl)-3-(2-fluoro-2-methylpropoxy)-3-methyl-indolin-2-one A solution of 2-fluoro-2-methylpropan-1-ol (49 mg, 0.54 mmol) in 5 mL of DMF was treated with 60% sodium hydride (21 mg, 0.54 mmol) at 0° C. The mixture was stirred for 30 min at 0° C., then 3-chloro-5-(9-ethyl-8-(2-methylpyrimidin-5-yl)-9H-purin-6-yl)-3-methylindolin-2-one (2B-3) (see Example 2B; 150 mg, 0.36 mmol) was added. The solution was stirred for another 30 min at 0° C. and then allowed to warmed to room temperature. The reaction mixture was quenched with water (10 mL) and extracted with EtOAc (3×10 mL). The combined organic layers was washed with brine (10 mL), dried (Na$_2$SO$_4$) and filtered. The filtrate was concentrated and purified by chromatography on SiO$_2$ (0%-10% MeOH/DCM) to afford the racemic product.

Step 2 (R or S)- and (S or R)-5-(9-Ethyl-8-(2-methylpyrimidin-5-yl)-9H-purin-6-yl)-3-(2-fluoro-2-methylpropoxy)-3-methylindolin-2-one (2-55 and 2-56)

The racemic material from step 1 (20 mg, 0.042 mmol) was resolved using chiral column chromatography [Column: ChiralPak™ IC; 20×250 mm, 254/220 nm detection; 20 mL/min flow rate; 30% IPA/hexanes]. The faster eluting enantiomer came at a retention time of 12.8 min (2-55), while the slower eluting enantiomer came at a retention time of 18.4 min (2-56). Characterization data for 2-55: $^1$H NMR (300 MHz, CD$_3$OD) δ 9.20 (s, 2H), 8.92 (s, 1H), 8.86 (d, J=8.4 Hz, 1H), 8.80 (s, 1H), 7.10 (d, J=8.4 Hz, 1H), 4.54-4.47 (m, 2H), 3.22-3.01 (m, 2H), 2.82 (s, 3H), 1.60 (s, 3H), 1.45 (t, J=7.2 Hz, 3H), 1.30 (s, 3H), 1.24 (s, 3H). MS (ESI) calc'd for C$_{25}$H$_{27}$FN$_7$O$_2$ [M+H]$^+$, 476; found, 476. Characterization data for 2-56: $^1$H NMR (300 MHz, CD$_3$OD) δ 9.20 (s, 2H), 8.92 (s, 1H), 8.86 (d, J=8.4 Hz, 1H), 8.81 (s, 1H), 7.10 (d, J=8.4 Hz, 1H), 4.54-4.47 (m, 2H), 3.19-3.00 (m, 2H), 2.82 (s, 3H), 1.60 (s, 3H), 1.45 (t, J=7.2 Hz, 3H), 1.31 (s, 3H), 1.25 (s, 3H). MS (ESI) calc'd for C$_{25}$H$_{27}$FN$_7$O$_2$ [M+H]$^+$, 476; found, 476.

Example 2E Compounds 2-57 and 2-58

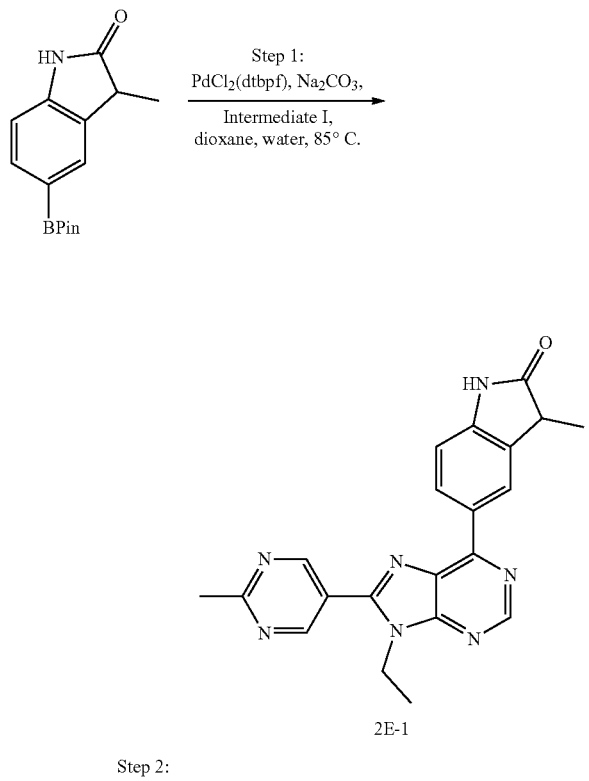

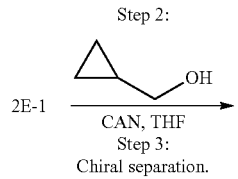

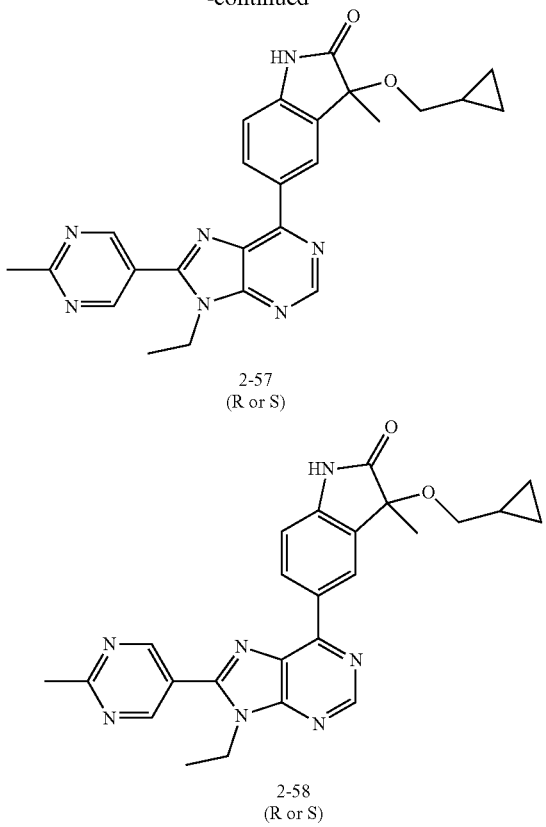

2-57 (R or S)

2-58 (R or S)

Step 1 5-(9-Ethyl-8-(2-methylpyrimidin-5-yl)-9H-purin-6-yl)-3-methylindolin-2-one (2E-1)

A 100 mL flask was charged with intermediate I (2.0 g, 7.3 mmol), 3-methyl-5-(4,4,5,5-tetramethyl-1,3,2-dioxaborolan-2-yl)indolin-2-one (2.0 g, 7.3 mmol), and PdCl$_2$(dtbpf) (480 mg, 0.73 mmol) and 15 mL of 1,4-dioxane. The mixture was evacuated and backfilled with nitrogen (3×). An aqueous solution of Na$_2$SO$_4$ (2 M, 7.3 mL, 15 mmol) was added and the mixture was again evacuated and backfilled with nitrogen (3×). The reaction was stirred under nitrogen at 85° C. for 2 h, then partitioned between DCM and water. The organic layer was dried (Na$_2$SO$_4$), filtered and concentrated. The residue was purified by reverse phase chromatography (MeCN/water gradient with 0.1% TFA modifier) to give 5-(9-ethyl-8-(2-methylpyrimidin-5-yl)-9H-purin-6-yl)-3-methylindolin-2-one (2E-1). MS (EI) calc'd for C$_{21}$H$_{20}$N$_7$O [M+H]$^+$, 386; found. 386.

Step 2 (R and S)-3-(Cyclopropylmethoxy)-5-(9-ethyl-8-(2-methylpyrimidin-5-yl)-9H-purin-6-yl)-3-methylindolin-2-one A mixture containing 5-(9-ethyl-8-(2-methylpyrimidin-5-yl)-9H-purin-6-yl)-3-methylindolin-2-one (2E-1) (150 mg, 0.389 mmol) in 3 mL of THF was treated with CAN (470 mg, 0.86 mmol) and cyclopropylmethanol (280 mg, 3.9 mmol). The suspension was stirred overnight, and then filtered through CELITE and concentrated. The residue was purified by mass-directed reverse phase chromatography (MeCN/water gradient with 0.1% TFA modifier) to give racemic 3-(cyclopropylmethoxy)-5-(9-ethyl-8-(2-methylpyrimidin-5-yl)-9H-purin-6-yl)-3-methylindolin-2-one. MS (EI) calc'd for $C_{25}H_{26}N_7O_2$ [M+H]$^+$, 456; found, 456.

Step 3 (R or S)- and (S or R)-3-(Cyclopropyl-methoxy)-5-(9-ethyl-8-(2-methylpyrimidin-5-yl)-9H-purin-6-yl)-3-methylindolin-2-one (2-57 and 2-58)

The racemic material from Step 2 was dissolved in MeOH and MeCN and resolved using chiral column chromatography [Column: Chiralcel™ OJ-H, 21×250 mm; 220 nm detection; 70 mL/min flow rate; 25% MeOH and 0.25% DMEA in $CO_2$]. The faster eluting enantiomer came at a retention time of 2.41 min (2-57). $^1$H NMR (600 MHz, DMSO-d$_6$) □ 10.90 (s, 1H), 9.26 (s, 2H), 9.02 (s, 1H), 8.92 (dd, J=8.3, 1.7 Hz, 1H), 8.80 (d, J=1.7 Hz, 1H), 7.11 (d, J=8.3 Hz, 1H), 4.47 (q, J=7.2 Hz, 2H), 3.18 (d, J=5.2 Hz, 1H), 3.02 (dd, J=9.5, 6.6 Hz, 1H), 2.80 (s, 3H), 2.09 (m, 1H), 1.50 (s, 3H), 1.41 (t, J=7.2 Hz, 3H), 0.35-0.42 (m, 2H), 0.06 (d, J=4.8 Hz, 2H). MS (EI) calc'd for $C_{25}H_{26}N_7O_2$ [M+H]$^+$, 456; found, 456. The slower eluting enantiomer came at a retention time of 3.15 min (2-58). $^1$H NMR (500 MHz, DMSO-d$_6$) □ 9.24 (s, 2H), 9.00 (s, 1H), 8.90 (dd, J=8.3, 1.7 Hz, 1H), 8.78 (d, J=1.7 Hz, 1H), 7.09 (d, J=8.0 Hz, 1H), 4.45 (q, J=7.1 Hz, 2H), 3.00 (dd, J=9.6, 6.6 Hz, 1H), 2.77 (dd, J=9.3, 6.9 Hz, 1H), 2.78 (s, 3H), 1.25 (m, 1H), 1.48 (s, 3H), 1.39 (t, J=7.4 Hz, 3H), 0.35-0.39 (m, 2H), 0.03 (m, 2H). MS (EI) calc'd for $C_{25}H_{26}N_7O_2$ [M+H]$^-$, 456; found, 456.

Example 2F Compound 2-77

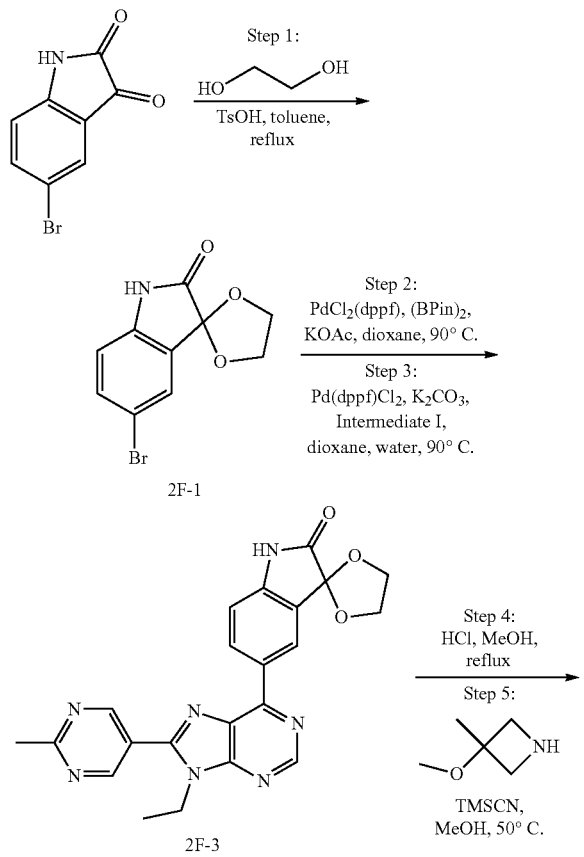

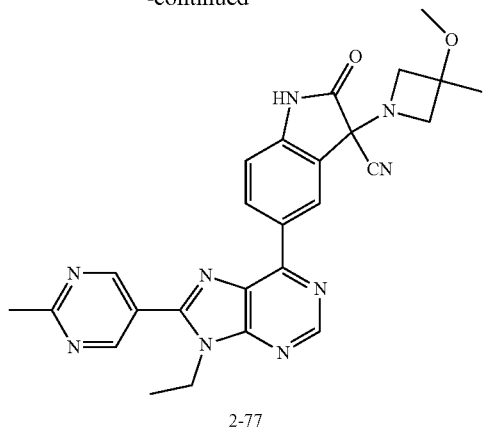

2-77

Step 1 5'-Bromospiro[[1,3]dioxolane-2,3'-indolin]-2'-one (2F-1)

A solution of 5-bromoindoline-2,3-dione (1.0 g, 4.4 mmol) in 20 mL of toluene was treated with ethane-1,2-diol (5.5 g, 88 mmol) and 4-methylbenzenesulfonic acid (76 mg, 0.44 mmol) and stirred for 12 h at 100° C. After cooling to room temperature, the mixture was quenched with water and extracted with EtOAc. The combined organic layers was washed with brine, dried (Na$_2$SO$_4$) and concentrated. The residue was purified by chromatography on SiO$_2$ (0%-20% EtOAc/hexane) to afford 5'-bromospiro[[1,3]dioxolane-2,3'-indolin]-2'-one (2F-1). $^1$H NMR (300 MHz, DMSO-d$_6$) δ 10.58 (brs, 1H), 7.53 (s, 1H), 7.50 (d, J=2.1 Hz, 1H), 6.82 (d, J=2.1 Hz, 1H), 4.48-4.24 (m, 4H).

Steps 2-3 5-(9-Ethyl-8-(2-methylpyrimidin-5-yl)-9H-purin-6-yl)spiro[indoline-3,2'-[1,3]dioxolan]-2-one (2F-3)

5'-Bromospiro[[1,3]dioxolane-2,3'-indolin]-2'-one (2F-1) was converted into the title compound (2F-3) by the two step borylation-Suzuki sequence outlined for Example 2B; using (BPin)$_2$, KOAc, PdCl$_2$(dppf) in dioxane at 90° C. for the borylation, then using Intermediate I, K$_2$CO$_3$ and PdCl$_2$(dppf) in dioxane/water at 90° C. for the Suzuki reaction. MS (EI) calc'd for $C_{22}H_{20}N_7O_3$ [M+H]$^+$, 430; found, 430.

Step 4 5-(9-Ethyl-8-(2-methylpyrimidin-5-yl)-9H-purin-6-yl)indoline-2,3-dione

A saturated solution of HCl gas in 10 mL of MeOH was treated with 5'-(9-ethyl-8-(2-methylpyrimidin-5-yl)-9H-purin-6-yl)spiro[[1,3]dioxolane-2,3'-indolin]-2'-one (0.30 g, 0.70 mmol). The reaction solution was stirred at 70° C. for 12 h. After cooling to room temperature, the mixture was quenched with water. The pH was adjusted to 8 with NaHCO$_3$ and the resulting mixture extracted with EtOAc. The combined organic layers were washed with brine, dried (Na$_2$SO$_4$) and concentrated. The residue was purified by chromatography on SiO$_2$ (0%-100% EtOAc/hexane) to afford 5-(9-ethyl-8-(2-methylpyrimidin-5-yl)-9H-purin-6-yl) indoline-2,3-dione. $^1$H NMR (300 MHz, DMSO-d$_6$) δ 11.37 (brs, 1H), 9.24 (s, 2H), 9.12 (d, J=8.4 Hz, 1H), 9.02 (s, 1H), 9.01 (s, 1H), 7.15 (d, J=8.4 Hz, 1H), 4.44 (q, J=7.2 Hz, 2H), 2.79 (s, 3H), 1.40 (t, J=8.4 Hz, 3H). MS (EI) calc'd for $C_{20}H_{16}N_7O_2$ [M+H]$^+$, 386; found, 386.

Step 5 5-(9-Ethyl-8-(2-methylpyrimidin-5-yl)-9H-purin-6-yl)-3-(3-methoxy-3-methylazetidin-1-yl)-2-oxoindoline-3-carbonitrile (2-77)

A solution of 5-(9-ethyl-8-(2-methylpyrimidin-5-yl)-9H-purin-6-yl) indoline-2,3-dione (30 mg, 0.08 mmol) in methanol (1 mL) was treated with 3-methoxy-3-methylazetidine (12 mg, 0.12 mmol) and TMSCN (12 mg, 0.12 mmol), then stirred for 5 h at 50° C. After cooling to room temperature, the mixture was quenched with water and extracted with EtOAc. The combined organic layers was washed with brine, dried ($Na_2SO_4$) and concentrated. The residue was purified by chromatography on $SiO_2$ (0%-100% EtOAc/hexane) to afford 5-(9-ethyl-8-(2-methylpyrimidin-5-yl)-9-purin-6-yl)-3-(3-methoxy-3-methylazetidin-1-yl)-2-oxoindoline-3-carbonitrile (2-77). $^1$H NMR (300 MHz, $CD_3OD$) δ 9.18 (s, 2H), 8.98-8.86 (m, 3H), 7.12 (d, J=8.4 Hz, 2H), 4.50 (q, J=7.2 Hz, 2H), 3.78-3.42 (m, 4H), 3.24 (s, 3H), 2.77 (s, 3H), 1.48 (t, J=8.4 Hz, 3H), 1.44 (s, 3H). MS (EI) calc'd for $C_{26}H_{26}N_9O_2$ [M+H]$^+$, 496; found, 496.

Example 2G Compounds 2-49 and 2-50

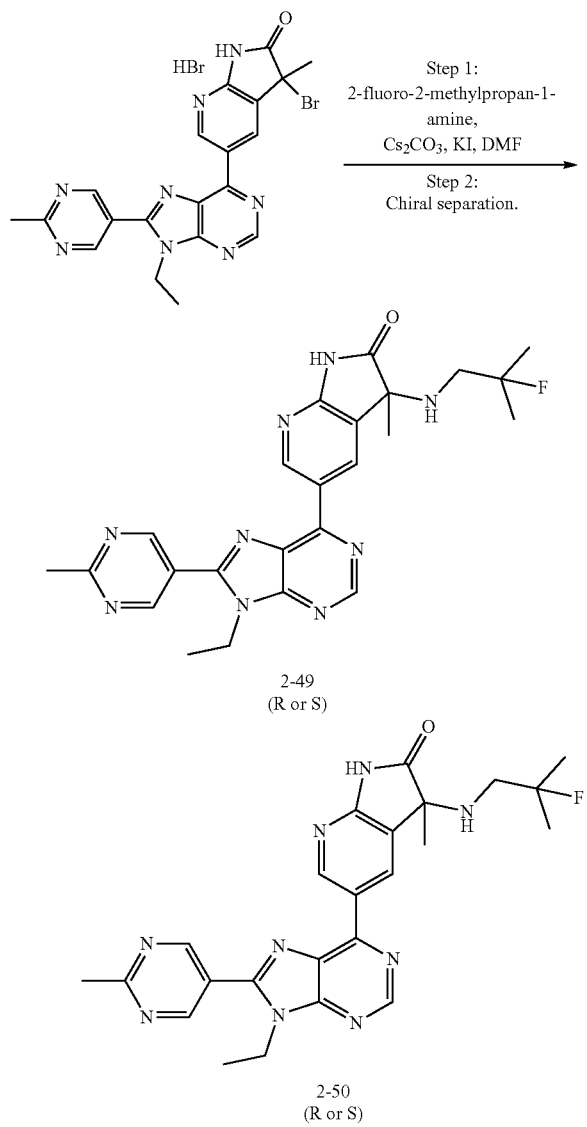

2-49
(R or S)

2-50
(R or S)

Steps 1-2 (R or S)- and (S or R)-5-(9-ethyl-8-(2-methylpyrimidin-5-yl)-9H-purin-6-yl)-3-((2-fluoro-2-methylpropyl)amino)-3-methyl-1,3-dihydro-2H-pyrrolo[2,3-b]pyridin-2-one (2-49 and 2-50)

A solution of intermediate 3-bromo-5-(9-ethyl-8-(2-methylpyrimidin-5-yl)-9H-purin-6-yl)-3-methyl-1,3-dihydro-2H-pyrrolo[2,3-b]pyridin-2-one HBr salt [previously described for the preparation of 2-43 and 2-44; Example 2C] (180 mg, 0.330 mmol) in 1 mL of DMF was treated with KI (5.5 mg, 0.033 mmol), 2-fluoro-2-methylpropan-1-amine hydrochloride (50 mg, 0.40 mmol), and $Cs_2CO_3$ (540 mg, 1.65 mmol). The reaction mixture was stirred for 2 h and filtered. The filtrate was concentrated and the residue purified by reverse phase chromatography (25% to 31% MeCN/water with 10 mM $NH_4CO_3$) to provide the racemic product. The racemic material was then resolved using chiral column chromatography [Column: ChiralPak™ IA; 20×250 mm; 15 mL/min flow rate; 50% EtOH/hexanes with 0.1% $Me_2NH$]. The faster eluting enantiomer came at a retention time of 18.8 min (2-49); while the slower eluting enantiomer came at a retention time of 27.8 min (2-50). Characterization data for 2-49: $^1$H NMR (300 MHz, DMSO-$d_6$) δ 11.38 (s, 1H), 9.68 (d, J=3 Hz, 1H), 9.24 (s, 2H), 9.04 (s, 1H), 8.91 (d, J=2 Hz, 1H), 4.50-4.44 (m, 2H), 2.87-2.82 (m, 1H), 2.79 (s, 3H), 2.50-2.46 (m, 1H), 2.15-2.0 (m, 1H), 1.45-1.38 (m, 6H), 1.25-1.15 (m, 6H). MS (EI) calc'd for $C_{24}H_{27}FN_9O$ [M+H]$^+$, 476; found, 476. Characterization data for 2-50: $^1$H NMR (300 MHz, DMSO-$d_6$) □ 11.37 (s, 1H), 9.68 (d, J=2 Hz, 1H), 9.24 (s, 2H), 9.04 (s, 1H), 8.91 (d, J=2 Hz, 1H), 4.50-4.44 (m, 2H), 2.88-2.82 (m, 1H), 2.79 (s, 3H), 2.50-2.44 (m, 1H), 2.15-2.0 (m, 1H), 1.45-1.38 (m, 6H), 1.24-1.15 (m, 6H). MS (EI) calc'd for $C_{24}H_{27}FN_9O$ [M+H]$^+$, 476; found, 476.

Compounds 2-3 Through 2-83

Compounds 2-3 and 2-4 were prepared in a fashion analogous to compounds 2-1 and 2-2, substituting 3-methoxy-3-methylazetidine for cis-2,6-dimethylmorpholine. The racemic product was then dissolved in MeOH and resolved using chiral column chromatography [Column: ChiralPak™ IF, 21×250 mm; 220 nm detection; 70 mL/min flow rate; 40% MeOH and 0.25% $Me_2NEt$ in $CO_2$]. The faster eluting enantiomer came at a retention time of 4.38 min (2-3); while the slower eluting enantiomer came at a retention time of 5.12 min (2-4).

Compounds 2-5 and 2-6 were prepared in a fashion analogous to compounds 2-1 and 2-2, substituting 3-methoxy-3-methylazetidine for 3-methylazetidine-3-carbonitrile. The racemic material was then dissolved in MeOH/MeCN and resolved using chiral column chromatography [Column: ChiralPak™ OJ-H, 21×250 mm; 220 nm detection; 70 mL/min flow rate; 20% MeOH and 0.25% $Me_2NEt$ in $CO_2$]. The faster eluting enantiomer came at a retention time of 3.20 min (2-5); while the slower eluting enantiomer came at a retention time of 3.86 min (2-6).

Compounds 2-7 and 2-8 were prepared in a fashion analogous to compounds 2-1 and 2-2, substituting 3-methoxy-3-methylazetidine for 1-oxa-6-azaspiro[3.3]heptane. The racemic product was then dissolved in MeOH and resolved using chiral column chromatography [Column: ChromegaChiral CCC™ (ES Industries, West Berlin, N.J. USA), 21×250 mm; 220 nm detection; 70 mL/min flow rate; 40% MeOH and 0.25% $Me_2NEt$ in $CO_2$]. The faster eluting enantiomer came at a retention time of 4.53 min (2-7); while the slower eluting enantiomer came at a retention time of 7.36 min (2-8).

Compounds 2-9 through to 2-28 were prepared in a fashion analogous to compounds 2-1 and 2-2, substituting 3-methoxy-3-methylazetidine for the appropriate amine. These were screened in the assay as mixtures of enantiomers or diastereomers, without further chiral separation.

Compounds 2-29 and 2-30 were prepared in a fashion analogous to compounds 2-1 and 2-2, substituting 3-methoxy-3-methylazetidine for cyclobutanamine. The racemic product was then dissolved in MeOH and resolved using chiral column chromatography [Column: Chromegabond® Pyridyl Amide (ES Industries, West Berlin, N.J. USA), 21×250 mm; 220 nm detection; 70 mL/min flow rate; 15% MeOH and 0.25% DMEA in $CO_2$]. The faster eluting enantiomer came at a retention time of 1.25 min (2-29); while the slower eluting enantiomer came at a retention time of 3.38 min (2-30).

Compounds 2-31 and 2-32 were prepared in a fashion analogous to compounds 2-1 and 2-2, substituting 3-methoxy-3-methylazetidine for isopropylamine. The racemic product was then dissolved in MeOH and resolved using chiral column chromatography [Column: ChiralPak™ AS-H, 21×250 mm; 220 nm detection; 70 mL/min flow rate; 20% MeOH and 0.25% DMEA in $CO_2$]. The faster eluting enantiomer came at a retention time of 3.83 min (2-31); while the slower eluting enantiomer came at a retention time of 4.52 min (2-32).

Compounds 2-33 and 2-34 were prepared in a fashion analogous to compounds 2-1 and 2-2, substituting 3-methoxy-3-methylazetidine for cyclopropylmethanamine. The racemic product was then dissolved in MeOH and resolved using chiral column chromatography [Column: ChiralPak™, 21×250 mm; 220 nm detection; 70 mL/min flow rate; 20% MeOH and 0.25% DMEA in $CO_2$]. The faster eluting enantiomer came at a retention time of 2.01 min (2-33); while the slower eluting enantiomer came at a retention time of 3.45 min (2-34).

Compounds 2-35 and 2-36 were prepared in a fashion analogous to compounds 2-1 and 2-2, substituting 3-methoxy-3-methylazetidine for (S)-tetrahydrofuran-3-amine. The racemic material was then dissolved in MeOH/MeCN and resolved using chiral column chromatography [Column: ChiralPak™ OJ-H, 21×250 mm; 220 nm detection; 70 mL/min flow rate; 25% MeOH and 0.25% $Me_2NEt$ in $CO_2$]. The faster eluting enantiomer came at a retention time of 2.22 min (2-35); while the slower eluting enantiomer came at a retention time of 3.54 min (2-36).

Compounds 2-39 and 2-40 were prepared in a fashion analogous to compounds 2-37 and 2-38, substituting 2-fluoro-2-methylpropan-1-amine for 3-amino-2,2-dimethylpropanenitrile. The racemic material was then resolved using chiral column chromatography [Column: ChiralPak™ AD-H; 20×250 mm; 15 mL/min flow rate; 40% EtOH/hexane]. The faster eluting enantiomer came at a retention time of 5 min (2-39); while the slower eluting enantiomer came at a retention time of 7 min (2-40).

Compounds 2-41 and 2-42 were prepared in a fashion analogous to compounds 2-37 and 2-38, substituting 2-fluoro-2-methylpropan-1-amine for 2,2-difluoro-propan-1-amine. The racemic material was then resolved using chiral column chromatography [Column: ChiralPak™ IA; 21×150 mm; 20 mL/min flow rate; 10% EtOH/hexane]. The faster eluting enantiomer came at a retention time of 12 min (2-41); while the slower eluting enantiomer came at a retention time of 17 min (2-42).

Compounds 2-45 and 2-46 were prepared in a fashion analogous to 2-43 and 2-44, substituting Intermediate I for Intermediate II. The racemic material was then resolved using chiral column chromatography [Column: ChiralPak™ IA; 20×250 mm; 20 mL/min flow rate; 70% MeOH/DCM]. The faster eluting enantiomer came at a retention time of 6.6 min (2-45); while the slower eluting enantiomer came at a retention time of 8.9 min (2-46).

Compounds 2-47 and 2-48 were prepared in a fashion analogous to 2-43 and 2-44, substituting (S)-tetrahydrofuran-3-amine for 3-methoxy-3-methylazetidine hydrochloride. The racemic material was then resolved using chiral column chromatography [Column: ChiralPak™ IA; 21×150 mm; 25 mL/min flow rate; 50% IPA/hexanes]. The faster eluting enantiomer came at a retention time of 6.6 min (2-47); while the slower eluting enantiomer came at a retention time of 9.1 min (2-48).

Compounds 2-51 and 2-52 were prepared in a fashion analogous to 2-43 and 2-44, substituting (S)-tetrahydrofuran-3-amine for cyclobutanamine. The racemic material was then resolved using chiral column chromatography [Column: ChiralPak™ IA; 20×250 mm; 20 mL/min flow rate; 15% IPA/hexanes with 0.2% $Me_2NH$]. The faster eluting enantiomer came at a retention time of 25 min (2-51); while the slower eluting enantiomer came at a retention time of 32 min (2-52).

Compounds 2-53 and 2-54 were prepared in a fashion analogous to 2-43 and 2-44, substituting (S)-tetrahydrofuran-3-amine for 3-amino-2,2-dimethylpropanenitrile. The racemic material was then resolved using chiral column chromatography [Column: ChiralPak™ IA; 20×250 mm; 20 mL/min flow rate; 50% IPA/hexanes]. The faster eluting enantiomer came at a retention time of 17.5 min (2-53); while the slower eluting enantiomer came at a retention time of 22.1 min (2-54).

Compounds 2-59 and 2-60 were prepared in a fashion analogous to 2-49 and 2-50, substituting Intermediate I for Intermediate II. The racemic material was then resolved using chiral column chromatography [Column: ChiralPak™ AS-H; 20×250 mm; 50 mL/min flow rate; 25% MeOH/$CO_2$]. The faster eluting enantiomer came at a retention time of 3.74 min (2-59); while the slower eluting enantiomer came at a retention time of 5.07 min (2-60).

Compounds 2-61 and 2-62 were prepared in a fashion analogous to the preparation of 2-1 and 2-2, using (3R,4R)-3,4-difluoropyrrolidine as the amine. The racemic material was then resolved using chiral column chromatography [Column: ChiralPak™ AS-H; 20×250 mm; 70 mL/min flow rate; 20% MeOH/$CO_2$]. The faster eluting enantiomer came at a retention time of 3.73 min (2-61), while the slower eluting enantiomer came at a retention time of 4.63 min (2-62).

Compounds 2-63 and 2-64 were prepared in a fashion analogous to the preparation of 2-1 and 2-2, using 3-fluoro-3-methylazetidine as the amine. The racemic material was then resolved using chiral column chromatography [Column: ChiralPak™ OJ-H; 21×250 mm; 70 mL/min flow rate; 15% MeOH/$CO_2$ with 0.25% $Me_2NEt$]. The faster eluting enantiomer came at a retention time of 4.0 min (2-63); while the slower eluting enantiomer came at a retention time of 4.7 min (2-64).

Compounds 2-65 and 2-66 were prepared in a fashion analogous to the preparation of 2-1 and 2-2, using 2-methylpropan-1-amine as the amine. The racemic material was then resolved using chiral column chromatography [Column: ChiralPak™ OJ-H; 21×250 mm; 70 mL/min flow rate; 20% MeOH/$CO_2$ with 0.25% $Me_2NEt$]. The faster eluting enantiomer came at a retention time of 2.2 min (2-65); while the slower eluting enantiomer came at a retention time of 2.6 min (2-66).

Compounds 2-67 and 2-68 were prepared in a fashion analogous to the preparation of 2-1 and 2-2, using 2-fluoro-2-methylpropan-1-amine as the amine and substituting Intermediate I for Intermediate II. The racemic material was then resolved using chiral column chromatography [Column: ChiralPak™ 21×250 mm; 70 mL/min flow rate; 15% MeOH/CO$_2$ with 0.25% Me$_2$NEt]. The faster eluting enantiomer came at a retention time of 4.8 min (2-67); while the slower eluting enantiomer came at a retention time of 5.8 min (2-68).

Compounds 2-69 and 2-70 were prepared in a fashion analogous to the preparation of 2-1 and 2-2, using 2,2-difluoropropan-1-amine as the amine and substituting intermediate I for Intermediate II. The racemic material was then resolved using chiral column chromatography [Column: ChiralPak™ 21×250 mm; 70 mL/min flow rate; 15% MeOH/CO$_2$ with 0.25% Me$_2$NEt]. The faster eluting enantiomer came at a retention time of 5.4 min (2-69); while the slower eluting enantiomer came at a retention time of 6.3 min (2-70).

Compounds 2-71 and 2-72 were prepared in a fashion analogous to the preparation of 2-1 and 2-2, using (3-fluorooxetan-3-yl)methanamine as the amine. The racemic material was then resolved using chiral column chromatography [Column: Phenomenex, Lux-4; 21×250 mm; 70 mL/min flow rate; 40% MeOH/CO$_2$ with 0.25% Me$_2$NEt]. The faster eluting enantiomer came at a retention time of 5.6 min (2-71); while the slower eluting enantiomer came at a retention time of 6.5 min (2-72).

Compounds 2-73, 2-74 and 2-75 were prepared in a fashion analogous to the preparation of compounds 2-57 and 2-58. For 2-73 and 2-74, isopropyl alcohol and cyclobutanol were used instead of hydroxymethylcyclopropane. For 2-75, Intermediate II was used instead of Intermediate I. All three were prepared as racemic materials and not resolved into separated enantiomers.

Compound 2-76 was prepared in a fashion analogous to compounds 2-1 and 2-2, substituting 3-methoxy-3-methylazetidine for (R)-3-aminotetrahydrofuran. Compound 2-76 was used as a racemate, without further chiral separation.

Compounds 2-78 and 2-79 were prepared in a fashion analogous to compounds 2-1 and 2-2, substituting 3-methoxy-3-methylazetidine for 3-methoxy-azetidine. The racemic material was then resolved using chiral column chromatography [Column: Chiralcel OD-H; 21×250 mm; 70 mL/min flow rate; 30% MeOH/CO$_2$ with 0.25% Me$_2$NEt]. The faster eluting enantiomer came at a retention time of 4.5 min (2-78); while the slower eluting enantiomer came at a retention time of 5.5 min (2-79).

Compounds 2-80 and 2-81 were prepared in a fashion analogous to compounds 2-37 and 2-37, substituting 2-fluoro-2-methylpropan-1-amine for 3-hydroxy-azetidine. The racemic material was then resolved using chiral column chromatography [Column: ChiralPak™ AD-H; 20×250 mm; 19 mL/min flow rate; 30% EtOH/hexane]. The faster eluting enantiomer came at a retention time of 10.5 min (2-80); while the slower eluting enantiomer came at a retention time of 14.8 min (2-81).

Compounds 2-82 and 2-83 were prepared in a fashion analogous to compounds 2-1 and 2-2, substituting 3-methoxy-3-methylazetidine for trans-3-methoxy-cyclobutan-1-amine. The racemic material was then resolved using chiral column chromatography [Column: Chiralcel OJ-H; 21×250 mm; 70 mL/min flow rate; 20% MeOH/CO$_2$ with 0.25% Me$_2$NEt]. The faster eluting enantiomer came at a retention time of 2.5 min (2-82); while the slower eluting enantiomer came at a retention time of 3.2 min (2-83).

Table 2 provides structures for compounds 2-1 through 2-83 which were synthesized by the methods described above or by analogous methods to those described above.

TABLE 2

| Compound | Structure | Name | Exact Mass [M + H]$^+$ |
|---|---|---|---|
| 2-1 | 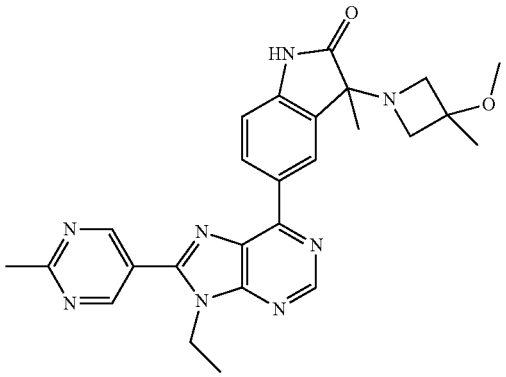 | (R or S)-5-[9-ethyl-8-(2-methylpyrimidin-5-yl)-9H-purin-6-yl]-3-(3-methoxy-3-methylazetidin-1-yl)-3-methyl-1,3-dihydro-2H-indol-2-one | Calc'd 485, found 485 |

TABLE 2-continued

| Compound | Structure | Name | Exact Mass [M + H]+ |
|---|---|---|---|
| 2-2 | 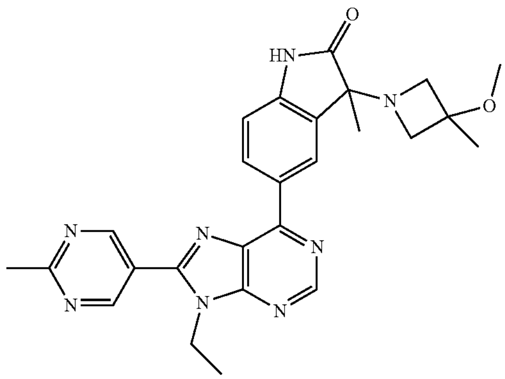 | (R or S)-5-[9-ethyl-8-(2-methylpyrimidin-5-yl)-9H-purin-6-yl]-3-(3-methoxy-3-methylazetidin-1-yl)-3-methyl-1,3-dihydro-2H-indol-2-one | Calc'd 485, found 485 |
| 2-3 | 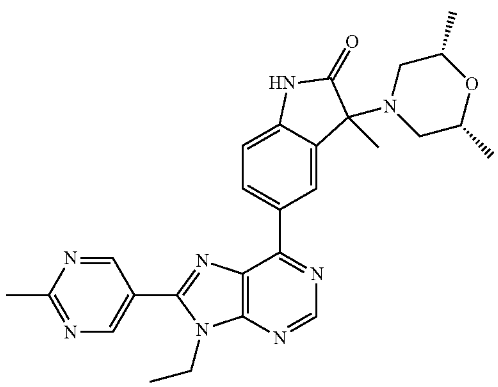 | (R or S)-3-[(cis)-2,6-dimethylmorpholin-4-yl]-5-[9-ethyl-8-(2-methylpyrimidin-5-yl)-9H-purin-6-yl]-3-methyl-1,3-dihydro-2H-indol-2-one | Calc'd 499, found 499 |
| 2-4 | 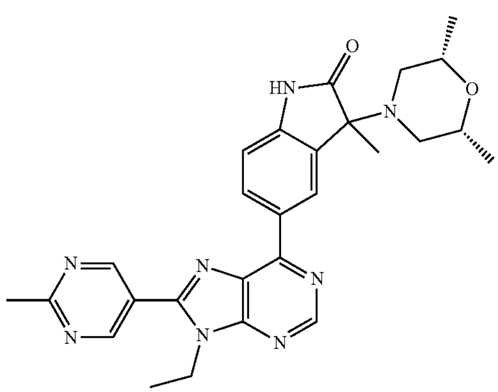 | (R or S)-3-[(cis)-2,6-dimethylmorpholin-4-yl]-5-[9-ethyl-8-(2-methylpyrimidin-5-yl)-9H-purin-6-yl]-3-methyl-1,3-dihydro-2H-indol-2-one | Calc'd 499, found 499 |
| 2-5 | 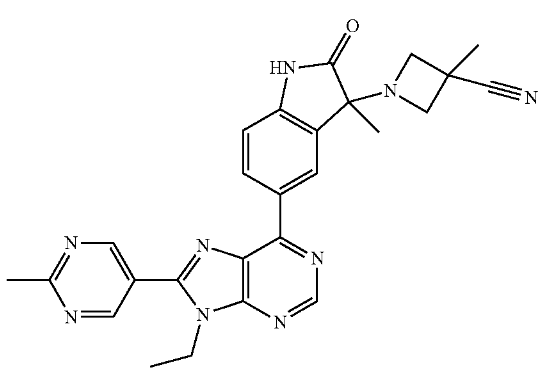 [SMILES: CCn1c(-c2cnc(C)nc2)nc2c(-c3ccc4c(c3)C(C)(N3CC(C)(C#N)C3)C(=O)N4)ncnc21] | (R or S)-1-{5-[9-ethyl-8-(2-methylpyrimidin-5-yl)-9H-purin-6-yl]-3-methyl-2-oxo-2,3-dihydro-1H-indol-3-yl}-3-methylazetidine-3-carbonitrile | Calc'd 480, found 480 |

TABLE 2-continued

| Compound | Structure | Name | Exact Mass [M + H]+ |
|---|---|---|---|
| 2-6 | 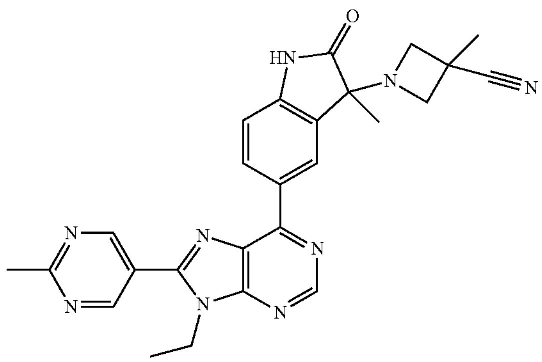 [SMILES: CCn1c(-c2cnc(C)nc2)nc2c(-c3ccc4c(c3)C(C)(N3CC(C)(C#N)C3)C(=O)N4)ncnc21] | (R or S)-1-{5-[9-ethyl-8-(2-methylpyrimidin-5-yl)-9H-purin-6-yl]-3-methyl-2-oxo-2,3-dihydro-1H-indol-3-yl}-3-methylazetidine-3-carbonitrile | Calc'd 480, found 480 |
| 2-7 | 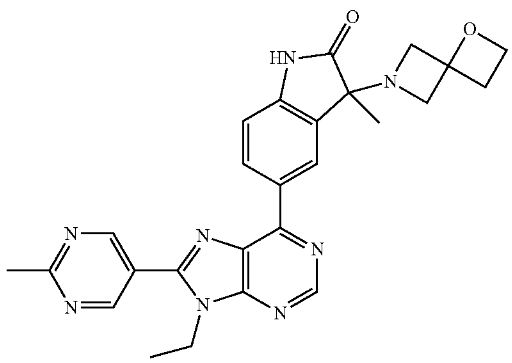 [SMILES: CCn1c(-c2cnc(C)nc2)nc2c(-c3ccc4c(c3)C(C)(N3CC5(CCO5)C3)C(=O)N4)ncnc21] | (R or S)-5-[9-ethyl-8-(2-methylpyrimidin-5-yl)-9H-purin-6-yl]-3-methyl-3-(1-oxa-6-azaspiro[3.3]hept-6-yl)-1,3-dihydro-2H-indol-2-one | Calc'd 483, found 483 |
| 2-8 | 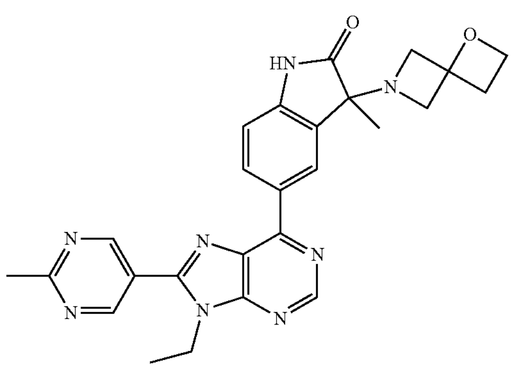 [SMILES: CCn1c(-c2cnc(C)nc2)nc2c(-c3ccc4c(c3)C(C)(N3CC5(CCO5)C3)C(=O)N4)ncnc21] | (R or S)-5-[9-ethyl-8-(2-methylpyrimidin-5-yl)-9H-purin-6-yl]-3-methyl-3-(1-oxa-6-azaspiro[3.3]hept-6-yl)-1,3-dihydro-2H-indol-2-one | Calc'd 483, found 483 |
| 2-9 | 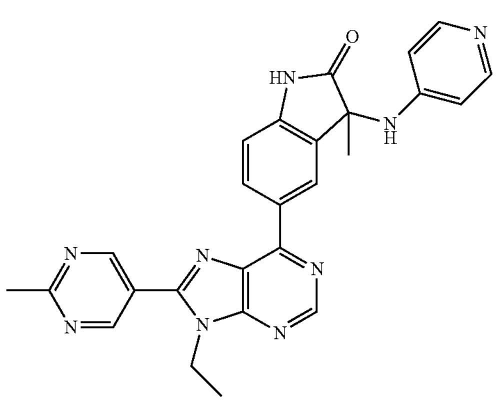 [SMILES: CCn1c(-c2cnc(C)nc2)nc2c(-c3ccc4c(c3)C(C)(Nc3ccncc3)C(=O)N4)ncnc21] | (R and S)-5-[9-ethyl-8-(2-methylpyrimidin-5-yl)-9H-purin-6-yl]-3-methyl-3-(pyridin-4-ylamino)-1,3-dihydro-2H-indol-2-one | Calc'd 478, found 478 |

TABLE 2-continued

| Compound | Structure | Name | Exact Mass [M + H]+ |
|---|---|---|---|
| 2-10 | 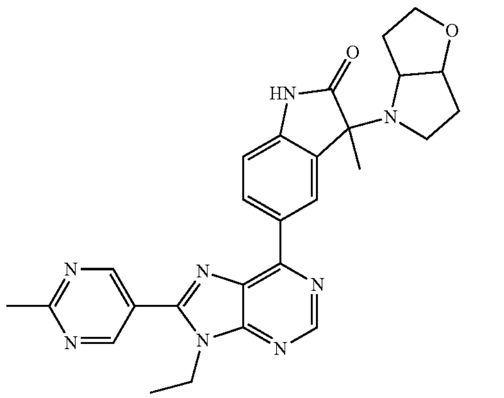 [SMILES: CCn1c(-c2cnc(C)nc2)nc2c(-c3ccc4c(c3)C(C)(N3CCC5OCCC53)C(=O)N4)ncnc21] | (R and S)-5-[9-ethyl-8-(2-methylpyrimidin-5-yl)-9H-purin-6-yl]-3-(hexahydro-4H-furo[3,2-b]pyrrol-4-yl)-3-methyl-1,3-dihydro-2H-indol-2-one | Calc'd 497, found 497 |
| 2-11 | 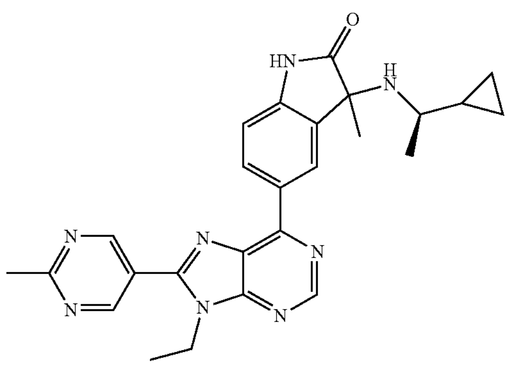 [SMILES: CCn1c(-c2cnc(C)nc2)nc2c(-c3ccc4c(c3)C(C)(N[C@H](C)C3CC3)C(=O)N4)ncnc21] | 3-{[(1R)-1-cyclopropylethyl]amino}-5-[9-ethyl-8-(2-methylpyrimidin-5-yl)-9H-purin-6-yl]-3(R and S)-methyl-1,3-dihydro-2H-indol-2-one | Calc'd 469, found 469 |
| 2-12 | 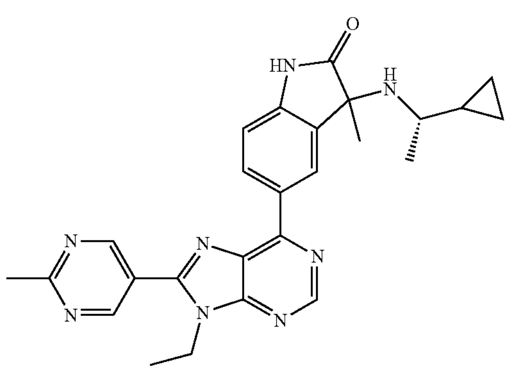 [SMILES: CCn1c(-c2cnc(C)nc2)nc2c(-c3ccc4c(c3)C(C)(N[C@@H](C)C3CC3)C(=O)N4)ncnc21] | 3-{[(1S)-1-cyclopropylethyl]amino}-5-[9-ethyl-8-(2-methylpyrimidin-5-yl)-9H-purin-6-yl]-3(R or S)-methyl-1,3-dihydro-2H-indol-2-one | Calc'd 469, found 469 |
| 2-13 | 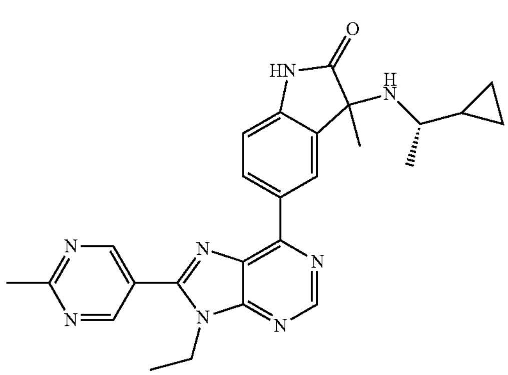 [SMILES: CCn1c(-c2cnc(C)nc2)nc2c(-c3ccc4c(c3)C(C)(N[C@@H](C)C3CC3)C(=O)N4)ncnc21] | 3-{[(1S)-1-cyclopropylethyl]amino}-5-[9-ethyl-8-(2-methylpyrimidin-5-yl)-9H-purin-6-yl]-3(R or S)-methyl-1,3-dihydro-2H-indol-2-one | Calc'd 469, found 469 |

TABLE 2-continued

| Compound | Structure | Name | Exact Mass [M + H]+ |
|---|---|---|---|
| 2-14 | 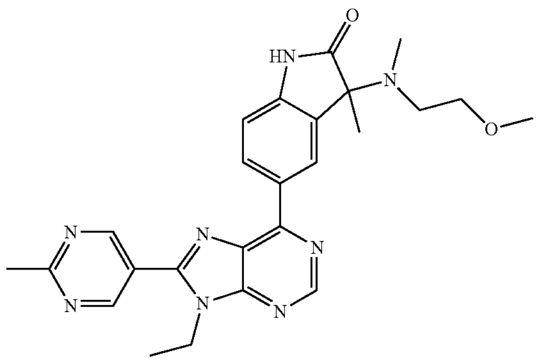 | (R and S)-5-[9-ethyl-8-(2-methylpyrimidin-5-yl)-9H-purin-6-yl]-3-[(2-methoxyethyl)(methyl)amino]-3-methyl-1,3-dihydro-2H-indol-2-one | Calc'd 473, found 473 |
| 2-15 | 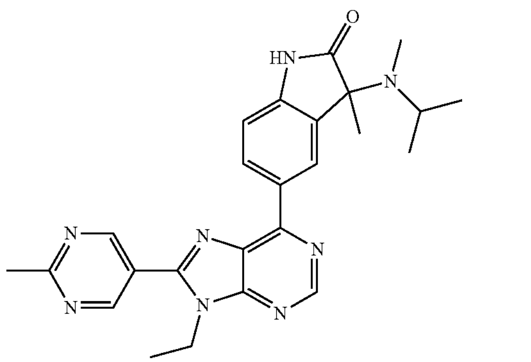 [SMILES: CCn1c(-c2cnc(C)nc2)nc2c(-c3ccc4c(c3)C(C)(N(C)C(C)C)C(=O)N4)ncnc21] | (R and S)-5-[9-ethyl-8-(2-methylpyrimidin-5-yl)-9H-purin-6-yl]-3-methyl-3-[methyl(1-methylethyl)amino]-1,3-dihydro-2H-indol-2-one | Calc'd 457, found 457 |
| 2-16 | 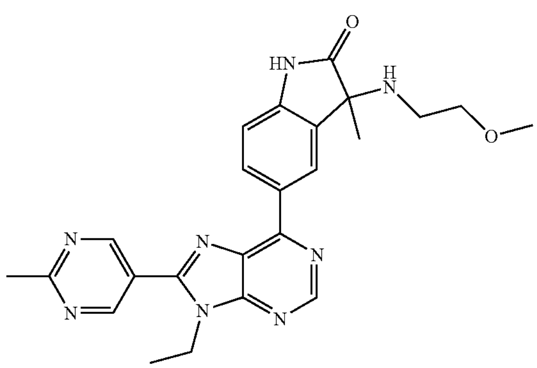 | (R and S)-5-[9-ethyl-8-(2-methylpyrimidin-5-yl)-9H-purin-6-yl]-3-[(2-methoxyethyl)amino]-3-methyl-1,3-dihydro-2H-indol-2-one | Calc'd 459, found 459 |
| 2-17 | 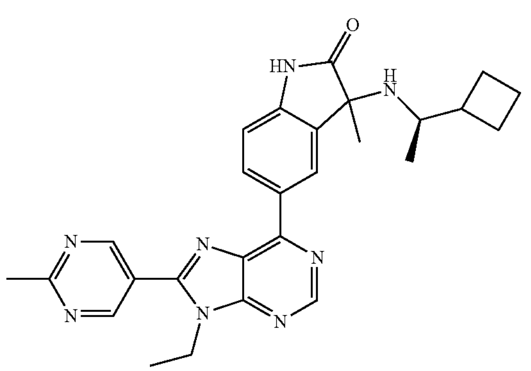 [SMILES: CCn1c(-c2cnc(C)nc2)nc2c(-c3ccc4c(c3)C(C)(N[C@H](C)C3CCC3)C(=O)N4)ncnc21] | 3-{[(1R)-1-cyclobutylethyl]amino}-5-[9-ethyl-8-(2-methylpyrimidin-5-yl)-9H-purin-6-yl]-3(R and S)-methyl-1,3-dihydro-2H-indol-2-one | Calc'd 483, found 483 |

TABLE 2-continued

| Compound | Structure | Name | Exact Mass [M + H]+ |
|---|---|---|---|
| 2-18 | 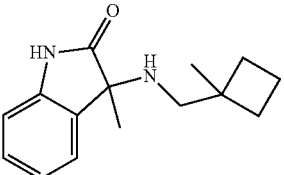 | (R and S)-5-[9-ethyl-8-(2-methylpyrimidin-5-yl)-9H-purin-6-yl]-3-methyl-3-{[(1-methylcyclobutyl)methyl]amino}-1,3-dihydro-2H-indol-2-one | Calc'd 483, found 483 |
| 2-19 | 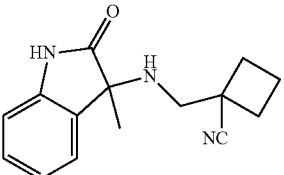 | (R and S)-1-[({5-[9-ethyl-8-(2-methylpyrimidin-5-yl)-9H-purin-6-yl]-3-methyl-2-oxo-2,3-dihydro-1H-indol-3-yl}amino)methyl]cyclobutanecarbonitrile | Calc'd 494, found 494 |
| 2-20 | 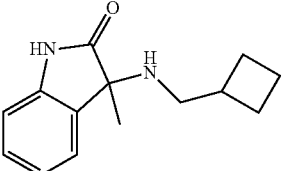 | (R and S)-3-[(cyclobutylmethyl)amino]-5-[9-ethyl-8-(2-methylpyrimidin-5-yl)-9H-purin-6-yl]-3-methyl-1,3-dihydro-2H-indol-2-one | Calc'd 469, found 469 |
| 2-21 | 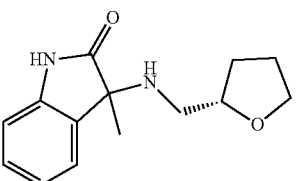 | 5-[9-ethyl-8-(2-methylpyrimidin-5-yl)-9H-purin-6-yl]-3(R and S)-methyl-3-{[(2S)-tetrahydrofuran-2-ylmethyl]amino}-1,3-dihydro-2H-indol-2-one | Calc'd 485, found 485 |

TABLE 2-continued

| Compound | Structure | Name | Exact Mass [M + H]+ |
|---|---|---|---|
| 2-22 | 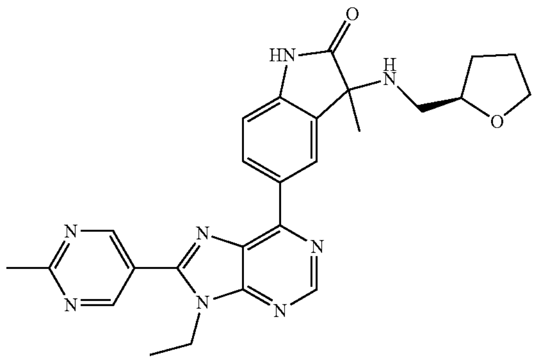 [SMILES: CCn1c(-c2cnc(C)nc2)nc2c(-c3ccc4c(c3)C(C)(NC[C@H]3CCCO3)C(=O)N4)ncnc21] | 5-[9-ethyl-8-(2-methylpyrimidin-5-yl)-9H-purin-6-yl]-3(R and S)-methyl-3-{[(2R)-tetrahydrofuran-2-ylmethyl]amino}-1,3-dihydro-2H-indol-2-one | Calc'd 485, found 485 |
| 2-23 | 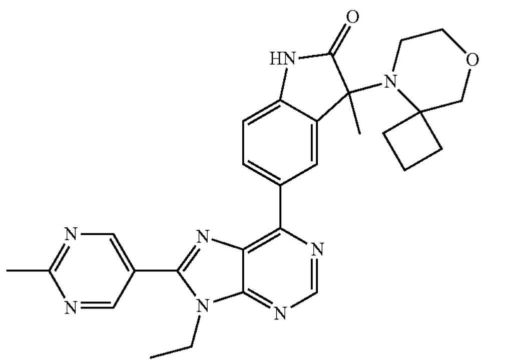 [SMILES: CCn1c(-c2cnc(C)nc2)nc2c(-c3ccc4c(c3)C(C)(N3CCOCC35CCC5)C(=O)N4)ncnc21] | (R and S)-5-[9-ethyl-8-(2-methylpyrimidin-5-yl)-9H-purin-6-yl]-3-methyl-3-(8-oxa-5-azaspiro[3.5]non-5-yl)-1,3-dihydro-2H-indol-2-one | Calc'd 511, found 511 |
| 2-24 | 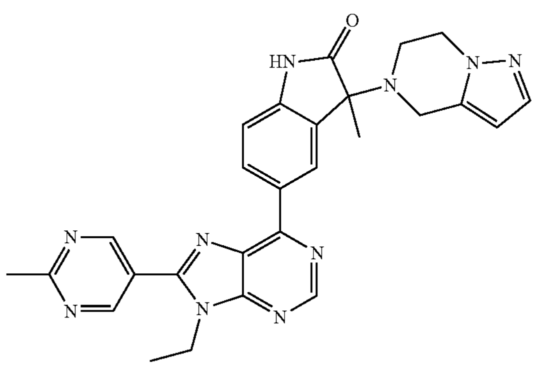 [SMILES: CCn1c(-c2cnc(C)nc2)nc2c(-c3ccc4c(c3)C(C)(N3CCn5nccc5C3)C(=O)N4)ncnc21] | (R and S)-3-(6,7-dihydropyrazolo[1,5-a]pyrazin-5(4H)-yl)-5-[9-ethyl-8-(2-methylpyrimidin-5-yl)-9H-purin-6-yl]-3-methyl-1,3-dihydro-2H-indol-2-one | Calc'd 507, found 507 |
| 2-25 | 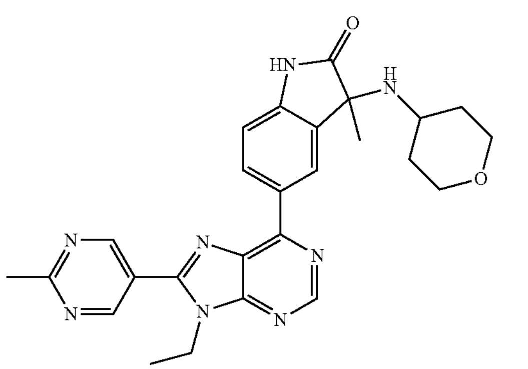 [SMILES: CCn1c(-c2cnc(C)nc2)nc2c(-c3ccc4c(c3)C(C)(NC3CCOCC3)C(=O)N4)ncnc21] | (R and S)-5-[9-ethyl-8-(2-methylpyrimidin-5-yl)-9H-purin-6-yl]-3-methyl-3-(tetrahydro-2H-pyran-4-ylamino)-1,3-dihydro-2H-indol-2-one | Calc'd 485, found 485 |

TABLE 2-continued

| Compound | Structure | Name | Exact Mass [M + H]+ |
|---|---|---|---|
| 2-26 | 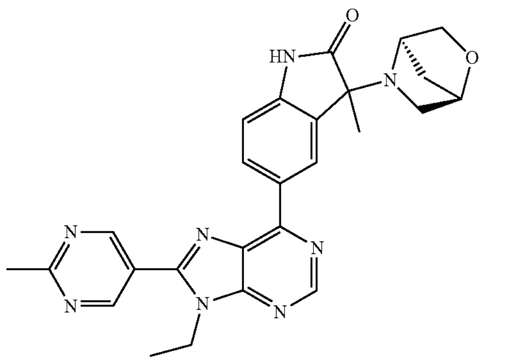 [SMILES: CCn1c(-c2cnc(C)nc2)nc2c(-c3ccc4c(c3)C(C)(N3C[C@H]5C[C@@H]3CO5)C(=O)N4)ncnc21] | 5-[9-ethyl-8-(2-methylpyrimidin-5-yl)-9H-purin-6-yl]-3(R and S)-methyl-3-[(1R,4R)-2-oxa-5-azabicyclo[2.2.1]hept-5-yl]-1,3-dihydro-2H-indol-2-one | Calc'd 483, found 483 |
| 2-27 | 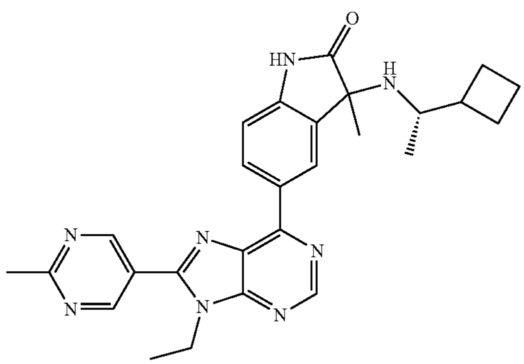 [SMILES: CCn1c(-c2cnc(C)nc2)nc2c(-c3ccc4c(c3)C(C)(N[C@@H](C)C3CCC3)C(=O)N4)ncnc21] | 3-{[(1S)-1-cyclobutylethyl]amino}-5-[9-ethyl-8-(2-methylpyrimidin-5-yl)-9H-purin-6-yl]-3(R and S)-methyl-1,3-dihydro-2H-indol-2-one | Calc'd 483, found 483 |
| 2-28 | 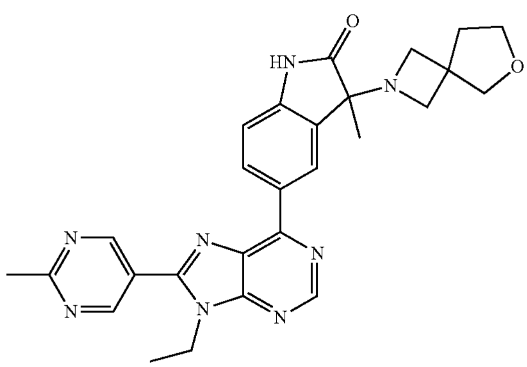 [SMILES: CCn1c(-c2cnc(C)nc2)nc2c(-c3ccc4c(c3)C(C)(N3CC5(CCOC5)C3)C(=O)N4)ncnc21] | (R and S)-5-[9-ethyl-8-(2-methylpyrimidin-5-yl)-9H-purin-6-yl]-3-methyl-3-(6-oxa-2-azaspiro[3.4]oct-2-yl)-1,3-dihydro-2H-indol-2-one | Calc'd 497, found 497 |
| 2-29 | 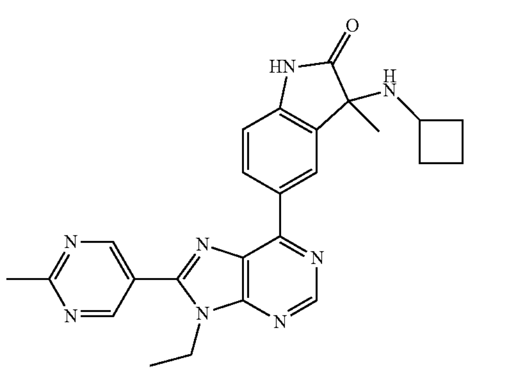 [SMILES: CCn1c(-c2cnc(C)nc2)nc2c(-c3ccc4c(c3)C(C)(NC3CCC3)C(=O)N4)ncnc21] | (R or S)-3-(cyclobutylamino)-5-[9-ethyl-8-(2-methylpyrimidin-5-yl)-9H-purin-6-yl]-3-methyl-1,3-dihydro-2H-indol-2-one | Calc'd 455, found 455 |

TABLE 2-continued

| Compound | Structure | Name | Exact Mass [M + H]⁺ |
|---|---|---|---|
| 2-30 | 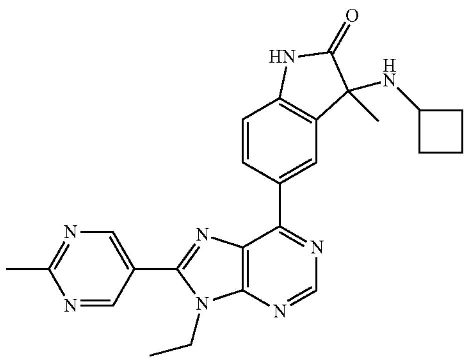 [SMILES: CCn1c(-c2cnc(C)nc2)nc2c(-c3ccc4c(c3)C(C)(NC3CCC3)C(=O)N4)ncnc21] | (R or S)-3-(cyclobutylamino)-5-[9-ethyl-8-(2-methylpyrimidin-5-yl)-9H-purin-6-yl]-3-methyl-1,3-dihydro-2H-indol-2-one | Calc'd 455, found 455 |
| 2-31 | 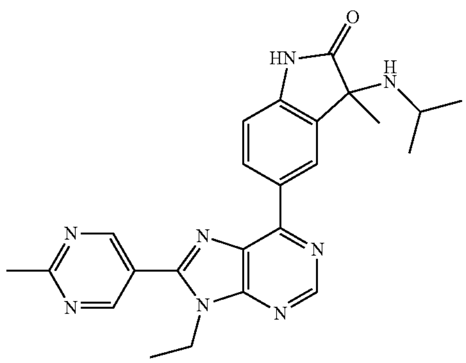 [SMILES: CCn1c(-c2cnc(C)nc2)nc2c(-c3ccc4c(c3)C(C)(NC(C)C)C(=O)N4)ncnc21] | (R or S)-5-[9-ethyl-8-(2-methylpyrimidin-5-yl)-9H-purin-6-yl]-3-methyl-3-[(1-methylethyl)amino]-1,3-dihydro-2H-indol-2-one | Calc'd 443, found 443 |
| 2-32 | 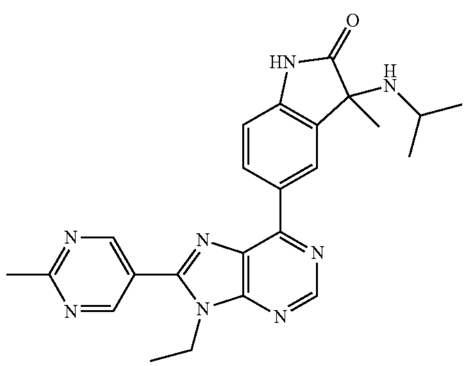 [SMILES: CCn1c(-c2cnc(C)nc2)nc2c(-c3ccc4c(c3)C(C)(NC(C)C)C(=O)N4)ncnc21] | (R or S)-5-[9-ethyl-8-(2-methylpyrimidin-5-yl)-9H-purin-6-yl]-3-methyl-3-[(1-methylethyl)amino]-1,3-dihydro-2H-indol-2-one | Calc'd 443, found 443 |
| 2-33 | 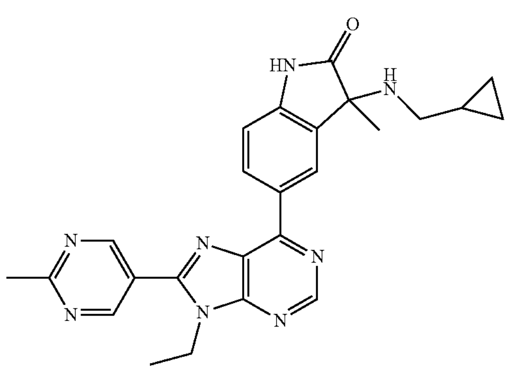 [SMILES: CCn1c(-c2cnc(C)nc2)nc2c(-c3ccc4c(c3)C(C)(NCC3CC3)C(=O)N4)ncnc21] | (R or S)-3-[(cyclopropylmethyl)amino]-5-[9-ethyl-8-(2-methylpyrimidin-5-yl)-9H-purin-6-yl]-3-methyl-1,3-dihydro-2H-indol-2-one | Calc'd 455, found 455 |

TABLE 2-continued

| Compound | Structure | Name | Exact Mass [M + H]+ |
|---|---|---|---|
| 2-34 | 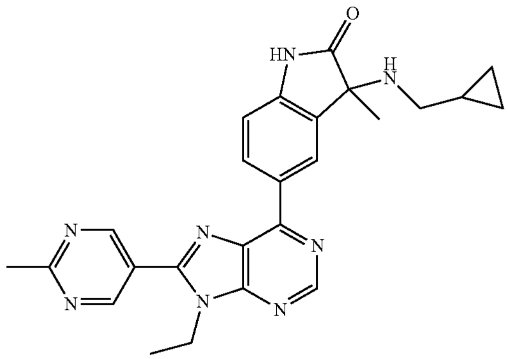 | (R or S)-3-[(cyclopropylmethyl)amino]-5-[9-ethyl-8-(2-methylpyrimidin-5-yl)-9H-purin-6-yl]-3-methyl-1,3-dihydro-2H-indol-2-one | Calc'd 455, found 455 |
| 2-35 | 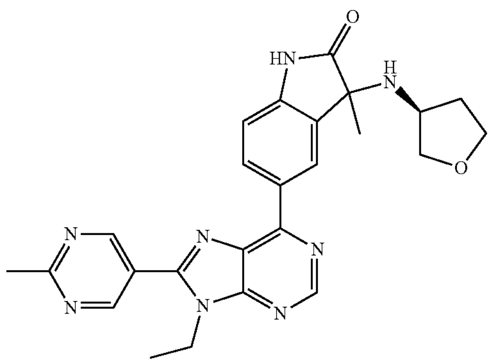 [SMILES: CCn1c(-c2cnc(C)nc2)nc2c(-c3ccc4c(c3)C(C)(N[C@H]3CCOC3)C(=O)N4)ncnc21] | 5-[9-ethyl-8-(2-methylpyrimidin-5-yl)-9H-purin-6-yl]-3(R or S)-methyl-3-[(3S)-tetrahydrofuran-3-ylamino]-1,3-dihydro-2H-indol-2-one | Calc'd 471, found 471 |
| 2-36 | 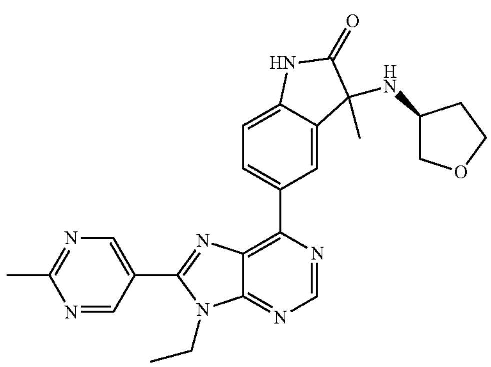 | 5-[9-ethyl-8-(2-methylpyrimidin-5-yl)-9H-purin-6-yl]-3(R or S)-methyl-3-[(3S)-tetrahydrofuran-3-ylamino]-1,3-dihydro-2H-indol-2-one | Calc'd 471, found 471 |
| 2-37 | 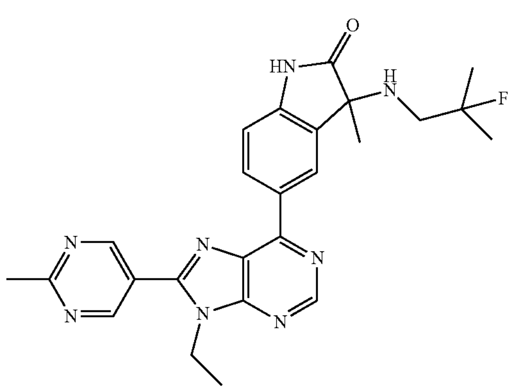 [SMILES: CCn1c(-c2cnc(C)nc2)nc2c(-c3ccc4c(c3)C(C)(NCC(C)(C)F)C(=O)N4)ncnc21] | (R or S)-5-(9-ethyl-8-(2-methylpyrimidin-5-yl)-9H-purin-6-yl)-3-((2-fluoro-2-methylpropyl)amino)-3-methylindolin-2-one | Calc'd 475, found 475 |

TABLE 2-continued

| Compound | Structure | Name | Exact Mass [M + H]+ |
|---|---|---|---|
| 2-38 | 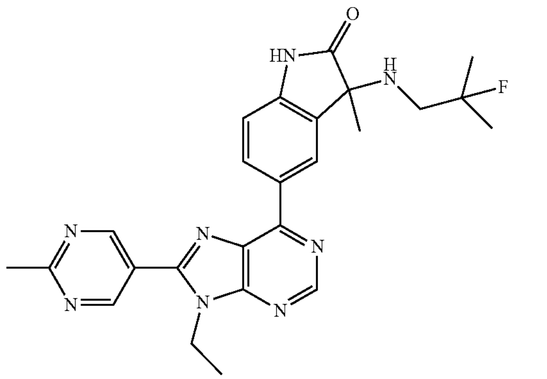 [SMILES: CCn1c(-c2cnc(C)nc2)nc2c(-c3ccc4c(c3)C(C)(NCC(C)(C)F)C(=O)N4)ncnc21] | (R or S)-5-(9-ethyl-8-(2-methylpyrimidin-5-yl)-9H-purin-6-yl)-3-((2-fluoro-2-methylpropyl)amino)-3-methylindolin-2-one | Calc'd 475, found 475 |
| 2-39 | 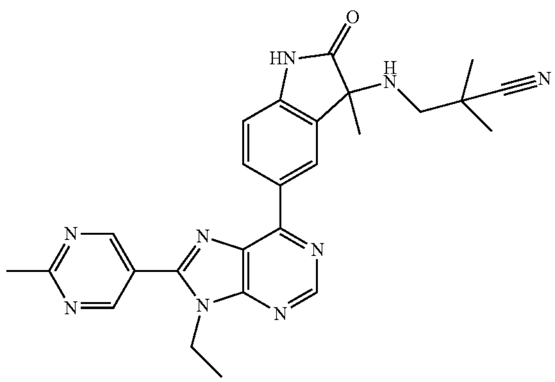 [SMILES: CCn1c(-c2cnc(C)nc2)nc2c(-c3ccc4c(c3)C(C)(NCC(C)(C)C#N)C(=O)N4)ncnc21] | (R or S)-3-((5-(9-ethyl-8-(2-methylpyrimidin-5-yl)-9H-purin-6-yl)-3-methyl-2-oxoindolin-3-yl)amino)-2,2-dimethylpropanenitrile | Calc'd 482, found 482 |
| 2-40 | 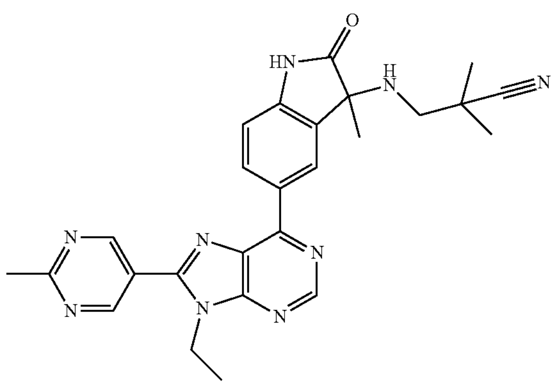 [SMILES: CCn1c(-c2cnc(C)nc2)nc2c(-c3ccc4c(c3)C(C)(NCC(C)(C)C#N)C(=O)N4)ncnc21] | (R or S)-3-((5-(9-ethyl-8-(2-methylpyrimidin-5-yl)-9H-purin-6-yl)-3-methyl-2-oxoindolin-3-yl)amino)-2,2-dimethylpropanenitrile | Calc'd 482, found 482 |
| 2-41 | 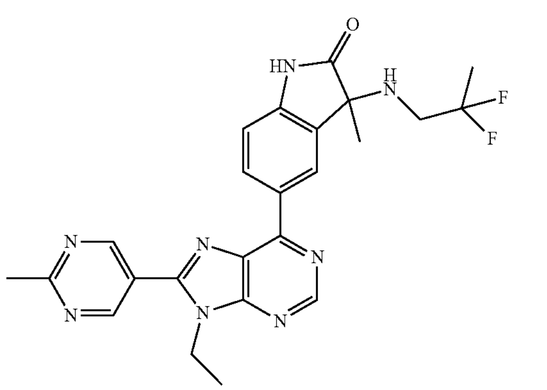 | (R or S)-3-((2,2-difluoropropyl)amino)-5-(9-ethyl-8-(2-methylpyrimidin-5-yl)-9H-purin-6-yl)-3-methylindolin-2-one | Calc'd 479, found 479 |

TABLE 2-continued

| Compound | Structure | Name | Exact Mass [M + H]+ |
|---|---|---|---|
| 2-42 | 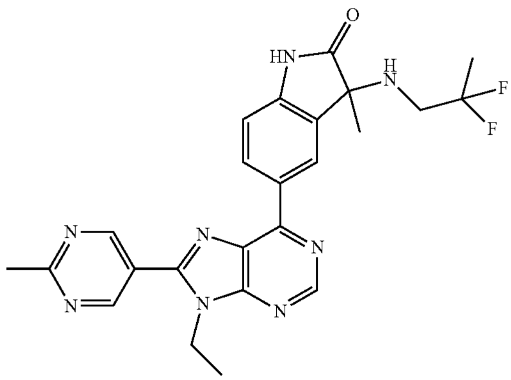 | (R or S)-3-((2,2-difluoropropyl)amino)-5-(9-ethyl-8-(2-methylpyrimidin-5-yl)-9H-purin-6-yl)-3-methylindolin-2-one | Calc'd 479, found 479 |
| 2-43 | 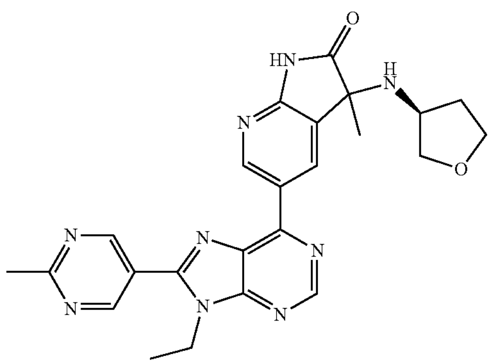 [SMILES: CCn1c(-c2cnc(C)nc2)nc2c(-c3cnc4c(c3)C(C)(N[C@H]3CCOC3)C(=O)N4)ncnc21] | (R or S)-5-(9-ethyl-8-(2-methylpyrimidin-5-yl)-9H-purin-6-yl)-3-methyl-3-(((S)-tetrahydrofuran-3-yl)amino)-1,3-dihydro-2H-pyrrolo[2,3-b]pyridin-2-one | Calc'd 472, found 472 |
| 2-44 | 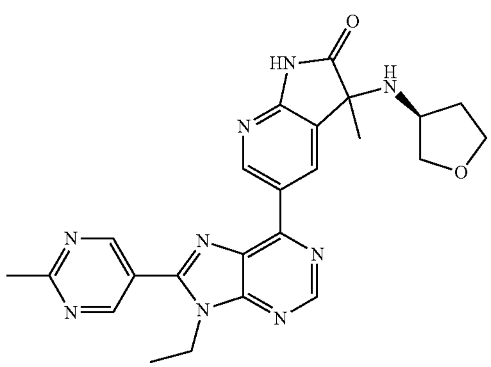 [SMILES: CCn1c(-c2cnc(C)nc2)nc2c(-c3cnc4c(c3)C(C)(N[C@H]3CCOC3)C(=O)N4)ncnc21] | (R or S)-5-(9-ethyl-8-(2-methylpyrimidin-5-yl)-9H-purin-6-yl)-3-methyl-3-(((S)-tetrahydrofuran-3-yl)amino)-1,3-dihydro-2H-pyrrolo[2,3-b]pyridin-2-one | Calc'd 472, found 472 |
| 2-45 | 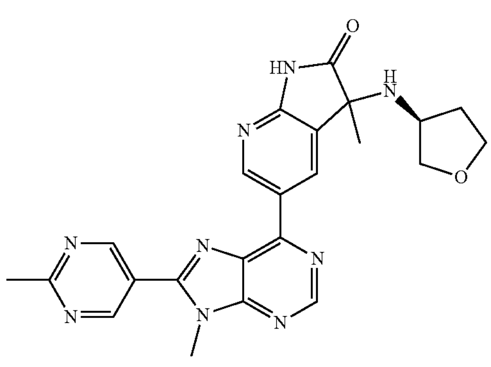 [SMILES: Cc1ncc(-c2nc3c(-c4cnc5c(c4)C(C)(N[C@H]4CCOC4)C(=O)N5)ncnc3n2C)cn1] | (R or S)-3-methyl-5-(9-methyl-8-(2-methylpyrimidin-5-yl)-9H-purin-6-yl)-3-(((S)-tetrahydrofuran-3-yl)amino)-1H-pyrrolo[2,3-b]pyridin-2(3H)-one | Calc'd 458, found 458 |

TABLE 2-continued

| Compound | Name | Exact Mass [M + H]+ |
|---|---|---|
| 2-46 | (R or S)-3-methyl-5-(9-methyl-8-(2-methylpyrimidin-5-yl)-9H-purin-6-yl)-3-(((S)-tetrahydrofuran-3-yl)amino)-1H-pyrrolo[2,3-b]pyridin-2(3H)-one | Calc'd 458, found 458 |
| 2-47 | (R or S)-5-(9-ethyl-8-(2-methylpyrimidin-5-yl)-9H-purin-6-yl)-3-(3-methoxy-3-methylazetidin-1-yl)-3-methyl-1H-pyrrolo[2,3-b]pyridin-2(3H)-one | Calc'd 486, found 486 |
| 2-48 | (R or S)-5-(9-ethyl-8-(2-methylpyrimidin-5-yl)-9H-purin-6-yl)-3-(3-methoxy-3-methylazetidin-1-yl)-3-methyl-1H-pyrrolo[2,3-b]pyridin-2(3H)-one | Calc'd 486, found 486 |
| 2-49 | (S or R)-5-(9-ethyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one | Calc'd 476, found 476 |

TABLE 2-continued

| Compound | Structure | Name | Exact Mass [M + H]+ |
|---|---|---|---|
| 2-50 | 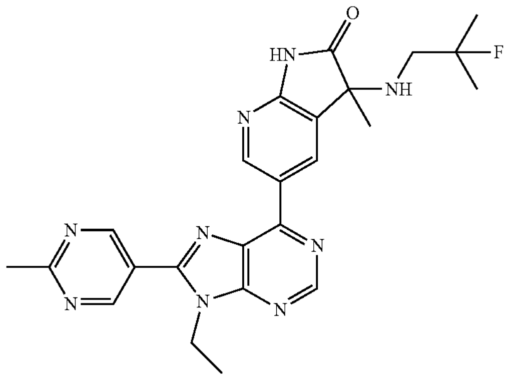 | (S or R)-5-(9-ethyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one | Calc'd 476, found 476 |
| 2-51 | 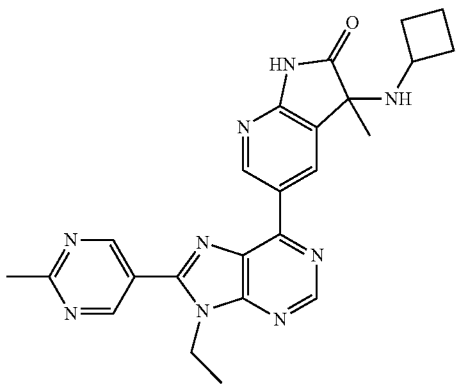 [SMILES: CCn1c(-c2cnc(C)nc2)nc2c(-c3cnc4c(c3)C(C)(NC3CCC3)C(=O)N4)ncnc21] | (S or R)-3-(cyclobutylamino)-5-(9-ethyl-8-(2-methylpyrimidin-5-yl)-9H-purin-6-yl)-3-methyl-1,3-dihydro-2H-pyrrolo[2,3-b]pyridin-2-one | Calc'd 456, found 456 |
| 2-52 | 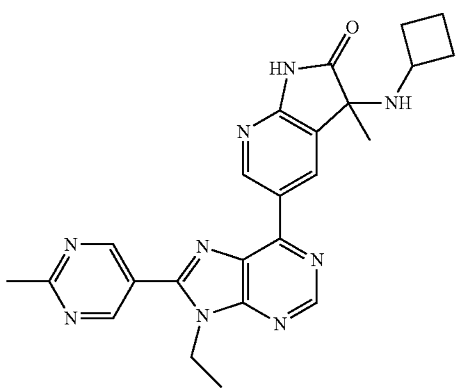 [SMILES: CCn1c(-c2cnc(C)nc2)nc2c(-c3cnc4c(c3)C(C)(NC3CCC3)C(=O)N4)ncnc21] | (S or R)-3-(cyclobutylamino)-5-(9-ethyl-8-(2-methylpyrimidin-5-yl)-9H-purin-6-yl)-3-methyl-1,3-dihydro-2H-pyrrolo[2,3-b]pyridin-2-one | Calc'd 456, found 456 |
| 2-53 | 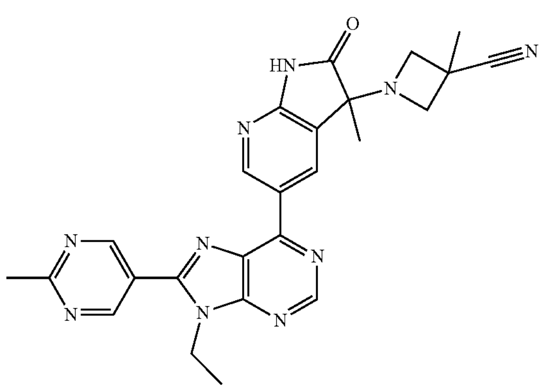 [SMILES: CCn1c(-c2cnc(C)nc2)nc2c(-c3cnc4c(c3)C(C)(N3CC(C)(C#N)C3)C(=O)N4)ncnc21] | (S or R)-1-(5-(9-ethyl-8-(2-methylpyrimidin-5-yl)-9H-purin-6-yl)-3-methyl-2-oxo-2,3-dihydro-1H-pyrrolo[2,3-b]pyridin-3-yl)-3-methylazetidine-3-carbonitrile | Calc'd 481, found 481 |

TABLE 2-continued

| Compound | Structure | Name | Exact Mass [M + H]+ |
|---|---|---|---|
| 2-54 | 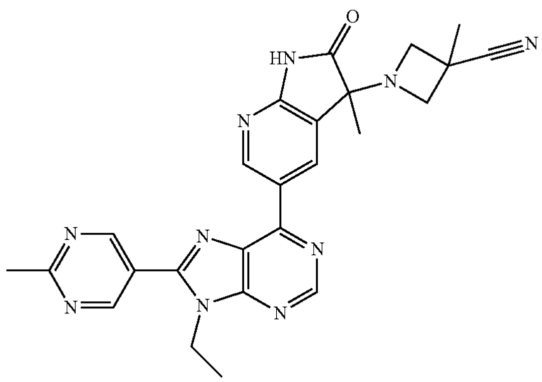 [SMILES: CCn1c(-c2cnc(C)nc2)nc2c(-c3cnc4c(c3)C(C)(N3CC(C)(C#N)C3)C(=O)N4)ncnc21] | (S or R)-1-(5-(9-ethyl-8-(2-methylpyrimidin-5-yl)-9H-purin-6-yl)-3-methyl-2-oxo-2,3-dihydro-1H-pyrrolo[2,3-b]pyridin-3-yl)-3-methylazetidine-3-carbonitrile | Calc'd 481, found 481 |
| 2-55 | 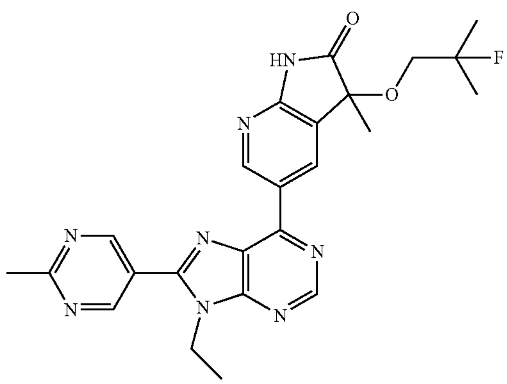 [SMILES: CCn1c(-c2cnc(C)nc2)nc2c(-c3cnc4c(c3)C(C)(OCC(C)(C)F)C(=O)N4)ncnc21] | (R or S)-5-(9-ethyl-8-(2-methylpyrimidin-5-yl)-9H-purin-6-yl)-3-(2-fluoro-2-methylpropoxy)-3-methylindolin-2-one | Calc'd 476, found 476 |
| 2-56 | 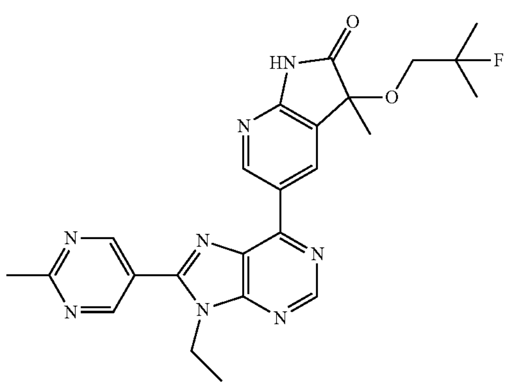 [SMILES: CCn1c(-c2cnc(C)nc2)nc2c(-c3cnc4c(c3)C(C)(OCC(C)(C)F)C(=O)N4)ncnc21] | (R or S)-5-(9-ethyl-8-(2-methylpyrimidin-5-yl)-9H-purin-6-yl)-3-(2-fluoro-2-methylpropoxy)-3-methylindolin-2-one | Calc'd 476, found 476 |
| 2-57 | 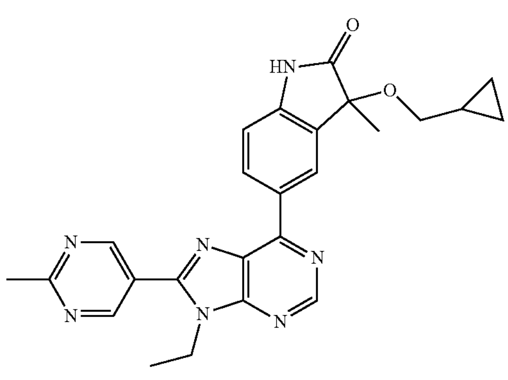 [SMILES: CCn1c(-c2cnc(C)nc2)nc2c(-c3ccc4c(c3)C(C)(OCC3CC3)C(=O)N4)ncnc21] | (R or S)-3-(cyclopropylmethoxy)-5-(9-ethyl-8-(2-methylpyrimidin-5-yl)-9H-purin-6-yl)-3-methylindolin-2-one | Calc'd 456, found 456 |

TABLE 2-continued

| Compound | Structure | Name | Exact Mass [M + H]+ |
|---|---|---|---|
| 2-58 | 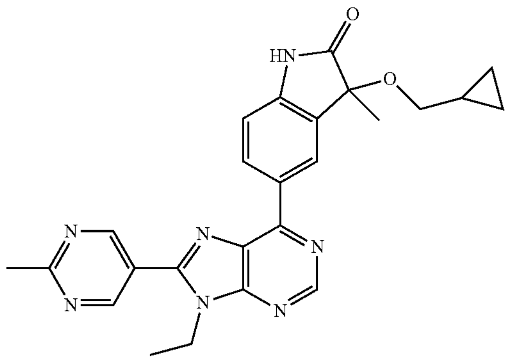 [SMILES: CCn1c(-c2cnc(C)nc2)nc2c(-c3ccc4c(c3)C(C)(OCC3CC3)C(=O)N4)ncnc21] | (R or S)-3-(cyclopropylmethoxy)-5-(9-ethyl-8-(2-methylpyrimidin-5-yl)-9H-purin-6-yl)-3-methylindolin-2-one | Calc'd 456, found 456 |
| 2-59 | 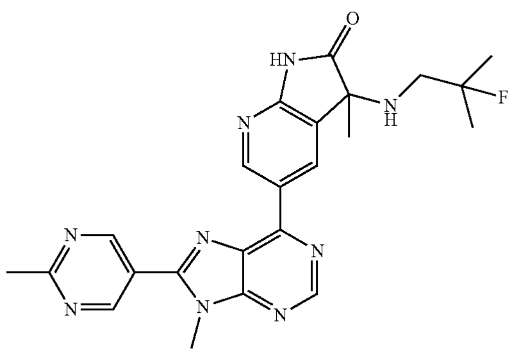 [SMILES: Cc1ncc(-c2nc3c(-c4cnc5c(c4)C(C)(NCC(C)(C)F)C(=O)N5)ncnc3n2C)cn1] | (S or R)-5-(9-methyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one | Calc'd 462, found 462 |
| 2-60 | 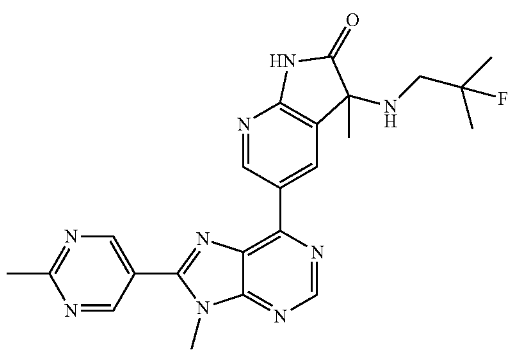 [SMILES: Cc1ncc(-c2nc3c(-c4cnc5c(c4)C(C)(NCC(C)(C)F)C(=O)N5)ncnc3n2C)cn1] | (S or R)-5-(9-methyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one | Calc'd 462, found 462 |
| 2-61 | 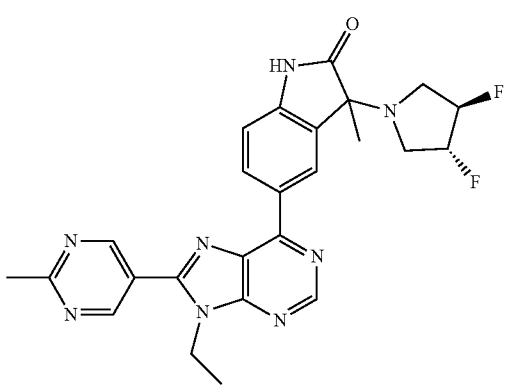 [SMILES: CCn1c(-c2cnc(C)nc2)nc2c(-c3ccc4c(c3)C(C)(N3C[C@@H](F)[C@H](F)C3)C(=O)N4)ncnc21] | 3-(R or S)-((3R,4R)-3,4-difluoropyrrolidin-1-yl)-5-(9-ethyl-8-(2-methylpyrimidin-5-yl)-9H-purin-6-yl)-3-methylindolin-2-one | Calc'd 491, found 491 |

TABLE 2-continued

| Compound | Structure | Name | Exact Mass [M + H]+ |
|---|---|---|---|
| 2-62 | 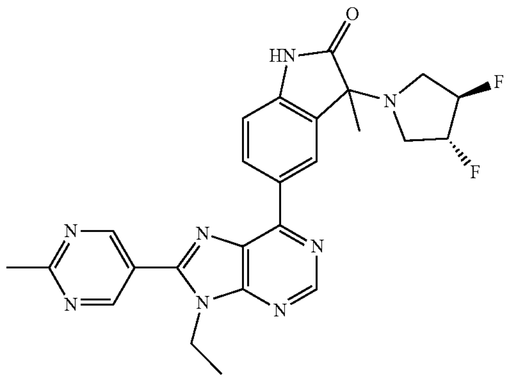 [SMILES: CCn1c(-c2cnc(C)nc2)nc2c(-c3ccc4c(c3)C(C)(N3C[C@@H](F)[C@H](F)C3)C(=O)N4)ncnc21] | 3-(R or S)-((3R,4R)-3,4-difluoropyrrolidin-1-yl)-5-(9-ethyl-8-(2-methylpyrimidin-5-yl)-9H-purin-6-yl)-3-methylindolin-2-one | Calc'd 491, found 491 |
| 2-63 | 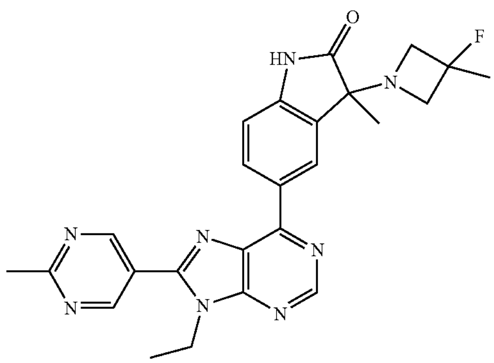 | (R or S)-5-(9-ethyl-8-(2-methylpyrimidin-5-yl)-9H-purin-6-yl)-3-(3-fluoro-3-methylazetidin-1-yl)-3-methylindolin-2-one | Calc'd 473, found 473 |
| 2-64 | 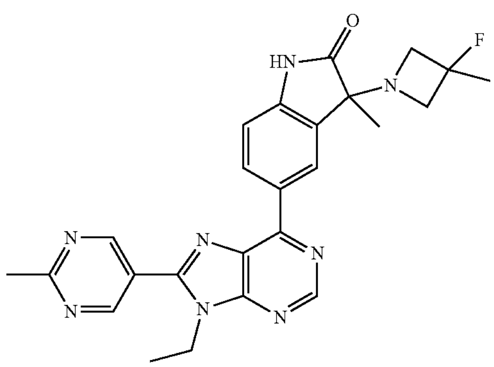 | (R or S)-5-(9-ethyl-8-(2-methylpyrimidin-5-yl)-9H-purin-6-yl)-3-(3-fluoro-3-methylazetidin-1-yl)-3-methylindolin-2-one | Calc'd 473, found 473 |
| 2-65 | 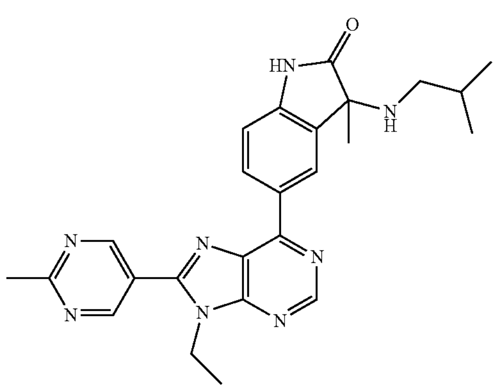 [SMILES: CCn1c(-c2cnc(C)nc2)nc2c(-c3ccc4c(c3)C(C)(NCC(C)C)C(=O)N4)ncnc21] | (R or S)-5-(9-ethyl-8-(2-methylpyrimidin-5-yl)-9H-purin-6-yl)-3-(isobutylamino)-3-methylindolin-2-one | Calc'd 457, found 457 |

TABLE 2-continued

| Compound | Structure | Name | Exact Mass [M + H]+ |
|---|---|---|---|
| 2-66 | 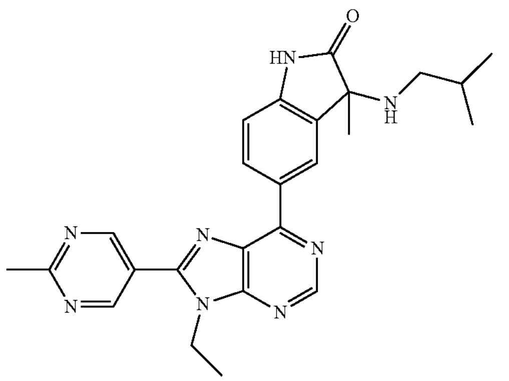 [SMILES: CCn1c(-c2cnc(C)nc2)nc2c(-c3ccc4c(c3)C(C)(NCC(C)C)C(=O)N4)ncnc21] | (R or S)-5-(9-ethyl-8-(2-methylpyrimidin-5-yl)-9H-purin-6-yl)-3-(isobutylamino)-3-methylindolin-2-one | Calc'd 457, found 457 |
| 2-67 | 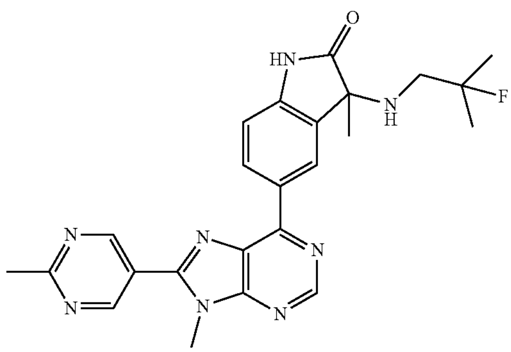 | (R or S)-3-((2-fluoro-2-methylpropyl)amino)-3-methyl-5-(9-methyl-8-(2-methylpyrimidin-5-yl)-9H-purin-6-yl)indolin-2-one | Calc'd 461, found 461 |
| 2-68 | 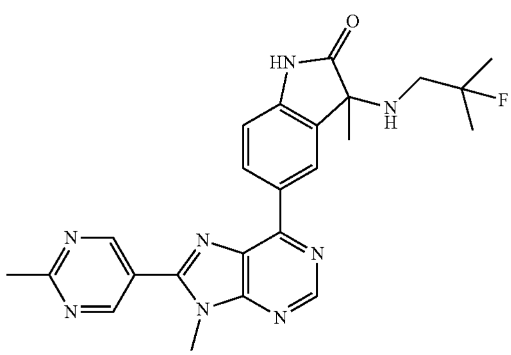 [SMILES: Cc1ncc(-c2nc3c(-c4ccc5c(c4)C(C)(NCC(C)(F)F)C(=O)N5)ncnc3n2C)cn1] | (R or S)-3-((2-fluoro-2-methylpropyl)amino)-3-methyl-5-(9-methyl-8-(2-methylpyrimidin-5-yl)-9H-purin-6-yl)indolin-2-one | Calc'd 461, found 461 |
| 2-69 | 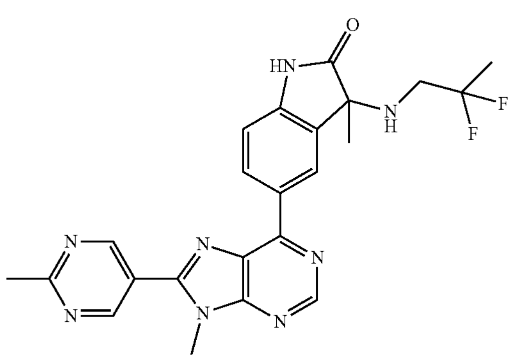 [SMILES: Cc1ncc(-c2nc3c(-c4ccc5c(c4)C(C)(NCC(C)(F)F)C(=O)N5)ncnc3n2C)cn1] | (R or S)-3-((2,2-difluoropropyl)amino)-3-methyl-5-(9-methyl-8-(2-methylpyrimidin-5-yl)-9H-purin-6-yl)indolin-2-one | Calc'd 465, found 465 |

TABLE 2-continued

| Compound | Structure | Name | Exact Mass [M + H]+ |
|---|---|---|---|
| 2-70 | 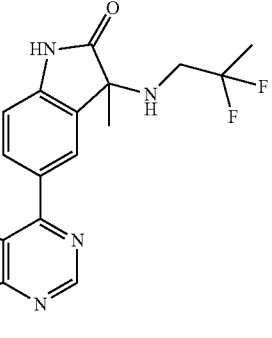 | (R or S)-3-((2,2-difluoropropyl)amino)-3-methyl-5-(9-methyl-8-(2-methylpyrimidin-5-yl)-9H-purin-6-yl)indolin-2-one | Calc'd 465, found 465 |
| 2-71 | 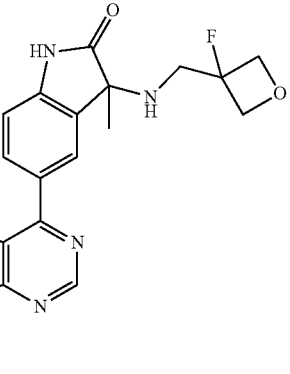 | (R or S)-5-(9-ethyl-8-(2-methylpyrimidin-5-yl)-9H-purin-6-yl)-3-(((3-fluorooxetan-3-yl)methyl)amino)-3-methylindolin-2-one | Calc'd 489, found 489 |
| 2-72 | 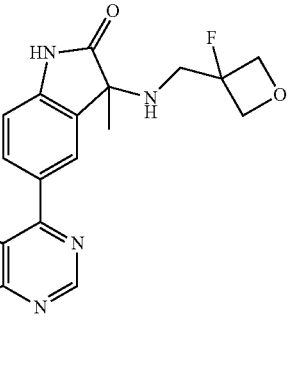 | (R or S)-5-(9-ethyl-8-(2-methylpyrimidin-5-yl)-9H-purin-6-yl)-3-(((3-fluorooxetan-3-yl)methyl)amino)-3-methylindolin-2-one | Calc'd 489, found 489 |
| 2-73 | 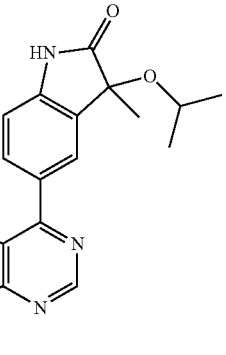 | 5-(9-ethyl-8-(2-methylpyrimidin-5-yl)-9H-purin-6-yl)-3-isopropoxy-3-methylindolin-2-one | Calc'd 444, found 444 |

TABLE 2-continued

| Compound | Structure | Name | Exact Mass [M + H]+ |
|---|---|---|---|
| 2-74 | 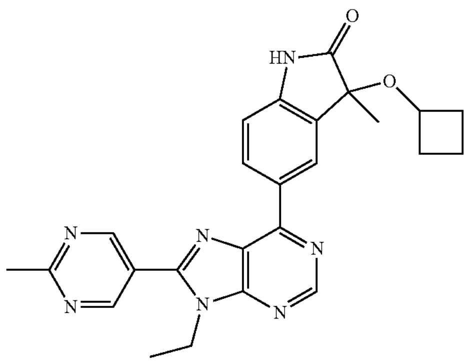 [SMILES: CCn1c(-c2cnc(C)nc2)nc2c(-c3ccc4c(c3)C(C)(OC3CCC3)C(=O)N4)ncnc21] | 3-cyclobutoxy-5-(9-ethyl-8-(2-methylpyrimidin-5-yl)-9H-purin-6-yl)-3-methylindolin-2-one | Calc'd 456, found 456 |
| 2-75 | 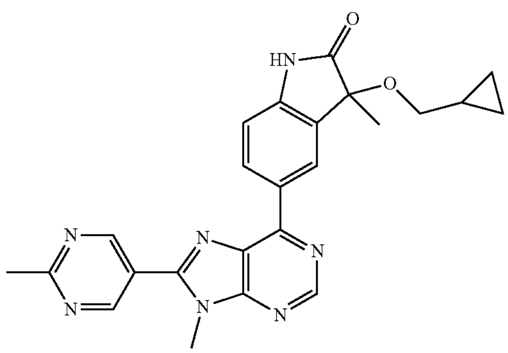 [SMILES: Cc1ncc(-c2nc3c(-c4ccc5c(c4)C(C)(OCC4CC4)C(=O)N5)ncnc3n2C)cn1] | 3-(cyclopropylmethoxy)-3-methyl-5-(9-methyl-8-(2-methylpyrimidin-5-yl)-9H-purin-6-yl)indolin-2-one | Calc'd 442, found 442 |
| 2-76 | 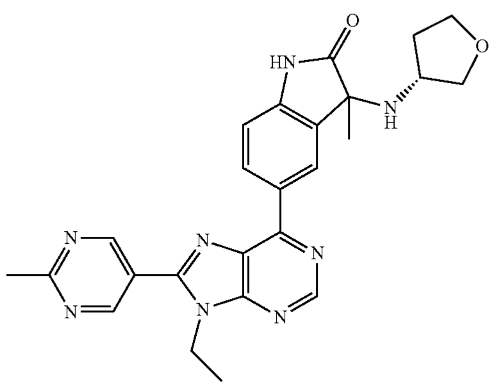 [SMILES: CCn1c(-c2cnc(C)nc2)nc2c(-c3ccc4c(c3)C(C)(N[C@@H]3CCOC3)C(=O)N4)ncnc21] | 5-(9-ethyl-8-(2-methylpyrimidin-5-yl)-9H-purin-6-yl)-3-(R and S)-methyl-3-(((R)-tetrahydrofuran-3-yl)amino)indolin-2-one | Calc'd 471, found 471 |
| 2-77 | 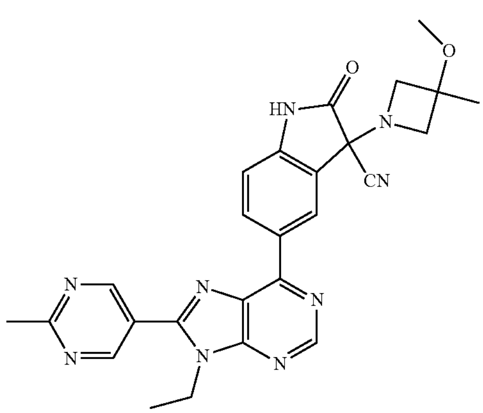 | 5-(9-ethyl-8-(2-methylpyrimidin-5-yl)-9H-purin-6-yl)-3-(3-methoxy-3-methylazetidin-1-yl)-2-oxoindoline-3-carbonitrile | Calc'd 496, found 496 |

TABLE 2-continued

| Compound | Structure | Name | Exact Mass [M + H]+ |
|---|---|---|---|
| 2-78 | 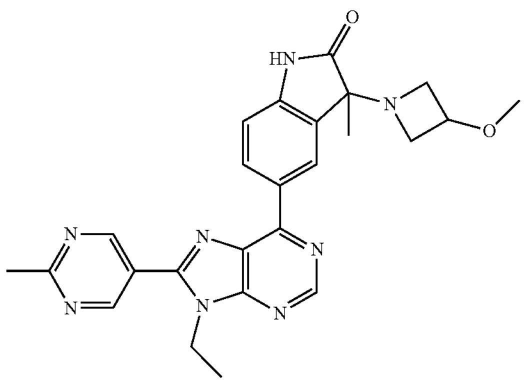 | (R or S)-5-(9-ethyl-8-(2-methylpyrimidin-5-yl)-9H-purin-6-yl)-3-(3-methoxyazetidin-1-yl)-3-methylindolin-2-one | Calc'd 471, found 471 |
| 2-79 | 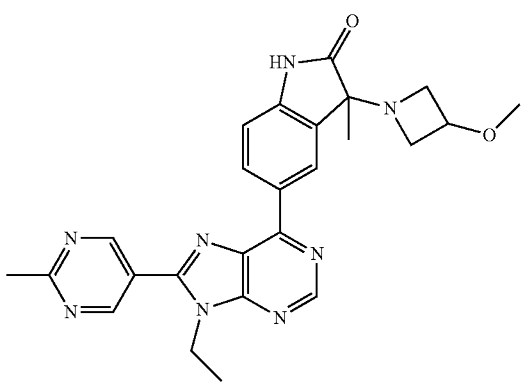 | (R or S)-5-(9-ethyl-8-(2-methylpyrimidin-5-yl)-9H-purin-6-yl)-3-(3-methoxyazetidin-1-yl)-3-methylindolin-2-one | Calc'd 471, found 471 |
| 2-80 | 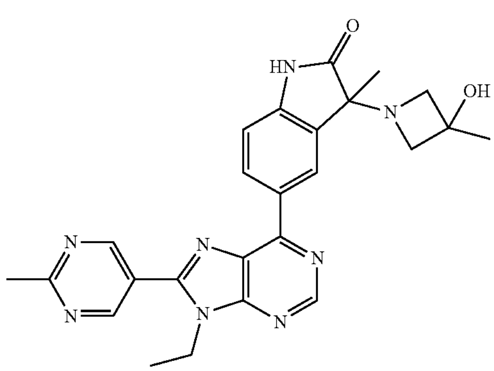 | (R or S)-5-(9-ethyl-8-(2-methylpyrimidin-5-yl)-9H-purin-6-yl)-3-(3-hydroxy-3-methylazetidin-1-yl)-3-methylindolin-2-one | Calc'd 471, found 471 |
| 2-81 | 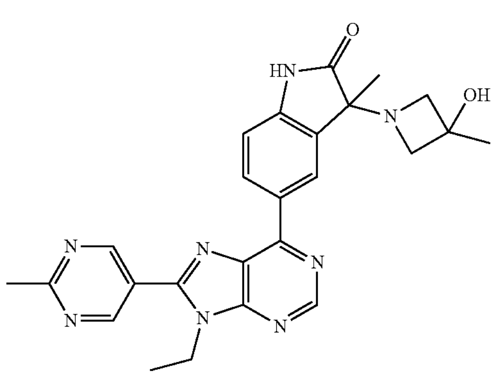 | (R or S)-5-(9-ethyl-8-(2-methylpyrimidin-5-yl)-9H-purin-6-yl)-3-(3-hydroxy-3-methylazetidin-1-yl)-3-methylindolin-2-one | Calc'd 471, found 471 |

TABLE 2-continued
| Compound | Structure | Name | Exact Mass [M + H]+ |
|---|---|---|---|
| 2-82 | 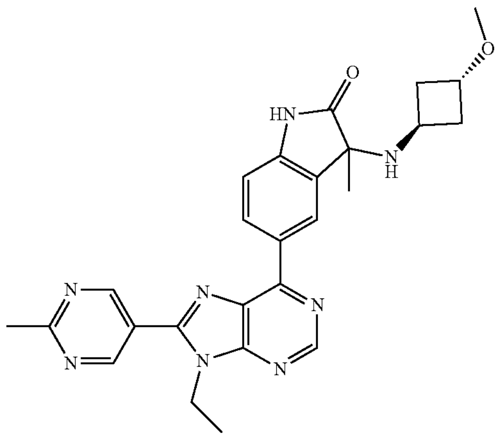 [SMILES: CCn1c(-c2cnc(C)nc2)nc2c(-c3ccc4c(c3)C(C)(N[C@H]3C[C@H](OC)C3)C(=O)N4)ncnc21] | 5-(9-ethyl-8-(2-methylpyrimidin-5-yl)-9H-purin-6-yl)-3-(((1R,3R)-3-methoxycyclobutyl)amino)-3(R or S)-methylindolin-2-one | Calc'd 485, found 485 |
| 2-83 | 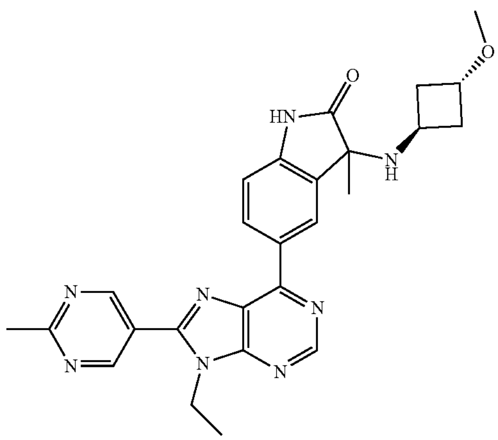 [SMILES: CCn1c(-c2cnc(C)nc2)nc2c(-c3ccc4c(c3)C(C)(N[C@H]3C[C@H](OC)C3)C(=O)N4)ncnc21] | 5-(9-ethyl-8-(2-methylpyrimidin-5-yl)-9H-purin-6-yl)-3-(((1R,3R)-3-methoxycyclobutyl)amino)-3(R or S)-methylindolin-2-one | Calc'd 485, found 485 |
Compound Examples of Table 3
Example 3A Compounds 3-4 and 3-2
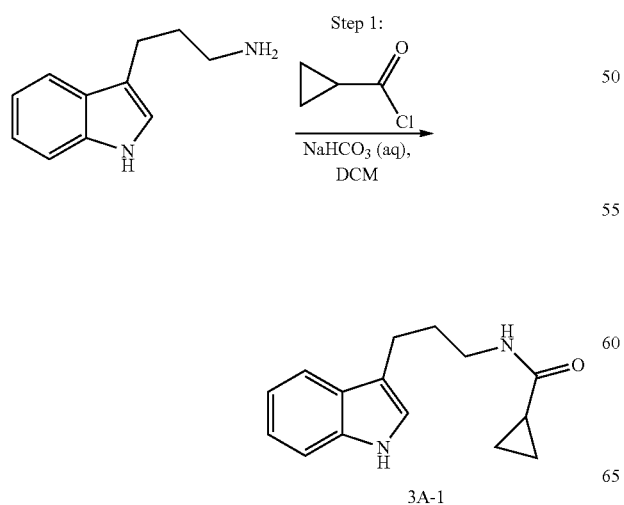

Step 5:
PdCl₂(dtbpf), K₃PO₄,
Intermediate I,
dioxane, water, 80° C.

3A-4 $\xrightarrow{\text{Step 6:}}$

Step 6:
HCl, EtOAc
Step 7:
Chiral separation

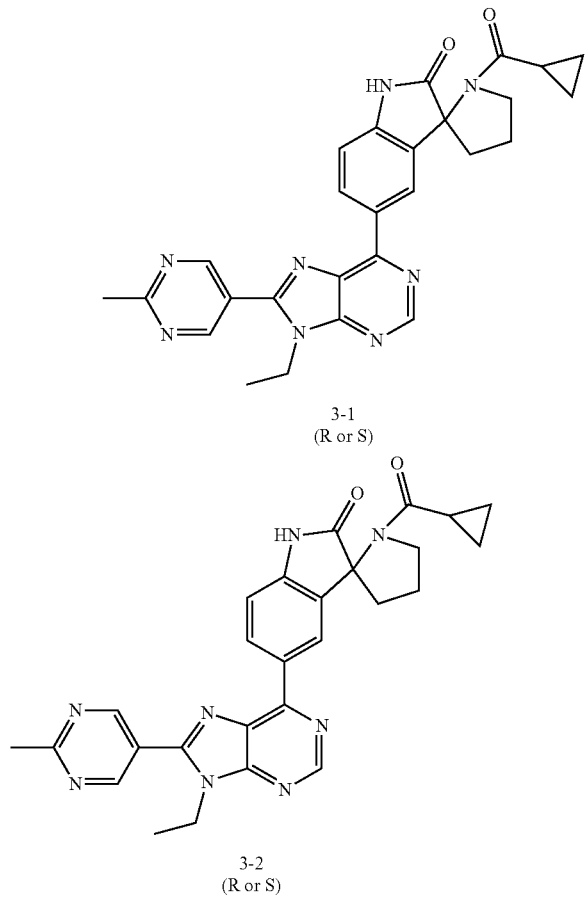

3-1
(R or S)

3-2
(R or S)

Step 1 N-(3-(1H-Indol-3-yl)propyl)cyclopropanecarboxamide (3A-1)

A mixture of 3-(1H-indol-3-yl)propan-1-amine (4.50 g, 25.8 mmol) in aqueous Na₂CO₃ (4.34 g, 51.7 mmol, dissolved in 60 mL of water) and DCM (100 mL) was treated dropwise at 0° C. with cyclopropanecarbonyl chloride (2.70 g, 25.8 mmol). The mixture was warmed to room temperature and stirred for 1 h. The reaction mixture was then diluted with DCM (300 mL), washed with brine (3×150 mL), dried over anhydrous Na₂SO₄ and filtered. The filtrate was concentrated under reduced pressure and purified by chromatography on SiO₂ (0% to 20% EtOAc/petroleum ether) to provide the title compound (3A-1). MS (EI) calc'd for $C_{15}H_{19}N_2O$ [M+H]⁺, 243; found, 243.

Step 2 5-Bromo-1'-(cyclopropanecarbonyl)spiro[indoline-3,2'-pyrrolidin]-2-one (3A-2)

A mixture N-(3-(1H-indol-3-yl)propyl)cyclopropanecarboxamide (3A-1) (5.50 g, 22.7 mmol) in THF (30 mL), t-BuOH (30 mL) and water (10 mL), was treated portionwise with NBS (12.1 g, 68.1 mmol). The mixture was stirred for 5 h, then concentrated under vacuum. The residue was then dissolved in DMF (80 mL), treated with Cs₂CO₃ (22.2 g, 68.1 mmol) and stirred for 30 min. The reaction mixture was quenched with water (100 mL) and extracted with DCM (3×150 mL). The combined organic layers were washed with brine 5×150 mL), dried (Na₂SO₄), filtered and concentrated. The residue was purified by chromatography on SiO₂ (25% EtOAc/petroleum ether) providing the title compound (3A-2). ¹H NMR (400 MHz, DMSO-d₆) 10.40 (s, 1H), 7.40 (s, 1H), 7.32 (dd, J=8.4, 2 Hz, 1H), 6.72 (d, J=8 Hz, 1H), 4.08-4.03 (m, 1H), 3.88-3.83 (m, 1H), 2.30-2.10 (m, 3H), 198-192 (m, 1H), 1.85-1.79 (m, 1H), 0.77-0.65 (m, 2H), 0.58 (m, 2H). MS (EI) calc'd for $C_{15}H_{16}BrN_2O_2$ [M+H]⁻, 335; found, 335, 337.

Step 3 tert-Butyl 5-Bromo-1'-(cyclopropanecarbonyl)-2-oxospiro[indoline-3,2'-pyrrolidine]-1-carboxylate (3A-4)

A solution of 5-bromo-1'-(cyclopropanecarbonyl)spiro[indoline-3,2'-pyrrolidin]-2-one (3A-2) (2.1 g, 6.3 mmol), NEt₃ (1.75 mL, 12.5 mmol) and DMAP (0.765 g, 6.26 mmol) in DCM (50 mL) was treated with di-tert-butyl dicarbonate (1.64 g, 7.52 mmol) and stirred for 2 h. The reaction mixture was quenched with water (100 mL) and extracted with DCM (2×100 mL). The combined organic layers were washed with brine (3×100 mL), dried (Na₂SO₄) and concentrated. The residue was purified by chromatography on SiO₂ (0-15% EtOAc/petroleum ether) to afford the product. MS (EI) calc'd for $C_{20}H_{24}BrN_2O_4$ [M+H]⁺, 435; found, 435.

Step 4 tert-Butyl-1'-(cyclopropanecarbonyl)-2-oxo-5-(4,4,5,5-tetramethyl-1,3,2-dioxaborolan-2-yl)spiro[indoline-3,2'-pyrrolidine]-1H-carboxylate (3A-4)

A mixture of tert-butyl 5-bromo-1'-(cyclopropanecarbonyl)-2-oxospiro[indoline-3,2'-pyrrolidine]-1-carboxylate (2.40 g, 5.51 mmol), (BPin)₂ (1.54 g, 6.06 mmol), KOAc (1.08 g, 11.0 mmol) and PdCl₂(dppf) (0.450 g, 0.551 mmol) in 1,4-dioxane (20 mL) was deoxygenated and stirred for 3 h at 80° C. The reaction mixture was filtered and concentrated. The residue was purified by chromatography on SiO₂ (0 to 15% EtOAc/petroleum ether) to afford the desired intermediate (3A-4). MS (EI) calc'd for $C_{26}H_{36}BN_2O_6$ [M+H]⁺, 483; found, 483.

Step 5 tert-Butyl 1'-(Cyclopropanecarbonyl)-5-(9-ethyl-8-(2-methylpyrimidin-5-yl)-9H-purin-6-yl)-2-oxospiro[indoline-3,2'-pyrrolidine]-1-carboxylate A mixture of tert-butyl 1'-(cyclopropanecarbonyl)-2-oxo-5-(4,4,5,5-tetramethyl-1,3,2-dioxaborolan-2-yl)spiro[indoline-3,2'-pyrrolidine]-1-carboxylate (3A-4) (120 g, 2.49 mmol), Intermediate I (0.683 g, 2.49 mmol), PdCl₂(dtbpf) (160 mg, 0.249 mmol) and K₃PO₄ (1.06 g, 4.98 mmol) in 1,4-dioxane (15 mL) and water (3 mL) was deoxygenated and stirred for 3 h at 80° C. After cooling to room temperature, the reaction mixture was diluted with EtOAc (100 mL), washed with brine (2×50 mL), dried (Na₂SO₄) and concentrated. The residue was purified by chromatography on SiO₂

(0 to 20% MeOH/DCM) to afford the desired product. MS (EI) calc'd for $C_{32}H_{35}N_8O_4$ [M+H]$^+$, 595; found, 595.

Step 6 1'-(Cyclopropanecarbonyl)-5-(9-ethyl-8-(2-methylpyrimidin-5-yl)-9H-purin-6-yl)spiro[indoline-3,2'-pyrrolidin]-2-one A stirred solution of tert-butyl 1'-(cyclopropanecarbonyl)-5-(9-ethyl-8-(2-methylpyrimidin-5-yl)-9H-purin-6-yl)-2-oxospiro[indoline-3,2'-pyrrolidine]-1-carboxylate (600 mg, 1.01 mmol) in EtOAc (100 ml) was treated with HCl gas by having the gas bubble through the solution for 2 h, then the resulting solution was stirred for another 3 h. The reaction was concentrated under reduced pressure and the pH adjusted to 9 with aqueous sodium carbonate (20 mL). The resulting suspension was filtered, the filter cake washed with methanol (3×30 mL). The solid was dried under reduced pressure to provide the title compound. $^1$H NMR (300 MHz, DMSO-$d_6$) δ10.75 (s, 1H), 9.26 (s, 2H), 8.97 (s, 1H), 8.90 (dd, J=8.1 Hz, 1.5 Hz, 1H), 8.60 (d, J=1.5 Hz, 1H), 7.01 (d, J=8.4 Hz, 1H), 4.45 (q, J=7.2 Hz, 2H), 4.16-4.11 (m, 1H), 3.95-3.92 (m, 1H), 2.79 (s, 3H), 2.32-2.18 (m, 3H), 2.07-2.02 (m, 1H), 1.86-1.84 (m, 1H), 1.39 (t, J=7.2 Hz, 3H), 0.77-0.56 (m, 4H). MS (EI) calc'd for $C_{27}H_{27}N_8O_2$ [M+H]$^+$, 495; found, 495.

Step 7 (R or S)- and (S or R)-1'-(Cyclopropanecarbonyl)-5-(9-ethyl-8-(2-methylpyrimidin-5-yl)-9H-purin-6-yl)spiro[indoline-3,2'-pyrrolidin]-2-one (3-1 and 3-2)

Racemic cyclopropanecarbonyl)-5-(9-ethyl-8-(2-methylpyrimidin-5-yl)-9H-purin-6-yl)spiro[indoline-3,2'-pyrrolidin]-2-one was dissolved in DMF and the enantiomers separated using chiral column chromatography [Column: ChiralPak™ IB, 21×250 mm; 220 nm detection; 70 mL/min flow rate; 30% MeOH and 0.25% Me$_2$NEt in CO$_2$]. The faster eluting enantiomer came at a retention time of 5.46 min (3-1); while the slower eluting enantiomer came at a retention time of 6.29 min (3-2). Characterization data for 3-1: $^1$H NMR (600 MHz, DMSO-$d_6$) δ 10.62 (s, 1H), 9.22 (s, 2H), 8.94 (s, 1H), 8.86 (d, 8.2 Hz, 1H), 8.57 (s, 1H), 6.97 (d, J=8.2 Hz, 1H), 4.42 (q, J=7.3 Hz, 2H), 4.12-4.09 (m, 1H), 3.92-3.88 (m, 1H), 2.75 (s, 3H), 2.27-2.25 (m, 2H), 2.18-2.13 (m, 1H), 2.03-2.00 (m, 1H), 1.83-1.82 (m, 1H), 1.35 (t, J=7.0 Hz, 3H), 0.72 (m, 1H), 0.63 (m, 1H), 0.54 (m, 1H), 0.51 (m, 1H). MS (EI) calc'd for $C_{27}H_{27}N_8O_2$ [M+H]$^+$, 495; found, 495. Characterization data for 3-2: $^1$H NMR (600 MHz, DMSO-$d_6$) δ 10.62 (s, 1H), 9.21 (s, 2H), 8.93 (s, 1H), 8.86 (d, J=7.9 Hz, 1H), 8.57 (s, 1H), 6.97 (d, J=8.2 Hz, 1H), 4.41 (q, J=7.0 Hz, 2H), 4.11-4.09 (m, 1H), 3.90-3.89 (m, 1H), 2.75 (s, 3H), 2.27-2.23 (m, 2H), 2.18-2.14 (m, 1H), 2.03-2.00 (m, 1H), 1.82-1.81 (m, 1H), 1.35 (t, J=7.3 Hz, 3H), 0.72 (m, 1H), 0.63 (m, 1H), 0.54 (m, 1H), 0.51 (m, 1H). MS (EI) calc'd for $C_{27}H_{27}N_8O_2$ [M+H]$^+$, 495; found, 495.

Example 3B Compounds 3-3 and 3-4

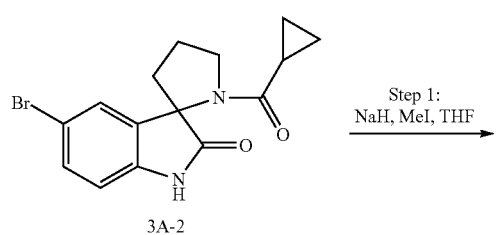

3A-2

Step 1: NaH, MeI, THF

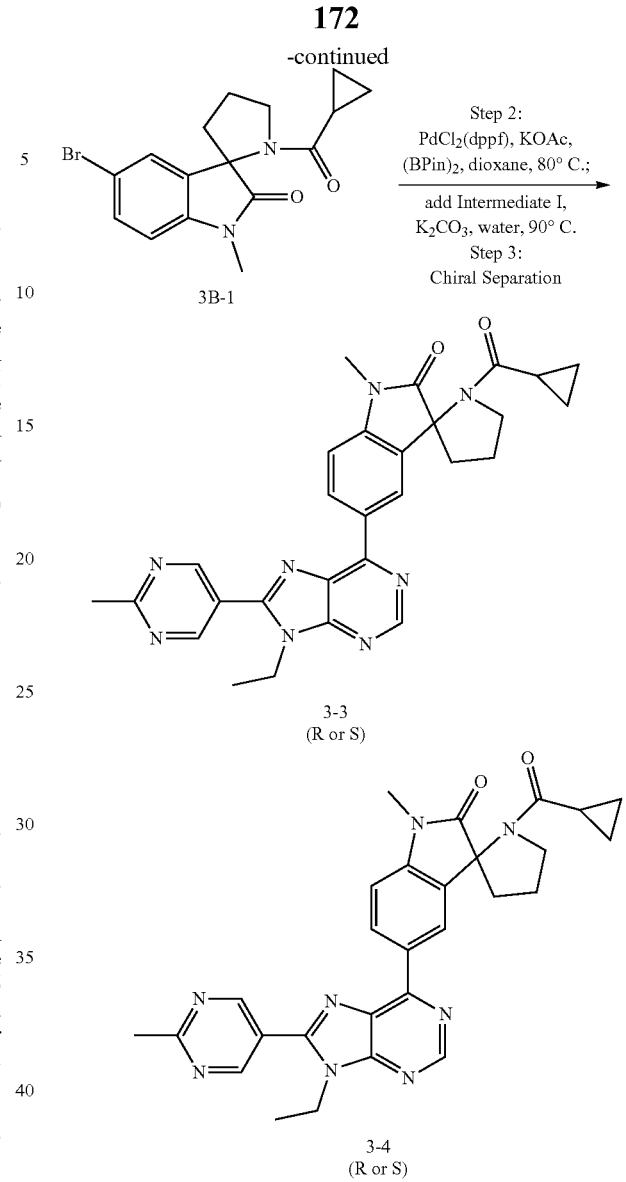

Step 1 5-Bromo-1'-(cyclopropanecarbonyl)-1-methylspiro[indoline-3,2'-pyrrolidin]-2-one (3B-1)

A solution of 5-bromo-1'-(cyclopropanecarbonyl)spiro[indoline-3,2'-pyrrolidin]-2-one (3A-2) (200 mg, 0.59 mmol; prepared as described in Example 3A) in THF (6 mL) was treated with 60% NaH (48 mg, 1.2 mmol) at 0° C. The resulting mixture was stirred for 20 min at 0° C., then treated with iodomethane (0.050 mL, 0.72 mmol). The reaction mixture was stirred for 5 h at RT and then quenched with water (5 mL). The resulting mixture was extracted with EtOAc (3×15 mL) and the combined organic layers washed with brine (2×15 mL), dried (Na$_2$SO$_4$) and concentrated. The residue was purified by chromatography on SiO$_2$ (1:30 MeOH/DCM) to provide the product (3B-1). MS (EI) calc'd for $C_{16}H_{18}BrN_2O_2$ [M+H]$^+$, 349; found, 349.

Step 2 1'-(Cyclopropanecarbonyl)-5-(9-ethyl-8-(2-methylpyrimidin-5-yl)-9H-purin-6-yl)-1-methylspiro[indoline-3,2'-pyrrolidin]-2-one A mixture of 5-bromo-1'-(cyclopropanecarbonyl)-1-methylspiro[indoline-3,2'-pyrrolidin]-2-one (150 mg, 0.430 mmol), KOAc (84 mg, 0.86 mmol), (BPin)$_2$ (120 mg, 0.472 mmol) and PdCl$_2$(dppf) (70 mg, 0.086 mmol) in 1,4-dioxane (2 mL) was deoxygenated and stirred for 2 h at 80° C. After cooling to room temperature, K$_2$CO$_3$ (119 mg, 0.859 mmol), Intermediate I (118 mg, 0.430 mmol) and water (0.4 mL) were added and the reaction mixture stirred for 3 h at 90° C. The reaction mixture was diluted with EtOAc (30 mL), washed with brine (3×15 mL), dried over anhydrous sodium sulfate and filtered. The filtrate was concentrated and the residue purified by chromatography on SiO$_2$ (1:15 MeOH/DCM) to provide the desired product. MS (EI) calc'd for C$_{28}$H$_{29}$N$_8$O$_2$ [M+H]$^+$, 509; found, 509.

Step 3 (R or S)- and (S or R)-1'-(Cyclopropanecarbonyl)-5-(9-ethyl-8-(2-methylpyrimidin-5-yl)-9H-purin-6-yl)-1-methylspiro[indoline-3,2'-pyrrolidin]-2-one (3-3 and 3-4)

The racemic material from step 2 was separated by chiral column chromatography [Column: (R,R) WHELK-O™ 1 (Regis Technologies, Inc., Morton Grove, Ill. USA) 5/100 Kromasil 21×250 mm; MeOH with 0.1% diethylamine; Flow rate: 20 mL/min; Detector 220 nm; Retention time 1: 15.0 min; Retention time 2: 18.0 min]. The faster-eluting enantiomer of the title compound (3-3) was obtained at 15.0 min. $^1$H NMR (300 MHz, DMSO-d$_6$) δ 9.26 (s, 2H), 8.99 (s, 1H), 8.97 (d, J=7.2 Hz, 1H), 8.65 (d, J=1.5 Hz, 1H), 7.21 (d, J=8.1 Hz, 1H), 4.49-4.42 (m, 2H), 4.17-4.14 (m, 1H), 3.97-3.94 (m, 1H), 3.18 (s, 3H), 2.78 (s, 3H), 2.34-2.03 (m, 4H), 1.88-1.83 (m, 1H), 1.39 (t, J=7.2. Hz, 3H), 0.69-0.51 (m, 4H). MS (EI) calc'd for C$_{28}$H$_{29}$N$_8$O$_2$ [M+H]$^+$, 509; found, 509. The slower-eluting enantiomer of the title compound (3-4) was obtained at 18.0 min. $^1$H NMR (300 MHz, DMSO-d$_6$) δ 9.26 (s, 2H), 8.99 (s, 1H), 8.97 (d, J=7.2 Hz, 1H), 8.65 (d, J=1.5 Hz, 1H), 7.21 (d, J=8.1 Hz, 1H), 4.49-4.42 (m, 2H), 4.17-4.14 (m, 1H), 3.97-3.94 (m, 1H), 3.18 (s, 3H), 2.78 (s, 3H), 2.34-2.03 (m, 4H), 1.88-1.83 (m, 1H), 1.39 (t, J=7.2. Hz, 3H), 0.69-0.51 (m, 4H). MS (EI) calc'd for C$_{28}$H$_{29}$N$_8$O$_2$ [M+H]$^+$, 509; found, 509.

Example 3C Compounds 3-5 and 3-6

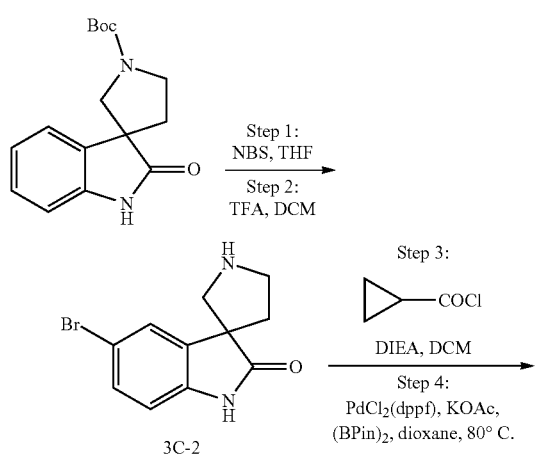

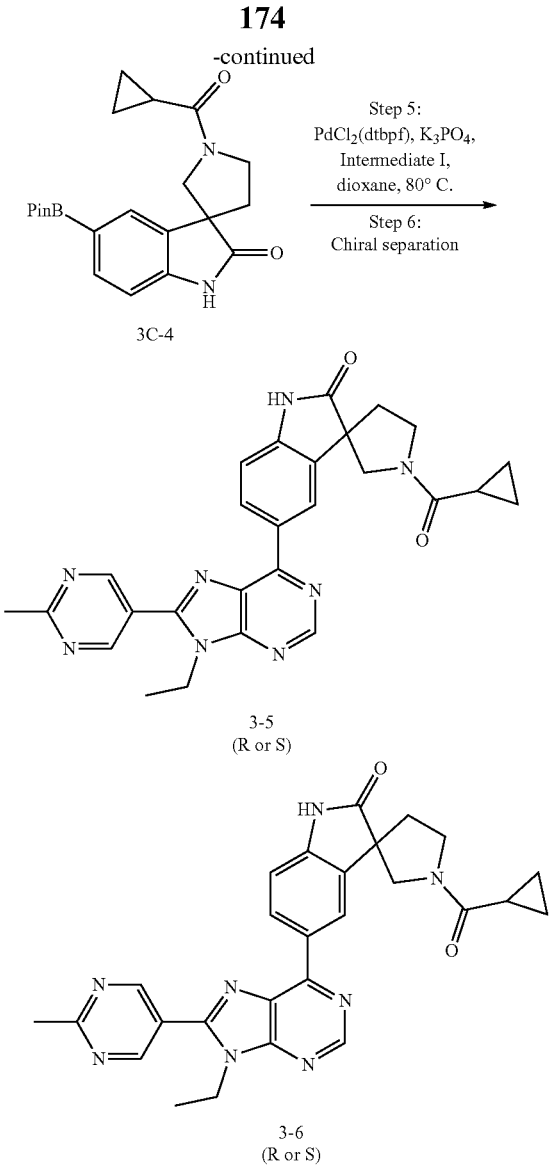

Steps 1-2 5-Bromospiro[indoline-3,3'-pyrrolidin]-2-one (3C-2)

A mixture containing commercially available tert-butyl 2-oxospiro[indoline-3,3'-pyrrolidine]-1'-carboxylate (391 mg, 1.36 mmol) and NBS (290 mg, 1.63 mmol) in THF (5 mL) was heated to reflux and stirred for 20 h. The reaction mixture was then cooled, quenched with water, and extracted with EtOAc. The organic layer was concentrated and purified by chromatography on SiO$_2$ (2-20% MeOH/DCM) to provide tert-butyl 5-bromo-2-oxospiro[indoline-3,3'-pyrrolidine]-1'-carboxylate. MS (EI) calc'd for C$_{16}$H$_{20}$BrN$_2$O$_3$ [M+H]$^+$, 367; found, 367.

A solution of tert-butyl 5-bromo-2-oxospiro[indoline-3,3'-pyrrolidine]-1'-carboxylate (300 mg, 0.817 mmol) in 5 mL of DCM was treated with 1 mL of TFA and stirred for 1 h. The reaction mixture was concentrated to give 5-bromospiro[indoline-3,3'-pyrrolidin]-2-one (3C-2) as a TFA salt. MS (EI) calc'd for C$_{11}$H$_{12}$BrN$_2$O [M+H]$^+$, 267; found, 267.

Steps 3-4 1'-(Cyclopropanecarbonyl)-5-(4,4,5,5-tetramethyl-1,3,2-dioxaborolan-2-yl)spiro[indoline-3,3'-pyrrolidin]-2-one (3C-4)

A solution of 5-bromospiro[indoline-3,3'-pyrrolidin]-2-one (3C-2) (150 mg, 0.412 mmol) in 5 mL in DCM was treated at 0° C. with NEt$_3$ (0.34 mL, 2.5 mmol) and cyclopropanecarbonyl chloride (43 mg, 0.41 mmol). The mixture was stirred for 30 min, then partitioned between EtOAc and water. The organic layer was dried (MgSO$_4$) and concentrated. The residue was purified by chromatography on SiO$_2$ (70% EtOAc/hexanes) to give 5-bromo-1'-(cyclopropanecarbonyl)spiro[indoline-3,3'-pyrrolidin]-2-one. MS (EI) calc'd for C$_{15}$H$_{16}$BrN$_2$O$_2$ [M+H]$^+$, 335; found, 335.

A mixture of 5-bromo-1'-(cyclopropanecarbonyl)spiro[indoline-3,3'-pyrrolidin]-2-one (137 mg, 0.409 mmol), (BPin)$_2$ (125 mg, 0.490 mmol), KOAc (100 mg, 1.02 mmol) and SPhos biphenyl precatalyst (32 mg, 0.041 mmol) in dioxane (4 mL) was deoxygenated by exchanging vacuum and nitrogen gas. The mixture was stirred at 85° C. for 2 h, filtered through CELITE and concentrated. The residue was purified by chromatography on SiO$_2$ (2-20% MeOH/DCM) to give 1'-(cyclopropanecarbonyl)-5-(4,4,5,5-tetramethyl-1,3,2-dioxaborolan-2-yl)spiro[indoline-3,3'-pyrrolidin]-2-one (3C-4). MS (EI) calc'd for C$_{21}$H$_{28}$BN$_2$O$_4$ [M+H]$^+$, 383; found, 383.

Steps 5-6 (R or S)- and (S or R)-1'-(Cyclopropanecarbonyl)-5-(9-ethyl-8-(2-methylpyrimidin-5-yl)-9H-purin-6-yl)spiro[indoline-3,3'-pyrrolidin]-2-one (3-5 and 3-6)

A mixture of 1'-(cyclopropanecarbonyl)-5-(4,4,5,5-tetramethyl-1,3,2-dioxaborolan-2-yl)spiro[indoline-3,3'-pyrrolidin]-2-one (3C-4) (56 mg, 0.15 mmol), Intermediate I (40 mg, 0.15 mmol), and PdCl$_2$(dtbpf)/K$_3$PO$_4$ complex (13 mg, 0.015 mmol) in 2 mL of dioxane was deoxygenated by exchanging vacuum and nitrogen. A 2 M solution of Na$_2$CO$_3$ (0.15 mL, 0.29 mmol) was added and the reaction stirred overnight at 80° C. The mixture was partitioned between DCM and water, and the organic layer dried (Na$_2$SO$_4$) and concentrated. Reverse phase chromatography (MeCN/water with 0.1% TFA) gave racemic 1'-(cyclopropanecarbonyl)-5-(9-ethyl-8-(2-methylpyrimidin-5-yl)-9H-purin-6-yl)spiro[indoline-3,3'-pyrrolidin]-2-one. MS (EI) calc'd for C$_{27}$H$_{27}$N$_8$O$_2$ [M+H]$^+$, 495; found, 495.

The racemic material was then dissolved in MeOH/MeCN and resolved using chiral column chromatography [Column: ChiralPak™ AS-H, 21×250 mm; 220 nm detection; 70 mL/min flow rate; 35% MeOH and 0.25% DMEA in CO$_2$]. The faster eluting enantiomer came at a retention time of 2.86 min (3-5), while the slower eluting enantiomer came at a retention time of 3.67 min (3-6). Characterization data for 3-5: $^1$H NMR (600 MHz, DMSO-d$_6$) δ 10.87 (m, 1H), 9.18 (m, 2H), 8.92 (m, 1H), 8.64-8.88 (m, 2H), 7.06 (m, 1H), 437 (m, 2H), 4.01-4.07 (m, 1H), 3.89 (m, 1H), 3.72 (m, 1H), 3.55 (m, 1H), 2.72 (m, 3H), 2.10-2.40 (m, 2H), 1.65-1.80 (m, 1H), 1.32 (t, J=7.0 Hz, 3H), 0.65-0.75 (m, 3H), 0.50-0.65 (m, 1H); MS (EI) calc'd for C$_{27}$H$_{27}$N$_8$O$_2$ [M+H]$^-$, 495; found, 495. Characterization data for 3-6: $^1$H NMR (600 MHz, DMSO-d$_6$) δ 10.93 (m, 1H), 9.24 (m, 2H), 8.97 (m, 1H), 8.70-8.93 (m, 2H), 7.12 (m, 1H), 4.41-4.45 (m, 2H), 3.98-4.12 (m, 1H), 3.92 (m, 1H), 3.77 (m, 1H), 3.58-3.64 (m, 1H), 2.77 (m, 3H), 2.17-2.41 (m, 2H), 1.75-1.82 (m, 1H), 1.38 (t, J=7.2 Hz, 3H), 0.70-0.75 (m, 3H), 0.56-0.63 (m, 1H). MS (EI) calc'd for C$_{27}$H$_{27}$N$_8$O$_2$ [M+H]$^+$, 495; found, 495.

Example 3D Compounds 3-7 and 3-8

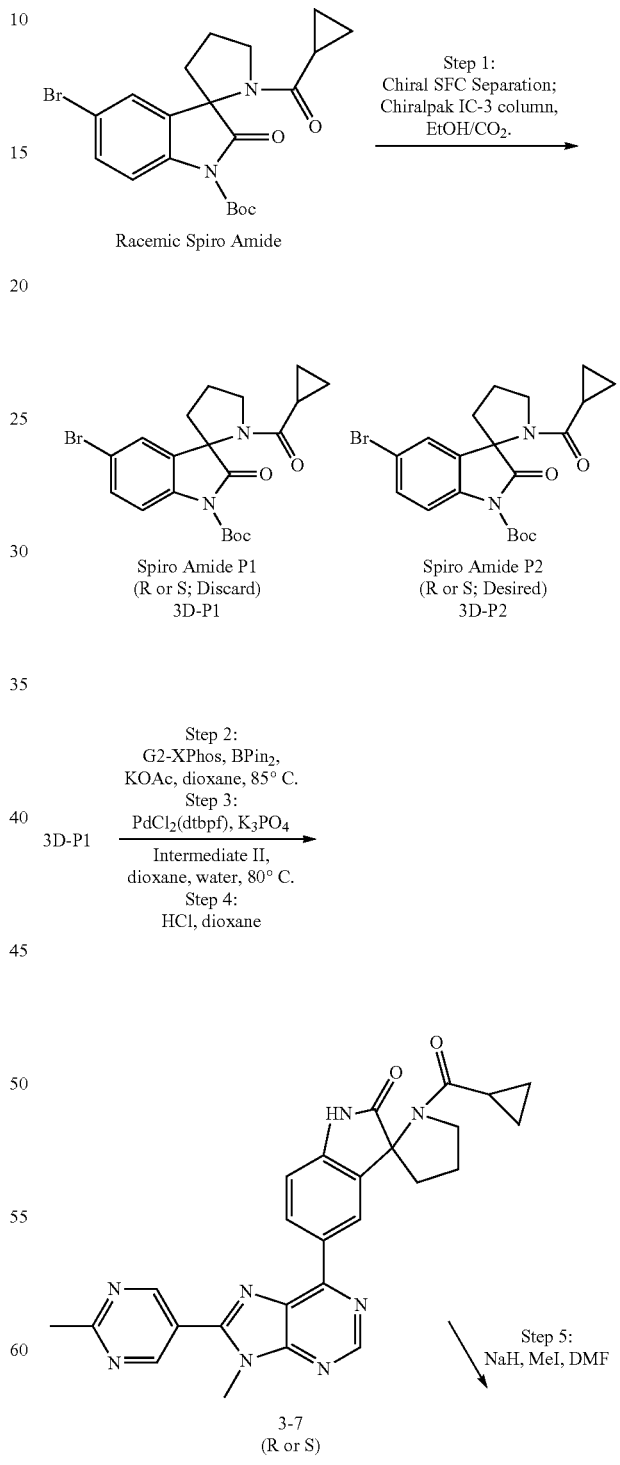

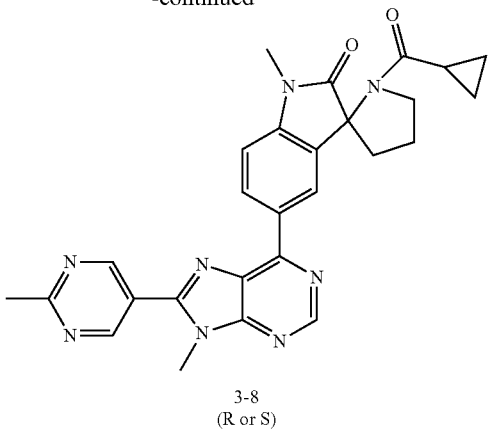

3-8
(R or S)

Step 1 (R or S)-tert-Butyl 5-Bromo-1'-(cyclopropanecarbonyl)-2-oxospiro[indoline-3,2'-pyrrolidine]-1-carboxylate (3D-P1 and 3D-P2)

Racemic tert-butyl 5-bromo-1'-(cyclopropanecarbonyl)-2-oxospiro[indoline-3,2'-pyrrolidine]-1-carboxylate, the synthesis of which was described earlier for Example 3A, was resolved into separate enantiomers using chiral SFC chromatography [Column: ChiralPak™ IC-3 3 μm; 25% EtOH with 0.05% isopropylamine and 75% CO$_2$; Flow rate: 4 mL/min; Detector 220 nm; Retention time 1: 1.07 min; Retention time 2: 1.42 min]. The faster-eluting enantiomer came at a retention time of 1.07 min, and was discarded (3D-P2). The slower-eluting enantiomer came at a retention time of 1.42 min and was collected and carried forward through the synthesis as non-racemic material (30-P2).

Steps 2-4 (R or S)-1'-(Cyclopropanecarbonyl)-5-(9-methyl-8-(2-methylpyrimidin-5-yl)-9H-purin-6-yl)spiro[indoline-3,2'-pyrrolidin]-2-one (3-7)

A suspension of (R or S)-tert-butyl 5-bromo-1'-(cyclopropanecarbonyl)-2-oxospiro[indoline-3,2'-pyrrolidine]-1-carboxylate (3D-P2) (Spiro Amide P2; 2.5 g, 5.8 mmol), G2-XPhos (200 mg, 0.250 mmol), KOAc (800 mg, 8.2 mmol) and (BPin)$_2$ (2.0 g, 7.9 mmol) in 15 mL of dioxane was deoxygenated by bubbling nitrogen for 10 min. The reaction mixture was warmed to 85° C. and stirred for 24 h, then filtered and concentrated. The residue was then dissolved in dioxane (20 mL) and treated with Intermediate II (1.5 g, 5.8 mmol), PdCl$_2$(dtbpf) (180 mg, 0.28 mmol) and 2 M aqueous K$_3$PO$_4$ (4.7 mL, 9.4 mmol). The resulting suspension was deoxygenated by bubbling nitrogen for 10 min and stirred overnight at 80° C. The mixture was diluted with DCM and washed with water. The organic layer was dried (Na$_2$SO$_4$) and concentrated to dryness. Chromatography on SiO$_2$ (7-60% EtOAc/DCM then 2 to 20% MeOH/DCM) gave the desired Boc-protected intermediate. MS (EI) calc'd for C$_{31}$H$_{33}$N$_8$O$_4$ [M+H]$^+$, 581; found, 581.

A solution of (R or S)-tert-butyl 1'-(cyclopropanecarbonyl)-5-(9-methyl-8-(2-methylpyrimidin-5-yl)-9H-purin-6-yl)-2-oxospiro[indoline-3,2'-pyrrolidine]-1-carboxylate (615 mg, 1.06 mmol) in 15 mL of DCM was treated with a 4 M solution of HCl in dioxane (3.0 mL, 12 mmol) and stirred for 2 h. The mixture was concentrated and dried under vacuum to provide the HCl salt of 3-7. $^1$H NMR (600 MHz, DMSO-d$_6$) δ 10.63 (s, 1H), 9.28 (s, 2H), 8.93 (s, 1H), 8.87 (d, J=8.2 Hz, 1H), 8.57 (s, 1H), 6.98 (d, J=8.2 Hz, 1H), 4.10 (m, 1H), 3.95 (s, 3H), 3.90 (q, J=9.7 Hz, 1H), 2.74 (s, 3H), 2.26 (m, 2H), 2.16 (m, 1H), 2.02 (m, 1H), 1.82 (m, 1H), 0.71 (m, 1H), 0.63 (m, 1H), 0.54 (m, 1H), 0.50 (m, 1H). MS (EI) calc'd for C$_{26}$H$_{25}$N$_8$O$_2$ [M+H]$^+$, 481; found, 481.

Step 5 (R or S)-1'-(Cyclopropanecarbonyl)-1-methyl-5-(9-methyl-8-(2-methyl pyrimidin-5-yl)-9H-purin-6-yl)spiro[indoline-3,2'-pyrrolidin]-2-one (3-8)

A mixture containing 1'-(cyclopropanecarbonyl)-5-(9-methyl-8-(2-methylpyrimidin-5-yl)-9H-purin-6-yl)spiro[indoline-3,2'-pyrrolidin]-2-one (compound 3-7; 80 mg, 0.17 mmol) in dioxane (1 mL) was treated with 60% sodium hydride (10 mg, 0.42 mmol), stirred for 10 min, then treated with iodomethane (70 mg, 0.49 mmol). The reaction mixture was stirred for 4 hours, then concentrated, suspended in DMSO and filtered. Reverse phase chromatography (MeCN/water with 0.1% NH$_4$OH modifier) gave the desired product 3-8. $^1$H NMR (600 MHz, DMSO-d$_6$) δ 9.29 (s, 2H), 8.97 (dd, J=8.2, 1.5 Hz, 1H), 8.94 (s, 1H), 8.62 (s, 1H), 7.18 (d, J=8.2 Hz, 1H), 4.12 (m, 1H), 3.96 (s, 3H), 3.92 (q, J=10 Hz, 1H), 3.14 (s, 3H), 2.74 (s, 3H), 2.29 (m, 2H), 2.17 (m, 1H), 2.04 (m, 1H), 1.82 (m, 1H), 0.71 (m, 1H), 0.63 (m, 1H), 0.54 (m, 1H), 0.49 (m, 1H). MS (EI) calc'd for C$_{27}$H$_{27}$N$_8$O$_2$ [M+H]$^+$, 495; found, 495.

Example 3E Compounds 3-11 and 3-12

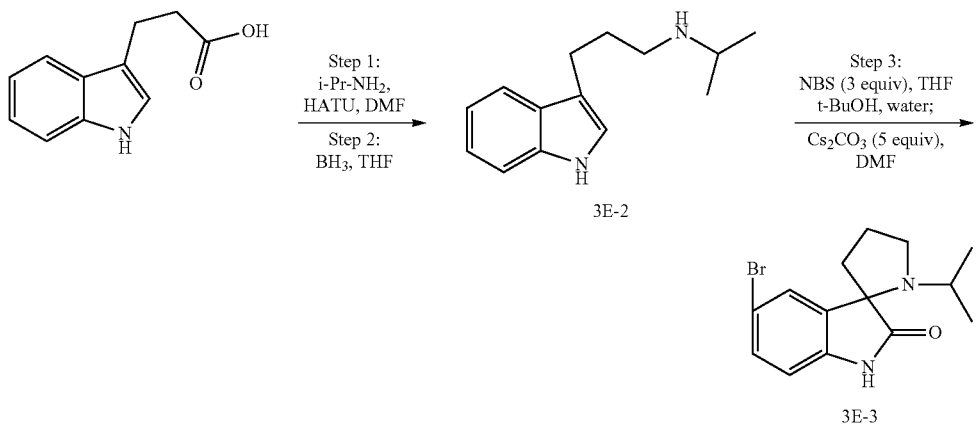

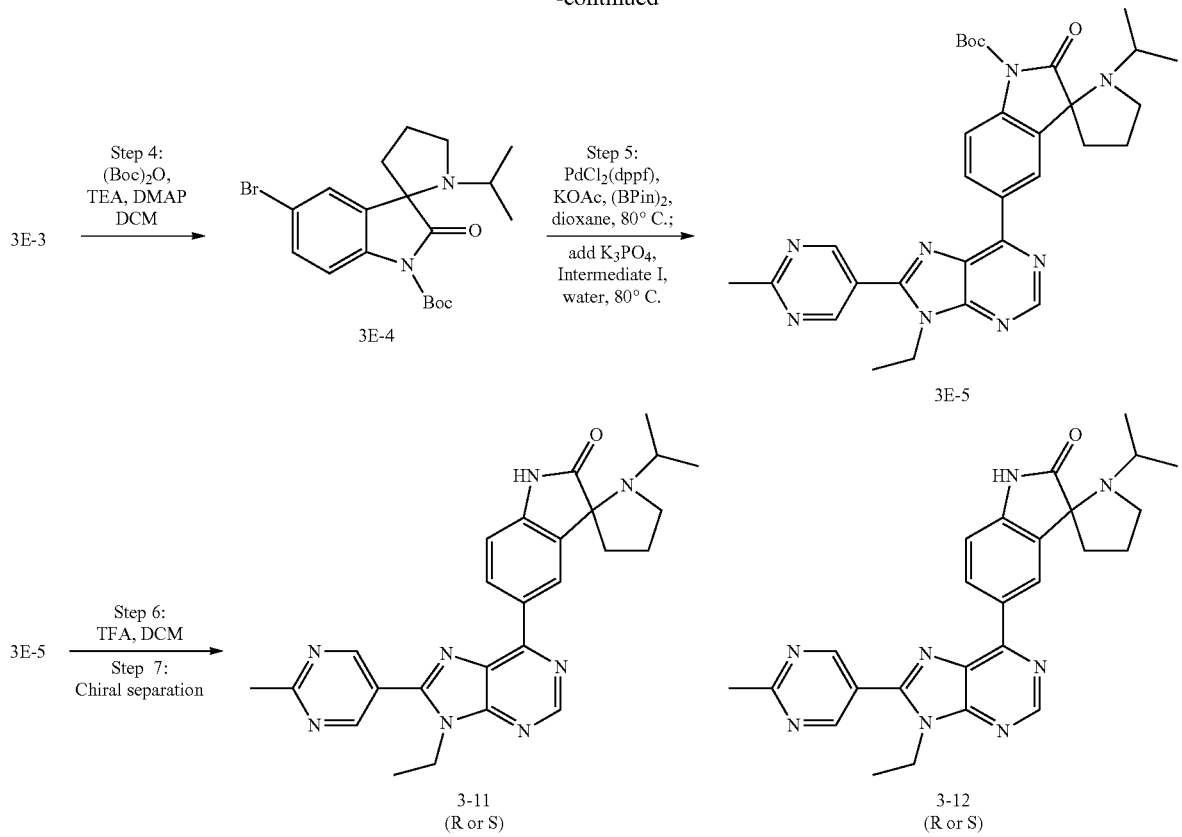

Steps 1-2 3-(1H-Indol-3-yl)-N-isopropylpropan-1-amine (3E-2)

A solution of 3-(1H-indol-3-yl)propanoic acid (500 mg, 2.64 mmol) in DMF (10 mL) was treated with isopropylamine (0.300 mL, 3.50 mmol) and HATU (1.20 g, 3.16 mmol). The reaction mixture was stirred for 3 hours, then concentrated to dryness. The residue was then taken-up into EtOAc and washed with 1 N HCl and sat'd NaHCO$_3$, the organic layer was dried (Na$_2$SO$_4$) and concentrated to dryness. The residue was dissolved in THF (10 mL) and treated with a 1 M THF solution of borane-THF complex (4.0 mL, 4.0 mmol) and stirred overnight at 70° C. Once cool, the reaction was quenched dropwise with methanol and concentrated. The residue was purified by chromatography on SiO$_2$ (0-50% MeOH/DCM) to provide the desired amine (3E-2). MS (EI) calc'd for C$_{14}$H$_{21}$N$_2$ [M+H]$^+$, 217; found, 217.

Step 3 5-Bromo-1'-isopropylspiro[indoline-3,2'-pyrrolidin]-2-one (3E-3)

A solution of 3-(1H-indol-3-yl)-N-isopropylpropan-1-amine (3E-2) (400 mg, 1.85 mmol) in THF (4 mL), tert-butyl alcohol (4 mL) and water (2 mL) was treated with NBS (1.0 g, 5.6 mmol) and the reaction mixture stirred for 10 min. The mixture was concentrated to dryness, dissolved into DMF (5 mL), then treated with cesium carbonate (3.0 g, 9.2 mmol) and stirred for 30 min. The suspension was filtered through a pad of CELITE and concentrated to dryness. The solid residue was suspended in DCM, filtered and concentrated. The desired product is soluble in DCM. The crude material was purified by reverse phase chromatography (MeCN/water with 0.1% TFA modifier) to provide the desired spirocycle (3E-3) as a TFA salt. MS (EI) calc'd for C$_{14}$H$_{18}$BrN$_2$O [M+H]$^+$, 309; found, 309.

Step 4 tert-Butyl 5-Bromo-1'-isopropyl-2-oxospiro [indoline-3,2'-pyrrolidine]-1'-carboxylate (3E-4)

A solution of 5-bromo-1'-isopropylspiro[indoline-3,2'-pyrrolidin]-2-one (3E-3), TFA salt (110 mg, 0.260 mmol) in DCM (1 mL) was treated with DMAP (6 mg, 0.05 mmol), Boc$_2$O (75 mg, 0.34 mmol) and Hunig's base (0.10 mL, 0.57 mmol), then stirred for 3 h. The mixture was concentrated to dryness and purified by chromatography on SiO$_2$ (0-20% MeOH/DCM) to provide the desired product (3E-4). MS (EI) calc'd for C$_{19}$H$_{26}$BrN$_2$O$_3$[M+H]$^+$, 409; found, 409.

Step 5 tert-Butyl 5-(9-Ethyl-8-(2-methylpyrimidin-5-yl)-9H-purin-6-yl)-1'-isopropyl-2-oxospiro[indoline-3,2'-pyrrolidine]-1-carboxylate (3E-5)

A mixture containing tert-butyl 5-bromo-1'-isopropyl-2-oxospiro[indoline-3,2'-pyrrolidine]-1-carboxylate (3E-4) (105 mg, 0.257 mmol) in dioxane (1 mL) was treated with PdCl$_2$(dppf) (20 mg, 0.024 mmol), KOAc (35 mg, 0.36 mmol) and (BPin)$_2$ (75 mg, 0.30 mmol). The reaction was stirred for 3 hours at 100° C. and cooled to RT. The mixture was treated with more PdCl$_2$(dppf) (20 mg, 0.024 mmol), Intermediate I (60 mg, 0.22 mmol) and 1 M aqueous K$_3$PO$_4$ (0.60 mL, 0.60 mmol) and stirred overnight at 80° C. The mixture was filtered and purified by reverse phase chromatography (MeCN/water with 0.1% TFA) to provide the desired product (3E-5).

Steps 6-7 (R or S)- and (S or R)-5-(9-ethyl-8-(2-methylpyrimidin-5-yl)-9H-purin-6-yl)-1'-isopropyl-spiro[indoline-3,2'-pyrrolidin]-2-one (3-11 and 3-12)

A solution of tert-butyl 5-(9-ethyl-8-(2-methylpyrimidin-5-yl)-9H-purin-6-yl)-1'-isopropyl-2-oxospiro[indoline-3,2'-pyrrolidine]-1-carboxylate (3E-5) (35 mg, 0.051 mmol) in 1 mL of 1:1 TFA/DCM and stirred for 30 min. The residue was concentrated to an oil and resolved using chiral column chromatography [Column: ChiralPak™ AS-H; 25% MeOH with 0.25% Me$_2$NEt and 75% CO$_2$; Flow rate: 70 mL/min; Detector 220 nm; Retention time 1: 4.39 min; Retention time 2: 6.48 min]. The faster-eluting enantiomer (retention time 4.39 min) became identified as compound 3-11, while the slower-eluting enantiomer (retention time 6.48 min) became identified as compound 3-12. Characterization data for 3-11: $^1$H NMR (600 MHz, DMSO-d$_6$) □ 10.57 (s, 1H), 9.20 (s, 2H), 8.94 (s, 1H), 8.80 (dd, J=8.2, 1.5 Hz, 1H), 8.71 (s, 1H), 7.00 (d, J=7.9 Hz, 1H), 4.21 (q, J=7.3 Hz, 2H), 3.25 (m, 1H), 3.16 (m, 1H), 2.74 (s, 3H), 2.73 (m, 1H), 2.00-2.10 (m, 3H), 1.91 (m, 1H), 1.35 (t, J=7.0 Hz, 3H), 0.82 (d, J=6.2 Hz, 3H), 0.80 (d, J=6.5 Hz, 3H). MS (EI) calc'd for C$_{26}$H$_{29}$N$_8$O [M+H]$^+$, 469; found, 469. Characterization data for 3-12: $^1$H NMR (600 MHz, DMSO-d$_6$) δ 10.57 (s, 1H), 9.20 (s, 2H), 8.95 (s, 1H), 8.80 (dd, J=8.2, 1.8 Hz, 1H), 8.71 (s, 1H), 7.00 (d, J=8.2 Hz, 1H), 4.42 (q, J=7.3 Hz, 2H), 3.25 (m, 1H), 3.16 (m, 1H), 2.75 (s, 3H), 2.73 (m, 1H), 2.00-2.10 (m, 3H), 1.91 (m, 1H), 1.35 (t, J=7.0 Hz, 3H), 0.82 (d, J=6.5 Hz, 3H), 0.80 (d, J=6.5 Hz, 3H). MS (EI) calc'd for C$_{26}$H$_{29}$N$_8$O [M+H]$^+$, 469; found, 469.

Example 3F Compound 3-17

Steps 1-2 (R or S)-1'-(Cyclopropanecarbonyl)-1-(2-hydroxy-2-methylpropyl)-5-(9-methyl-8-(2-methylpyrimidin-5-yl)-9H-purin-6-yl)spiro[indoline-3,2'-pyrrolidin]-2-one (3-17)

A solution of (R or S)-1'-(cyclopropanecarbonyl)-5-(9-methyl-8-(2-methylpyrimidin-5-yl)-9H-purin-6-yl)spiro[indoline-3,2'-pyrrolidin]-2-one hydrochloride (compound 3-7; 0.30 g, 0.58 mmol) in 5 mL of DMF was treated at 0° C. with 60% NaH in mineral oil (58 mg, 1.5 mmol). After stirring for 10 min, 3-bromo-2-methylprop-1-ene (86 mg, 0.64 mmol) was added and the mixture stirred for another 4 h. The reaction was quenched with water and extracted with EtOAc. The organic layer was washed with brine, dried (Na$_2$SO$_4$) and concentrated. The residue was purified by chromatography on SiO$_2$ (0%-6% MeOH/DCM) to afford (R or S)-1'-(cyclopropanecarbonyl)-1-(2-hydroxy-2-methylpropyl)-5-(9-methyl-8-(2-methylpyrimidin-5-yl)-9H-purin-6-yl)spiro[indoline-3,2'-pyrrolidin]-2-one. MS (ESI) calc'd for C$_{30}$H$_{31}$N$_8$O$_2$ [M+H]$^+$, 535; found, 535.

A solution of (R or S)-1'-(cyclopropanecarbonyl)-5-(9-methyl-8-(2-methylpyrimidin-5-yl)-9H-purin-6-yl)-1-(2-methylallyl)spiro[indoline-3,2'-pyrrolidin]-2-one (50 mg, 0.090 mmol) in aqueous of hydrogen chloride (2.0 mL, 12 mmol, 6 M in water) was stirred for 3 h at 90° C. After cooling to room temperature, the pH of the reaction was adjusted to 8 by the addition of saturated aqueous of sodium bicarbonate (10 mL). The mixture was extracted with EtOAc, washed with brine, dried (Na$_2$SO$_4$) and filtered. The filtrate was concentrated and the residue purified by Prep-HPLC [Column: XBridge® Prep C18 OBD (Waters Corporation, Milford Mass. USA), 5 μm; 25%-57% MeCN/water with 10 mM NH$_4$HCO$_3$; Flow rate: 20 mL/min; Detector 254, 220 nm; Retention time: 3 min] to provide 3-17. $^1$H NMR (300 MHz, DMSO-d$_6$) δ 9.33 (s, 2H), 8.98 (s, 1H), 8.93 (d, J=8.4 Hz, 1H), 8.63 (d, J=1.8 Hz, 1H), 7.38 (d, J=8.4 Hz, 1H), 4.59 (s, 1H), 4.19-4.15 (m, 1H), 4.00-3.96 (m, 4H), 3.75-3.71 (m, 1H), 3.55-3.50 (m, 1H), 2.78 (s, 3H), 2.34-2.21 (m, 3H), 2.15-2.09 (m, 1H),1.89-1.85 (m, 1H), 1.20 (s, 3H), 1.12 (s, 3H), 0.80-0.65 (m, 2H), 0.59-0.51 (m, 2H). MS (ESI) calc'd for C$_{30}$H$_{33}$N$_8$O$_3$ [M+H]$^+$, 553; found, 553.

Example 3G Compound 3-18

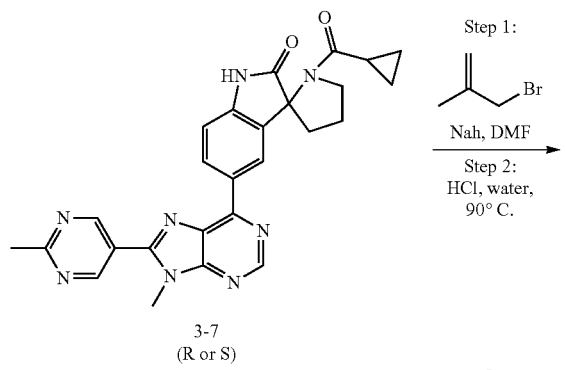

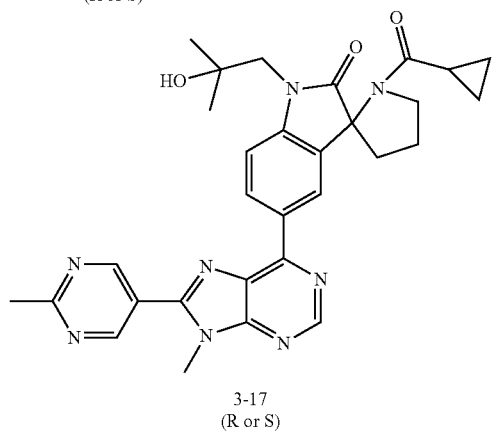

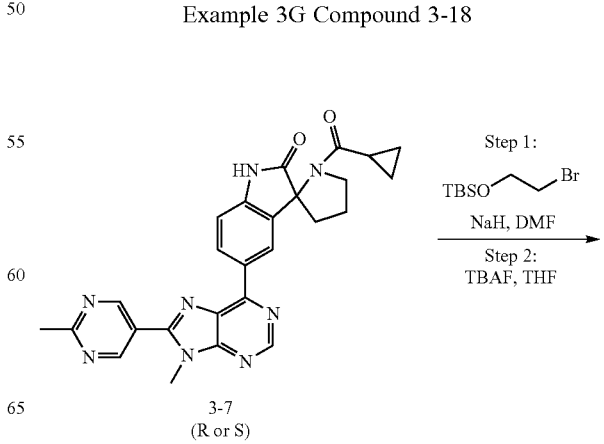

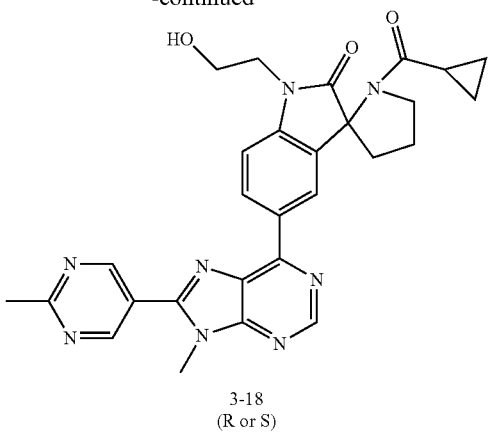

3-18
(R or S)

Steps 1-2 (R or S)-1'-(Cyclopropanecarbonyl)-1-(2-hydroxyethyl)-5-(9-methyl-8-(2-methylpyrimidin-5-yl)-9H-purin-6-yl)spiro[indoline-3,2'-pyrrolidin]-2-one (3-18)

A solution of 1'-(cyclopropanecarbonyl)-5-(9-methyl-8-(2-methylpyrimidin-5-yl)-9H-purin-6-yl)spiro[indoline-3,2'-pyrrolidin]-2-one hydrochloride (Compound 3-7; 0.20 g, 0.42 mmol) in DMF (10 mL) was treated with 60% NaH in mineral oil (30 mg, 1.2 mmol) at 0° C. The mixture was stirred for 10 min at 0° C., then (2-bromoethoxy)-(tert-butyl) dimethylsilane (110 mg, 0.46 mmol) was added. The mixture was stirred for 16 h at room temperature, quenched with water (5 mL), and extracted with EtOAc. The combined organic layers were washed with brine, dried ($Na_2SO_4$) and filtered. The filtrate was concentrated and the residue purified by chromatography on $SiO_2$ (0%-10% MeOH/DCM) to afford 1-(2-((tert-butyldimethylsilyl)oxy)ethyl)-1'-(cyclopropanecarbonyl)-5-(9-methyl-8-(2-methylpyrimidin-5-yl)-9H-purin-6-yl)spiro[indoline-3,2'-pyrrolidin]-2-one. MS (EI) calc'd for $C_{34}H_{43}N_8O_3Si$ $[M+H]^+$, 639; found, 639.

A solution of 1-(2-((tert-butyldimethylsilyl)oxy)ethyl)-1'-(cyclopropanecarbonyl)-5-(9-methyl-8-(2-methylpyrimidin-5-yl)-9H-purin-6-yl)spiro[indoline-3,2'-pyrrolidin]-2-one (50 mg, 0.080 mmol) in THF (2 mL) was treated with a 1 M THF solution of TBAF (0.16 mL, 0.16 mmol). The solution was stirred for 16 h at room temperature and concentrated. The residue was purified by chromatography on $SiO_2$ (5% MeOH/DCM) to afford crude product. The crude product was further purified by Prep-HPLC [Column: XBridge Prep C18 OBD, 10 μm; 22%-55% MeCN/water with 10 mM $NH_4HCO_3$; Flow rate: 20 mL/min; Detector 254, 220 nm] to provide 3-18. $^1H$ NMR (300 MHz, DMSO-$d_6$) δ 9.32 (s, 2H), 8.98-8.95 (m, 2H), 8.65 (d, J=1.5 Hz, 1H), 7.27 (d, J=8.4 Hz, 1H), 4.71-4.69 (m, 1H), 4.18-4.13 (m, 1H), 3.99-3.87 (m, 4H), 3.85-3.69 (m, 1H), 3.67-3.57 (m, 3H), 2.78 (s, 3H), 2.32-2.11 (m, 4H), 1.91-1.86 (m, 1H), 0.81-0.60 (m, 4H). MS (EI) calc'd for $C_{28}H_{29}N_8O_3$ $[M+H]^+$, 525; found, 525.

Example 3H Compound 3-19 and 3-20

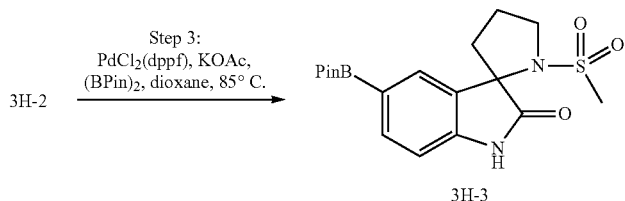

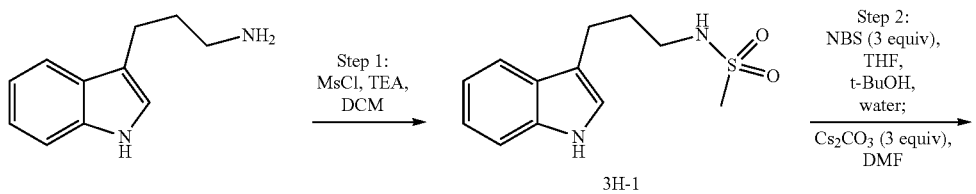

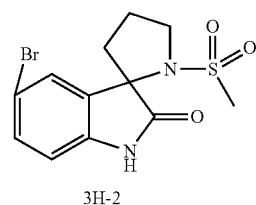

3H-2

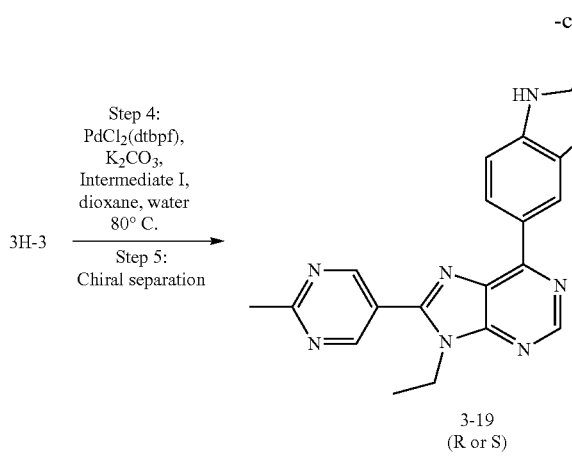

3-19
(R or S)

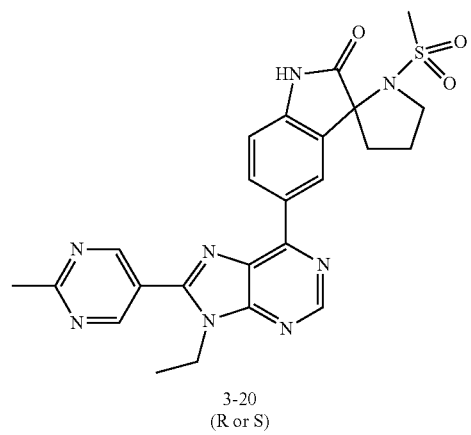

3-20
(R or S)

Step 4:
PdCl₂(dtbpf),
K₂CO₃,
Intermediate I,
dioxane, water
80° C.

3H-3 →

Step 5:
Chiral separation

Step 1 N-(3-(1H-Indol-3-yl)propyl)methanesulfonamide (3H-1)

A solution of 3-(1H-indol-3-yl)propan-1-amine (1.00 g, 5.74 mmol) and NEt₃ (1.6 mL, 12 mmol) in DCM (10 mL) was treated dropwise with MsCl (0.48 mL, 6.3 mmol) at 0° C. The solution was stirred for 1.5 h at room temperature and concentrated. The residue was purified by chromatography on SiO₂ (20%-40% EtOAc/petroleum ether) to afford N-(3-(1H-indol-3-yl)propyl)methanesulfonamide (3H-1). MS (EI) calc'd for $C_{12}H_{17}N_2O_2S$ [M+H]⁺, 253; found, 253.

Step 2 5-Bromo-1'-(methylsulfonyl)spiro[indoline-3,2'-pyrrolidin]-2-one (3H-2)

A solution of N-(3-(1H-indol-3-yl)propyl)methanesulfonamide (3H-1) (1.30 g, 5.15 mmol) in t-BuOH (6 mL), THF (6 mL) and water (2 mL) was treated with NBS (2.75 g, 15.5 mmol) at 0° C. The mixture was stirred for 5 h at room temperature and concentrated. The residue was taken-up in DMF (10 mL), treated with Cs₂CO₃ (5.04 g, 15.5 mmol) and the resulting suspension stirred for 3 h. The suspension was diluted with water and extracted with EtOAc. The combined organic layers were washed with brine, dried (Na₂SO₄) and concentrated. The residue was purified by chromatography on SiO₂ (40%-80% EtOAc/petroleum ether) to afford 5-bromo-1'-(methylsulfonyl)spiro[indoline-3,2'-pyrrolidin]-2-one (3H-2). MS (EI) calc'd for $C_{12}H_{14}BrN_2O_3S$ [M+H]⁺, 345; found, 345.

Step 3 1'-(Methylsulfonyl)-5-(4,4,5,5-tetramethyl-1,3,2-dioxaborolan-2-yl) spiro[indoline-3,2'-pyrrolidin]-2-one (3H-3)

A solution of 5-bromo-1'-(methylsulfonyl)spiro[indoline-3,2'-pyrrolidin]-2-one (3H-2) (0.30 g, 0.87 mmol) in dioxane (3 mL) was treated with KOAc (170 mg, 1.74 mmol), PdCl₂(dppf) (63 mg, 0.090 mmol) and (BPin)₂ (0.24 g, 0.96 mmol). The resulting mixture was stirred for 3 h at 85° C. and concentrated. The residue was purified by chromatography on SiO₂ (30%-60% EtOAc/petroleum ether) to afford 1'-(methylsulfonyl)-5-(4,4,5,5-tetramethyl-1,3,2-dioxaborolan-2-yl)spiro[indoline-3,2'-pyrrolidin]-2-one (3H-3). MS (EI) calc'd for $C_{18}H_{26}BN_2O_5S$ [M+H]⁺, 393; found, 393.

Steps 4-5 (R or S)- and (S or R)-5-(9-Ethyl-8-(2-methylpyrimidin-5-yl)-9H-purin-6-yl)-1'-(methylsulfonyl)spiro[indoline-3,2'-pyrrolidin]-2-one (3-19 and 3-20)

A solution of Intermediate I (3H-3) (110 mg, 0.40 mmol) in dioxane/water (2/0.2 mL) was treated with PdCl₂(dtbpf) (13 mg, 0.020 mmol), 1'-(methylsulfonyl)-5-(4,4,5,5-tetramethyl-1,3,2-dioxaborolan-2-yl)spiro[indoline-3,2'-pyrrolidin]-2-one (160 mg, 0.40 mmol) and K₂CO₃ (110 mg, 0.80 mmol). The resulting mixture was stirred for 2 h at 80° C. After cooling to room temperature, water (2 mL) was added and the mixture filtered, washing the solids with MeOH. The solid residue was collected and purified by Prep-Chiral HPLC [Column: CHIRAL ART™ Cellulose-SB (YMC Europe GMBH, Dinslaken, Germany), 250×20 mm; 40% EtOH/hexanes; Flow rate: 20 mL/min; Detection 254/220 nm; Retention time 1: 21.3 min; Retention time 2: 23.7 min). The faster-eluting enantiomer (3-19) was obtained at 21.3 min: ¹H NMR (300 MHz, CD₃OD) δ 9.22 (s, 2H), 8.92 (s, 1H), 8.86-8.83 (m, 2H), 7.08-7.05 (m, 1H), 4.57-4.48 (m, 2H), 3.89-3.76 (m, 2H), 2.90 (s, 3H), 2.82 (s, 3H), 2.45-2.33 (m, 3H), 2.26-2.22 (m, 1H), 1.50-1.46 (m, 3H). MS (EI) calc'd for $C_{24}H_{25}N_8O_3S$ [M+H]⁺, 505; found, 505. The slower-eluting enantiomer (3-20) was obtained at 23.7 min: ¹H NMR (300 MHz, CD₃OD) δ 9.22 (s, 2H), 8.92 (s, 1H), 8.86-8.83 (m, 2H), 7.08-7.05 (m, 1H), 4.55-4.50 (m, 2H), 3.85-3.75 (m, 2H), 2.92 (s, 3H), 2.82 (s, 3H), 2.44-2.35 (m, 3H), 2.26-2.22 (m, 1H), 1.50-1.46 (m, 3H). MS (EI) calc'd for $C_{24}H_{25}N_8O_3S$ [M+H]⁺, 505; found, 505.

Example 3I Compound 3-23 and 3-24

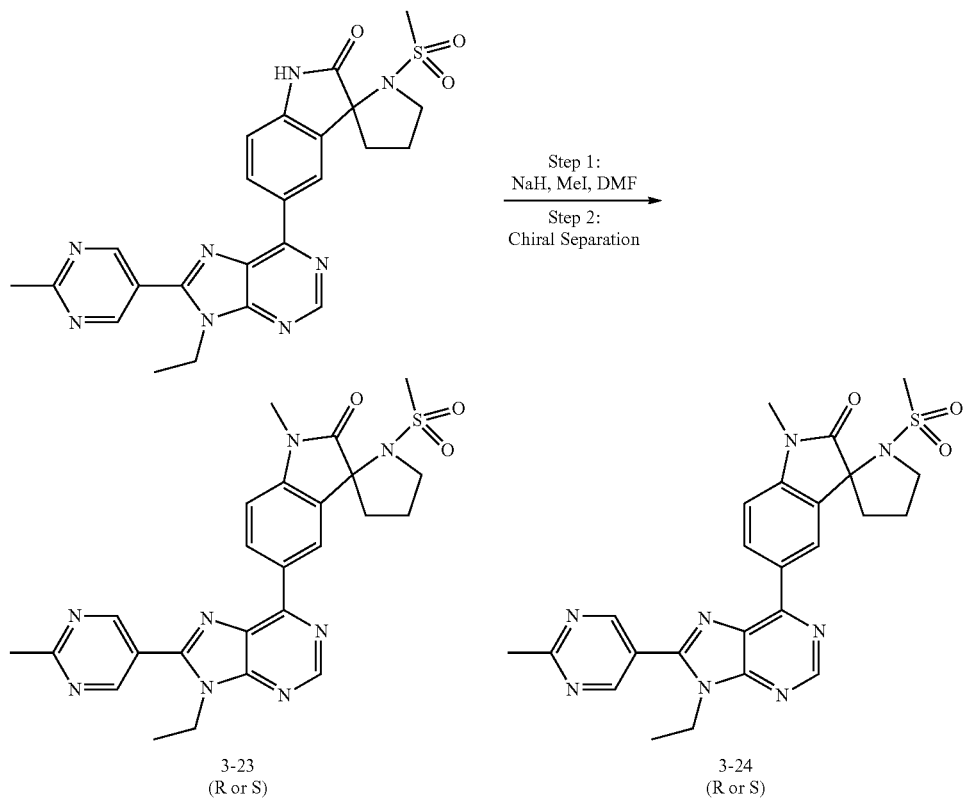

Steps 1-2 (R or S)- and (S or R)-5-(9-Ethyl-8-(2-methylpyrimidin-5-yl)-9H-purin-6-yl)-1-methyl-1'-(methylsulfonyl)spiro[indoline-3,2'-pyrrolidin]-2-one (3-23 and 3-24)

A solution of 5-(9-ethyl-8-(2-methylpyrimidin-5-yl)-9H-purin-6-yl)-1'-(methylsulfonyl)-spiro[indoline-3,2'-pyrrolidin]-2-one (60 mg, 0.12 mmol; synthesis of which is described in Example 3H) in DMF (1 mL) was treated with 60% NaH (8.8 mg, 0.24 mmol) at 0° C. The solution was stirred for 15 min at 0° C., then iodomethane (25 mg, 0.18 mmol) was added and the resulting mixture stirred another 1 h at room temperature. The reaction was quenched with water (0.5 mL) and concentrated. The residue was purified by Prep-HPLC [Column: X Select™ CSH Prep C18 OBD (Waters Corporation, Milford Mass., USA); 19×150 mm; 20 mL/min flow rate; 20% to 60% MeCN in water with 0.05% TFA] to provide racemic product. The racemate was then resolved by Prep-Chiral HPLC [Column: ChiralPak™ IA; 21×250 mm; 20 mL/min flow rate; 65% IPA in hexane; RT1 10.4 min; RT2 16.3 min] to provide the resolved enantiomers. The faster-eluting enantiomer (3-23) was obtained at a retention time of 10.4 min, while the slower eluting enantiomer (3-24) came at a retention time of 16.3 min. Characterization data for 3-23: $^1$H NMR (300 MHz, CD$_3$OD) δ 9.22 (s, 2H), 8.96 (d, J=1.5 Hz, 1H), 8.93 (s, 1H), 8.87 (d, J=1.5 Hz, 1H), 7.20 (d, J=8.4 Hz, 1H), 4.52 (q, J=7.2 Hz, 2H), 3.85-3.74 (m, 2H), 3.35-3.33 (m, 3H), 2.89 (s, 3H), 2.82 (s, 3H), 2.45-2.35 (m, 3H), 2.25-2.23 (m, 1H), 1.48 (t, J=7.2 Hz, 3H). MS (EI) calc'd for C$_{25}$H$_{27}$N$_8$O$_3$S [M+H]$^+$, 519; found, 519. Characterization data for 3-24: $^1$H NMR (300 MHz, CD$_3$OD) δ 9.22 (s, 2H), 8.96 (d, J=1.5 Hz, 1H), 8.94 (s, 1H), 8.87 (d, J=1.8 Hz, 1H), 7.20 (d, J=8.4 Hz, 1H), 4.52 (q, J=7.2 Hz, 2H), 3.85-3.78 (m, 2H), 3.35-3.32 (m, 3H), 2.89 (s, 3H), 2.82 (s, 3H), 2.41-2.38 (m, 3H), 2.25-2.23 (m, 1H), 1.48 (t, J=7.2 Hz, 3H). MS (EI) calc'd for C$_{25}$H$_{27}$N$_8$O$_3$S [M+H]$^+$, 519; found, 519.

Examples for Compounds 3-9, 3-10, 3-13 to 3-16, 3-21, 3-22, 3-25 to 3-36

Compounds 3-9 and 3-10 were prepared from compound 3-1 in a fashion analogous to the preparation of compound 3-8 from compound 3-7, substituting methyl iodide for ethyl iodide and isopropyl iodide, respectively.

Compounds 3-13 and 3-14 were prepared in a fashion analogous to the preparation of compounds 3-11 and 3-12, in which intermediate I was replaced by Intermediate II. The racemic material was then resolved using chiral column chromatography [Column: ChiralPak™ AS-H; 21×250 mm; 70 mL/min flow rate; 35% MeOH in CO$_2$ with 0.25% Me$_2$NEt]. The faster eluting enantiomer came at a retention time of 2.91 min (3-13); while the slower eluting enantiomer came at a retention time of 4.38 min (3-14).

Compound 3-15 was prepared in a fashion analogous to the preparation of compound 3-7, in which Intermediate II was replaced by Intermediate III.

Compound 3-16 was prepared in a fashion analogous to the preparation of compound 3-8, in which iodomethane and sodium hydride were replaced by 4-(2-bromoethyl)morpholine hydrobromide and potassium carbonate, respectively.

Compounds 3-21 and 3-22 were prepared in a fashion analogous to the preparation of compounds 3-19 and 3-20, in which methanesulfonyl chloride was replaced by trifluoromethanesulfonic anhydride in Step 1. The racemic material was then dissolved in 3:1 MeOH/MeCN and resolved using chiral column chromatography [Column: ChiralPak™ AS-H; 21×250 mm; 70 mL/min flow rate; 30% MeOH in $CO_2$ with 0.25% $Me_2NEt$]. The faster eluting enantiomer came at a retention time of 2.60 min (3-21); while the slower eluting enantiomer came at a retention time of 3.08 min (3-22).

Compound 3-25 was prepared in a fashion analogous to the preparation of 3-5 in Example 3C, in which Intermediate II was used in place of Intermediate I, and achiral 5-bromospiro[indoline-3,4'-piperidin]-2-one was used instead of chiral 5-bromospiro[indoline-3,3'-pyrrolidin]-2-one.

Compounds 3-26 and 3-27 were prepared in a fashion analogous to the preparation of 3-11 and 3-12, in which ethyl amine was used in Step 1 of the synthesis. The racemic material was then dissolved in MeOH and resolved using chiral column chromatography [Column: ChiralPak™ AS-H; 21×250 mm; 70 mL/min flow rate; 25% MeOH in $CO_2$ with 0.25% $Me_2NEt$]. The faster eluting enantiomer came at a retention time of 4.4 min (3-26); while the slower eluting enantiomer came at a retention time of 5.8 min (3-27).

Compounds 3-28 and 3-29 were prepared in a fashion analogous to the preparation of 3-13 and 3-14, in which ethyl amine was used in Step 1 of the synthesis. The racemic material was then dissolved in 2:1 MeOH/MeCN and resolved using chiral column chromatography [Column: ChiralPak™ AS-H; 21×250 mm; 70 mL/min flow rate; 30% MeOH in $CO_2$ with 0.25% $Me_2NEt$]. The faster eluting enantiomer came at a retention time of 3.70 min (3-28); while the slower eluting enantiomer came at a retention time of 5.20 min (3-29).

Compounds 3-30 and 3-31 were prepared in a fashion analogous to the preparation of 3-11 and 3-12, in which 3-(1H-indol-3-yl)-N-isopropylpropan-1-amine was replaced by 3-(1H-indol-3-yl)propan-1-ol as the spirocyclization precursor. The racemic material was then dissolved in 12 mL of 1:1 MeOH/MeCN and resolved using chiral column chromatography [Column: ChiralPak™ AS-H; 21×250 mm; 70 mL/min flow rate; 40% MeOH in $CO_2$ with 0.25% $Me_2NEt$]. The faster eluting enantiomer came at a retention time of 2.1 min (3-30); while the slower eluting enantiomer came at a retention time of 2.7 min (3-31).

Compounds 3-32 and 3-33 were prepared in a fashion analogous to the preparation of 3-1 and 3-2, in which N-(3-(1H-indol-3-yl)propyl)cyclopropanecarboxamide was replaced by tert-butyl (3-(1H-indol-3-yl)propyl)carbamate as the spirocyclization precursor. After Suzuki coupling to Intermediate I, the Boc-protective group was cleaved by treatment with a saturated solution of HCl gas in EtOAc and concentrated. The racemic material was then resolved using chiral column chromatography [Column: ChiralPak™ IA; 21×150 mm; 18 ml/min flow rate; 30% EtOH in MTBE with 0.1% $Me_2NEt$]. The faster eluting enantiomer came at a retention time of 6.0 min (3-32); while the slower eluting enantiomer came at a retention time of 11.4 min (3-33).

Compound 3-34 was prepared in a fashion analogous to the preparation of 3-5 and 3-6, substituting 5-bromo-1'-(cyclopropanecarbonyl)spiro[indoline-3,3'-pyrrolidin]-2-one for the known spirocycle 5'-bromospiro[cyclopentane-1,3'-indolin]-2'-one. Being achiral, no chiral separation on 3-34 was performed.

Compounds 3-35 and 3-36 were prepared in a fashion analogous to the preparation of 3-5 and 3-6, substituting 5-bromo-1'-(cyclopropanecarbonyl)spiro[indoline-3,3'-pyrrolidin]-2-one for 5-bromo-1'-isopropylspiro[indoline-3,3'-pyrrolidin]-2-one. 5-Bromo-1'-isopropylspiro[indoline-3,3'-pyrrolidin]-2-one was prepared as follows: A solution of 5-bromospiro[indoline-3,3'-pyrrolidin]-2-one (267 mg, 1.00 mmol) in 2 mL of DCE was treated with $NaHB(OAc)_3$, AcOH (0.060 mL, 1.00 mmol) and acetone (1 mL). The reaction mixture was stirred for 1 h, poured in EtOAc and washed with sat'd $NaHCO_3$ and brine. The organic layer was dried ($MgSO_4$) and concentrated. The residue was purified by chromatography on $SiO_2$ (2-20% MeOH/DCM) to give 5-bromo-1'-isopropylspiro[indoline-3,3'-pyrrolidin]-2-one which was then used for Step 4 in the sequence; MS (EI) calc'd for $C_{14}H_{18}BrN_2O$ $[M+H]^+$, 311; found, 311. After steps 4-5, involving the coupling to Intermediate I, the racemic material was then dissolved in MeOH and resolved using chiral column chromatography [Column: ChiralPak™ AD-H; 21×150 mm; 70 mL/min flow rate; 30% MeOH in $CO_2$ with 0.25% $Me_2NEt$]. The faster eluting enantiomer came at a retention time of 3.7 min (3-35); while the slower eluting enantiomer came at a retention time of 5.0 min (3-36).

Table 3 provides structures for compounds 3-1 through 3-36 which were synthesized directly by the methods described above or by analogous methods to those described above.

TABLE 3

| Compound | Structure | Name | Exact Mass $[M + H]^+$ |
|---|---|---|---|
| 3-1 | 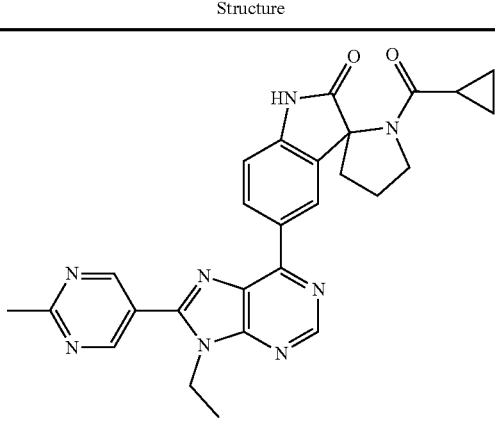 | (R or S)-1'-(cyclopropylcarbonyl)-5-[9-ethyl-8-(2-methylpyrimidin-5-yl)-9H-purin-6-yl]spiro[indole-3,2'-pyrrolidin]-2(1H)-one | Calc'd 495, found 495 |

TABLE 3-continued

| Compound | Structure | Name | Exact Mass [M + H]+ |
|---|---|---|---|
| 3-2 | 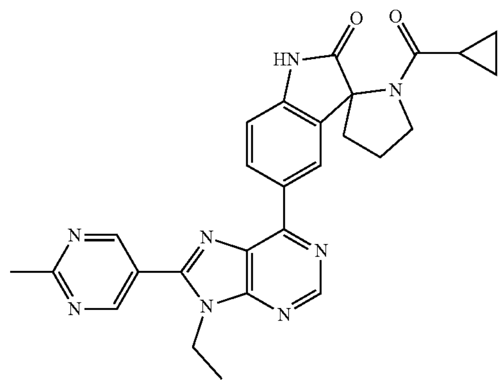 [SMILES: CCn1c(-c2cnc(C)nc2)nc2c(-c3ccc4c(c3)C3(CCCN3C(=O)C3CC3)C(=O)N4)ncnc21] | (R or S)-1'-(cyclopropylcarbonyl)-5-[9-ethyl-8-(2-methylpyrimidin-5-yl)-9H-purin-6-yl]spiro[indole-3,2'-pyrrolidin]-2(1H)-one | Calc'd 495, found 495 |
| 3-3 | 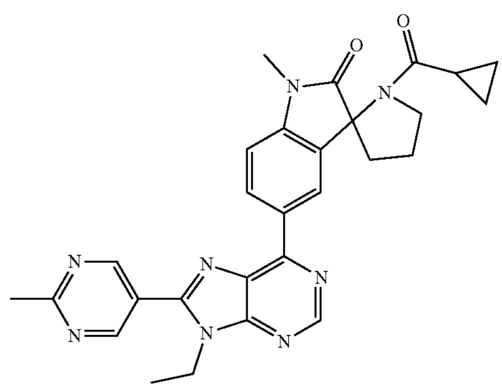 [SMILES: CCn1c(-c2cnc(C)nc2)nc2c(-c3ccc4c(c3)C3(CCCN3C(=O)C3CC3)C(=O)N4C)ncnc21] | (R or S)-1'-(cyclopropylcarbonyl)-5-[9-ethyl-8-(2-methylpyrimidin-5-yl)-9H-purin-6-yl]-1-methylspiro[indole-3,2'-pyrrolidin]-2(1H)-one | Calc'd 509, found 509 |
| 3-4 | 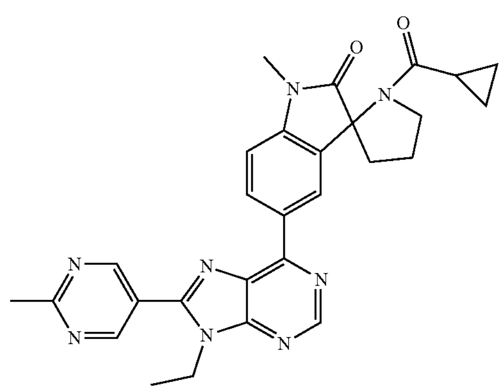 [SMILES: CCn1c(-c2cnc(C)nc2)nc2c(-c3ccc4c(c3)C3(CCCN3C(=O)C3CC3)C(=O)N4C)ncnc21] | (R or S)-1'-(cyclopropylcarbonyl)-5-[9-ethyl-8-(2-methylpyrimidin-5-yl)-9H-purin-6-yl]-1-methylspiro[indole-3,2'-pyrrolidin]-2(1H)-one | Calc'd 509, found 509 |
| 3-5 | 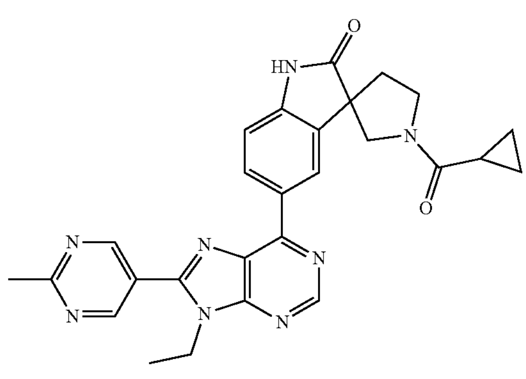 [SMILES: CCn1c(-c2cnc(C)nc2)nc2c(-c3ccc4c(c3)C3(CCN(C(=O)C5CC5)C3)C(=O)N4)ncnc21] | (R or S)-1'-(cyclopropanecarbonyl)-5-(9-ethyl-8-(2-methylpyrimidin-5-yl)-9H-purin-6-yl)spiro[indoline-3,3'-pyrrolidin]-2-one | Calc'd 495, found 495 |

TABLE 3-continued

| Compound | Structure | Name | Exact Mass [M + H]+ |
|---|---|---|---|
| 3-6 | 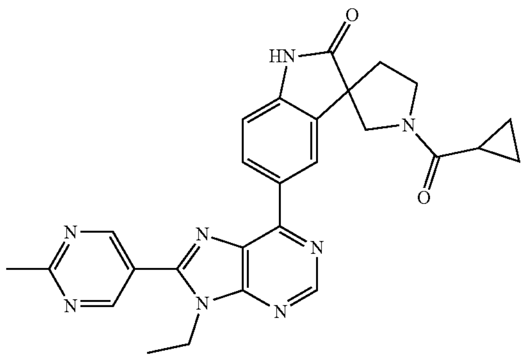 [SMILES: CCn1c(-c2cnc(C)nc2)nc2c(-c3ccc4c(c3)C3(CCN(C(=O)C5CC5)C3)C(=O)N4)ncnc21] | (R or S)-1'-(cyclopropanecarbonyl)-5-(9-ethyl-8-(2-methylpyrimidin-5-yl)-9H-purin-6-yl)spiro[indoline-3,3'-pyrrolidin]-2-one | Calc'd 495, found 495 |
| 3-7 | 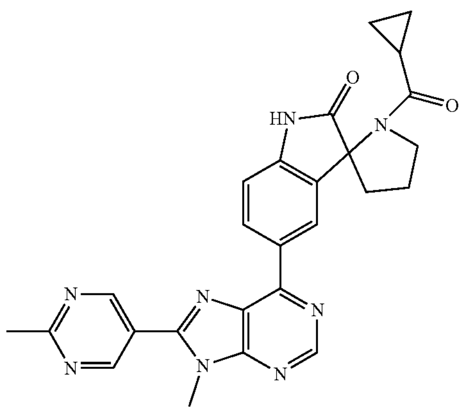 [SMILES: Cc1ncc(-c2nc3c(-c4ccc5c(c4)C4(CCCN4C(=O)C4CC4)C(=O)N5)ncnc3n2C)cn1] | (R or S)-1'-(cyclopropanecarbonyl)-5-(9-methyl-8-(2-methylpyrimidin-5-yl)-9H-purin-6-yl)spiro[indoline-3,2'-pyrrolidin]-2-one | Calc'd 481, found 481 |
| 3-8 | 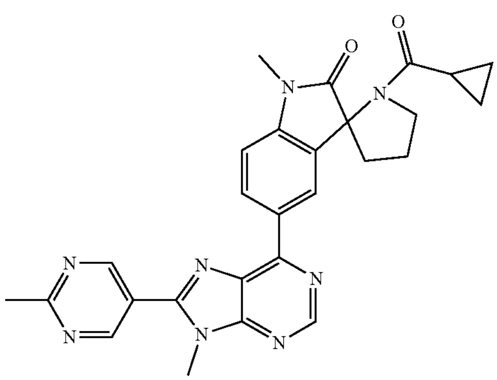 [SMILES: Cc1ncc(-c2nc3c(-c4ccc5c(c4)C4(CCCN4C(=O)C4CC4)C(=O)N5C)ncnc3n2C)cn1] | (R or S)-1'-(cyclopropanecarbonyl)-1-methyl-5-(9-methyl-8-(2-methylpyrimidin-5-yl)-9H-purin-6-yl)spiro[indoline-3,2'-pyrrolidin]-2-one | Calc'd 495, found 495 |
| 3-9 | 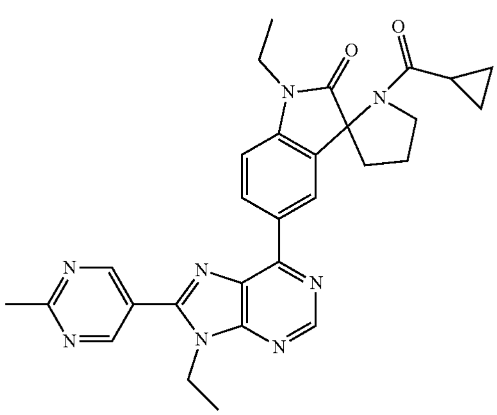 [SMILES: CCN1C(=O)C2(CCCN2C(=O)C2CC2)c2cc(-c3ncnc4c3nc(-c3cnc(C)nc3)n4CC)ccc21] | (R or S)-1'-(cyclopropanecarbonyl)-1-ethyl-5-(9-ethyl-8-(2-methylpyrimidin-5-yl)-9H-purin-6-yl)spiro[indoline-3,2'-pyrrolidin]-2-one | Calc'd 523, found 523 |

TABLE 3-continued

| Compound | Structure | Name | Exact Mass [M + H]+ |
|---|---|---|---|
| 3-10 | 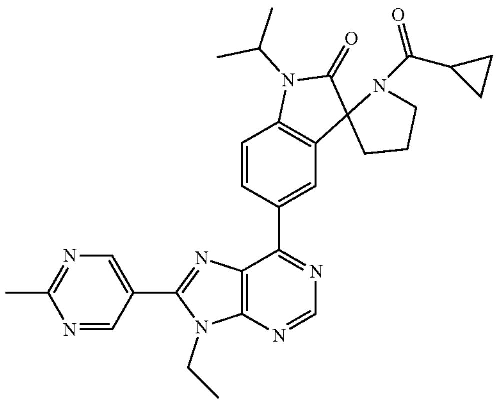 [SMILES: CCn1c(-c2cnc(C)nc2)nc2c(-c3ccc4c(c3)C3(CCCN3C(=O)C3CC3)C(=O)N4C(C)C)ncnc21] | (R or S)-1'-(cyclopropanecarbonyl)-5-(9-ethyl-8-(2-methylpyrimidin-5-yl)-9H-purin-6-yl)-1-isopropylspiro[indoline-3,2'-pyrrolidin]-2-one | Cal'd 537, found 537 |
| 3-11 | 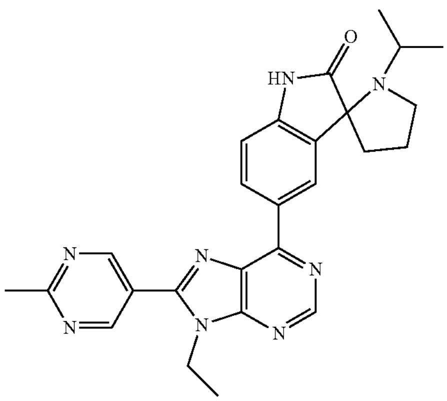 [SMILES: CCn1c(-c2cnc(C)nc2)nc2c(-c3ccc4c(c3)C3(CCCN3C(C)C)C(=O)N4)ncnc21] | (R or S)-5-(9-ethyl-8-(2-methylpyrimidin-5-yl)-9H-purin-6-yl)-1'-isopropylspiro[indoline-3,2'-pyrrolidin]-2-one | Calc'd 469, found 469 |
| 3-12 | 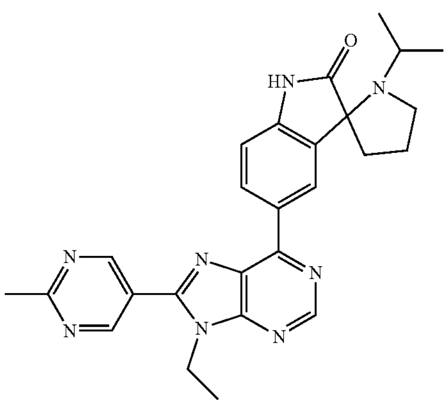 [SMILES: CCn1c(-c2cnc(C)nc2)nc2c(-c3ccc4c(c3)C3(CCCN3C(C)C)C(=O)N4)ncnc21] | (R or S)-5-(9-ethyl-8-(2-methylpyrimidin-5-yl)-9H-purin-6-yl)-1'-isopropylspiro[indoline-3,2'-pyrrolidin]-2-one | Calc'd 469, found 469 |
| 3-13 | 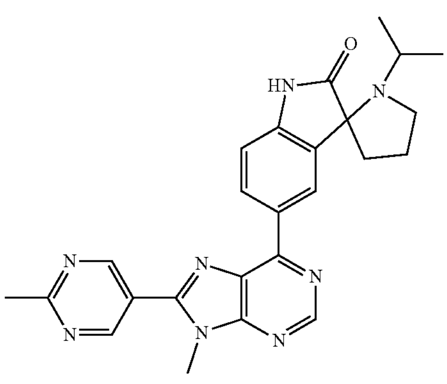 [SMILES: Cc1ncc(-c2nc3c(-c4ccc5c(c4)C4(CCCN4C(C)C)C(=O)N5)ncnc3n2C)cn1] | (R or S)-1'-isopropyl-5-(9-methyl-8-(2-methylpyrimidin-5-yl)-9H-purin-6-yl)spiro[indoline-3,2'-pyrrolidin]-2-one | Calc'd 455, found 455 |

TABLE 3-continued

| Compound | Structure | Name | Exact Mass [M + H]+ |
|---|---|---|---|
| 3-14 | 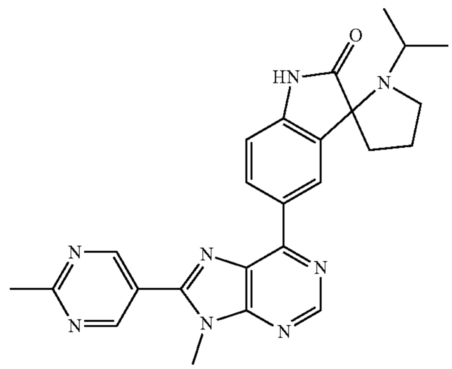 [SMILES: Cc1ncc(-c2nc3c(-c4ccc5c(c4)C4(CCCN4C(C)C)C(=O)N5)ncnc3n2C)cn1] | (R or S)-1'-isopropyl-5-(9-methyl-8-(2-methylpyrimidin-5-yl)-9H-purin-6-yl)spiro[indoline-3,2'-pyrrolidin]-2-one | Calc'd 455, found 455 |
| 3-15 | 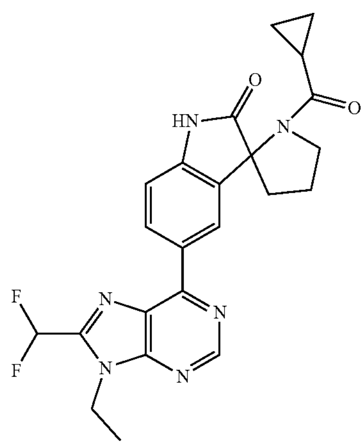 [SMILES: CCn1c(C(F)F)nc2c(-c3ccc4c(c3)C3(CCCN3C(=O)C3CC3)C(=O)N4)ncnc21] | (R or S)-1'-(cyclopropanecarbonyl)-5-(8-(difluoromethyl)-9-ethyl-9H-purin-6-yl)spiro[indoline-3,2'-pyrrolidin]-2-one | Calc'd 453, found 453 |
| 3-16 | 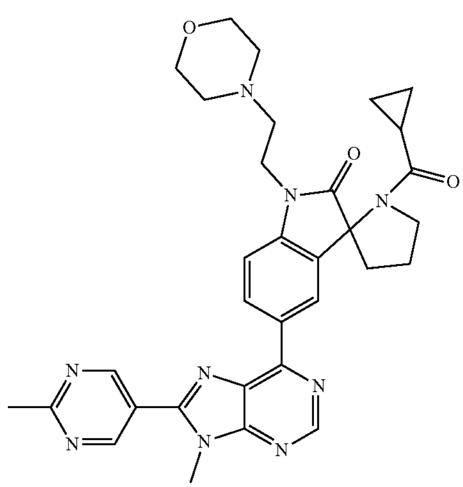 [SMILES: Cc1ncc(-c2nc3c(-c4ccc5c(c4)C4(CCCN4C(=O)C4CC4)C(=O)N5CCN4CCOCC4)ncnc3n2C)cn1] | (R or S)-1'-(cyclopropanecarbonyl)-5-(9-methyl-8-(2-methylpyrimidin-5-yl)-9H-purin-6-yl)-1-(2-morpholinoethyl)spiro[indoline-3,2'-pyrrolidin]-2-one | Calc'd 594, found, 594 |

TABLE 3-continued

| Compound | Structure | Name | Exact Mass [M + H]+ |
|---|---|---|---|
| 3-17 | 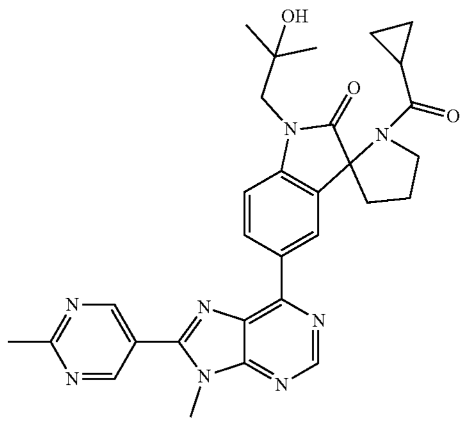 [SMILES: Cc1ncc(-c2nc3c(-c4ccc5c(c4)C4(CCCN4C(=O)C4CC4)C(=O)N5CC(C)(C)O)ncnc3n2C)cn1] | (R or S)-1'-(cyclopropanecarbonyl)-1-(2-hydroxy-2-methylpropyl)-5-(9-methyl-8-(2-methylpyrimidin-5-yl)-9H-purin-6-yl)spiro[indoline-3,2'-pyrrolidin]-2-one | Calc'd 553, found, 553 |
| 3-18 | 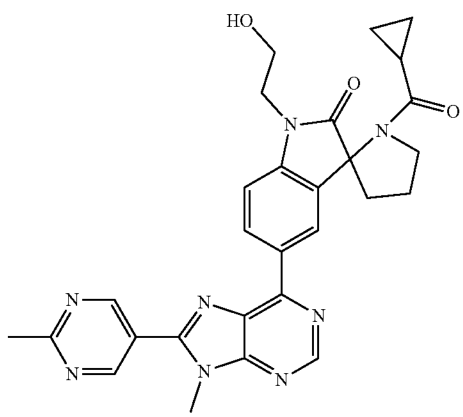 [SMILES: Cc1ncc(-c2nc3c(-c4ccc5c(c4)C4(CCCN4C(=O)C4CC4)C(=O)N5CCO)ncnc3n2C)cn1] | (R or S)-1'-(cyclopropanecarbonyl)-1-(2-hydroxyethyl)-5-(9-methyl-8-(2-methylpyrimidin-5-yl)-9H-purin-6-yl)spiro[indoline-3,2'-pyrrolidin]-2-one | Calc'd 525, found, 525 |
| 3-19 | 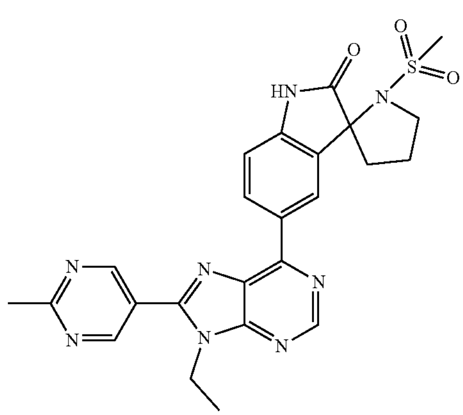 [SMILES: CCn1c(-c2cnc(C)nc2)nc2c(-c3ccc4c(c3)C3(CCCN3S(C)(=O)=O)C(=O)N4)ncnc21] | (R or S)-5-(9-ethyl-8-(2-methylpyrimidin-5-yl)-9H-purin-6-yl)-1'-(methylsulfonyl)spiro[indoline-3,2'-pyrrolidin]-2-one | Calc'd 505, found, 505 |

TABLE 3-continued

| Compound | Structure | Name | Exact Mass [M + H]+ |
|---|---|---|---|
| 3-20 | 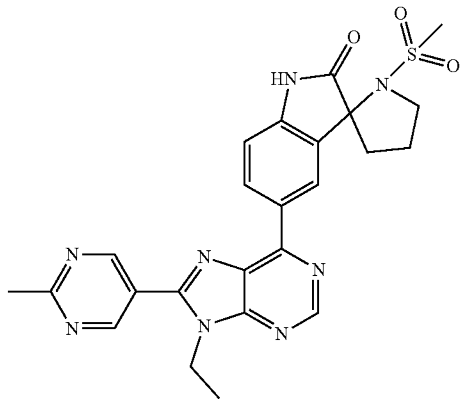 [SMILES: CCn1c(-c2cnc(C)nc2)nc2c(-c3ccc4c(c3)C3(CCCN3S(C)(=O)=O)C(=O)N4)ncnc21] | (R or S)-5-(9-ethyl-8-(2-methylpyrimidin-5-yl)-9H-purin-6-yl)-1'-(methylsulfonyl)spiro[indoline-3,2'-pyrrolidin]-2-one | Calc'd 505, found, 505 |
| 3-21 | 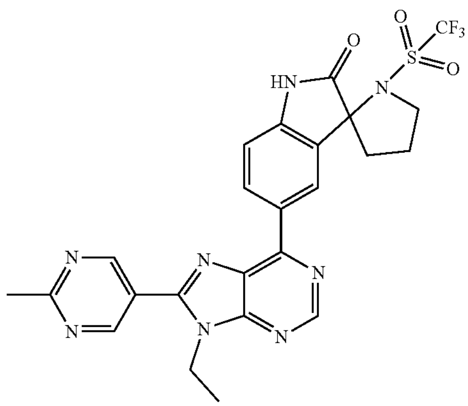 [SMILES: CCn1c(-c2cnc(C)nc2)nc2c(-c3ccc4c(c3)C3(CCCN3S(=O)(=O)C(F)(F)F)C(=O)N4)ncnc21] | (R or S)-5-(9-ethyl-8-(2-methylpyrimidin-5-yl)-9H-purin-6-yl)-1'-((trifluoromethyl)sulfonyl)spiro[indoline-3,2'-pyrrolidin]-2-one | Calc'd 559, found, 559 |
| 3-22 | 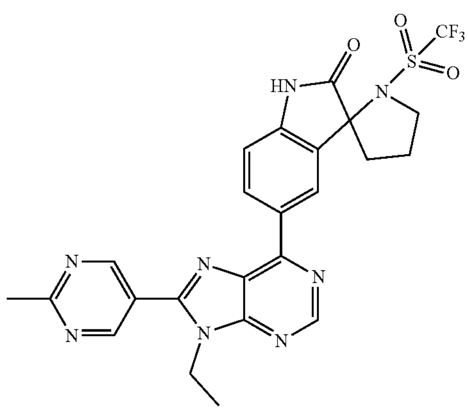 [SMILES: CCn1c(-c2cnc(C)nc2)nc2c(-c3ccc4c(c3)C3(CCCN3S(=O)(=O)C(F)(F)F)C(=O)N4)ncnc21] | (R or S)-5-(9-ethyl-8-(2-methylpyrimidin-5-yl)-9H-purin-6-yl)-1'-((trifluoromethyl)sulfonyl)spiro[indoline-3,2'-pyrrolidine]-2-one | Calc'd 559, found, 559 |
| 3-23 | 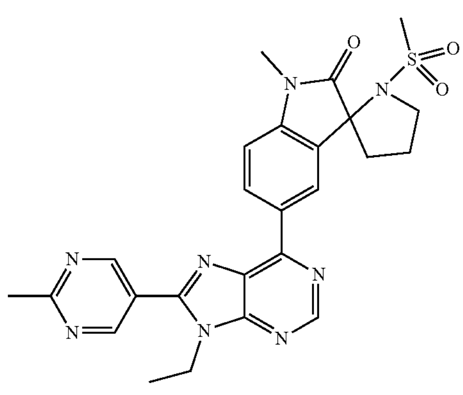 [SMILES: CCn1c(-c2cnc(C)nc2)nc2c(-c3ccc4c(c3)C3(CCCN3S(C)(=O)=O)C(=O)N4C)ncnc21] | (R or S)-5-(9-ethyl-8-(2-methylpyrimidin-5-yl)-9H-purin-6-yl)-1-methyl-1'-(methylsulfonyl)spiro[indoline-3,2'-pyrrolidin]-2-one | Calc'd 519, found, 519 |

TABLE 3-continued

| Compound | Structure | Name | Exact Mass [M + H]+ |
|---|---|---|---|
| 3-24 | 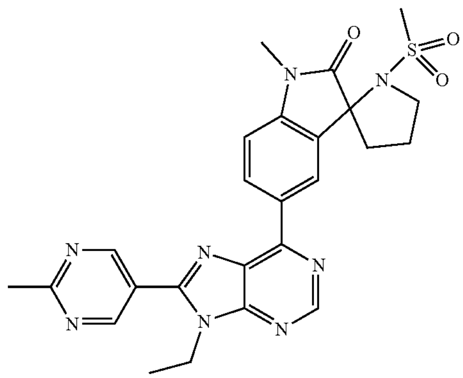 [SMILES: CCn1c(-c2cnc(C)nc2)nc2c(-c3ccc4c(c3)C3(CCCN3S(C)(=O)=O)C(=O)N4C)ncnc21] | (R or S)-5-(9-ethyl-8-(2-methylpyrimidin-5-yl)-9H-purin-6-yl)-1-methyl-1'-(methylsulfonyl)spiro[indoline-3,2'-pyrrolidin]-2-one | Calc'd 519, found, 519 |
| 3-25 | 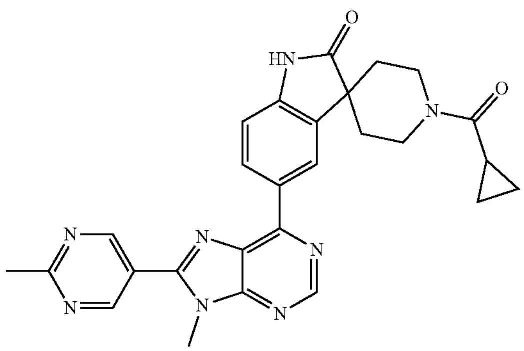 [SMILES: Cc1ncc(-c2nc3c(-c4ccc5c(c4)C4(CCN(C(=O)C6CC6)CC4)C(=O)N5)ncnc3n2C)cn1] | 1'-(cyclopropanecarbonyl)-5-(9-methyl-8-(2-methylpyrimidin-5-yl)-9H-purin-6-yl)spiro[indoline-3,4'-piperidin]-2-one | Calc'd 495, found, 495 |
| 3-26 | 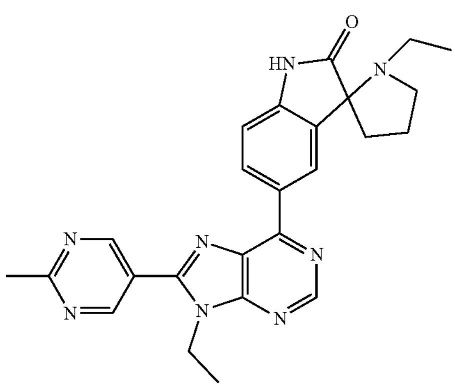 [SMILES: CCN1CCCC12C(=O)Nc1ccc(-c3ncnc4c3nc(-c3cnc(C)nc3)n4CC)cc12] | (R or S)-1'-ethyl-5-(9-ethyl-8-(2-methylpyrimidin-5-yl)-9H-purin-6-yl)spiro[indoline-3,2'-pyrrolidin]-2-one | Calc'd 455, found, 455 |
| 3-27 | 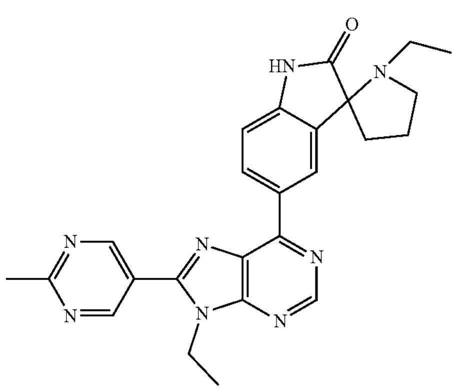 [SMILES: CCN1CCCC12C(=O)Nc1ccc(-c3ncnc4c3nc(-c3cnc(C)nc3)n4CC)cc12] | (R or S)-1'-ethyl-5-(9-ethyl-8-(2-methylpyrimidin-5-yl)-9H-purin-6-yl)spiro[indoline-3,2'-pyrrolidin]-2-one | Calc'd 455, found, 455 |

TABLE 3-continued

| Compound | Structure | Name | Exact Mass [M + H]+ |
|---|---|---|---|
| 3-28 | 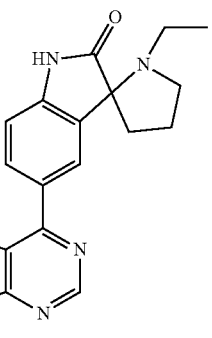 | (R or S)-1'-ethyl-5-(9-methyl-8-(2-methylpyrimidin-5-yl)-9H-purin-6-yl)spiro[indoline-3,2'-pyrrolidin]-2-one | Calc'd 441, found, 441 |
| 3-29 | 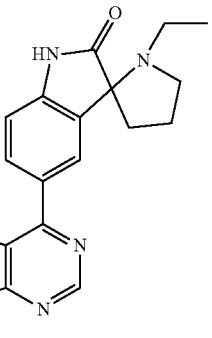 | (R or S)-1'-ethyl-5-(9-methyl-8-(2-methylpyrimidin-5-yl)-9H-purin-6-yl)spiro[indoline-3,2'-pyrrolidin]-2-one | Calc'd 441, found, 441 |
| 3-30 | 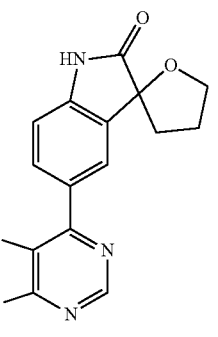 | (R or S)-5'-(9-ethyl-8-(2-methylpyrimidin-5-yl)-9H-purin-6-yl)-4,5-dihydro-3H-spiro[furan-2,3'-indolin]-2'-one | Calc'd 428, found, 428 |
| 3-31 | 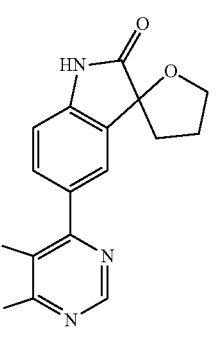 | (R or S)-5'-(9-ethyl-8-(2-methylpyrimidin-5-yl)-9H-purin-6-yl)-4,5-dihydro-3H-spiro[furan-2,3'-indolin]-2'-one | Calc'd 428, found, 428 |

TABLE 3-continued

| Compound | Structure | Name | Exact Mass [M + H]+ |
|---|---|---|---|
| 3-32 | 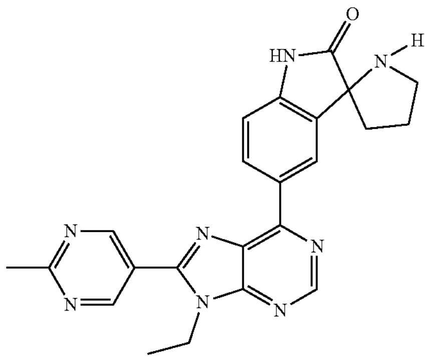 [SMILES: CCn1c(-c2cnc(C)nc2)nc2c(-c3ccc4c(c3)C3(CCCN3)C(=O)N4)ncnc21] | (R or S)-5-(9-ethyl-8-(2-methylpyrimidin-5-yl)-9H-purin-6-yl)spiro[indoline-3,2'-pyrrolidin]-2-one | Calc'd 427, found, 427 |
| 3-33 | 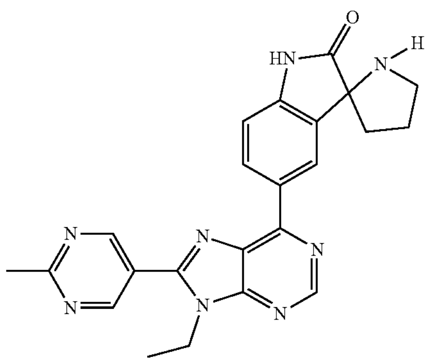 [SMILES: CCn1c(-c2cnc(C)nc2)nc2c(-c3ccc4c(c3)C3(CCCN3)C(=O)N4)ncnc21] | (R or S)-5-(9-ethyl-8-(2-methylpyrimidin-5-yl)-9H-purin-6-yl)spiro[indoline-3,2'-pyrrolidin]-2-one | Calc'd 427, found, 427 |
| 3-34 | 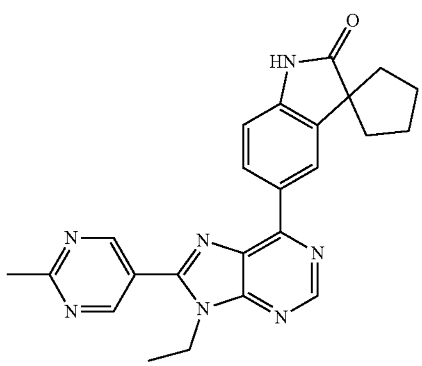 [SMILES: CCn1c(-c2cnc(C)nc2)nc2c(-c3ccc4c(c3)C3(CCCC3)C(=O)N4)ncnc21] | 5'-(9-ethyl-8-(2-methylpyrimidin-5-yl)-9H-purin-6-yl)spiro[cyclopentane-1,3'-indolin]-2'-one | Calc'd 426, found, 426 |
| 3-35 | 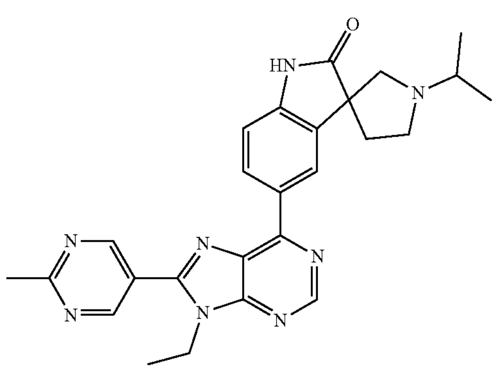 [SMILES: CCn1c(-c2cnc(C)nc2)nc2c(-c3ccc4c(c3)C3(CCN(C(C)C)C3)C(=O)N4)ncnc21] | (R or S)-5-(9-ethyl-8-(2-methylpyrimidin-5-yl)-9H-purin-6-yl)-1'-isopropylspiro[indoline-3,3'-pyrrolidin]-2-one | Calc'd 469, found, 469 |

TABLE 3-continued
| Compound | Structure | Name | Exact Mass [M + H]+ |
|---|---|---|---|
| 3-36 | 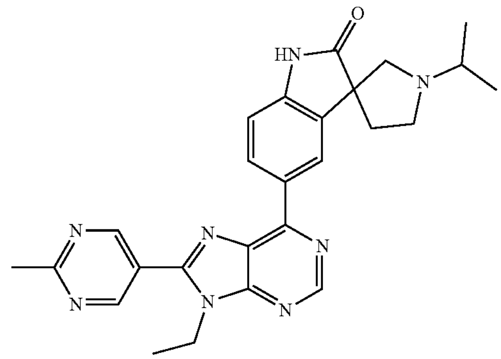 [SMILES: CCn1c(-c2cnc(C)nc2)nc2c(-c3ccc4c(c3)C3(CCN(C(C)C)C3)C(=O)N4)ncnc21] | (R or S)-5-(9-ethyl-8-(2-methylpyrimidin-5-yl)-9H-purin-6-yl)-1'-isopropylspiro[indoline-3,3'-pyrrolidin]-2-one | Calc'd 469, found, 469 |
Compound Examples of Table 4
Example 4A Compounds 4-1 and 4-2
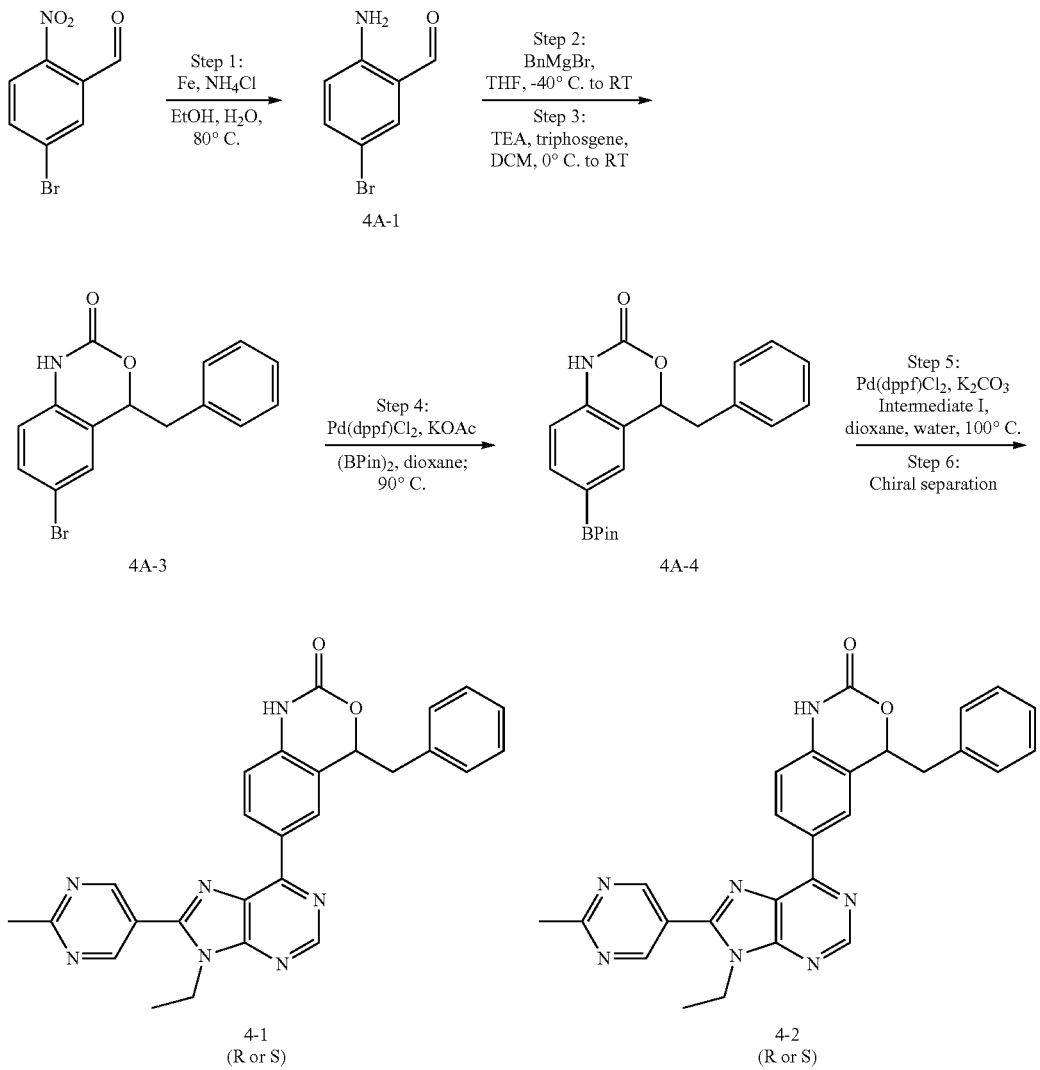
4-1 (R or S)
4-2 (R or S)

Step 1 2-Amino-5-bromobenzaldehyde (4A-1)

To a solution of 5-bromo-2-nitrobenzaldehyde (3.00 g, 13.0 mmol) in ethanol/water 40 mL/10 mL), were added ammonium chloride (0.84 g, 16 mmol) and iron (powdered, 3.64 g, 65.2 mmol). The mixture was stirred for 1 h at 80° C. After cooling to room temperature, the reaction mixture was filtered. The filtrate was extracted with EtOAc (2×50 mL). The combined organic layers were washed with brine (2×50 mL), dried ($Na_2SO_4$) and concentrated. The residue was purified by chromatography on $SiO_2$ (0% to 30% EtOAc/petroleum ether) to afford 2-amino-5-bromobenzaldehyde (4A-1). MS (EI) calc'd for $C_7H_7BrNO$ [M+H]$^+$, 200; found, 200.

Steps 2-3 4-Benzyl-6-bromo-1H-benzo[d][1,3]oxazin-2(4H)-one (4A-3)

To a solution of 2-amino-5-bromobenzaldehyde (4A-1) (0.50 g, 2.5 mmol) in THF (5 mL) was added a THF solution of benzylmagnesium bromide (8.3 mL, 7.5 mmol) at −40° C. The reaction was stirred for 2 h at room temperature. The reaction mixture was quenched with water (5 mL) and the resulting solution was extracted with EtOAc (3×10 mL). The combined organic layers was washed with brine (10 mL), dried ($Na_2SO_4$) and concentrated. The residue was purified by chromatography on $SiO_2$ (0% to 50% EtOAc/petroleum ether) to afford 1-(2-amino-5-bromophenyl)-2-phenylethanol. MS (EI) calc'd for $C_{14}H_{15}BrNO$ [M+H]$^+$, 292; found, 292.

To a solution of 1-(2-amino-5-bromophenyl)-2-phenylethanol (80 mg, 0.27 mmol) in DCM (5 mL), was added slowly triphosgene (98 mg, 0.33 mmol) at 0° C. and the mixture stirred at 0° C. for 20 min. Then, triethylamine (0.11 mL, 0.82 mmol) was added to the above solution at 0° C. The reaction mixture was allowed to stir at room temperature for another 1 h, and the resulting mixture poured into crushed ice and extracted with EtOAc (2×5 mL). The combined organic layers were washed with brine (5 mL), dried ($Na_2SO_4$) and concentrated. The residue was purified by chromatography on $SiO_2$ (0% to 50% EtOAc/petroleum ether) to afford 4-benzyl-6-bromo-1H-benzo[d][1,3]oxazin-2(4H)-one (4A-3). MS (EI) calc'd for $C_{15}H_{13}BrNO_2$ [M+H]$^+$, 318; found, 318.

Step 4 4-Benzyl-6(4,4,5,5-tetramethyl-1,3,2-dioxaborolan-2-yl)-1H-benzo[d][1,3]oxazin-2(4H)-one To a solution of 4-benzyl-6-bromo-1H-benzo[d][1,3]oxazin-2(4H)-one (4A-3) (66 mg, 0.21 mmol) in dioxane (2 mL), were added KOAc (40 mg, 0.42 mmol), (BPin)$_2$ (63 mg, 0.25 mmol) and PdCl$_2$(dppf) (15 mg, 0.02 mmol). The resulting mixture was deoxygenated with nitrogen and stirred for 2 h at 90° C. After cooling to room temperature, the reaction mixture was diluted with water (2 mL) and extracted with EtOAc (3×5 mL). The combined organic layers was washed with brine (5 mL), dried ($Na_2SO_4$) and concentrated. The residue was purified by chromatography on $SiO_2$ (0% to 25% EtOAc/petroleum ether) to afford 4-benzyl-6-(4,4,5,5-tetramethyl-1,3,2-dioxaborolan-2-yl)-1H-benzo[d][1,3]oxazin-2(4H)-one (4A-4). MS (EI) calc'd for $C_{21}H_{25}BNO_4$ [M+H]$^+$, 366; found, 366.

Steps 5-6 (R or S)- and (S or R)-4-Benzyl-6-(9-ethyl-8-(2-methylpyrimidin-5-yl)-9H-purin-6-yl)-1H-benzo[d][1,3]oxazin-2(4H)-one (4-1 and 4-2)

To a solution of 4-benzyl-6-(4,4,5,5-tetramethyl-1,3,2-dioxaborolan-2-yl)-1H-benzo[d][1,3]oxazin-2(4H)-one (50 mg, 0.14 mmol) in dioxane/water (3 mL/1 mL), were added Intermediate I (38 mg, 0.14 mmol), potassium carbonate (38 mg, 0.27 mmol) and PdCl$_2$(dppf)-CH$_2$Cl$_2$ (11 mg, 0.01 mmol). The mixture was deoxygenated with nitrogen and stirred for 2 h at 100° C. After cooling to room temperature, the reaction mixture was diluted with water (2 mL) and extracted with ethyl acetate (2×5 mL). The combined organic layers was washed with brine (5 mL), dried over anhydrous sodium sulfate and filtered. The filtrate was concentrated under reduced pressure and the residue was purified by Prep-HPLC [Column: X Bridge RP C18, 19×150 mm, 5 um; 30-50% MeCN/water with 10 mM NH$_4$HCO$_3$; Flow rate: 20 mL/min] to give the racemic title compound.

The racemate was separated by Prep-Chiral-HPLC [Column: ChiralPak™ IB 2×25 cm, 5 um; 30% EtOH/hexane; Flow rate: 20 mL/min; 254/220 nm; Retention Time 1: 11 min; Retention Time 2: 14 min]. The faster-eluting enantiomer of the title compound (4-1) was obtained at 11.0 min. $^1$H NMR (400 MHz, CDCl$_3$) δ 9.20-9.17 (m, 2H), 9.07 (s, 1H), 8.98 (s, 1H), 8.73 (s, 1H), 7.61 (s, 1H), 7.28-7.16 (m, 5H), 6.93 (d, J=8.0 Hz, 1H), 5.81 (s, 1H), 4.53 (s, 2H), 3.35-3.39 (m, 2H); 2.93 (s, 3H), 1.81-1.78 (m, 3H). MS (EI) calc'd for $C_{27}H_{24}N_7O_2$ [M+H]$^+$, 478; found, 478. The slower-eluting enantiomer of the title compound (4-2) was obtained at 14.0 min. $^1$H NMR (400 MHz, CDCl$_3$) δ 9.17-9.13 (m, 3H), 8.98 (s, 1H), 8.76 (s, 1H), 7.64 (s, 1H), 7.24-7.15 (m, 5H), 6.98 (d, J=8.0 Hz, 1H), 5.80 (s, 1H), 4.55 (s, 2H), 3.35-3.39 (m, 2H), 2.95 (s, 3H), 1.81-1.78 (m, 3H). MS (EI) calc'd for $C_{27}H_{24}N_7O_2$ [M+H]$^+$, 478; found, 478.

Example 4B Compounds 4-3 and 4-4

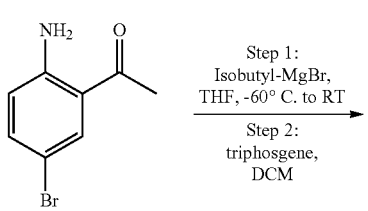
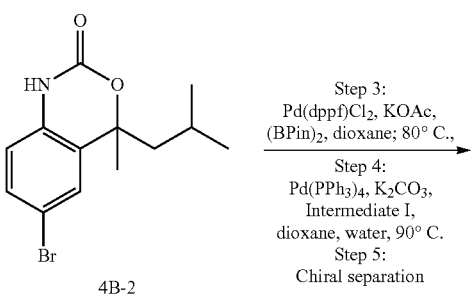

4B-2

Step 1: Isobutyl-MgBr, THF, −60° C. to RT
Step 2: triphosgene, DCM
Step 3: Pd(dppf)Cl$_2$, KOAc, (BPin)$_2$, dioxane; 80° C.,
Step 4: Pd(PPh$_3$)$_4$, K$_2$CO$_3$, Intermediate I, dioxane, water, 90° C.
Step 5: Chiral separation

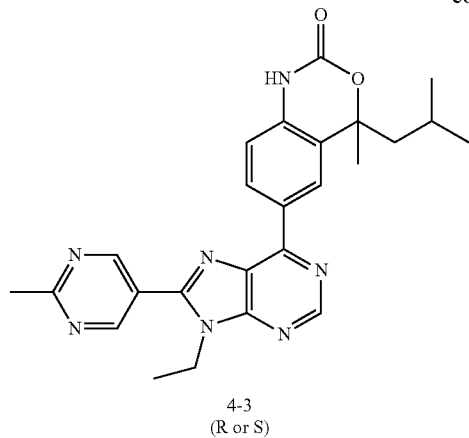

4-3
(R or S)

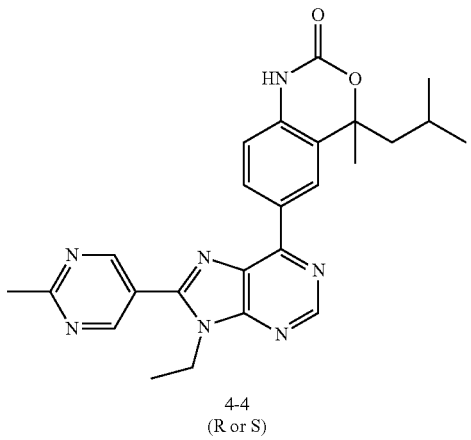

4-4
(R or S)

Step 1
2-(2-Amino-5-bromophenyl)-4-methylpentan-2-ol

To a solution of 1-(2-amino-5-bromophenyl)ethanone (3.0 g, 14 mmol) in THF (40 mL), was added dropwise a 2 M solution of isobutylmagnesium bromide (21 ml, 42 mmol) in THF within 30 min at −60° C. The resulting solution was stirred for 30 min at −60° C., then warmed to room temperature and stirred for 1 h. The mixture was cooled to 0° C. and quenched with saturated ammonium chloride (40 mL). The resulting mixture was extracted with EtOAc (3×150 mL) and the combined organic layers was washed with brine (3×100 mL), dried ($Na_2SO_4$) and concentrated. The residue was purified by chromatography on $SiO_2$ (0 to 20% EtOAc/petroleum ether) to afford 2-(2-amino-5-bromophenyl)-4-methylpentan-2-ol, MS (EI) calc'd for $C_{12}H_{19}BrNO$ [M+H]$^+$, 272; found, 272.

Step 2 6-Bromo-4-isobutyl-4-methyl-1H-benzo[d][1,3]oxazin-2(4H)-one (4B-2)

To a solution of 2-(2-amino-5-bromophenyl)-4-methylpentan-2-ol (2.0 g, 7.6 mmol) in DCM (30 mL), was added bis(trichloromethyl) carbonate (0.87 g, 2.9 mmol) portionwise. The resulting mixture was stirred for 2 h at 25° C., then quenched with saturated sodium bicarbonate (30 mL). The resulting mixture was extracted DCM with (3×50 mL). The combined organic layers were washed with brine (2×50 mL), dried ($Na_2SO_4$) and concentrated. The residue was purified by chromatography on $SiO_2$ (0 to 25% EtOAc/petroleum ether) to afford 6-bromo-4-isobutyl-4-methyl-1H-benzo[d][1,3]oxazin-2(4H)-one (4B-2). MS (EI) calc'd for $C_{13}H_{17}BrNO_2$ [M+H]$^+$, 298; found, 298.

Steps 3-5 (R or S)- and (S or R)-6-(9-Ethyl-8-(2-methylpyrimidin-5-yl)-9H-purin-6-yl)-4-isobutyl-4-methyl-1H-benzo[d][1,3]oxazin-2(4H)-one (4-3 and 4-4)

A mixture of 6-bromo-4-isobutyl-4-methyl-1H-benzo[d][1,3]oxazin-2(4H)-one (4B-2) (300 mg, 1.01 mmol), $PdCl_2$(dppf) (74 mg, 0.10 mmol), KOAc (247 mg, 2.52 mmol) and (BPin)$_2$ (281 mg, 1.11 mmol) in 1,4-dioxane (10 ml) was deoxygenated with nitrogen and stirred for 2 h at 80° C. Next, Intermediate I (276 mg, 1.01 mmol), Pd(Ph$_3$P)$_4$ (116 mg, 0.101 mmol), potassium carbonate (278 mg, 2.01 mmol) and water (2 mL) were added. The resulting mixture was stirred for 16 h at 90° C. After cooling to room temperature, the reaction mixture was diluted with water (10 mL) and extracted with ethyl acetate (3×20 mL). The combined organic layers was washed with brine (2×20 mL), dried ($Na_2SO_4$) and concentrated. The residue was purified by chromatography on $SiO_2$ (20 to 50% EtOAc/petroleum ether) to afford 6-(9-ethyl-8-(2-methylpyrimidin-5-yl)-9H-purin-6-yl)-4-isobutyl-4-methyl-1H-benzo[d][1,3]oxazin-2(4H)-one.

The racemate was separated by Chiral-HPLC [Column: ChiralPak™ IC-3, 2×25 cm, 5 um; 40% EtOH/hexane; Flow rate: 18 mL/min; 254/220 nm; Retention Time 1: 18.25 min; Retention Time 2: 23.15 min). The faster-eluting enantiomer of the title compound (4-3) was obtained at 18.25 min. $^1$H NMR (400 MHz, DMSO-d$_6$) δ 10.54 (s, 1H), 9.26 (s, 1H), 9.00 (s, 1H), 8.82 (d, J=1.6 Hz, 1H), 8.77 (dd, J=8.4 Hz, 2.0 Hz, 1H), 7.09 (d, J=8.4 Hz, 1H), 4.47 (q, J=7.2 Hz, 2H), 2.78 (s, 3H), 2.03-1.97 (m, 1H), 1.84-1.81 (m, 2H), 1.67 (s, 3H), 1.39 (t, J=7.2 Hz, 3H), 0.87 (2d, J=6.4 Hz, 6H). MS (EI) calc'd for $C_{25}H_{28}N_7O_2$ [M+H]$^+$, 458; found, 458. The slower-eluting enantiomer of the title compound (4-4) was obtained at 23.15 min. $^1$H NMR (400 MHz, DMSO-d$_6$) δ 10.54 (s, 1H), 9.26 (s, 1H), 9.00 (s, 1H), 8.82 (d, J=1.6 Hz, 1H), 8.77 (dd, J=8.4 Hz, 2.0 Hz, 1H), 7.09 (d, J=8.4 Hz, 1H), 4.47 (q, J=7.2 Hz, 2H), 2.78 (s, 3H), 2.03-1.97 (m, 1H), 1.84-1.81 (m, 2H), 1.67 (s, 3H), 1.39 (t, J=7.2 Hz, 3H), 0.87 (2d, J=6.4 Hz, 6H). MS (EI) calc'd for $C_{25}H_{28}N_7O_2$ [M+H]$^+$, 458; found, 458.

Example 4C Compounds 4-5 and 4-6

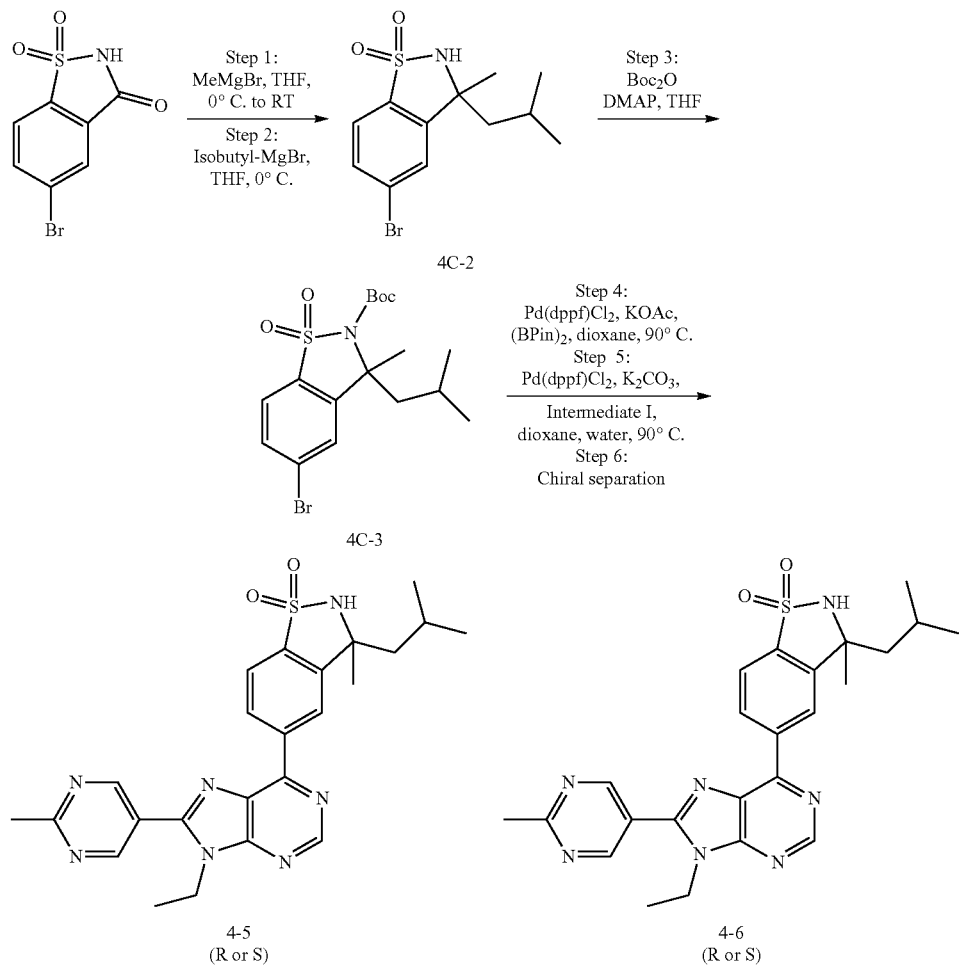

Step 1 5-Bromo-3-methylbenzo[d]isothiazole-1,1-dioxide

To a solution of 5-bromobenzo[d]isothiazol-3(2H)-one 1,1-dioxide (2.0 g, 7.6 mmol) in THF (60 mL) was added a 3 M THF solution of MeMgCl (5.3 mL, 16 mmol) at 0° C. The solution was warmed to ambient temperature for 2 h and stirred for an additional 12 h. Aqueous ammonium chloride (200 mL) was added and the mixture was extracted with ethyl acetate (3×50 mL). The combined organic fractions were washed with brine (3×20 mL), dried ($Na_2SO_4$), filtered and the solvent evaporated under reduced pressure. The residue was purified by chromatography on $SiO_2$ (1-25% EtOAc/isohexane) to give 5-bromo-3-methylbenzo[d]isothiazole 1,1-dioxide. MS (EI) calc'd for $C_8H_7BrNO_2S$ $[M+H]^+$, 260; found, 260.

Step 2 5-Bromo-3-isobutyl-3-methyl-2,3-dihydrobenzo[d]isothiazole-1,1-dioxide (4C-2)

To a solution of 5-bromo-3-methylbenzo[d]isothiazole 1,1-dioxide (500 mg, 1.92 mmol) in THF (10 ml) was added a 2 M THF solution of isobutylmagnesium bromide (1.15 mL, 2.30 mmol) at 0° C. The solution was stirred at 0° C. for 1 h, then aqueous ammonium chloride (saturated, 30 mL was added and the mixture was extracted with ethyl acetate (3×20 mL). The combined organic fractions were washed with brine (2×10 mL), dried ($Na_2SO_4$), filtered, and the solvent was evaporated under reduced pressure. The residue was purified by preparative HPLC [C-18 column; 20% to 90% MeCN/water; Flow 40 mL/min], 5 g) to give 5-bromo-3-isobutyl-3-methyl-2,3-dihydrobenzo[d]isothiazole 1,1-dioxide (4C-2). MS (EI) calc'd for $C_{12}H_{17}BrNO_2S$ $[M+H]^+$, 318; found, 318.

Step 3 tert-Butyl 5-Bromo-3-isobutyl-3-methylbenzo[d]isothiazole-2(3H)-carboxylate-1,1-dioxide (4C-3)

A solution of 5-bromo-3-isobutyl-3-methyl-2,3-dihydrobenzo[d]isothiazole 1,1-dioxide (4C-2) (50 mg, 0.16 mmol), di-tert-butyl dicarbonate (51 mg, 0.24 mmol) and N,N-dimethylpyridin-4-amine (58 mg, 0.47 mmol) in THF (3 mL) was stirred at ambient temperature for 3 h. The mixture was diluted with ethyl acetate (30 mL), washed with brine (2×5 mL), dried ($Na_2SO_4$), filtered and the solvent evaporated under reduced pressure. The residue was purified by chromatography on $SiO_2$ (1-20% EtOAc/isohexane) to give tert-butyl 5-bromo-3-isobutyl-3-methylbenzo[d]isothiazole-2(3H)-carboxylate-1,1-dioxide (4C-3). MS (EI) calc'd for $C_{17}H_{25}BrNO_4S$ $[M+H]^+$, 418; found, 418.

Steps 4-6 (R or S)- and (S or R)-5-(9-Ethyl-8-(pyrimidin-5-yl)-9H-purin-6-yl)-3-isobutyl-3-methyl-2,3-dihydrobenzo[d]isothiazole-1,1-dioxide (4-5 and 4-6)

A mixture of tert-butyl 5-bromo-3-isobutyl-3-methyl-benzo[d]isothiazole-2(3H)-carboxylate-1,1-dioxide (200 mg, 0.478 mmol), PdCl$_2$(dppf) (35 mg, 0.048 mmol), KOAc (94 mg, 0.96 mmol) and (BPin)$_2$ (150 mg, 0.57 mmol) in dioxane (10 mL) was stirred at 90° C. for 3 h. The mixture was cooled to ambient temperature, then treated with Intermediate I (160 mg, 0.57 mmol), K$_2$CO$_3$ (130 mg, 0.96 mmol) and water (2 mL). The mixture was then stirred at 90° C. for 12 h. The mixture was cooled to ambient temperature, ethyl acetate (30 mL) was added, then the organic layer was washed with brine (2×10 mL), dried (Na$_2$SO$_4$), filtered and the solvent evaporated under reduced pressure. The residue was purified by chromatography on SiO$_2$ (1-90% EtOAc/isohexane) to give racemic 5-(9-ethyl-8-(2-methylpyrimidin-5-yl)-9H-purin-6-yl)-3-isobutyl-3-methyl-2,3-dihydrobenzo[d]isothiazole-1,1-dioxide.

The racemate was then separated by Prep-Chiral HPLC [Column: ChiralPak™ IC 2×25 cm, 5 um; 40% EtOH/hexane; Flow rate: 17 mL/min; 254/220 nm; Retention Time 1: 21.2 min, Retention Time 2: 29.9 min]. The faster-eluting enantiomer of the title compound (4-5) was obtained at 21.2 min. $^1$H NMR (400 MHz, DMSO-d$_6$) δ 9.28 (s, 2H), 9.14 (s, 1H), 9.06 (d, J=8.4 Hz, 1H), 8.94 (s, 1H), 8.06 (s, 1H), 8.02 (d, J=8.4 Hz, 1H), 4.50 (q, J=7.2 Hz, 2H), 2.79 (s, 3H), 1.90-1.80 (m, 2H), 1.71-1.68 (m, 1H), 1.60 (s, 3H), 1.42 (d, J=7.2 Hz, 3H), 0.91 (d, J=6.4 Hz, 3H), 0.62 (d, J=6.4 Hz, 3H). MS (EI) calc'd for C$_{24}$H$_{28}$N$_7$O$_2$S [M+H]$^+$, 478; found, 478. The slower-eluting enantiomer of the title compound (4-6) was obtained at 29.9 min. $^1$H NMR (400 MHz, DMSO-d$_6$) δ 9.28 (s, 2H), 9.14 (s, 1H), 9.06 (d, J=8.4 Hz, 1H), 8.94 (s, 1H), 8.06 (s, 1H), 8.02 (d, J=8.4 Hz, 1H), 4.50 (q, J=7.2 Hz, 2H), 2.79 (s, 3H), 1.88-1.84 (m, 2H), 1.71-1.68 (m, 1H), 1.59 (s, 3H), 1.42 (d, J=7.2 Hz, 3H), 0.91 (d, J=6.4 Hz, 3H), 0.62 (d, J=6.4 Hz, 3H). MS (EI) calc'd for C$_{24}$H$_{28}$N$_7$O$_2$S [M+H]$^+$, 478; found, 478.

Example 4D Compound 4-7 and 4-8

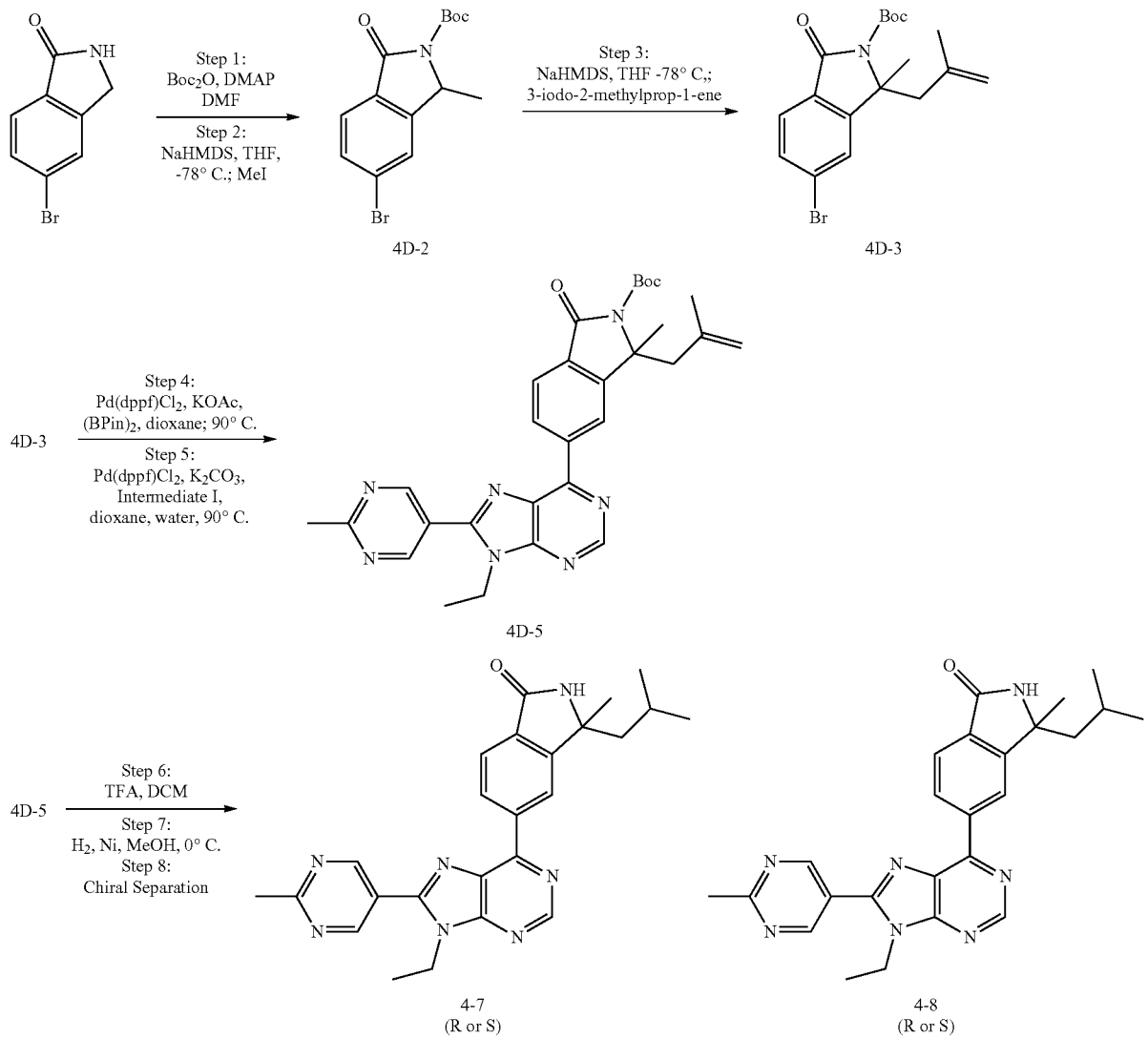

Step 1 tert-Butyl 5-Bromo-1-oxoisoindoline-2-carboxylate

A solution of 5-bromoisoindolin-1-one (2.0 g, 9.4 mmol), N,N-dimethylpyridin-4-amine (0.23 g, 1.9 mmol) and di-tert-butyl dicarbonate (2.47 g, 11.3 mmol) in DMF (20 ml) was stirred at ambient temperature for 2 h. Water (100 mL) was then added and the mixture was extracted with EtOAc (3×30 mL). The combined organic fractions were washed with brine (3×10 mL), dried ($Na_2SO_4$), filtered and the solvent evaporated under reduced pressure. The residue was purified by chromatography on $SiO_2$ (1-90% EtOAc/isohexane) to give tert-butyl 5-bromo-1-oxoisoindoline-2-carboxylate. MS (EI) calc'd for $C_{13}H_{15}Br NO_3$ $[M+H]^-$, 312; found, 312.

Step 2 tert-Butyl 5-Bromo-3-methyl-1-oxoisoindoline-2-carboxylate (4D-2)

To a solution of tert-butyl 5-bromo-1-oxoisoindoline-2-carboxylate (2.6 g, 8.3 mmol) in THF (50 mL) were added NaHMDS (1.99 g, 10.8 mmol) followed by iodomethane (1.8 g, 12 mmol) at −78° C. The solution was stirred at −78° C. for 1 h, then warmed to ambient temperature and aqueous ammonium chloride (100 mL) was added. The mixture was extracted with ethyl acetate (3×30 mL). The combined organic fractions were washed with brine (3×20 mL), dried ($Na_2SO_4$), filtered and the solvent evaporated under reduced pressure. The residue was purified by reverse phase chromatography [C-18 column; 40-70% MeCN/water] to give tert-butyl 5-bromo-3-methyl-1-oxoisoindoline-2-carboxylate (4D-2). MS (EI) calc'd for $C_{14}H_{17}BrNO_3$ $[M+H]^+$, 326; found, 326.

Step 3 tert-Butyl 6-Bromo-1-methyl-1-(2-methylallyl)-3-oxoisoindoline-2-carboxylate (4D-3)

To a solution of tert-butyl 5-bromo-3-methyl-1-oxoisoindoline-2-carboxylate (4D-2) (400 mg, 1.23 mmol) and 3-iodo-2-methylprop-1-ene (446 mg, 2.45 mmol) in THF (10 mL) was added a 2 M THF solution of NaHMDS (0.80 ml, 1.6 mmol) at −78° C. The solution was stirred at −78° C. for 1 h and then warmed to ambient temperature. Water (30 mL) was added and the mixture was extracted with ethyl acetate (3×10 mL). The combined organic fractions were washed with brine (2×5 mL), dried ($Na_2SO_4$), filtered and the solvent evaporated under reduced pressure. The residue was purified by chromatography on $SiO_2$ (1-90% EtOAc/isohexane) to give tert-butyl 6-bromo-1-methyl-1-(2-methylallyl)-3-oxoisoindoline-2-carboxylate (4D-3). MS (EI) calc'd for $C_{18}H_{23}Br NO_3$ $[M+H]^+$, 380; found, 380.

Steps 4-5 tert-Butyl 6-(9-Ethyl-8-(2-methylpyrimidin-5-yl)-9H-purin-6-yl)-1-methyl-1-(2-methylallyl)-3-oxoisoindoline-2-carboxylate (4D-5)

To a solution of tert-butyl 6-bromo-1-methyl-1-(2-methylallyl)-3-oxoisoindoline-2-carboxylate (4D-2) (0.30 g, 0.80 mmol) in dioxane (10 mL) were added $PdCl_2(dppf)$ (58 mg, 0.080 mmol), KOAc (155 mg, 1.58 mmol) and $(BPin)_2$ (0.24 g, 0.95 mmol). The resulting mixture was stirred at 90° C. for 3 h. After cooling to room temperature, Intermediate I (0.26 g, 0.95 mmol), $K_2CO_3$ (0.22 g, 1.6 mmol) and water (2 mL) were added to the above mixture. The resulting mixture was stirred at 90° C. for 12 h. After cooling to room temperature, the reaction mixture was diluted with ethyl acetate (30 mL), washed with brine (2×10 mL), dried over anhydrous sodium sulfate and filtered. The filtrate was concentrated under reduced pressure and the residue purified by chromatography on $SiO_2$ (0% to 25% EtOAc/hexane) to afford tert-butyl 6-(9-ethyl-8-(2-methylpyrimidin-5-yl)-9H-purin-6-yl)-1-methyl-1-(2-methylallyl)-3-oxoisoindoline-2-carboxylate (4D-5). MS (EI) calc'd for $C_{30}H_{34}N_7O_3$ $[M+H]^+$, 540; found, 540.

Step 6 5-(9-Ethyl-8-(2-methylpyrimidin-5-yl)-9H-purin-6-yl)-3-methyl-3-(2-methylallyl)isoindolin-1-one A solution of tert-butyl 6-(9-ethyl-8-(2-methylpyrimidin-5-yl)-9H-purin-6-yl)-1-methyl-1-(2-methylallyl)-3-oxoisoindoline-2-carboxylate (4D-5) (300 mg, 0.556 mmol) and TFA (2.1 mL, 28 mmol) in DCM (10 ml) was stirred at ambient temperature for 1 h. The solution was adjusted pH of 8-9 with the addition of aqueous sodium hydrogen carbonate, then extracted with DCM (2×20 mL). The combined organic fractions were washed with brine (2×10 mL), dried ($Na_2SO_4$), filtered and the solvent evaporated under reduced pressure to give 5-(9-ethyl-8-(2-methylpyrimidin-5-yl)-9H-purin-6-yl)-3-methyl-3-(2-methylallyl)isoindolin-1-one. MS (EI) calc'd for $C_{25}H_{26}N_7O$ $[M+H]^+$, 440; found, 440.

Steps 7-8 (R or S)- and (S or R)-5-(9-Ethyl-8-(2-methylpyrimidin-5-yl)-9H-purin-6-yl)-3-isobutyl-3-methylisoindolin-1-one (4-7 and 4-8)

A mixture of 5-(9-ethyl-8-(2-methylpyrimidin-5-yl)-9H-purin-6-yl)-3-methyl-3-(2-methylallyl)isoindolin-1-one (80 mg, 0.18 mmol) and nickel (21 mg, 0.036 mmol) in MeOH (3 mL) was stirred at 0° C. for 15 h with $H_2$ (3 atm). The mixture was filtered, washed with MeOH (10 mL) and concentrated. The residue was purified by preparative reverse phase HPLC [C-18 column; 20-70% MeCN/water with 0.05% TFA; Flow rate: 20 mL/min, 254 nm) to give 5-(9-ethyl-8-(2-methylpyrimidin-5-yl)-9H-purin-6-yl)-3-isobutyl-3-methylisoindolin-1-one. The racemate was then resolved using prep-chiral HPLC [Column: ChiralPak™ IC 2×25 cm, 5 um; 30% EtOH/hexane; Flow rate: 18 mL/min; 254/220 nm; Retention Time 1: 17.9 min; Retention Time 2: 22.1 min). The faster-eluting enantiomer of the title compound (4-7) was obtained at 17.9 min. $^1$H NMR (300 MHz, $CD_3OD$) δ 9.22 (s, 2H), 9.02 (s, 1H), 8.97 (d, J=8.1 Hz, 1H), 8.89 (s, 1H), 7.89 (d, J=7.8 Hz, 1H), 4.54 (q, J=7.2 Hz, 2H), 2.82 (s, 3H), 2.04-1.89 (m, 2H), 1.56 (s, 3H), 1.49 (t, J=7.2 Hz, 3H), 1.33-1.23 (m, 1H), 0.85 (d, J=7.2 Hz, 3H), 0.55 (d, J=7.2 Hz, 3H). MS (EI) calc'd for $C_{25}H_{28}N_7O$ $[M+H]^+$, 442; found, 442. The slower-eluting enantiomer of the title compound (4-8) was obtained at 22.1 min. $^1$H NMR (300 MHz, $CD_3OD$) δ 9.22 (s, 2H), 9.01 (s, 1H), 8.96 (d, J=8.1 Hz, 1H), 8.89 (s, 1H), 7.88 (d, J=7.8 Hz, 1H), 4.53 (q, J=7.2 Hz, 2H), 2.82 (s, 3H), 2.04-1.89 (m, 2H), 1.56 (s, 3H), 1.49 (t, J=7.2 Hz, 3H), 1.33-1.22 (m, 1H), 0.85 (d, J=7.2 Hz, 3H), 0.55 (d, J=7.2 Hz, 3H). MS (EI) calc'd for $C_{13}H_{15}BrNO_3$ $[M+H]^+$, 442; found, 442.

Example 4E Compound 4-9

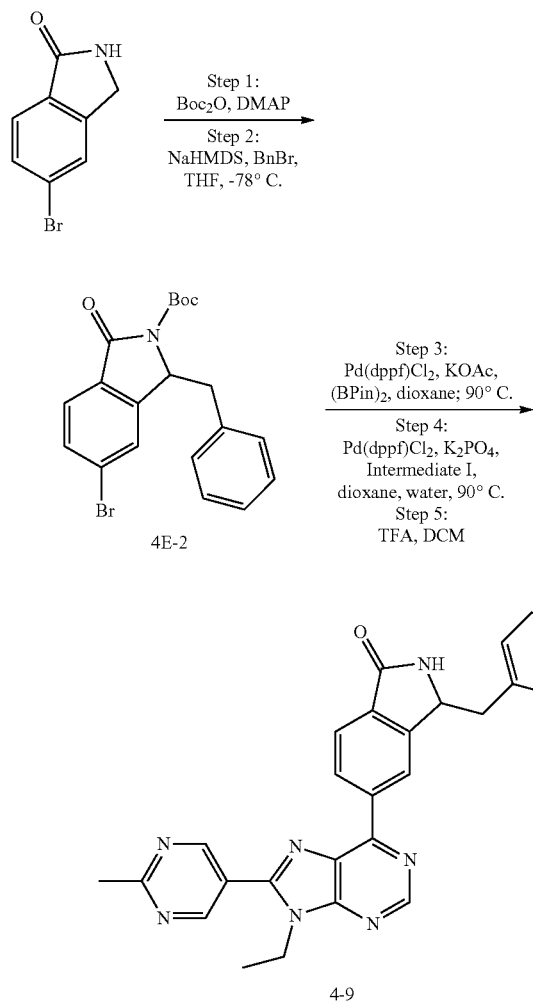

4-9

Step 1 tert-Butyl 5-Bromo-1-oxoisoindoline-2-carboxylate

A suspension of 5-bromoisoindolin-1-one (1.0 g, 4.7 mmol) in DMF (10 mL) was treated with DMAP (0.10 g, 0.82 mmol) followed by Boc$_2$O (1.2 g, 5.5 mmol). The suspension was stirred until homogeneous, about 2 hours, then concentrated to dryness. The residue was dissolved into DCM, washed with water, dried (Na$_2$SO$_4$) and concentrated. Chromatography on SiO$_2$ (0-100% EtOAc/DCM) gave the desired product. MS (EI) calc'd for C$_9$H$_7$BrNO$_3$ [M+H–tBu]$^+$, 256; found, 256.

Step 2 tert-Butyl 3-Benzyl-5-bromo-1-oxoisoindoline-2-carboxylate (4E-2)

A solution of tert-butyl 5-bromo-1-oxoisoindoline-2-carboxylate (0.50 g, 1.6 mmol) in THF (5 mL) was cooled to –78° C. and treated dropwise with a 1 M THF solution of NaHMDS (2.0 mL, 2.0 mmol). The mixture was stirred 5 min, then treated dropwise with (bromomethyl)benzene (0.41 g, 2.4 mmol). After stirring for 1 hour, the reaction mixture was quenched with EtOAc and washed with water. The organic layer was dried (Na$_2$SO$_4$) and concentrated to dryness. Chromatography on SiO$_2$ (0-100% EtOAc/DCM) gave the desired product (4E-2). MS (EI) calc'd for C$_{16}$H$_{13}$BrNO$_3$ [M+H–tBu]$^+$, 346; found, 346.

Step 3-5 (R and S)-3-Benzyl-5-(9-ethyl-8-(2-methylpyrimidin-5-yl)-9H-purin-6-yl)isoindolin-1-one (4-9)

A mixture containing tert-butyl 3-benzyl-5-bromo-1-oxoisoindoline-2-carboxylate (4E-2) (75 mg, 0.19 mmol) in dioxane (1 mL) was treated with KOAc (40 mg, 0.41 mmol), (BPin)$_2$ (75 mg, 0.30 mmol), PdCl$_2$(dppf) (15 mg, 0.018 mmol) and stirred for 2 hours at 90° C. Next, Intermediate I (50 mg, 0.18 mmol), K$_3$PO$_4$ (100 mg, 0.47 mmol) and water (0.2 mL) were added and the reaction mixture stirred overnight at 80° C. The reaction was cooled to RT, diluted with DCM, washed with water, dried (Na$_2$SO$_4$) and concentrated. Chromatography on SiO$_2$ (0-20% MeOH/DCM) gave the desired intermediate product. The residue was dissolved in 1 mL of 1:1 DCM/TFA and stirred for 2 hours, then concentrated to dryness. Reverse phase chromatography (MeCN/water using 0.1% TFA) provided the desired product 4-9 as a TFA salt. $^1$H NMR (600 MHz, DMSO-d$_6$) δ 9.22 (s, 2H), 9.05 (s, 1H), 8.90-8.87 (m, 2H), 8.81 (s, 1H), 7.70 (d, J=7.9 Hz, 1H), 7.11-7.08 (m, 4H), 7.03-7.01 (m, 1H), 5.03 (t, J=5.6 Hz, 2H), 4.43 (q, J=7.3 Hz, 2H), 3.18 (dd, J=14, 5.3 Hz, 1H), 3.09 (dd, J=13.8, 5.9 Hz, 1H), 2.76 (s, 3H), 1.37 (t, J=7.3 Hz, 3H); MS (EI) calc'd for C$_{27}$H$_{24}$N$_7$O [M+H]$^+$, 462; found, 462.

Example 4F Compound 4-10 and 4-11

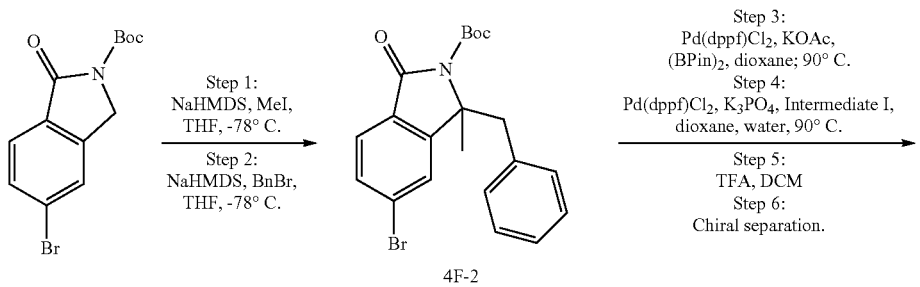

4F-2

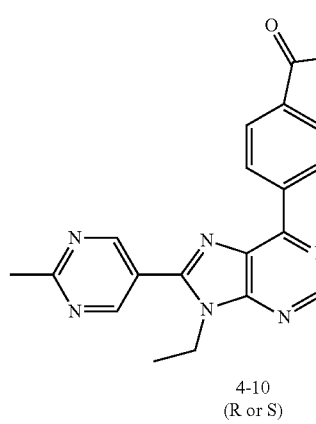

4-10
(R or S)

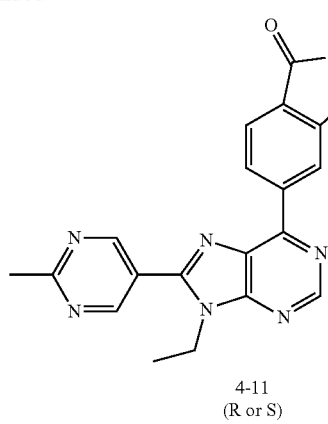

4-11
(R or S)

Step 1 tert-butyl 5-Bromo-3-methyl-1-oxoisoindoline-2-carboxylate (4F-2)

A solution of tert-butyl 5-bromo-1-oxoisoindoline-2-carboxylate (0.50 g, 1.6 mmol) in THF (10 mL) was treated at −78° C. with a 1 M THF solution of NaHMDS (2.0 mL, 2.0 mmol), the reaction stirred 10 min, then treated with methyl iodide (0.20 mL, 3.2 mmol). The mixture was stirred for 1 hour at −78° C., then quenched with water and extracted with EtOAc. The organic layer was dried ($Na_2SO_4$) and concentrated. Chromatography on $SiO_2$ (0-100% EtOAc/DCM) gave the desired product. MS (EI) calc'd for $C_{10}H_9BrNO_3$ [M+H−tBu]$^+$, 270; found, 270.

Step 2 tert-Butyl 1-Benzyl-6-bromo-1-methyl-3-oxoisoindoline-2-carboxylate (4F-2)

A solution of tert-butyl 5-bromo-3-methyl-1-oxoisoindoline-2-carboxylate (375 mg, 1.15 mmol) in THF (10 mL) and treated at −78° C. with a 1 M THF solution of NaHMDS (2.0 mL, 2.0 mmol). The mixture was stirred for 5 min, then treated with (bromomethyl)benzene (0.41 g, 2.4 mmol). The reaction mixture was stirred at −78° C. for 1 hour, then quenched with water and extracted with EtOAc. The organic layer was dried ($Na_2SO_4$) filtered and concentrated. Chromatography on $SiO_2$ (0-100% EtOAc/DCM) gave the desired product (4F-2). MS (EI) calc'd for $C_{17}H_{15}BrNO_3$ [M+H−tBu]$^+$, 360; found, 360.

Step 3-6 (R or S)- and (S or R)-3-Benzyl-5-(9-ethyl-8-(2-methylpyrimidin-5-yl)-9H-purin-6-yl)-3-methylisoindolin-1-one (4-10 and 4-yl)

A mixture containing tert-butyl 1-benzyl-6-bromo-1-methyl-3-oxoisoindoline-2-carboxylate (75 mg, 0.19 mmol) in dioxane (1 mL) was treated with KOAc (40 mg, 0.41 mmol), (BPin)$_2$ (75 mg, 0.30 mmol), PdCl$_2$(dppf) (15 mg, 0.018 mmol) and stirred for 2 hours at 90° C. Next, Intermediate I (50 mg, 0.18 mmol), K$_3$PO$_4$ (100 mg, 0.47 mmol) and water (0.2 mL) were added and the reaction mixture stirred overnight at 80° C. The reaction was cooled to RT, diluted with DCM, washed with water, dried ($Na_2SO_4$) and concentrated. Chromatography on $SiO_2$ (0-20% MeOH/DCM) gave the desired intermediate product. The residue was dissolved in 1 mL of 1:1 DCM/TFA and stirred for 2 hours, then concentrated to dryness. Reverse phase chromatography (MeCN/water using 0.1% TFA) provided the desired product as a TFA salt. MS (EI) calc'd for $C_{28}H_{26}N_7O$ [M+H]$^+$, 476; found, 476.

The racemic material was then dissolved in 4 mL of MeOH/MeCN and resolved using chiral column chromatography [Column: ChiralPak™ IA, 21×250 mm; 220 nm detection; 70 mL/min flow rate; 40% MeOH, 0.25% Me$_2$NEt in CO$_2$]. The faster eluting enantiomer came at a retention time of 6.10 min (4-10); while the slower eluting enantiomer came at a retention time of 8.41 min (4-11). Data for 4-10: $^1$H NMR (600 MHz, DMSO-d$_6$) δ 9.25 (s, 2H), 9.10 (s, 1H), 9.00 (s, 1H), 8.87 (dd, J=7.9, 1.2 Hz, 1H), 8.77 (s, 1H), 7.55 (d, J=7.9 Hz, 1H), 6.98-6.97 (m, 3H), 6.90-6.88 (m, 2H), 4.46 (q, J=7.3 Hz, 2H), 3.30-3.27 (m, 1H), 3.13-3.09 (m, 1H), 2.75 (s, 3H), 1.61 (s, 3H), 1.39 (t, J=7.0 Hz, 3H); MS (EI) calc'd for $C_{28}H_{26}N_7O$ [M+H]$^+$, 476; found, 476. Data for 4-11: $^1$H NMR (600 MHz, DMSO-d$_6$) δ 9.25 (s, 2H), 9.10 (s, 1H), 9.00 (s, 1H), 8.87 (dd, J=7.9, 1.2 Hz, 1H), 8.77 (s, 1H), 7.55 (d, J=7.9 Hz, 1H), 6.98-6.97 (m, 3H), 6.90-6.88 (m, 2H), 4.46 (q, J=7.3 Hz, 2H), 3.30-3.27 (m, 1H), 3.13-3.09 (m, 1H), 2.75 (s, 3H), 1.61 (s, 3H), 1.39 (t, J=7.0 Hz, 3H); MS (EI) calc'd for $C_{28}H_{26}N_7O$ [M+H]$^+$, 476; found, 476.

Example 4G Compound 4-12

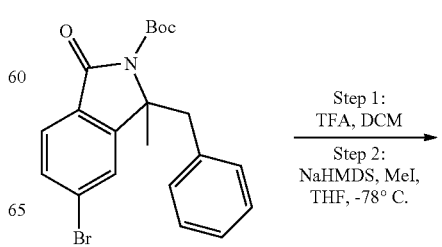

Step 1: TFA, DCM
Step 2: NaHMDS, MeI, THF, -78° C.

-continued

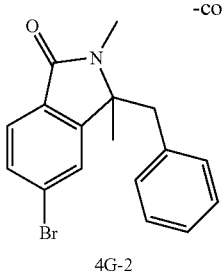

4G-2

Step 3: Pd(dppf)Cl₂, KOAc, (BPin)₂, dioxane; 85° C.

Step 4: Pd(dppf)Cl₂, K₃PO₄, Intermediate I, dioxane, water, 85° C.

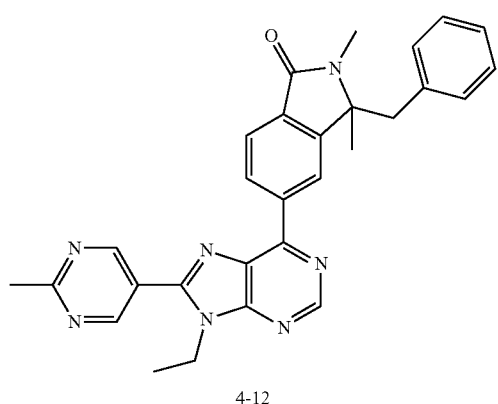

4-12

Step 1 3-Benzyl-5-bromo-3-methylisoindolin-1-one

A solution containing tert-butyl 1-benzyl-6-bromo-1-methyl-3-oxoisoindoline-2-carboxylate described for the synthesis of 4-10 and 4-11 (350 mg, 0.87 mmol) in DCM (2 mL) was treated with TFA (0.5 mL) and stirred for 1 h. The reaction mixture was concentrated to dryness, then taken up into DCM and washed with sat'd NaHCO₃. The organic layer was dried (Na₂SO₄), filtered and concentrated to dryness. MS (EI) calc'd for $C_{16}H_{15}BrNO$ [M+H]⁺, 316; found, 316.

Step 2 3-Benzyl-5-bromo-2,3-dimethylisoindolin-1-one (4G-2)

A solution of 3-benzyl-5-bromo-3-methylisoindolin-1-one (100 mg, 0.316 mmol) in THF (1 mL) was treated at −78° C. with a 1 M THF solution of NaHMDS (0.50 mL, 0.50 mmol). The mixture was stirred for 5 min, then treated dropwise with methyl iodide (0.10 mL, 1.6 mmol). The cooling bath was removed, the reaction was allowed to warm to RT and stirred overnight. The mixture was diluted with DCM, washed with water and dried (Na₂SO₄) to afford compound (4G-2). MS (EI) calc'd for $C_{17}H_{17}BrNO$ [M+H]⁻, 330; found, 330.

Steps 3-4 (R and S)-3-Benzyl-5-(9-ethyl-8-(2-methylpyrimidin-5-yl)-9H-purin-6-yl)-3-methylisoindolin-1-one (4-12)

A solution containing 3-benzyl-5-bromo-2,3-dimethylisoindolin-1-one (85 mg, 0.26 mmol) in dioxane (1 mL) was treated with KOAc (50 mg, 0.51 mmol), (BPin)₂ (80 mg, 0.32 mmol) and PdCl₂(dppf) (20 mg, 0.024 mmol). The mixture was stirred at 85° C. for 12 hours and cooled to RT. Next, Intermediate I (75 mg, 0.27 mmol), K₃PO₄ (100 mg, 0.47 mmol), more PdCl₂(dppf) (20 mg, 0.024 mmol) and water (0.2 mL) were added. The reaction mixture was stirred overnight at 85° C. Once cool, the mixture was diluted with DCM and washed with water. The organic layer was dried (Na₂SO₄), filtered and concentrated. The residue was then purified by reverse phase chromatography (MeCN/water with 0.1% TFA) to provide the title compound 4-12. ¹H NMR (600 MHz, DMSO-d₆) 9.26 (s, 2H), 9.10 (s, 1H), 9.05 (d, J=0.6 Hz, 1H), 8.88 (dd, J=7.9, 1.2 Hz, 1H), 7.58 (d, J=7.9 Hz, 1H), 6.93-6.91 (m, 3H), 6.71-6.69 (m, 2H), 4.46 (q, J=7.3 Hz, 2H), 3.36 (d, J=14 Hz, 1H), 3.29 (d, J=14 Hz, 1H), 3.05 (s, 3H), 2.75 (s, 3H), 1.63 (s, 3H), 1.39 (t, J=7.3 Hz, 3H); MS (EI) calc'd for $C_{29}H_{28}N_7O$ [M+H]⁺, 490; found, 490.

Example Compounds 4-13 to 4-16

Compound 4-13 was prepared in a fashion analogous to the preparation of 4-5 and 4-6. In this case, tert-butyl 5-bromo-3-isobutyl-3-methylbenzo[d]isothiazole-2(3H)-carboxylate 1,1-dioxide was substituted with the known and readily available 5-bromo-2,3-dihydrobenzo[d]isothiazole 1,1-dioxide. Since 4-13 is achiral, it did not require a chiral separation.

Compound 4-14 was prepared in a fashion analogous to the preparation of 4-5 and 4-6. In this case, tert-butyl 5-bromo-3-isobutyl-3-methylbenzo[d]isothiazole-2(3H)-carboxylate 1,1-dioxide was substituted with the known and readily available 5-bromo-2-methyl-2,3-dihydrobenzo[d]isothiazole 1,1-dioxide. Since 4-14 is achiral, it did not require a chiral separation.

Compound 4-15 was prepared in a fashion analogous to the preparation of 4-9. In this case, tert-butyl 3-benzyl-5-bromo-1-oxoisoindoline-2-carboxylate was substituted with the known and readily available 5-bromoisoindolin-1-one. Since 4-15 is achiral, it did not require a chiral separation.

Compound 4-16 was prepared in a fashion analogous to the preparation of 4-3 and 4-4. In this case, isobutyl magnesium bromide was replaced by phenyl magnesium bromide. Since 4-16 is chiral and used without chiral separation.

Table 4 provides structures for compounds 4-1 through 4-16 which were synthesized directly by the methods described above or by analogous methods to those described above.

TABLE 4

| Compound | Structure | Name | Exact Mass [M + H]+ |
|---|---|---|---|
| 4-1 | 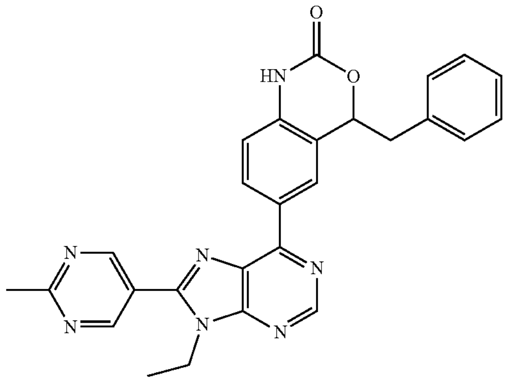 [SMILES: CCn1c(-c2cnc(C)nc2)nc2c(-c3ccc4c(c3)C(Cc3ccccc3)OC(=O)N4)ncnc21] | (R or S)-4-benzyl-6-[9-ethyl-8-(2-methylpyrimidin-5-yl)-9H-purin-6-yl]-1,4-dihydro-2H-3,1-benzoxazin-2-one | Calc'd 478, found 478 |
| 4-2 | 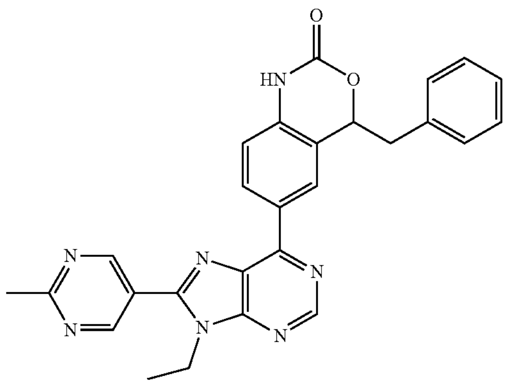 [SMILES: CCn1c(-c2cnc(C)nc2)nc2c(-c3ccc4c(c3)C(Cc3ccccc3)OC(=O)N4)ncnc21] | (R or S)-4-benzyl-6-[9-ethyl-8-(2-methylpyrimidin-5-yl)-9H-purin-6-yl]-1,4-dihydro-2H-3,1-benzoxazin-2-one | Calc'd 478, found 478 |
| 4-3 | 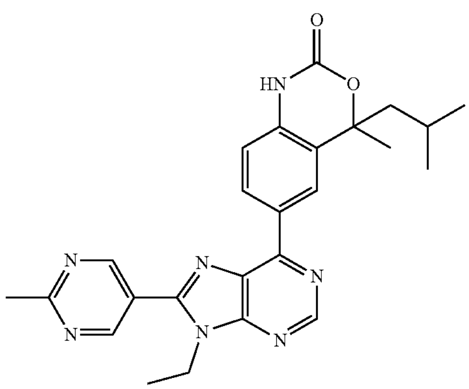 [SMILES: CCn1c(-c2cnc(C)nc2)nc2c(-c3ccc4c(c3)C(C)(CC(C)C)OC(=O)N4)ncnc21] | (R or S)-6-[9-ethyl-8-(2-methylpyrimidin-5-yl)-9H-purin-6-yl]-4-methyl-4-(2-methylpropyl)-1,4-dihydro-2H-3,1-benzoxazin-2-one | Calc'd 458, found 458 |
| 4-4 | 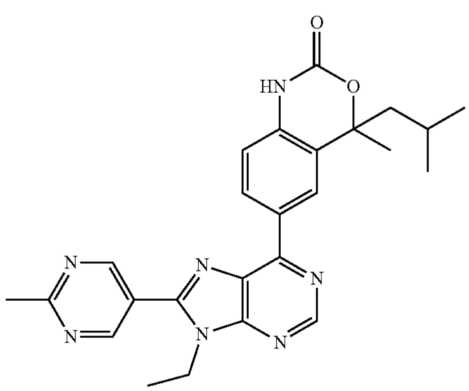 [SMILES: CCn1c(-c2cnc(C)nc2)nc2c(-c3ccc4c(c3)C(C)(CC(C)C)OC(=O)N4)ncnc21] | (R or S)-6-[9-ethyl-8-(2-methylpyrimidin-5-yl)-9H-purin-6-yl]-4-methyl-4-(2-methylpropyl)-1,4-dihydro-2H-3,1-benzoxazin-2-one | Calc'd 458, found 458 |

TABLE 4-continued

| Compound | Structure | Name | Exact Mass [M + H]+ |
|---|---|---|---|
| 4-5 | 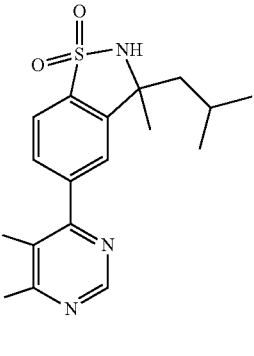 | (R or S)-9-ethyl-6-[3-methyl-3-(2-methylpropyl)-1,1-dioxido-2,3-dihydro-1,2-benzisothiazol-5-yl]-8-(2-methylpyrimidin-5-yl)-9H-purine | Calc'd 478, found 478 |
| 4-6 | 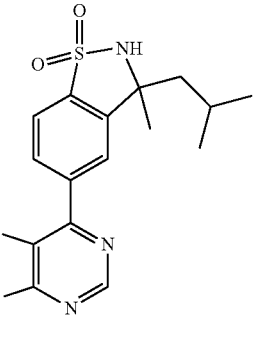 | (R or S)-9-ethyl-6-[3-methyl-3-(2-methylpropyl)-1,1-dioxido-2,3-dihydro-1,2-benzisothiazol-5-yl]-8-(2-methylpyrimidin-5-yl)-9H-purine | Calc'd 478, found 478 |
| 4-7 | 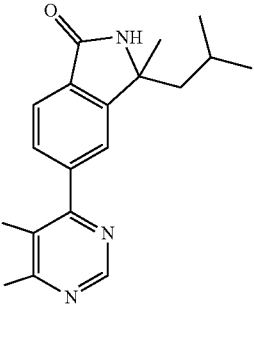 | (R or S)-5-[9-ethyl-8-(2-methylpyrimidin-5-yl)-9H-purin-6-yl]-3-methyl-3-(2-methylpropyl)-2,3-dihydro-1H-isoindol-1-one | Calc'd 442, found 442 |
| 4-8 | 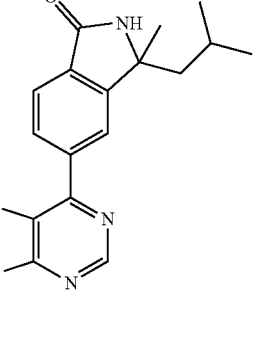 | (R or S)-5-[9-ethyl-8-(2-methylpyrimidin-5-yl)-9H-purin-6-yl]-3-methyl-3-(2-methylpropyl)-2,3-dihydro-1H-isoindol-1-one | Calc'd 442, found 442 |

TABLE 4-continued

| Compound | Structure | Name | Exact Mass [M + H]+ |
|---|---|---|---|
| 4-9 | 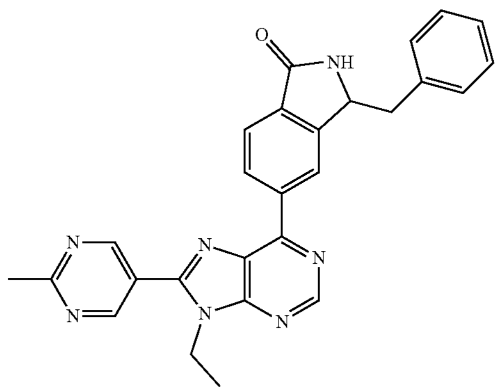 [SMILES: CCn1c(-c2cnc(C)nc2)nc2c(-c3ccc4c(c3)C(Cc3ccccc3)NC4=O)ncnc21] | (R or S)-3-benzyl-5-[9-ethyl-8-(2-methylpyrimidin-5-yl)-9H-purin-6-yl]-2,3-dihydro-1H-isoindol-1-one | Calc'd 462, found 462 |
| 4-10 | 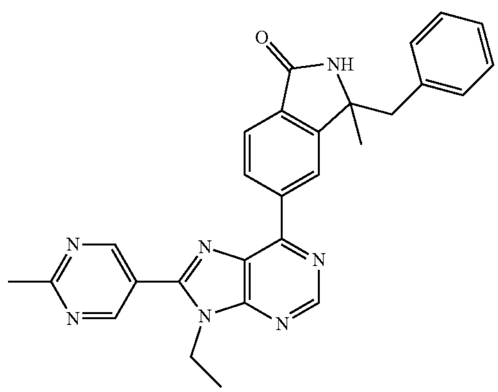 [SMILES: CCn1c(-c2cnc(C)nc2)nc2c(-c3ccc4c(c3)C(C)(Cc3ccccc3)NC4=O)ncnc21] | (R or S)-3-benzyl-5-[9-ethyl-8-(2-methylpyrimidin-5-yl)-9H-purin-6-yl]-3-methyl-2,3-dihydro-1H-isoindol-1-one | Calc'd 476, found 476 |
| 4-11 | 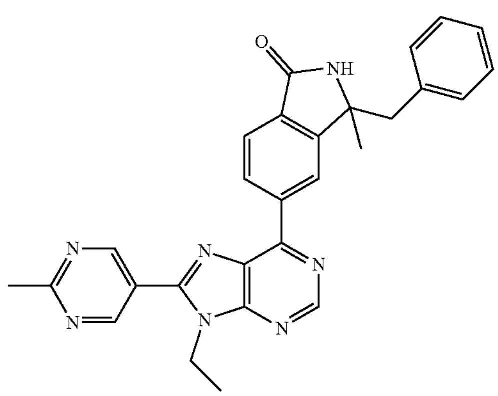 [SMILES: CCn1c(-c2cnc(C)nc2)nc2c(-c3ccc4c(c3)C(C)(Cc3ccccc3)NC4=O)ncnc21] | (R or S)-3-benzyl-5-[9-ethyl-8-(2-methylpyrimidin-5-yl)-9H-purin-6-yl]-3-methyl-2,3-dihydro-1H-isoindol-1-one | Calc'd 476, found 476 |
| 4-12 | 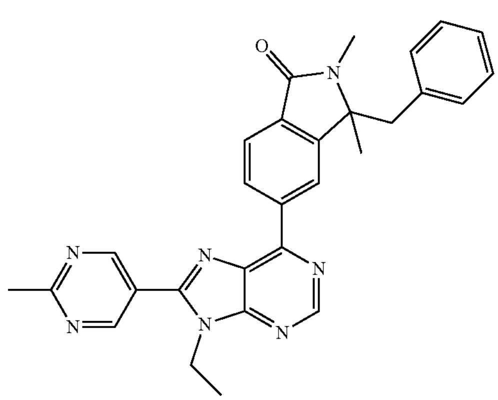 [SMILES: CCn1c(-c2cnc(C)nc2)nc2c(-c3ccc4c(c3)C(C)(Cc3ccccc3)N(C)C4=O)ncnc21] | (R or S)-3-benzyl-5-[9-ethyl-8-(2-methylpyrimidin-5-yl)-9H-purin-6-yl]-2,3-dimethyl-2,3-dihydro-1H-isoindol-1-one | Calc'd 490, found 490 |

TABLE 4-continued

| Compound | Structure | Name | Exact Mass [M + H]⁺ |
|---|---|---|---|
| 4-13 | 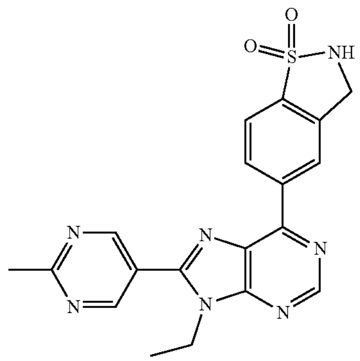 [SMILES: CCn1c(-c2cnc(C)nc2)nc2c(-c3ccc4c(c3)CNS4(=O)=O)ncnc21] | 5-(9-ethyl-8-(2-methylpyrimidin-5-yl)-9H-purin-6-yl)-2,3-dihydrobenzo[d]isothiazole 1,1-dioxide | Calc'd 408, found 408 |
| 4-14 | 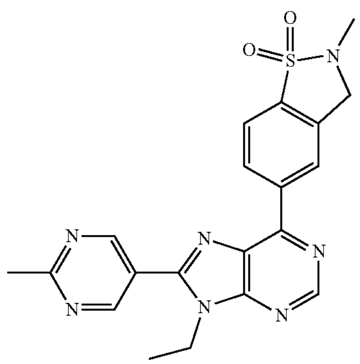 | 5-(9-ethyl-8-(2-methylpyrimidin-5-yl)-9H-purin-6-yl)-2-methyl-2,3-dihydrobenzo[d]isothiazole 1,1-dioxide | Calc'd 408, found 408 |
| 4-15 | 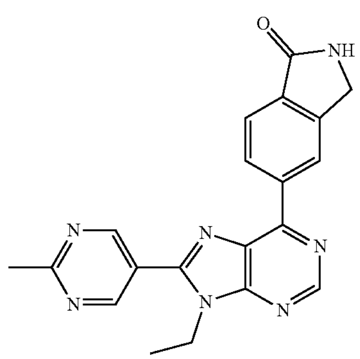 [SMILES: CCn1c(-c2cnc(C)nc2)nc2c(-c3ccc4c(c3)CNC4=O)ncnc21] | 5-(9-ethyl-8-(2-methylpyrimidin-5-yl)-9H-purin-6-yl)isoindolin-1-one | Calc'd 372, found 372 |
| 4-16 | 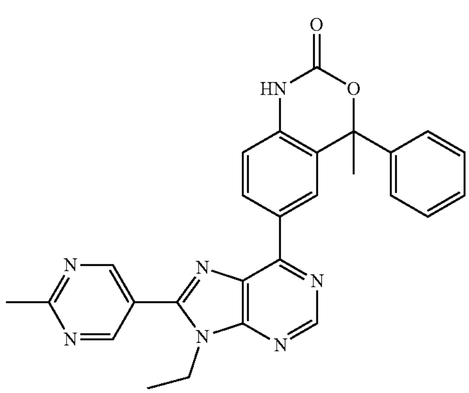 [SMILES: CCn1c(-c2cnc(C)nc2)nc2c(-c3ccc4c(c3)C(C)(c3ccccc3)OC(=O)N4)ncnc21] | 6-(9-ethyl-8-(2-methylpyrimidin-5-yl)-9H-purin-6-yl)-4-methyl-4-phenyl-1,4-dihydro-2H-benzo[d][1,3]oxazin-2-one | Calc'd 478, found 478 |

Compound Examples of Table 5

Example 5A Compound 5-1 and 5-2

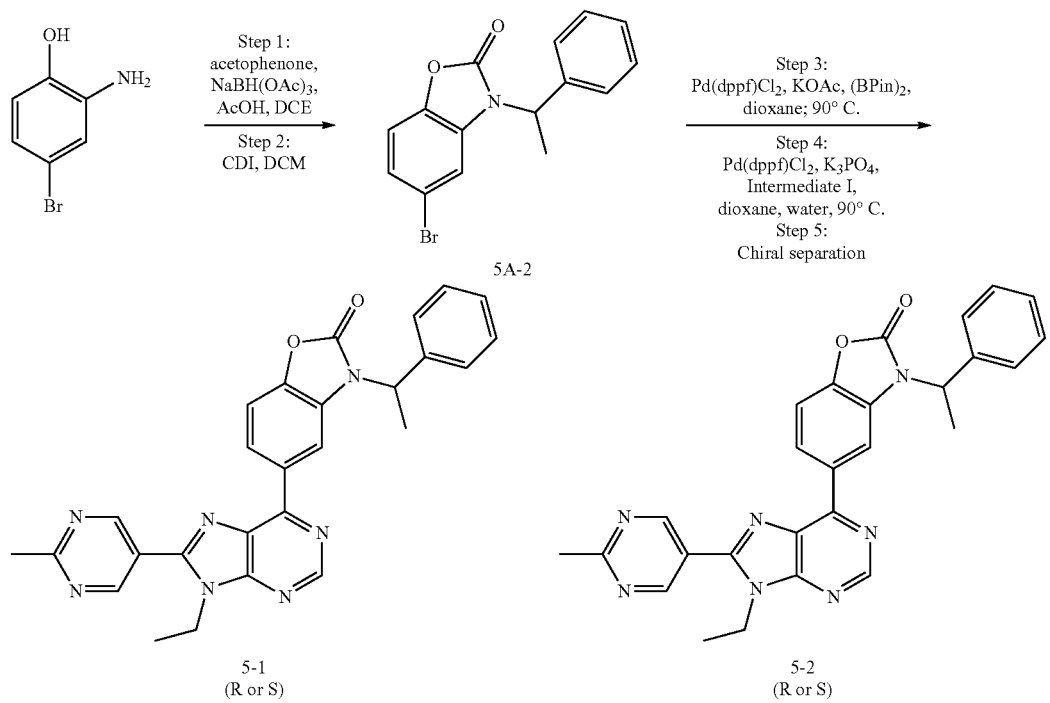

Step 1 4-Bromo-2-((1-phenylethyl)amino)phenol

To a solution of 2-amino-4-bromophenol (1.00 g, 5.32 mmol) in 1,2-dichloroethane (20 mL), were added acetophenone (0.77 g, 6.4 mmol), acetic acid (0.30 mL, 5.3 mmol) and sodium triacetoxyborohydride (2.25 g, 10.6 mmol). The resulting mixture was stirred for 3 h at room temperature. The reaction mixture was quenched with saturated aqueous sodium bicarbonate (100 mL) and extracted with DCM (3×100 mL). The combined organic layers was washed with brine (100 mL), dried ($Na_2SO_4$) and concentrated. The residue was purified by chromatography on $SiO_2$ (0% to 25% EtOAc/hexane) to afford 4-bromo-2-((1-phenylethyl)amino)phenol. MS (EI) calc'd for $C_{14}H_{15}BrNO$ [M+H]$^+$, 292; found, 292.

Step 2 5-Bromo-3-(1-phenylethyl)benzo[d]oxazol-2(3H)-one (5A-2)

To a solution of 4-bromo-2-((1-phenylethyl)amino)phenol (0.50 g, 1.7 mmol) in dichloromethane (10 mL) was added 1,1'-carbonyldiimidazole (0.42 g, 2.6 mmol) at room temperature. The resulting mixture was stirred for 12 h at room temperature and concentrated under reduced pressure. The residue was purified by chromatography on $SiO_2$ (0%-15% EtOAc/hexane) to afford 5-bromo-3-(1-phenylethyl)benzo[d]oxazol-2(3H)-one (5A-2). MS (EI) calc'd for $C_{15}H_{13}BrNO_2$ [M+H]$^+$, 318; found, 318.

Step 3 3-(1-Phenylethyl)-5-(4,4,5,5-tetramethyl-1,3,2-dioxaborolan-2-yl)benzo[d]oxazol-2(3H)-one A deoxygenated solution of 5-bromo-3-(1-phenylethyl)benzo[d]oxazol-2(3H)-one (260 mg, 0.82 mmol), (BPin)$_2$ (250 mg, 0.98 mmol) and KOAc (160 mg, 1.63 mmol) in 1,4-dioxane (10 mL) was treated with $PdCl_2$(dppf)-$CH_2Cl_2$ (67 mg, 0.082 mmol) at ambient temperature under nitrogen. The mixture was stirred for 2 h at 80° C. and concentrated to dryness. Chromatography on $SiO_2$ (0-15% EtOAc/hexanes) provided 3-(1-phenylethyl)-5-(4,4,5,5-tetramethyl-1,3,2-dioxaborolan-2-yl)benzo[d]oxazol-2(3H)-one. MS (EI) calc'd for $C_{21}H_{25}BNO_4$ [M+H]$^+$, 366; found, 366.

Steps 4 and 5 (R or S)- and (S or R)-5-(9-Ethyl-8-(2-methylpyrimidin-5-yl)-9H-purin-6-yl)-3-(1-phenylethyl)benzo[d]oxazol-2(3H)-one (5-1) and (5-2)

A solution of Intermediate I (75 mg, 0.27 mmol) and 3-(1-phenylethyl)-5-(4,4,5,5-tetramethyl-1,3,2-dioxaborolan-2-yl)benzo[d]oxazol-2(3H)-one (100 mg, 0.274 mmol) in 1,4-dioxane (5 mL) and water (1 mL) was treated with KOAc (76 mg, 0.55 mmol) and Pd(PPh$_3$)$_2$Cl$_2$ (19 mg, 0.027 mmol) at ambient temperature under nitrogen. The mixture was stirred for 3 h at 90° C. and concentrated. The residue was then purified by chromatography on $SiO_2$ (0-8% MeOH/DCM). The crude product was then purified by CHIRAL-Prep-SFC [Column: ChiralPak™ AD-H SFC 5×25 cm, 5 µm; 50% EtOH/CO$_2$; Flow rate: 190 mL/min; 230 nm; Retention Time 1: 6.25 min; Retention Time 2: 10.85 min]. The faster-eluting enantiomer of the title compound (5-1) was obtained at 6.25 min: $^1$H NMR (300 MHz, CD$_3$OD) δ 9.23 (s, 2H), 8.93 (s, 1H), 8.71-8.64 (m, 2H), 7.53-7.44 (m, 3H), 7.36-7.26 (m, 3H), 5.78-5.69 (m, 1H), 4.57-4.48 (m, 2H), 2.88 (s, 3H), 2.03 (d, J=7.2 Hz, 3H), 1.50 (t, J=7.2 Hz, 3H). MS (EI) calc'd for $C_{27}H_{24}N_7O_2$ [M+H]$^+$, 478; found, 478. The slower-eluting enantiomer of the title compound (5-2) was obtained at 10.85 min: $^1$H NMR (300 MHz, CD$_3$OD) δ 9.23 (s, 2H), 8.93 (s, 1H), 8.71-8.64 (m, 2H), 7.53-7.44 (m, 3H), 7.36-7.26 (m, 3H), 5.78-5.69 (m, 1H), 4.56-4.49 (m, 2H), 2.88 (s, 3H), 2.03 (d, J=7.2 Hz, 3H), 1.50 (t, J=7.2 Hz, 3H). MS (EI) calc'd for $C_{27}H_{24}N_7O_2$ [M+H]$^+$ 478; found, 478.

Example 5B Compound 5-7 and 5-8

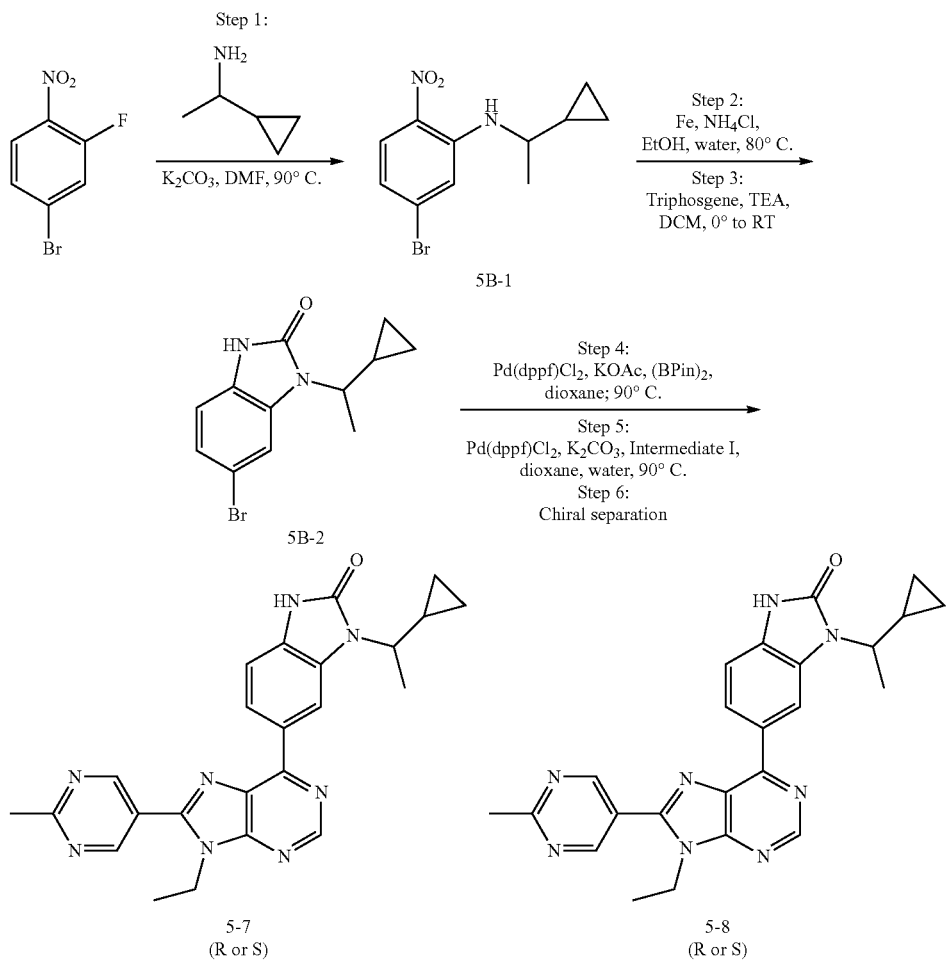

Step 1 5-Bromo-N-(1-cyclopropylethyl)-2-nitroaniline (5B-1)

A solution of 4-bromo-2-fluoro-1-nitrobenzene (1.29 g, 5.87 mmol) in DMF (10 mL) as treated with $K_2CO_3$ (2.44 g, 17.6 mmol), 1-cyclopropylethanamine (0.50 g, 5.87 mmol) at room temperature. The resulting mixture was stirred for 3 h at 90° C., cooled, then quenched with water (20 mL) and extracted with EtOAc (3×30 mL). The combined organic layers was washed with brine (30 mL), dried ($Na_2SO_4$) and concentrated to afford 5-bromo-N-(1-cyclopropylethyl)-2-nitroaniline (5B-1). MS (EI) calc'd for $C_{11}H_{14}BrN_2O_2$ $[M+H]^+$, 285; found, 285.

Step 2 5-Bromo-N-(1-cyclopropylethyl)benzene-1,2-diamine (5B-2)

A solution of 5-bromo-N-(1-cyclopropylethyl)-2-nitroaniline (5B-1) (1.5 g, 5.3 mmol) in EtOH (10 mL) and water (10 mL) was treated with $NH_4Cl$ (1.41 g, 26.3 mmol) and iron (0.881 g, 15.8 mmol). The resulting mixture was stirred for 3 h at 80° C., then quenched with water (100 mL) and filtered. The aqueous layer was extracted with DCM (3×100 mL), the combined organic layers was washed with brine (100 mL), dried ($Na_2SO_4$) and concentrated. The residue was purified by chromatography on $SiO_2$ (0-20% EtOAc/hexane) to afford 5-bromo-N1-(1-cyclopropylethyl)benzene-1,2-diamine (5B-2). MS (EI) calc'd for $C_{11}H_{16}BrN_2$ $[M+H]^+$, 255; found; 255.

Step 3 6-Bromo-1-(1-cyclopropylethyl)-1H-benzo[d]imidazol-2(3H)-one

A solution of 5-bromo-N-(1-cyclopropylethyl)benzene-1,2-diamine (0.30 g, 1.2 mmol) in DCM (10 mL) was treated with triethylamine (0.50 mL, 3.5 mmol) and triphosgene (0.14 g, 0.47 mmol) at 0° C. The resulting solution was stirred for 1 h at room temperature, then quenched with water (10 mL). The resulting mixture was extracted with DCM (3×10 mL) and the combined organic layers was washed with brine (10 mL), dried ($Na_2SO_4$) and concentrated to afford 6-bromo-1-(1-cyclopropylethyl)-1H-benzo[d]imidazol-2(3H)-one. MS (EI) calc'd for $C_{12}H_{14}BrN_2O$ $[M+H]^+$, 281; found, 281.

Steps 4-6 (R or S)- and (S or R)-1-(1-Cyclopropylethyl)-6-(9-ethyl-8-(2-methyl pyrimidin-5-yl)-9H-purin-6-yl)-1H-benzo[d]imidazol-2(3H)-one (5-7 and 5-8)

A racemic mixture containing 5-7 and 5-8 was prepared from 6-bromo-1-(1-cyclopropylethyl)-1H-benzo[d]imidazol-2(3H)-one and Intermediate I in a fashion analogous to Example 5A. The racemate was separated by Prep-Chiral-HPLC [Column: ChiralPak™ IA 2×25 cm, 5 um; 10% EtOH/MTBE; Flow rate: 20 mL/min; 254/220 nm, Retention Time 1: 10 min; Retention Time 2: 21 min). The faster-eluting enantiomer of the title compound (5-7) was obtained at 10 min. $^1$H NMR (300 MHz, DMSO-$d_6$) δ 11.20 (s, 1H), 9.26 (s, 2H), 8.99 (s, 1H), 8.97 (s, 1H), 8.67-8.64 (m, 1H), 7.20 (d, J=8.1 Hz, 1H), 4.47 (q, J=7.2 Hz, 2H), 3.78-3.72 (m, 1H), 2.79 (s, 3H), 1.60-1.57 (m, 4H), 1.40 (t, J=7.2 Hz, 3H), 0.67-0.30 (m, 4H). MS (EI) calc'd for $C_{24}H_{25}N_8O$ [M+H]$^+$, 441; found, 441. The slower-eluting enantiomer of the title compound (5-8) was obtained at 21 min. $^1$H NMR (300 MHz, DMSO-$d_6$) δ 11.20 (s, 1H), 9.26 (s, 2H), 8.99 (s, 1H), 8.97 (s, 1H), 8.67-8.64 (m, 1H), 7.20 (d, J=8.1 Hz, 1H), 4.47 (q, J=7.2 Hz, 2H), 3.78-3.72 (m, 1H), 2.79 (s, 3H), 1.60-1.57 (m, 4H), 1.40 (t, J=7.2 Hz, 3H), 0.67-0.30 (m, 4H). MS (EI) calc'd for $C_{24}H_{25}N_8O$ [M+H]$^+$, 441; found, 441.

Example Compounds 5-3, 5-5, 5-6 and 5-9

Compounds 5-3 and 5-4 were prepared in a fashion analogous to compound 5-1, substituting acetophenone for benzaldehyde in Step 1 in the case of 5-3, and tetrahydro-2H-pyran-4-carbaldehyde in the case of 5-4.

Compounds 5-5 and 5-6 were prepared in a fashion analogous to compounds 5-1 and 5-2, substituting acetophenone for cyclopropylethanone. The racemic product was separated by Prep-Chiral-HPLC [Column: ChiralPak™ IA 2×25 cm, 5 um; 10% EtOH/MTBE; Flow rate: 20 mL/min; 254/220 nm, Retention Time 1: 11 min; Retention Time 2: 18 min]. The faster-eluting enantiomer (5-5) was obtained at 11 min. The slower-eluting enantiomer (5-6) was obtained at 18 min.

Compound 5-9 was prepared in a fashion analogous to the preparation of 5-1 and 5-2, substituting acetophenone for dihydro-2H-pyran-4(3H)-one in the reductive amination step. Being achiral, compound 5-9 did not require chiral separation.

Table 5 provides structures for compounds 5-1 through 5-9 which were synthesized directly by the methods described above or by analogous methods to those described above.

TABLE 5

| Compound | Structure | Name | Exact Mass [M + H]$^+$ |
|---|---|---|---|
| 5-1 | 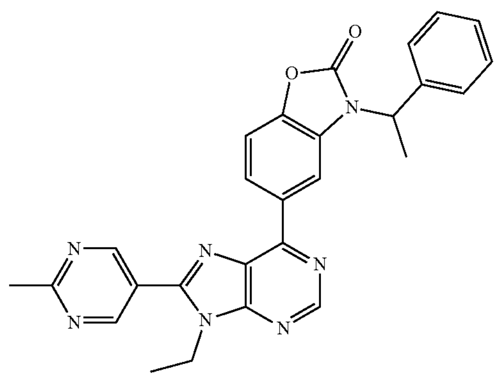 [SMILES: CCn1c(-c2cnc(C)nc2)nc2c(-c3ccc4oc(=O)n(C(C)c5ccccc5)c4c3)ncnc21] | (R or S)-5-[9-ethyl-8-(2-methylpyrimidin-5-yl)-9H-purin-6-yl]-3-(1-phenylethyl)-1,3-benzoxazol-2(3H)-one | Calc'd 478, found 478 |
| 5-2 | 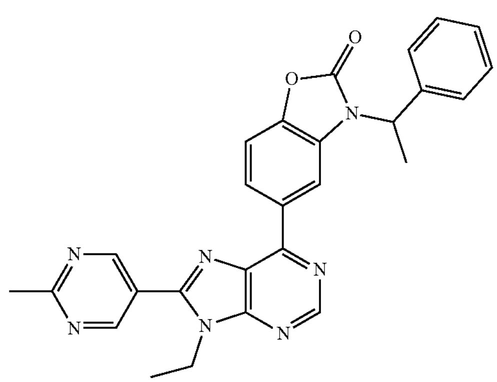 [SMILES: CCn1c(-c2cnc(C)nc2)nc2c(-c3ccc4oc(=O)n(C(C)c5ccccc5)c4c3)ncnc21] | (R or S)-5-[9-ethyl-8-(2-methylpyrimidin-5-yl)-9H-purin-6-yl]-3-(1-phenylethyl)-1,3-benzoxazol-2(3H)-one | Calc'd 478, found 478 |

TABLE 5-continued

| Compound | Structure | Name | Exact Mass [M + H]+ |
|---|---|---|---|
| 5-3 | 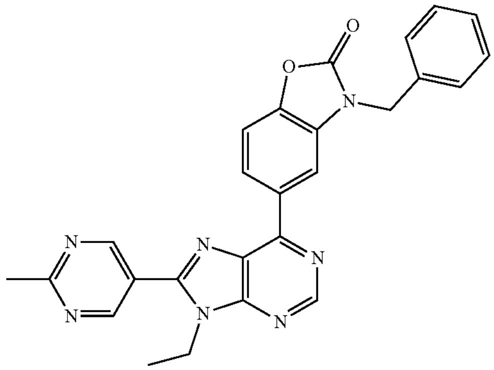 [SMILES: CCn1c(-c2cnc(C)nc2)nc2c(-c3ccc4oc(=O)n(Cc5ccccc5)c4c3)ncnc21] | 3-benzyl-5-[9-ethyl-8-(2-methylpyrimidin-5-yl)-9H-purin-6-yl]-1,3-benzoxazol-2(3H)-one | Calc'd 464, found 464 |
| 5-4 | 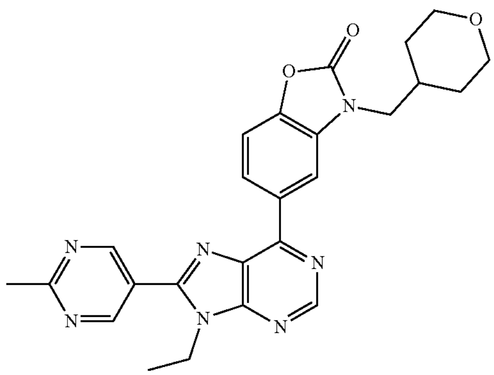 [SMILES: CCn1c(-c2cnc(C)nc2)nc2c(-c3ccc4oc(=O)n(CC5CCOCC5)c4c3)ncnc21] | 5-[9-ethyl-8-(2-methylpyrimidin-5-yl)-9H-purin-6-yl]-3-(tetrahydro-2H-pyran-4-ylmethyl)-1,3-benzoxazol-2(3H)-one | Calc'd 472, found 472 |
| 5-5 | 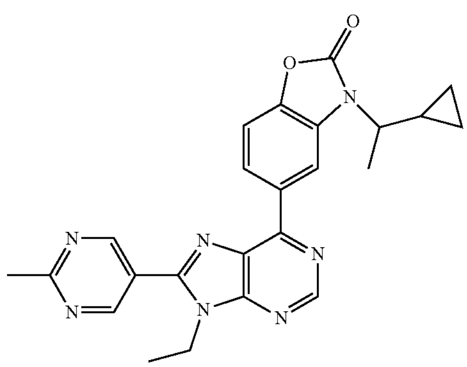 [SMILES: CCn1c(-c2cnc(C)nc2)nc2c(-c3ccc4oc(=O)n(C(C)C5CC5)c4c3)ncnc21] | (R or S)-3-(1-cyclopropylethyl)-5-[9-ethyl-8-(2-methylpyrimidin-5-yl)-9H-purin-6-yl]-1,3-benzoxazol-2(3H)-one | Calc'd 442, found 442 |
| 5-6 | 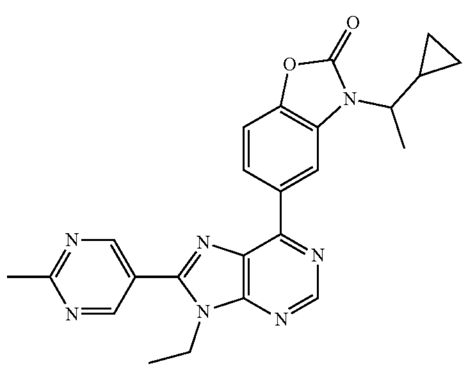 [SMILES: CCn1c(-c2cnc(C)nc2)nc2c(-c3ccc4oc(=O)n(C(C)C5CC5)c4c3)ncnc21] | (R or S)-3-(1-cyclopropylethyl)-5-[9-ethyl-8-(2-methylpyrimidin-5-yl)-9H-purin-6-yl]-1,3-benzoxazol-2(3H)-one | Calc'd 442, found 442 |

TABLE 5-continued

| Compound | Structure | Name | Exact Mass [M + H]+ |
|---|---|---|---|
| 5-7 | 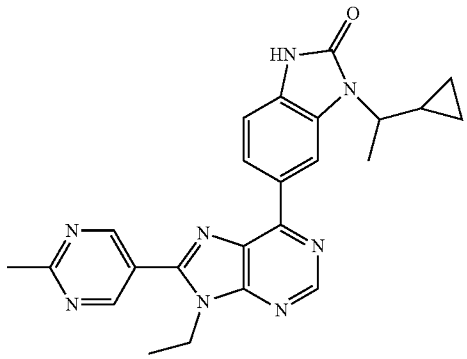 [SMILES: CCn1c(-c2cnc(C)nc2)nc2c(-c3ccc4[nH]c(=O)n(C(C)C5CC5)c4c3)ncnc21] | (R or S)-1-(1-cyclopropylethyl)-6-[9-ethyl-8-(2-methylpyrimidin-5-yl)-9H-purin-6-yl]-1,3-dihydro-2H-benzimidazol-2-one | Calc'd 441, found 441 |
| 5-8 | 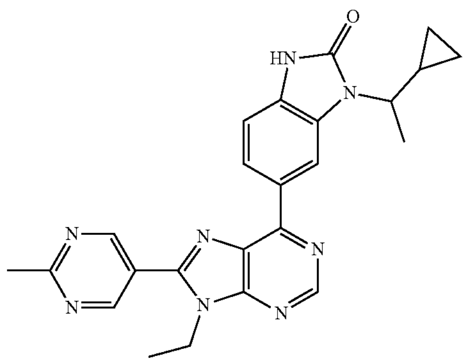 [SMILES: CCn1c(-c2cnc(C)nc2)nc2c(-c3ccc4[nH]c(=O)n(C(C)C5CC5)c4c3)ncnc21] | (R or S)-1-(1-cyclopropylethyl)-6-[9-ethyl-8-(2-methylpyrimidin-5-yl)-9H-purin-6-yl]-1,3-dihydro-2H-benzimidazol-2-one | Calc'd 441, found 441 |
| 5-9 | 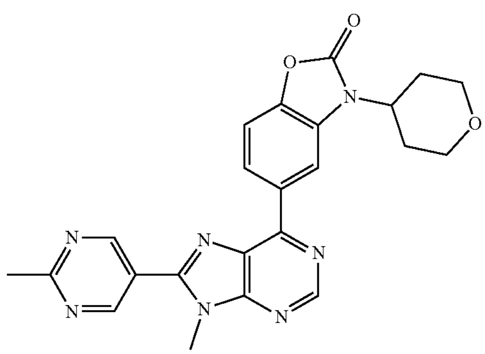 [SMILES: Cc1ncc(-c2nc3c(-c4ccc5oc(=O)n(C6CCOCC6)c5c4)ncnc3n2C)cn1] | 5-(9-ethyl-8-(2-methylpyrimidin-5-yl)-9H-purin-6-yl)-3-(tetrahydro-2H-pyran-4-yl)benzo[d]oxazol-2(3H)-one | Calc'd 458, found 458 |

HTRF PI3K Biochemical Assay to Measure Intrinsic Potency of Compound Inhibitors

The PI3-Kinase biochemical assays were developed to measure the intrinsic potency and compound dependent inhibition of the alpha, beta, delta, and gamma PI3K isoform enzymes. This assay was developed and further optimized from a kit produced by Upstate (Millipore catalog #33-047) and has been configured for HTS and SAR screening. Briefly, this procedure exploits the exquisite specificity and high affinity binding of enzyme reaction substrate phosphatidyl(3,4,5)triphosphate (PIP3) to the GRP1 pleckstrin homology (PH) domain to generate the signal. In the absence of PIP3, an HTRF (Homogeneous Time-Resolved Fluorescence energy transfer) complex is formed consisting of europium (Eu)-labeled anti-GST, GSTtagged GRP1-PH domain, biotin-PIP3 and streptavidin conjugated APC. The native PIP3 produced by PI3-Kinase activity disrupts, in a competitive manner, the biotin-PIP3 from the PH domain, resulting in the loss of energy transfer (HTRF complex) and a decrease in the signal. The format of this assay is the same for all 4 isoforms of PI3K; the differences lie in the concentration of enzyme used to achieve robust assay window. The alpha, beta, and delta assays are run at 0.5, 1, and 0.3 nM enzymes and the gamma assay is run at 5 nM enzyme. The ATP concentration is 100 uM in the alpha, beta, and delta assays and 50 uM ATP in the gamma assay. All reactions are run at 50 uM PIP2.

Assay Protocol

Compounds are serially diluted (3-fold in 100% DMSO) across a 384-well polypropylene source plated from column 3 to column 12 and column 13 to column 22, to yield 10 concentration dose response for each test compound. Columns 1, 2, 23 and 24 contain either only DMSO or pharmacological known control inhibitor. Once titrations are made, 2.5 nL of the compounds on 384 well plates are reformatted and transferred by acoustic dispense in quadruplicates to a 1536 assay plate (Greiner) to assay across all four PI3K isoform enzymes.

The PI3-Kinase biochemical assay was optimized using the HTRF kit provided by Upstate (Millipore). The assay kit contains six reagents: 1) 4× Reaction Buffer; 2) native PIP2 (substrate); 3) Stop (EDTA); 4) Detection Mix A (Streptavidin-APC); 5) Detection Mix B (Eu-labeled Anti-GST plus GST-tagged PH-domain); 6) Detection Mix C. In addition, the following items were obtained or purchased; PI3Kinase (alpha 14-602, beta 14-603, gamma 14-558 and delta 14-604 from Upstate; Millipore), dithiothreitol (Sigma, D-5545), Adenosine-5' triphosphate (InVitrogen, Cat # AS001A), native PIP3 (PI(3,4,5)P3, diC8, H⁺, CELLSIGNALS, INC. Cat #907) DMSO (Sigma, 472301).

PI3Kinase Reaction Buffer was prepared by dilution the stock 1:4 with de-ionized water. DTT, PIP2 and Biotin-PIP3 were added to 1536 assay plate at a final concentration of 5 mM, 5 mM and 25 nM on the day of use. Enzyme addition and compound pre-incubation were initiated by the addition of 1.25 ul of PI3K (at twice its final concentration) in the 1× reaction buffer to all wells using a BioRaptor. Plates were incubated at room temperature for 15 minutes. Reactions are initiated by addition of 1.25 ul of 2× substrate solution (PIP2 and ATP in 1× reaction buffer) using BioRaptor. Plates were incubated in humidified chamber at room temperature for one hour. Reactions were quenched by addition of 0.625 uL of stop solution to all wells using the BioRaptor. The quenched reactions are then processed to detect product formation by adding 0.625 uL of Detection Solution to all wells using the BioRaptor (Detection mix C, Detection Mix A, and Detection Mix B combined together in an 18:1:1 ratio prepared 2 hours prior to use). Following a one hour incubation in the dark, the HTRF signal was measured on the Envision plate reader set for 330 nm excitation and dual emission detection at 620 nM (Eu) and 665 nM (APC).

Data Analysis

The loss of the HTRF signal is due to the displacement of biotinylated-PIP3 from the PH domain by the PI3K-dependent conversion of PIP2 to PIP3. This loss of signal is nonlinear with respect to both increasing product and time. This non-linear detection will impact accuracy of $IC_{50}$ calculations; therefore, there is a need for a correction factor to obtain more accurate $IC_{50}$ values. This correction is derived from a PIP3 standard curve run in a separate assay plate. All data were calculated using the ratio of acceptor (APC) to donor (Europium) fluorescence in each well of the assay plate. The percent inhibition for each compound concentration was calculated as follows: % inhibition=100× (fluorescence ratio−CtrlB)/(CtrlA−CtrlB) where CtrlA=PI3Kinase reaction+known reference inhibitor and CtrlB=PI3K+DMSO. An $IC_{50}$ was then calculated fitting the % inhibition data to the equation: % inhibition=min+(Max−min)/1+([inhibitor]/IC50)^n) where min is the % inhibition with inhibitor, max is the signal in DMSO control, and n is the Hill slope.

BIOLOGICAL DATA

The following table tabulates the biological data disclosed for the instant invention. The biological data was collected using the methodology described above. For each compound, PI3Kdelta $IC_{50}$ values are listed along with the relative selectivity versus PI3Kalpha, as well as the physical form of the compound dosed in this assay.

The determination of relative selectivity for a given compound is defined as the relative ratio of the (PI3K-alpha$IC_{50}$ value/PI3K-delta $IC_{50}$ value).

| Compound | Form Screened | PI3Kdelta IC$_{50}$ (nM) | Relative Selectivity versus PI3Kalpha |
|---|---|---|---|
| 1-1 | neutral | 4 | >10 |
| 1-2 | neutral | 121 | >10 |
| 1-3 | neutral | 94 | >10 |
| 1-4 | neutral | 10 | >10 |
| 1-5 | neutral | 177 | 3 |
| 1-6 | neutral | 15 | >10 |
| 1-7 | neutral | 120 | 6 |
| 1-8 | neutral | 12 | >10 |
| 1-9 | neutral | 17 | >10 |
| 1-10 | neutral | 194 | >10 |
| 1-11 | neutral | 49 | >10 |
| 1-12 | neutral | 9 | >10 |
| 1-13 | neutral | 370 | >10 |
| 1-14 | neutral | 16 | >10 |
| 1-15 | neutral | 224 | >10 |
| 1-16 | neutral | 250 | 7 |
| 1-17 | neutral | 2 | >10 |
| 1-18 | TFA salt | 25 | >10 |
| 1-19 | TFA salt | 87 | >10 |
| 1-20 | neutral | 477 | 3 |
| 1-21 | neutral | 4 | >10 |
| 1-22 | TFA salt | 36 | >10 |
| 1-23 | neutral | 27 | >10 |
| 1-24 | neutral | 658 | >10 |
| 1-25 | TFA salt | 4 | >10 |
| 1-26 | neutral | 50 | >10 |
| 1-27 | neutral | 5 | >10 |
| 1-28 | neutral | 60 | >10 |
| 1-29 | neutral | 8,800 | 1 |
| 1-30 | neutral | 7 | >10 |
| 1-31 | neutral | 159 | >10 |
| 1-32 | neutral | 3 | >10 |
| 1-33 | TFA salt | 42 | >10 |
| 1-34 | neutral | 48 | 8 |
| 1-35 | neutral | 5 | >10 |
| 1-36 | neutral | 143 | 6 |
| 1-37 | neutral | 3 | >10 |
| 1-38 | neutral | 80 | >10 |
| 1-39 | neutral | 85 | >10 |
| 1-40 | neutral | 142 | >10 |
| 1-41 | neutral | 23 | >10 |
| 2-1 | neutral | 2 | >10 |
| 2-2 | neutral | 176 | >10 |
| 2-3 | neutral | 145 | 4 |
| 2-4 | neutral | 5 | >10 |
| 2-5 | neutral | 73 | >10 |
| 2-6 | neutral | 3 | >10 |
| 2-7 | neutral | 8 | >10 |
| 2-8 | neutral | 129 | >10 |
| 2-9 | TFA salt | 144 | >10 |
| 2-10 | TFA salt | 14 | >10 |
| 2-11 | TFA salt | 15 | >10 |
| 2-12 | TFA salt | 5 | >10 |
| 2-13 | TFA salt | 32 | >10 |
| 2-14 | TFA salt | 46 | >10 |
| 2-15 | TFA salt | 46 | >10 |
| 2-16 | TFA salt | 43 | >10 |
| 2-17 | TFA salt | 10 | >10 |
| 2-18 | TFA salt | 8 | >10 |
| 2-19 | TFA salt | 22 | >10 |
| 2-20 | TFA salt | 23 | >10 |
| 2-21 | TFA salt | 22 | >10 |
| 2-22 | TFA salt | 26 | >10 |
| 2-23 | TFA salt | 7 | >10 |
| 2-24 | TFA salt | 67 | >10 |
| 2-25 | TFA salt | 28 | >10 |
| 2-26 | TFA salt | 58 | >10 |
| 2-27 | TFA salt | 13 | >10 |
| 2-28 | TFA salt | 49 | >10 |
| 2-29 | neutral | 569 | >10 |
| 2-30 | neutral | 2 | >10 |
| 2-31 | neutral | 479 | >10 |
| 2-32 | neutral | 27 | >10 |
| 2-33 | neutral | 2749 | >4 |
| 2-34 | neutral | 29 | >10 |
| 2-35 | neutral | 1334 | 2 |
| 2-36 | neutral | 4 | >10 |
| 2-37 | neutral | 349 | >10 |

| Compound | Form Screened | PI3Kdelta IC$_{50}$ (nM) | Relative Selectivity versus PI3Kalpha |
|---|---|---|---|
| 2-38 | neutral | 9 | >10 |
| 2-39 | neutral | 3 | >10 |
| 2-40 | neutral | 179 | >10 |
| 2-41 | neutral | 5 | >10 |
| 2-42 | neutral | 207 | >10 |
| 2-43 | neutral | 5 | >10 |
| 2-44 | neutral | 616 | >10 |
| 2-45 | neutral | 7 | >10 |
| 2-46 | neutral | 748 | >10 |
| 2-47 | neutral | 4 | >10 |
| 2-48 | neutral | 509 | 9 |
| 2-49 | neutral | 3 | >10 |
| 2-50 | neutral | 898 | >10 |
| 2-51 | neutral | 6 | >10 |
| 2-52 | neutral | 504 | >10 |
| 2-53 | neutral | 4 | >10 |
| 2-54 | neutral | 168 | >10 |
| 2-55 | neutral | 200 | >10 |
| 2-56 | neutral | 3 | >10 |
| 2-57 | neutral | 264 | >10 |
| 2-58 | neutral | 7 | >10 |
| 2-59 | neutral | 2 | >10 |
| 2-60 | neutral | 133 | 8 |
| 2-61 | neutral | 35 | >10 |
| 2-62 | neutral | 6 | >10 |
| 2-63 | neutral | 87 | >10 |
| 2-64 | neutral | 6 | >10 |
| 2-65 | neutral | 79 | >10 |
| 2-66 | neutral | 1 | >10 |
| 2-67 | neutral | 344 | >10 |
| 2-68 | neutral | 2 | >10 |
| 2-69 | neutral | 788 | 5 |
| 2-70 | neutral | 4 | >10 |
| 2-71 | neutral | 219 | >10 |
| 2-72 | neutral | 3 | >10 |
| 2-73 | TFA salt | 35 | >10 |
| 2-74 | TFA salt | 21 | >10 |
| 2-75 | TFA salt | 7 | >10 |
| 2-76 | TFA salt | 34 | >10 |
| 2-77 | neutral | 7 | >10 |
| 2-78 | neutral | 238 | >10 |
| 2-79 | neutral | 15 | >10 |
| 2-80 | neutral | 7 | >10 |
| 2-81 | neutral | 26 | >10 |
| 2-82 | neutral | 1568 | 8 |
| 2-83 | neutral | 21 | >10 |
| 3-1 | neutral | 1 | >10 |
| 3-2 | neutral | 39 | >10 |
| 3-3 | neutral | 1227 | 2 |
| 3-4 | neutral | 2 | >10 |
| 3-5 | neutral | 63 | >10 |
| 3-6 | neutral | 26 | >10 |
| 3-7 | TFA salt | 1 | >10 |
| 3-8 | neutral | 9 | >10 |
| 3-9 | TFA salt | 5 | >10 |
| 3-10 | TFA salt | 3 | >10 |
| 3-11 | neutral | 34 | >10 |
| 3-12 | neutral | 3 | >10 |
| 3-13 | neutral | 45 | >10 |
| 3-14 | neutral | 2 | >10 |
| 3-15 | neutral | 5 | >10 |
| 3-16 | neutral | 2 | >10 |
| 3-17 | neutral | 2.5 | >10 |
| 3-18 | neutral | 1.9 | >10 |
| 3-19 | neutral | 0.7 | >10 |
| 3-20 | neutral | 55 | >10 |
| 3-21 | neutral | 69 | 2 |
| 3-22 | neutral | 4 | >10 |
| 3-23 | neutral | 6 | >10 |
| 3-24 | neutral | 32 | >10 |
| 3-25 | TFA salt | 48 | >10 |
| 3-26 | neutral | 29 | >10 |
| 3-27 | neutral | 9 | >10 |
| 3-28 | neutral | 99 | >10 |
| 3-29 | neutral | 15 | >10 |
| 3-30 | neutral | 156 | 5 |
| 3-31 | neutral | 99 | >10 |
| 3-32 | neutral | 169 | >10 |
| 3-33 | neutral | 67 | >10 |
| 3-34 | TFA salt | 64 | >10 |
| 3-35 | neutral | 14 | >10 |
| 3-36 | neutral | 26 | >10 |
| 4-1 | neutral | 97 | 2 |
| 4-2 | neutral | 35 | >10 |
| 4-3 | neutral | 59 | 6 |
| 4-4 | neutral | 4 | >10 |
| 4-5 | neutral | 6 | >10 |
| 4-6 | neutral | 55 | >10 |
| 4-7 | neutral | 7 | >10 |
| 4-8 | neutral | 128 | >10 |
| 4-9 | TFA salt | 22 | >10 |
| 4-10 | neutral | 5 | >10 |
| 4-11 | neutral | 323 | >10 |
| 4-12 | TFA salt | 14 | >10 |
| 4-13 | neutral | 177 | 9 |
| 4-14 | neutral | 147 | >10 |
| 4-15 | TFA salt | 121 | 7 |
| 4-16 | neutral | 3 | >10 |
| 5-1 | neutral | 14 | >10 |
| 5-2 | neutral | 37 | >10 |
| 5-3 | neutral | 25 | >10 |
| 5-4 | neutral | 24 | >10 |
| 5-5 | neutral | 42 | >10 |
| 5-6 | neutral | 5 | >10 |
| 5-7 | neutral | 3 | >10 |
| 5-8 | neutral | 24 | >10 |
| 5-9 | neutral | 151 | >10 |

What is claimed is:

1. A compound of formula I or a pharmaceutically acceptable salt or stereoisomer thereof:

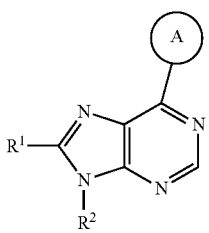

wherein is selected from the group consisting of

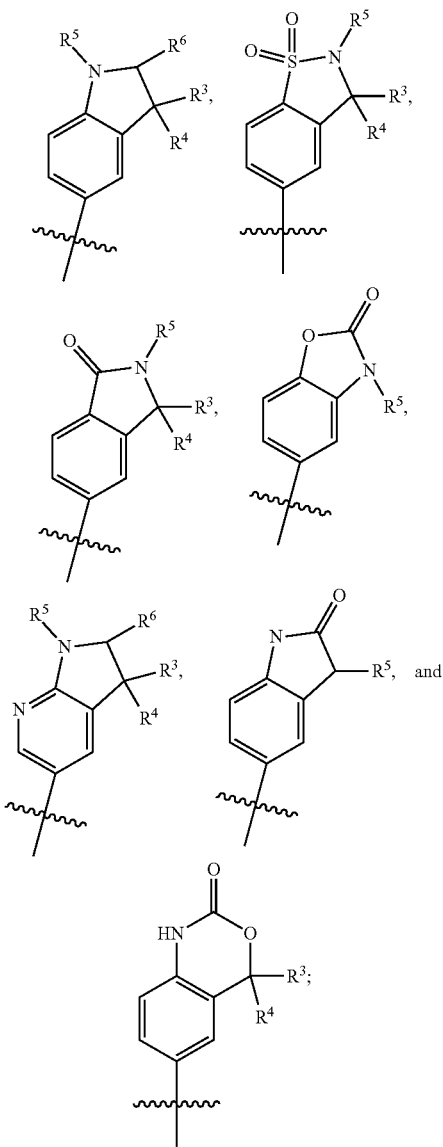

R¹ is selected from the group consisting of hydrogen, a 5- to 6-membered heteroaryl, $C_{1-6}$alkyl, and $C_{1-6}$haloalkyl, wherein said heteroaryl and alkyl is substituted with 0, 1, 2, or 3 moieties each independently selected from the group consisting of $C_{1-6}$alkyl, halogen, and OH;
R² is hydrogen or $C_{1-6}$ alkyl;
R³ is selected the group consisting of from hydrogen, $C_{1-6}$alkyl, and cyano;
R⁴ is selected from the group consisting of
 hydrogen,
 cyano,
 $C_{1-6}$alkyl,
 $C_{1-6}$heteroalkyl,
 $C_{3-12}$heterocycloalkyl$C_{0-6}$alkyl,
 $C_{3-12}$cycloalkyl$C_{0-6}$alkyl,
 aryl$C_{0-6}$alkyl,
 heteroaryl$C_{0-6}$alkyl,
 spirocyclyl$C_{0-6}$alkyl,
 $C_{3-12}$cycloalkyl$C_{0-10}$alkyloxy,
 amino,
 -amino($C_{1-10}$ alkyl)$_{1-2}$,
 $C_{3-12}$cycloalkyl$C_{0-10}$alkylamino,
 heteroaryl$C_{0-10}$alkylamino,
 $C_{3-12}$heterocycloalkyl$C_{0-10}$alkylamino,
 aryl$C_{0-10}$alkylamino,
 hydroxy,
 —($C_{1-10}$ alkyl)OH, and
 $C_{1-10}$ alkoxy;
wherein R⁴ is substituted with 0, 1, 2, or 3 groups selected from the group consisting of $C_{1-6}$alkyl, cyano, halogen, hydroxy, —O—$C_{1-6}$alkyl, and —($C_{1-10}$alkyl)OH;
further wherein, optionally, R³ and R⁴ along with the carbon to which they are attached may join together to form a 4 to 6 membered saturated ring system substituted with 0, 1, or 2 moieties selected from the group consisting of $C_{1-6}$alkyl, halogen, hydroxy, —O—$C_{1-6}$alkyl, —($C_{1-10}$ alkyl)OH, —SO$_2$C$_{1-6}$alkyl, —SO$_2$CF$_3$, —SO$_2$CF$_2$H, and $C_{3-12}$cycloalkyl$C_{0-10}$alkylcarbonyl;
R⁵ is selected from the group consisting of
 hydrogen,
 $C_{1-6}$ alkyl,
 $C_{1-10}$alkylcarbonyl,
 $C_{3-12}$cycloalkyl$C_{0-10}$alkyl,
 $C_{3-12}$heterocycloalkyl$C_{0-10}$alkyl,
 aryl$C_{0-10}$alkyl, and
 —($C_{1-10}$ alkyl)OH; and
R⁶ is hydrogen, oxo (=O), or $C_{1-3}$alkyl.

2. The compound according to claim 1, wherein R¹ is selected from the group consisting of hydrogen, difluoromethyl, pyrimidinyl, pyrazolyl wherein said pyrimidinyl and said pyrazolyl are each substituted with 0, 1, 2, or 3 moieties each independently selected from the group consisting of $C_{1-6}$alkyl, halogen and OH.

3. The compound according to claim 2, wherein R² is selected from the group consisting of hydrogen and $C_{1-6}$alkyl.

4. The compound according to claim 3, wherein R² is selected from the group consisting of methyl, ethyl, and hydrogen.

5. The compound according to claim 3, wherein R² is hydrogen.

6. The compound according to claim 1, wherein R³ is selected from the group consisting of hydrogen, $C_{1-6}$alkyl, and cyano.

7. The compound according to claim 6, wherein R³ is selected from the group consisting of hydrogen, methyl, and cyano.

8. The compound according to claim 1, wherein R⁴ is selected from the group consisting of
 hydrogen,
 cyano,
 $C_{1-6}$alkyl,
 $C_{3-12}$heterocycloalkyl$C_{0-6}$alkyl,
 $C_{3-12}$cycloalkyl$C_{0-6}$alkyl,
 aryl$C_{0-6}$alkyl,
 heteroaryl$C_{0-6}$alkyl,
 spirocyclyl$C_{0-6}$alkyl,
 $C_{3-12}$cycloalkyl$C_{0-10}$alkyloxy,
 -amino($C_{1-10}$ alkyl)$_{1-2}$,
 $C_{3-12}$cycloalkyl$C_{0-10}$alkylamino,
 heteroaryl$C_{0-10}$alkylamino,
 $C_{3-12}$heterocycloalkyl$C_{0-10}$alkylamino, and
 —($C_{1-10}$ alkyl)OH;
wherein said aryl is a 6-membered aryl and said heteroaryl is a 5- to 6-membered heteroaryl and further wherein R⁴ is substituted with 0, 1, 2, or 3 groups selected from the group consisting of $C_{1-6}$ alkyl, cyano, halogen, hydroxy, and methoxy.

9. The compound according to claim 6, wherein $R^4$ is selected from the group consisting of 2-methylpropyl, oxetanylmethyl, oxetan-3-ylmethyl, cyclopropylmethyl, benzyl, methylpyrimidinyl, methylpyrimidin-5-yl, tetrahydro-2H-pyranyl, phenyl, ethyl, 2-hydroxy-2-methylpropyl, azetidinyl, azetidin-1-yl, morpholinyl, oxa-6-azaspiro[3.3]heptyl, 1-oxa-6-azaspiro[3.3]hept-6-yl, pyridinylamino, hexahydro-4H-furo[3,2-b]pyrrol-4-yl, (1-cyclopropylethyl)amino, (methyl)(ethyl)amino, (methyl)(isopropyl)amino, (ethyl) amino, (1-cyclobutylethyl)amino, (cyclobutylmethyl) amino, (tetrahydrofuranylmethyl)amino, (tetrahydrofuran-2-ylmethyl)amino, 8-oxa-5-azaspiro[3.5]non-5-yl, 6,7-dihydropyrazolo[1.5-a]pyrazin-5(4H)-yl, tetrahydropyranylamino, tetrahydro-2H-pyra-4-ylamino, 2-oxa-5-azabicyclo[2.2.1]hept-5-yl, oxaazabicyclo[2.2.1] heptyl, 6-oxa-2-azaspiro[3.4]oct-2-yl, cyclobutylamino, isopropylamino, (cyclopropylmethyl)amino, tetrahydrofuranylamino, tetrahydrofuran-3-ylamino, isobutylamino, propylamino, azetidinyl, azetidin-1-yl, isobutoxy, cycloproylmethoxy, pyrrolidinyl, (oxetanylmethyl)amino, (oxetan-3-ylmethyl)amino, isopropoxy, cyclobutoxy, hydrogen, and 1-phenylethyl; wherein $R^4$ is substituted with 0, 1, 2, or 3 groups selected from the group consisting of $C_{1-4}$ alkyl, cyano, halogen, hydroxy, and methoxy.

10. The compound according to claim 1, wherein $R^3$ and $R^4$ along with the carbon to which they are attached may join together to form a 4- to 6-membered saturated ring system selected from the group consisting of pyrrolidinyl, pyrrolidin-2-yl, piperidinyl, tetrahydrofuranyl, and cyclopentyl, said 4- to 6-membered saturated ring system is substituted with 0, 1, or 2 moieties selected from the group consisting of $C_{1-6}$alkyl, halogen, —$SO_2C_{1-6}$alkyl, $C_{3-6}$cycloalkylcarbonyl, and —$SO_2CF_3$.

11. The compound according to claim 9, wherein $R^5$ is selected from the group consisting of hydrogen, methyl, methylcarbonyl, ethyl, isopropyl, morpholinoethyl, 2-hydroxy-2-methylpropyl, 2-hydroxyethyl, 1-phenylethyl, benzyl, tetrahydro-2H-pyranylmethyl, 1-cyclopropylethyl, and tetrahydro-2H-pyranyl.

12. The compound according to claim 11, wherein $R^6$ is hydrogen or oxo.

13. The compound according to claim 1, wherein

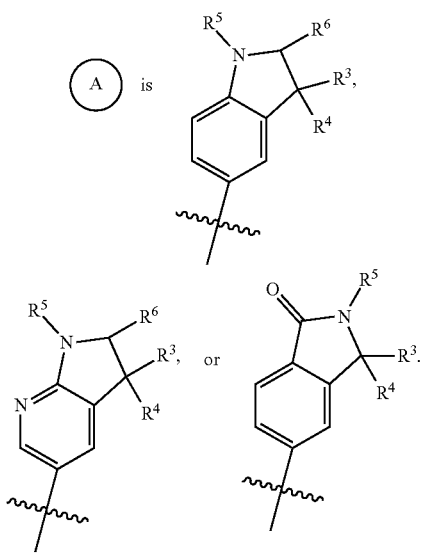

14. The compound or a pharmaceutically acceptable salt, wherein the compound is selected from the group consisting of 5-[9-ethyl-8-(2-methylpyrimidin-5-yl)-9H-purin-6-yl]-3-methyl-3-(2-methylpropyl)-1,3-dihydro-2H-indol-2-one;

(R)-5-[9-ethyl-8-(2-methylpyrimidin-5-yl)-9H-purin-6-yl]-3-methyl-3-(2-methylpropyl)-1,3-dihydro-2H-indol-2-one;

(S)-5-[9-ethyl-8-(2-methylpyrimidin-5-yl)-9H-purin-6-yl]-3-methyl-3-(2-methylpropyl)-1,3-dihydro-2H-indol-2-one;

5-[9-ethyl-8-(2-methylpyrimidin-5-yl)-9H-purin-6-yl]-3-methyl-3-(oxetan-3-ylmethyl)-1,3-dihydro-2H-indol-2-one;

(R)-5-[9-ethyl-8-(2-methylpyrimidin-5-yl)-9H-purin-6-yl]-3-methyl-3-(oxetan-3-ylmethyl)-1,3-dihydro-2H-indol-2-one;

(S)-5-[9-ethyl-8-(2-methylpyrimidin-5-yl)-9H-purin-6-yl]-3-methyl-3-(oxetan-3-ylmethyl)-1,3-dihydro-2H-indol-2-one;

5-[9-ethyl-8-(2-methylpyrimidin-5-yl)-9H-purin-6-yl]-3-methyl-3-[(3-methyloxetan-3-yl)methyl]-1,3-dihydro-2H-indol-2-one;

(R)-5-[9-ethyl-8-(2-methylpyrimidin-5-yl)-9H-purin-6-yl]-3-methyl-3-[(3-methyloxetan-3-yl)methyl]-1,3-dihydro-2H-indol-2-one;

(S)-5-[9-ethyl-8-(2-methylpyrimidin-5-yl)-9H-purin-6-yl]-3-methyl-3-[(3-methyloxetan-3-yl)methyl]-1,3-dihydro-2H-indol-2-one;

3-(cyclopropylmethyl)-5-(9-ethyl-8-(2-methylpyrimidin-5-yl)-9H-purin-6-yl)-3-methylindolin-2-one;

(R)-3-(cyclopropylmethyl)-5-(9-ethyl-8-(2-methylpyrimidin-5-yl)-9H-purin-6-yl)-3-methylindolin-2-one;

(S)-3-(cyclopropylmethyl)-5-(9-ethyl-8-(2-methylpyrimidin-5-yl)-9H-purin-6-yl)-3-methylindolin-2-one;

3-(cyclopropylmethyl)-5-(9-ethyl-8-(2-methylpyrimidin-5-yl)-9H-purin-6-yl)-1,3-dimethylindolin-2-one;

(R)-3-(cyclopropylmethyl)-5-(9-ethyl-8-(2-methylpyrimidin-5-yl)-9H-purin-6-yl)-1,3-dimethylindolin-2-one;

(S)-3-(cyclopropylmethyl)-5-(9-ethyl-8-(2-methylpyrimidin-5-yl)-9H-purin-6-yl)-1,3-dimethylindolin-2-one;

5-(9-ethyl-8-(2-methylpyrimidin-5-yl)-9H-purin-6-yl)-3-isobutyl-2-oxoindoline-3-carbo nitrile;

5-(9-ethyl-8-(2-methylpyrimidin-5-yl)-9H-purin-6-yl)-3-isobutyl-3-methyl-1,3-dihydro-2H-pyrrolo[2,3-b]pyridin-2-one;

(R)-5-(9-ethyl-8-(2-methylpyrimidin-5-yl)-9H-purin-6-yl)-3-isobutyl-3-methyl-1,3-dihydro-2H-pyrrolo[2,3-b]pyridin-2-one;

(S)-5-(9-ethyl-8-(2-methylpyrimidin-5-yl)-9H-purin-6-yl)-3-isobutyl-3-methyl-1,3-dihydro-2H-pyrrolo[2,3-b]pyridin-2-one;

3-(cyclopropylmethyl)-5-(9-ethyl-8-(2-methylpyrimidin-5-yl)-9H-purin-6-yl)-3-methyl-1,3-dihydro-2H-pyrrolo[2,3-b]pyridin-2-one;

(R)-3-(cyclopropylmethyl)-5-(9-ethyl-8-(2-methylpyrimidin-5-yl)-9H-purin-6-yl)-3-methyl-1,3-dihydro-2H-pyrrolo[2,3-b]pyridin-2-one;

(S)-3-(cyclopropylmethyl)-5-(9-ethyl-8-(2-methylpyrimidin-5-yl)-9H-purin-6-yl)-3-methyl-1,3-dihydro-2H-pyrrolo[2,3-b]pyridin-2-one;

3-benzyl-5-(9-ethyl-8-(2-methylpyrimidin-5-yl)-9H-purin-6-yl)-3-methylindolin-2-one;

(R)-3-benzyl-5-(9-ethyl-8-(2-methylpyrimidin-5-yl)-9H-purin-6-yl)-3-methylindolin-2-one;
(S)-3-benzyl-5-(9-ethyl-8-(2-methylpyrimidin-5-yl)-9H-purin-6-yl)-3-methylindolin-2-one;
6-(3-benzyl-3-methylindolin-5-yl)-9-ethyl-8-(2-methylpyrimidin-5-yl)-9H-purine;
1-(3-benzyl-5-(9-ethyl-8-(2-methylpyrimidin-5-yl)-9H-purin-6-yl)-3-methylindolin-1-yl)ethan-1-one;
3-benzyl-5-(9-ethyl-8-(2-methylpyrimidin-5-yl)-9H-purin-6-yl)-1,3-dimethylindolin-2-one;
(R)-3-benzyl-5-(9-ethyl-8-(2-methylpyrimidin-5-yl)-9H-purin-6-yl)-1,3-dimethylindolin-2-one;
(S)-3-benzyl-5-(9-ethyl-8-(2-methylpyrimidin-5-yl)-9H-purin-6-yl)-1,3-dimethylindolin-2-one;
6-(3-benzyl-1,3-dimethylindolin-5-yl)-9-ethyl-8-(2-methylpyrimidin-5-yl)-9H-purine;
benzyl-5-(8-(difluoromethyl)-9-ethyl-9H-purin-6-yl)-3-methylindolin-2-one;
(R)-benzyl-5-(8-(difluoromethyl)-9-ethyl-9H-purin-6-yl)-3-methylindolin-2-one;
(S)-benzyl-5-(8-(difluoromethyl)-9-ethyl-9H-purin-6-yl)-3-methylindolin-2-one;
3-(cyclopropylmethyl)-5-(9-ethyl-8-(1-ethyl-5-methyl-1H-pyrazol-4-yl)-9H-purin-6-yl)-3-methylindolin-2-one;
(R)-3-(cyclopropylmethyl)-5-(9-ethyl-8-(1-ethyl-5-methyl-1H-pyrazol-4-yl)-9H-purin-6-yl)-3-methylindolin-2-one;
(S)-3-(cyclopropylmethyl)-5-(9-ethyl-8-(1-ethyl-5-methyl-1H-pyrazol-4-yl)-9H-purin-6-yl)-3-methylindolin-2-one;
3-isobutyl-3-methyl-5-(9-methyl-8-(2-methylpyrimidin-5-yl)-9H-purin-6-yl)-1,3-dihydro-2H-pyrrolo[2,3-b]pyridin-2-one;
(R)-3-isobutyl-3-methyl-5-(9-methyl-8-(2-methylpyrimidin-5-yl)-9H-purin-6-yl)-1,3-dihydro-2H-pyrrolo[2,3-b]pyridin-2-one;
(S)-3-isobutyl-3-methyl-5-(9-methyl-8-(2-methylpyrimidin-5-yl)-9H-purin-6-yl)-1,3-dihydro-2H-pyrrolo[2,3-b]pyridin-2-one;
3-benzyl-3-methyl-5-(9-methyl-9H-purin-6-yl)indolin-2-one;
(R)-3-benzyl-3-methyl-5-(9-methyl-9H-purin-6-yl)indolin-2-one;
(S)-3-benzyl-3-methyl-5-(9-methyl-9H-purin-6-yl)indolin-2-one;
5-(9-ethyl-8-(2-methylpyrimidin-5-yl)-9H-purin-6-yl)-3-methyl-3-(oxetan-2-ylmethyl)indolin-2-one;
(R,R)-5-(9-ethyl-8-(2-methylpyrimidin-5-yl)-9H-purin-6-yl)-3-methyl-3-(oxetan-2-ylmethyl)indolin-2-one;
(R,S)-5-(9-ethyl-8-(2-methylpyrimidin-5-yl)-9H-purin-6-yl)-3-methyl-3-(oxetan-2-ylmethyl)indolin-2-one;
(S,S)-5-(9-ethyl-8-(2-methylpyrimidin-5-yl)-9H-purin-6-yl)-3-methyl-3-(oxetan-2-ylmethyl)indolin-2-one;
(S,R)-5-(9-ethyl-8-(2-methylpyrimidin-5-yl)-9H-purin-6-yl)-3-methyl-3-(oxetan-2-ylmethyl)indolin-2-one;
5-(9-ethyl-8-(2-methylpyrimidin-5-yl)-9H-purin-6-yl)-3-methyl-3-(pyrimidin-5-ylmethyl)indolin-2-one;
5-(9-ethyl-8-(2-methylpyrimidin-5-yl)-9H-purin-6-yl)-3-methyl-3-(tetrahydro-2H-pyran-4-yl)indolin-2-one;
(R)-5-(9-ethyl-8-(2-methylpyrimidin-5-yl)-9H-purin-6-yl)-3-methyl-3-(tetrahydro-2H-pyran-4-yl)indolin-2-one;
(S)-5-(9-ethyl-8-(2-methylpyrimidin-5-yl)-9H-purin-6-yl)-3-methyl-3-(tetrahydro-2H-pyran-4-yl)indolin-2-one;
5-(9-ethyl-8-(2-methylpyrimidin-5-yl)-9H-purin-6-yl)-3-methyl-3-phenylindolin-2-one;
(R)-5-(9-ethyl-8-(2-methylpyrimidin-5-yl)-9H-purin-6-yl)-3-methyl-3-phenylindolin-2-one;
(S)-5-(9-ethyl-8-(2-methylpyrimidin-5-yl)-9H-purin-6-yl)-3-methyl-3-phenylindolin-2-one;
3-ethyl-5-(9-ethyl-8-(2-methylpyrimidin-5-yl)-9H-purin-6-yl)-3-methylindolin-2-one;
(R)-3-ethyl-5-(9-ethyl-8-(2-methylpyrimidin-5-yl)-9H-purin-6-yl)-3-methylindolin-2-one;
(S)-3-ethyl-5-(9-ethyl-8-(2-methylpyrimidin-5-yl)-9H-purin-6-yl)-3-methylindolin-2-one;
5-(9-ethyl-8-(2-methylpyrimidin-5-yl)-9H-purin-6-yl)-3-(2-hydroxy-2-methylpropyl)-3-methylindolin-2-one;
(R)-5-(9-ethyl-8-(2-methylpyrimidin-5-yl)-9H-purin-6-yl)-3-(2-hydroxy-2-methylpropyl)-3-methylindolin-2-one;
(S)-5-(9-ethyl-8-(2-methylpyrimidin-5-yl)-9H-purin-6-yl)-3-(2-hydroxy-2-methylpropyl)-3-methylindolin-2-one;
5-[9-ethyl-8-(2-methylpyrimidin-5-yl)-9H-purin-6-yl]-3-(3-methoxy-3-methylazetidin-1-yl)-3-methyl-1,3-dihydro-2H-indol-2-one;
(R)-5-[9-ethyl-8-(2-methylpyrimidin-5-yl)-9H-purin-6-yl]-3-(3-methoxy-3-methylazetidin-1-yl)-3-methyl-1,3-dihydro-2H-indol-2-one;
(S)-5-[9-ethyl-8-(2-methylpyrimidin-5-yl)-9H-purin-6-yl]-3-(3-methoxy-3-methylazetidin-1-yl)-3-methyl-1,3-dihydro-2H-indol-2-one;
3-[2,6-dimethylmorpholin-4-yl]-5-[9-ethyl-8-(2-methylpyrimidin-5-yl)-9H-purin-6-yl]-3-methyl-1,3-dihydro-2H-indol-2-one;
(R)-3-[(cis)-2,6-dimethylmorpholin-4-yl]-5-[9-ethyl-8-(2-methylpyrimidin-5-yl)-9H-purin-6-yl]-3-methyl-1,3-dihydro-2H-indol-2-one;
(S)-3-[(cis)-2,6-dimethylmorpholin-4-yl]-5-[9-ethyl-8-(2-methylpyrimidin-5-yl)-9H-purin-6-yl]-3-methyl-1,3-dihydro-2H-indol-2-one;
1-{5-[9-ethyl-8-(2-methylpyrimidin-5-yl)-9H-purin-6-yl]-3-methyl-2-oxo-2,3-dihydro-1H-indol-3-yl}-3-methylazetidine-3-carbonitrile;
(R)-1-{5-[9-ethyl-8-(2-methylpyrimidin-5-yl)-9H-purin-6-yl]-3-methyl-2-oxo-2,3-dihydro-1H-indol-3-yl}-3-methylazetidine-3-carbonitrile;
(S)-1-{5-[9-ethyl-8-(2-methylpyrimidin-5-yl)-9H-purin-6-yl]-3-methyl-2-oxo-2,3-dihydro-1H-indol-3-yl}-3-methylazetidine-3-carbonitrile;
5-[9-ethyl-8-(2-methylpyrimidin-5-yl)-9H-purin-6-yl]-3-methyl-3-(1-oxa-6-azaspiro[3.3]hept-6-yl)-1,3-dihydro-2H-indol-2-one;
(R)-5-[9-ethyl-8-(2-methylpyrimidin-5-yl)-9H-purin-6-yl]-3-methyl-3-(1-oxa-6-azaspiro[3.3]hept-6-yl)-1,3-dihydro-2H-indol-2-one;
(S)-5-[9-ethyl-8-(2-methylpyrimidin-5-yl)-9H-purin-6-yl]-3-methyl-3-(1-oxa-6-azaspiro[3.3]hept-6-yl)-1,3-dihydro-2H-indol-2-one;
5-[9-ethyl-8-(2-methylpyrimidin-5-yl)-9H-purin-6-yl]-3-methyl-3-(pyridin-4-ylamino)-1,3-dihydro-2H-indol-2-one;
(R)-5-[9-ethyl-8-(2-methylpyrimidin-5-yl)-9H-purin-6-yl]-3-methyl-3-(pyridin-4-ylamino)-1,3-dihydro-2H-indol-2-one;
(S)-5-[9-ethyl-8-(2-methylpyrimidin-5-yl)-9H-purin-6-yl]-3-methyl-3-(pyridin-4-ylamino)-1,3-dihydro-2H-indol-2-one;

5-[9-ethyl-8-(2-methylpyrimidin-5-yl)-9H-purin-6-yl]-3-(hexahydro-4H-furo[3,2-b]pyrrol-4-yl)-3-methyl-1,3-dihydro-2H-indol-2-one;

(R)-5-[9-ethyl-8-(2-methylpyrimidin-5-yl)-9H-purin-6-yl]-3-(hexahydro-4H-furo[3,2-b]pyrrol-4-yl)-3-methyl-1,3-dihydro-2H-indol-2-one;

(S)-5-[9-ethyl-8-(2-methylpyrimidin-5-yl)-9H-purin-6-yl]-3-(hexahydro-4H-furo[3,2-b]pyrrol-4-yl)-3-methyl-1,3-dihydro-2H-indol-2-one;

3-{[1-cyclopropylethyl]amino}-5-[9-ethyl-8-(2-methylpyrimidin-5-yl)-9H-purin-6-yl]-3-methyl-1,3-dihydro-2H-indol-2-one;

3-{[(1R)-1-cyclopropylethyl]amino}-5-[9-ethyl-8-(2-methylpyrimidin-5-yl)-9H-purin-6-yl]-3 (R)-methyl-1,3-dihydro-2H-indol-2-one;

3-{[(1R)-1-cyclopropylethyl]amino}-5-[9-ethyl-8-(2-methylpyrimidin-5-yl)-9H-purin-6-yl]-3(S)-methyl-1,3-dihydro-2H-indol-2-one;

3-{[(1S)-1-cyclopropylethyl]amino}-5-[9-ethyl-8-(2-methylpyrimidin-5-yl)-9H-purin-6-yl]-3 (R)-methyl-1,3-dihydro-2H-indol-2-one;

3-{[(1S)-1-cyclopropylethyl]amino}-5-[9-ethyl-8-(2-methylpyrimidin-5-yl)-9H-purin-6-yl]-3(S)-methyl-1,3-dihydro-2H-indol-2-one;

5-[9-ethyl-8-(2-methylpyrimidin-5-yl)-9H-purin-6-yl]-3-[(2-methoxyethyl)(methyl)amino]-3-methyl-1,3-dihydro-2H-indol-2-one;

(R)-5-[9-ethyl-8-(2-methylpyrimidin-5-yl)-9H-purin-6-yl]-3-[(2-methoxyethyl)(methyl)amino]-3-methyl-1,3-dihydro-2H-indol-2-one;

(S)-5-[9-ethyl-8-(2-methylpyrimidin-5-yl)-9H-purin-6-yl]-3-[(2-methoxyethyl)(methyl)amino]-3-methyl-1,3-dihydro-2H-indol-2-one;

5-[9-ethyl-8-(2-methylpyrimidin-5-yl)-9H-purin-6-yl]-3-methyl-3-[methyl(2-methylethyl)amino]-1,3-dihydro-2H-indol-2-one;

(R)-5-[9-ethyl-8-(2-methylpyrimidin-5-yl)-9H-purin-6-yl]-3-methyl-3-[methyl(1-methylethyl)amino]-1,3-dihydro-2H-indol-2-one;

(S)-5-[9-ethyl-8-(2-methylpyrimidin-5-yl)-9H-purin-6-yl]-3-methyl-3-[methyl(1-methylethyl)amino]-1,3-dihydro-2H-indol-2-one;

5-[9-ethyl-8-(2-methylpyrimidin-5-yl)-9H-purin-6-yl]-3-[(2-methoxyethyl)amino]-3-methyl-1,3-dihydro-2H-indol-2-one;

(R)-5-[9-ethyl-8-(2-methylpyrimidin-5-yl)-9H-purin-6-yl]-3-[(2-methoxyethyl)amino]-3-methyl-1,3-dihydro-2H-indol-2-one;

(S)-5-[9-ethyl-8-(2-methylpyrimidin-5-yl)-9H-purin-6-yl]-3-[(2-methoxyethyl)amino]-3-methyl-1,3-dihydro-2H-indol-2-one;

3-{[1-cyclobutylethyl]amino}-5-[9-ethyl-8-(2-methylpyrimidin-5-yl)-9H-purin-6-yl]-3-methyl-1,3-dihydro-2H-indol-2-one;

3-{[(1R)-1-cyclobutylethyl]amino}-5-[9-ethyl-8-(2-methylpyrimidin-5-yl)-9H-purin-6-yl]-3 (R)-methyl-1,3-dihydro-2H-indol-2-one;

3-{[(1S)-1-cyclobutylethyl]amino}-5-[9-ethyl-8-(2-methylpyrimidin-5-yl)-9H-purin-6-yl]-3(S)-methyl-1,3-dihydro-2H-indol-2-one;

5-[9-ethyl-8-(2-methylpyrimidin-5-yl)-9H-purin-6-yl]-3-methyl-3-{[(1-methylcyclobutyl)methyl]amino}-1,3-dihydro-2H-indol-2-one;

(R)-5-[9-ethyl-8-(2-methylpyrimidin-5-yl)-9H-purin-6-yl]-3-methyl-3-{[(1-methylcyclobutyl)methyl]amino}-1,3-dihydro-2H-indol-2-one;

(S)-5-[9-ethyl-8-(2-methylpyrimidin-5-yl)-9H-purin-6-yl]-3-methyl-3-{[(1-methylcyclobutyl)methyl]amino}-1,3-dihydro-2H-indol-2-one;

1-[({5-[9-ethyl-8-(2-methylpyrimidin-5-yl)-9H-purin-6-yl]-3-methyl-2-oxo-2,3-dihydro-1H-indol-3-yl}amino)methyl]cyclobutanecarbonitrile;

(R)-1-[({5-[9-ethyl-8-(2-methylpyrimidin-5-yl)-9H-purin-6-yl]-3-methyl-2-oxo-2,3-dihydro-1H-indol-3-yl}amino)methyl]cyclobutanecarbonitrile;

(S)-1-[({5-[9-ethyl-8-(2-methylpyrimidin-5-yl)-9H-purin-6-yl]-3-methyl-2-oxo-2,3-dihydro-1H-indol-3-yl}amino)methyl]cyclobutanecarbonitrile;

3-[(cyclobutylmethyl)amino]-5-[9-ethyl-8-(2-methylpyrimidin-5-yl)-9H-purin-6-yl]-3-methyl-1,3-dihydro-2H-indol-2-one;

(R)-3-[(cyclobutylmethyl)amino]-5-[9-ethyl-8-(2-methylpyrimidin-5-yl)-9H-purin-6-yl]-3-methyl-1,3-dihydro-2H-indol-2-one;

(S)-3-[(cyclobutylmethyl)amino]-5-[9-ethyl-8-(2-methylpyrimidin-5-yl)-9H-purin-6-yl]-3-methyl-1,3-dihydro-2H-indol-2-one;

5-[9-ethyl-8-(2-methylpyrimidin-5-yl)-9H-purin-6-yl]-3-methyl-3-{[tetrahydrofuran-2-ylmethyl]amino}-1,3-dihydro-2H-indol-2-one;

5-[9-ethyl-8-(2-methylpyrimidin-5-yl)-9H-purin-6-yl]-3 (R)-methyl-3-{[(2R)-tetrahydrofuran-2-ylmethyl]amino}-1,3-dihydro-2H-indol-2-one;

5-[9-ethyl-8-(2-methylpyrimidin-5-yl)-9H-purin-6-yl]-3 (S)-methyl-3-{[(2R)-tetrahydrofuran-2-ylmethyl]amino}-1,3-dihydro-2H-indol-2-one;

5-[9-ethyl-8-(2-methylpyrimidin-5-yl)-9H-purin-6-yl]-3-methyl-3-(8-oxa-5-azaspiro[3.5]non-5-yl)-1,3-dihydro-2H-indol-2-one;

(R)-5-[9-ethyl-8-(2-methylpyrimidin-5-yl)-9H-purin-6-yl]-3-methyl-3-(8-oxa-5-azaspiro[3.5]non-5-yl)-1,3-dihydro-2H-indol-2-one;

(S)-5-[9-ethyl-8-(2-methylpyrimidin-5-yl)-9H-purin-6-yl]-3-methyl-3-(8-oxa-5-azaspiro[3.5]non-5-yl)-1,3-dihydro-2H-indol-2-one;

3-(6,7-dihydropyrazolo[1,5-a]pyrazin-5 (4H)-yl)-5-[9-ethyl-8-(2-methylpyrimidin-5-yl)-9H-purin-6-yl]-3-methyl-1,3-dihydro-2H-indol-2-one;

(R)-3-(6,7-dihydropyrazolo[1,5-a]pyrazin-5 (4H)-yl)-5-[9-ethyl-8-(2-methylpyrimidin-5-yl)-9H-purin-6-yl]-3-methyl-1,3-dihydro-2H-indol-2-one;

(S)-3-(6,7-dihydropyrazolo[1,5-a]pyrazin-5(4H)-yl)-5-[9-ethyl-8-(2-methylpyrimidin-5-yl)-9H-purin-6-yl]-3-methyl-1,3-dihydro-2H-indol-2-one;

5-[9-ethyl-8-(2-methylpyrimidin-5-yl)-9H-purin-6-yl]-3-methyl-3-(tetrahydro-2H-pyran-4-ylamino)-1,3-dihydro-2H-indol-2-one;

(R)-5-[9-ethyl-8-(2-methylpyrimidin-5-yl)-9H-purin-6-yl]-3-methyl-3-(tetrahydro-2H-pyran-4-ylamino)-1,3-dihydro-2H-indol-2-one;

(S)-5-[9-ethyl-8-(2-methylpyrimidin-5-yl)-9H-purin-6-yl]-3-methyl-3-(tetrahydro-2H-pyran-4-ylamino)-1,3-dihydro-2H-indol-2-one;

5-[9-ethyl-8-(2-methylpyrimidin-5-yl)-9H-purin-6-yl]-3-methyl-3-[2-oxa-5-azabicyclo[2.2.1]hept-5-yl]-1,3-dihydro-2H-indol-2-one;

5-[9-ethyl-8-(2-methylpyrimidin-5-yl)-9H-purin-6-yl]-3 (R)-methyl-3-[(1R,4R)-2-oxa-5-azabicyclo[2.2.1]hept-5-yl]-1,3-dihydro-2H-indol-2-one;

5-[9-ethyl-8-(2-methylpyrimidin-5-yl)-9H-purin-6-yl]-3 (S)-methyl-3-[(1R,4R)-2-oxa-5-azabicyclo[2.2.1]hept-5-yl]-1,3-dihydro-2H-indol-2-one;

3-{[1-cyclobutylethyl]amino}-5-[9-ethyl-8-(2-methylpyrimidin-5-yl)-9H-purin-6-yl]-3-methyl-1,3-dihydro-2H-indol-2-one;
3-{[(1S)-1-cyclobutylethyl]amino}-5-[9-ethyl-8-(2-methylpyrimidin-5-yl)-9H-purin-6-yl]-3 (R)-methyl-1,3-dihydro-2H-indol-2-one;
3-{[(1R)-1-cyclobutylethyl]amino}-5-[9-ethyl-8-(2-methylpyrimidin-5-yl)-9H-purin-6-yl]-3(S)-methyl-1,3-dihydro-2H-indol-2-one;
5-[9-ethyl-8-(2-methylpyrimidin-5-yl)-9H-purin-6-yl]-3-methyl-3-(6-oxa-2-azaspiro[3.4]oct-2-yl)-1,3-dihydro-2H-indol-2-one;
(R)-5-[9-ethyl-8-(2-methylpyrimidin-5-yl)-9H-purin-6-yl]-3-methyl-3-(6-oxa-2-azaspiro[3.4]oct-2-yl)-1,3-dihydro-2H-indol-2-one;
(S)-5-[9-ethyl-8-(2-methylpyrimidin-5-yl)-9H-purin-6-yl]-3-methyl-3-(6-oxa-2-azaspiro[3.4]oct-2-yl)-1,3-dihydro-2H-indol-2-one;
3-(cyclobutylamino)-5-[9-ethyl-8-(2-methylpyrimidin-5-yl)-9H-purin-6-yl]-3-methyl-1,3-dihydro-2H-indol-2-one;
(R)-3-(cyclobutylamino)-5-[9-ethyl-8-(2-methylpyrimidin-5-yl)-9H-purin-6-yl]-3-methyl-1,3-dihydro-2H-indol-2-one;
(S)-3-(cyclobutylamino)-5-[9-ethyl-8-(2-methylpyrimidin-5-yl)-9H-purin-6-yl]-3-methyl-1,3-dihydro-2H-indol-2-one;
5-[9-ethyl-8-(2-methylpyrimidin-5-yl)-9H-purin-6-yl]-3-methyl-3-[(1-methylethyl)amino]-1,3-dihydro-2H-indol-2-one;
(R)-5-[9-ethyl-8-(2-methylpyrimidin-5-yl)-9H-purin-6-yl]-3-methyl-3-[(1-methylethyl)amino]-1,3-dihydro-2H-indol-2-one;
(S)-5-[9-ethyl-8-(2-methylpyrimidin-5-yl)-9H-purin-6-yl]-3-methyl-3-[(1-methylethyl)amino]-1,3-dihydro-2H-indol-2-one;
3-[(cyclopropylmethyl)amino]-5-[9-ethyl-8-(2-methylpyrimidin-5-yl)-9H-purin-6-yl]-3-methyl-1,3-dihydro-2H-indol-2-one;
(R)-3-[(cyclopropylmethyl)amino]-5-[9-ethyl-8-(2-methylpyrimidin-5-yl)-9H-purin-6-yl]-3-methyl-1,3-dihydro-2H-indol-2-one;
(S)-3-[(cyclopropylmethyl)amino]-5-[9-ethyl-8-(2-methylpyrimidin-5-yl)-9H-purin-6-yl]-3-methyl-1,3-dihydro-2H-indol-2-one;
5-[9-ethyl-8-(2-methylpyrimidin-5-yl)-9H-purin-6-yl]-3-methyl-3-[tetrahydrofuran-3-ylamino]-1,3-dihydro-2H-indol-2-one;
5-[9-ethyl-8-(2-methylpyrimidin-5-yl)-9H-purin-6-yl]-3 (R)-methyl-3-[(3 S)-tetrahydrofuran-3-ylamino]-1,3-dihydro-2H-indol-2-one;
5-[9-ethyl-8-(2-methylpyrimidin-5-yl)-9H-purin-6-yl]-3 (S)-methyl-3-[(3 S)-tetrahydrofuran-3-ylamino]-1,3-dihydro-2H-indol-2-one;
5-(9-ethyl-8-(2-methylpyrimidin-5-yl)-9H-purin-6-yl)-3-((2-fluoro-2-methylpropyl)amino)-3-methylindolin-2-one;
(S)-5-(9-ethyl-8-(2-methylpyrimidin-5-yl)-9H-purin-6-yl)-3-((2-fluoro-2-methylpropyl)amino)-3-methylindolin-2-one;
(R)-5-(9-ethyl-8-(2-methylpyrimidin-5-yl)-9H-purin-6-yl)-3-((2-fluoro-2-methylpropyl)amino)-3-methylindolin-2-one;
3-((5-(9-ethyl-8-(2-methylpyrimidin-5-yl)-9H-purin-6-yl)-3-methyl-2-oxoindolin-3-yl)amino)-2,2-dimethylpropanenitrile;
(R)-3-((5-(9-ethyl-8-(2-methylpyrimidin-5-yl)-9H-purin-6-yl)-3-methyl-2-oxoindolin-3-yl)amino)-2,2-dimethylpropanenitrile;
(S)-3-((5-(9-ethyl-8-(2-methylpyrimidin-5-yl)-9H-purin-6-yl)-3-methyl-2-oxoindolin-3-yl)amino)-2,2-dimethylpropanenitrile;
3-((2,2-difluoropropyl)amino)-5-(9-ethyl-8-(2-methylpyrimidin-5-yl)-9H-purin-6-yl)-3-methylindolin-2-one;
(R)-3-((2,2-difluoropropyl)amino)-5-(9-ethyl-8-(2-methylpyrimidin-5-yl)-9H-purin-6-yl)-3-methylindolin-2-one;
(S)-3-((2,2-difluoropropyl)amino)-5-(9-ethyl-8-(2-methylpyrimidin-5-yl)-9H-purin-6-yl)-3-methylindolin-2-one;
5-(9-ethyl-8-(2-methylpyrimidin-5-yl)-9H-purin-6-yl)-3-methyl-3-((tetrahydrofuran-3-yl)amino)-1,3-dihydro-2H-pyrrolo[2,3-b]pyridin-2-one;
(R)-5-(9-ethyl-8-(2-methylpyrimidin-5-yl)-9H-purin-6-yl)-3-methyl-3-(((S)-tetrahydrofuran-3-yl)amino)-1,3-dihydro-2H-pyrrolo[2,3-b]pyridin-2-one;
(S)-5-(9-ethyl-8-(2-methylpyrimidin-5-yl)-9H-purin-6-yl)-3-methyl-3-(((S)-tetrahydrofuran-3-yl)amino)-1,3-dihydro-2H-pyrrolo[2,3-b]pyridin-2-one;
3-methyl-5-(9-methyl-8-(2-methylpyrimidin-5-yl)-9H-purin-6-yl)-3-((tetrahydrofuran-3-yl)amino)-1H-pyrrolo[2,3-b]pyridin-2(3H)-one;
(R)-3-methyl-5-(9-methyl-8-(2-methylpyrimidin-5-yl)-9H-purin-6-yl)-3-(((S)-tetrahydrofuran-3-yl)amino)-1H-pyrrolo[2,3-b]pyridin-2(3H)-one;
(S)-3-methyl-5-(9-methyl-8-(2-methylpyrimidin-5-yl)-9H-purin-6-yl)-3-(((S)-tetrahydrofuran-3-yl)amino)-1H-pyrrolo[2,3-b]pyridin-2(3H)-one;
5-(9-ethyl-8-(2-methylpyrimidin-5-yl)-9H-purin-6-yl)-3-(3-methoxy-3-methylazetidin-1-yl)-3-methyl-1H-pyrrolo[2,3-b]pyridin-2(3H)-one;
(R)-5-(9-ethyl-8-(2-methylpyrimidin-5-yl)-9H-purin-6-yl)-3-(3-methoxy-3-methylazetidin-1-yl)-3-methyl-1H-pyrrolo[2,3-b]pyridin-2(3H)-one;
(S)-5-(9-ethyl-8-(2-methylpyrimidin-5-yl)-9H-purin-6-yl)-3-(3-methoxy-3-methylazetidin-1-yl)-3-methyl-1H-pyrrolo[2,3-b]pyridin-2(3H)-one;
5-(9-ethyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one;
(S)-5-(9-ethyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one;
(R)-5-(9-ethyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one;
3-(cyclobutylamino)-5-(9-ethyl-8-(2-methylpyrimidin-5-yl)-9H-purin-6-yl)-3-methyl-1,3-dihydro-2H-pyrrolo[2,3-b]pyridin-2-one;
(S)-3-(cyclobutylamino)-5-(9-ethyl-8-(2-methylpyrimidin-5-yl)-9H-purin-6-yl)-3-methyl-1,3-dihydro-2H-pyrrolo[2,3-b]pyridin-2-one;
(R)-3-(cyclobutylamino)-5-(9-ethyl-8-(2-methylpyrimidin-5-yl)-9H-purin-6-yl)-3-methyl-1,3-dihydro-2H-pyrrolo[2,3-b]pyridin-2-one;
1-(5-(9-ethyl-8-(2-methylpyrimidin-5-yl)-9H-purin-6-yl)-3-methyl-2-oxo-2,3-dihydro-1H-pyrrolo[2,3-b]pyridin-3-yl)-3-methylazetidine-3-carbonitrile;
(S)-1-(5-(9-ethyl-8-(2-methylpyrimidin-5-yl)-9H-purin-6-yl)-3-methyl-2-oxo-2,3-dihydro-1H-pyrrolo[2,3-b]pyridin-3-yl)-3-methylazetidine-3-carbonitrile;

(R)-1-(5-(9-ethyl-8-(2-methylpyrimidin-5-yl)-9H-purin-6-yl)-3-methyl-2-oxo-2,3-dihydro-1H-pyrrolo[2,3-b]pyridin-3-yl)-3-methylazetidine-3-carbonitrile;
5-(9-ethyl-8-(2-methylpyrimidin-5-yl)-9H-purin-6-yl)-3-(2-fluoro-2-methylpropoxy)-3-methylindolin-2-one;
(R)-5-(9-ethyl-8-(2-methylpyrimidin-5-yl)-9H-purin-6-yl)-3-(2-fluoro-2-methylpropoxy)-3-methylindolin-2-one;
(S)-5-(9-ethyl-8-(2-methylpyrimidin-5-yl)-9H-purin-6-yl)-3-(2-fluoro-2-methylpropoxy)-3-methylindolin-2-one;
3-(cyclopropylmethoxy)-5-(9-ethyl-8-(2-methylpyrimidin-5-yl)-9H-purin-6-yl)-3-methylindolin-2-one;
(R)-3-(cyclopropylmethoxy)-5-(9-ethyl-8-(2-methylpyrimidin-5-yl)-9H-purin-6-yl)-3-methylindolin-2-one;
(S)-3-(cyclopropylmethoxy)-5-(9-ethyl-8-(2-methylpyrimidin-5-yl)-9H-purin-6-yl)-3-methylindolin-2-one;
5-(9-methyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one;
(S)-5-(9-methyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one;
(R)-5-(9-methyl-8-(2-methylpyrimidin-5-yl)-9H-purin-6-yl)-3-((2-fluoro-2-methylpropyl)amino)-3-methyl-1H-pyrrolo[2,3-b]pyridin-2(3H)-one;
3-(3,4-difluoropyrrolidin-1-yl)-5-(9-ethyl-8-(2-methylpyrimidin-5-yl)-9H-purin-6-yl)-3-methylindolin-2-one;
3-(R)-((3R,4R)-3,4-difluoropyrrolidin-1-yl)-5-(9-ethyl-8-(2-methylpyrimidin-5-yl)-9H-purin-6-yl)-3-methylindolin-2-one;
3-(S)-((3R,4R)-3,4-difluoropyrrolidin-1-yl)-5-(9-ethyl-8-(2-methylpyrimidin-5-yl)-9H-purin-6-yl)-3-methylindolin-2-one;
5-(9-ethyl-8-(2-methylpyrimidin-5-yl)-9H-purin-6-yl)-3-(3-fluoro-3-methylazetidin-1-yl)-3-methylindolin-2-one;
(R)-5-(9-ethyl-8-(2-methylpyrimidin-5-yl)-9H-purin-6-yl)-3-(3-fluoro-3-methylazetidin-1-yl)-3-methylindolin-2-one;
(S)-5-(9-ethyl-8-(2-methylpyrimidin-5-yl)-9H-purin-6-yl)-3-(3-fluoro-3-methylazetidin-1-yl)-3-methylindolin-2-one;
5-(9-ethyl-8-(2-methylpyrimidin-5-yl)-9H-purin-6-yl)-3-(isobutylamino)-3-methylindolin-2-one;
(R)-5-(9-ethyl-8-(2-methylpyrimidin-5-yl)-9H-purin-6-yl)-3-(isobutylamino)-3-methylindolin-2-one;
(S)-5-(9-ethyl-8-(2-methylpyrimidin-5-yl)-9H-purin-6-yl)-3-(isobutylamino)-3-methylindolin-2-one;
3-((2-fluoro-2-methylpropyl)amino)-3-methyl-5-(9-methyl-8-(2-methylpyrimidin-5-yl)-9H-purin-6-yl)indolin-2-one;
(S)-3-((2-fluoro-2-methylpropyl)amino)-3-methyl-5-(9-methyl-8-(2-methylpyrimidin-5-yl)-9H-purin-6-yl)indolin-2-one;
(R)-3-((2-fluoro-2-methylpropyl)amino)-3-methyl-5-(9-methyl-8-(2-methylpyrimidin-5-yl)-9H-purin-6-yl)indolin-2-one;
3-((2,2-difluoropropyl)amino)-3-methyl-5-(9-methyl-8-(2-methylpyrimidin-5-yl)-9H-purin-6-yl)indolin-2-one;
(R)-3-((2,2-difluoropropyl)amino)-3-methyl-5-(9-methyl-8-(2-methylpyrimidin-5-yl)-9H-purin-6-yl)indolin-2-one;
(S)-3-((2,2-difluoropropyl)amino)-3-methyl-5-(9-methyl-8-(2-methylpyrimidin-5-yl)-9H-purin-6-yl)indolin-2-one;
5-(9-ethyl-8-(2-methylpyrimidin-5-yl)-9H-purin-6-yl)-3-(((3-fluorooxetan-3-yl)methyl)amino)-3-methylindolin-2-one;
(R)-5-(9-ethyl-8-(2-methylpyrimidin-5-yl)-9H-purin-6-yl)-3-(((3-fluorooxetan-3-yl)methyl)amino)-3-methylindolin-2-one;
(S)-5-(9-ethyl-8-(2-methylpyrimidin-5-yl)-9H-purin-6-yl)-3-(((3-fluorooxetan-3-yl)methyl)amino)-3-methylindolin-2-one;
5-(9-ethyl-8-(2-methylpyrimidin-5-yl)-9H-purin-6-yl)-3-isopropoxy-3-methylindolin-2-one;
3-cyclobutoxy-5-(9-ethyl-8-(2-methylpyrimidin-5-yl)-9H-purin-6-yl)-3-methylindolin-2-one;
3-(cyclopropylmethoxy)-3-methyl-5-(9-methyl-8-(2-methylpyrimidin-5-yl)-9H-purin-6-yl)indolin-2-one;
5-(9-ethyl-8-(2-methylpyrimidin-5-yl)-9H-purin-6-yl)-3-methyl-3-((tetrahydrofuran-3-yl)amino)indolin-2-one;
5-(9-ethyl-8-(2-methylpyrimidin-5-yl)-9H-purin-6-yl)-3-(R)-methyl-3-(((R)-tetrahydrofuran-3-yl)amino)indolin-2-one;
5-(9-ethyl-8-(2-methylpyrimidin-5-yl)-9H-purin-6-yl)-3-(S)-methyl-3-(((R)-tetrahydrofuran-3-yl)amino)indolin-2-one;
5-(9-ethyl-8-(2-methylpyrimidin-5-yl)-9H-purin-6-yl)-3-(3-methoxy-3-methylazetidin-1-yl)-2-oxoindoline-3-carbonitrile;
5-(9-ethyl-8-(2-methylpyrimidin-5-yl)-9H-purin-6-yl)-3-(3-methoxyazetidin-1-yl)-3-methylindolin-2-one;
(R)-5-(9-ethyl-8-(2-methylpyrimidin-5-yl)-9H-purin-6-yl)-3-(3-methoxyazetidin-1-yl)-3-(3-methoxyazetidin-methylindolin-2-one;
(S)-5-(9-ethyl-8-(2-methylpyrimidin-5-yl)-9H-purin-6-yl)-3-(3-methoxyazetidin-1-yl)-3-methylindolin-2-one;
5-(9-ethyl-8-(2-methylpyrimidin-5-yl)-9H-purin-6-yl)-3-(3-hydroxy-3-methyl azetidin-1-yl)-3-methylindolin-2-one;
(R)-5-(9-ethyl-8-(2-methylpyrimidin-5-yl)-9H-purin-6-yl)-3-(3-hydroxy-3-methylazetidin-1-yl)-3-methylindolin-2-one;
(S)-5-(9-ethyl-8-(2-methylpyrimidin-5-yl)-9H-purin-6-yl)-3-(3-hydroxy-3-methylazetidin-1-yl)-3-methylindolin-2-one;
5-(9-ethyl-8-(2-methylpyrimidin-5-yl)-9H-purin-6-yl)-3-((3-methoxycyclobutyl)amino)-3-methylindolin-2-one;
5-(9-ethyl-8-(2-methylpyrimidin-5-yl)-9H-purin-6-yl)-3-(((1R,3R)-3-methoxycyclobutyl)amino)-3 (R)-methylindolin-2-one;
5-(9-ethyl-8-(2-methylpyrimidin-5-yl)-9H-purin-6-yl)-3-(((1R,3R)-3-methoxycyclobutyl)amino)-3(S)-methylindolin-2-one;
1'-(cyclopropylcarbonyl)-5-[9-ethyl-8-(2-methylpyrimidin-5-yl)-9H-purin-6-yl]spiro[indole-3,2'-pyrrolidin]-2(1H)-one;
(R)-1'-(cyclopropylcarbonyl)-5-[9-ethyl-8-(2-methylpyrimidin-5-yl)-9H-purin-6-yl]spiro[indole-3,2'-pyrrolidin]-2(1H)-one;
(S)-1'-(cyclopropylcarbonyl)-5-[9-ethyl-8-(2-methylpyrimidin-5-yl)-9H-purin-6-yl]spiro[indole-3,2'-pyrrolidin]-2(1H)-one;
1'-(cyclopropylcarbonyl)-5-[9-ethyl-8-(2-methylpyrimidin-5-yl)-9H-purin-6-yl]-1-methylspiro[indole-3,2'-pyrrolidin]-2(1H)-one;

(R)-1'-(cyclopropylcarbonyl)-5-[9-ethyl-8-(2-methylpyrimidin-5-yl]-9H-purin-6-yl]-1-methylspiro[indole-3,2'-pyrrolidin]-2(1H)-one;
(S)-1'-(cyclopropylcarbonyl)-5-[9-ethyl-8-(2-methylpyrimidin-5-yl]-9H-purin-6-yl]-1-methylspiro[indole-3,2'-pyrrolidin]-2(1H)-one;
1'-(cyclopropanecarbonyl)-5-(9-ethyl-8-(2-methylpyrimidin-5-yl)-9H-purin-6-yl)spiro[indoline-3,3'-pyrrolidin]-2-one;
(R)-1'-(cyclopropanecarbonyl)-5-(9-ethyl-8-(2-methylpyrimidin-5-yl)-9H-purin-6-yl)spiro[indoline-3,3'-pyrrolidin]-2-one;
(S)-1'-(cyclopropanecarbonyl)-5-(9-ethyl-8-(2-methylpyrimidin-5-yl)-9H-purin-6-yl)spiro[indoline-3,3'-pyrrolidin]-2-one;
1'-(cyclopropanecarbonyl)-5-(9-methyl-8-(2-methylpyrimidin-5-yl)-9H-purin-6-yl)spiro[indoline-3,2'-pyrrolidin]-2-one;
(R)-1'-(cyclopropanecarbonyl)-5-(9-methyl-8-(2-methylpyrimidin-5-yl)-9H-purin-6-yl)spiro[indoline-3,2'-pyrrolidin]-2-one;
(S)-1'-(cyclopropanecarbonyl)-5-(9-methyl-8-(2-methylpyrimidin-5-yl)-9H-purin-6-yl)spiro[indoline-3,2'-pyrrolidin]-2-one;
1'-(cyclopropanecarbonyl)-1-methyl-5-(9-methyl-8-(2-methylpyrimidin-5-yl)-9H-purin-6-yl)spiro[indoline-3,2'-pyrrolidin]-2-one;
(R)-1'-(cyclopropanecarbonyl)-1-methyl-5-(9-methyl-8-(2-methylpyrimidin-5-yl)-9H-purin-6-yl)spiro[indoline-3,2'-pyrrolidin]-2-one;
(S)-1'-(cyclopropanecarbonyl)-1-methyl-5-(9-methyl-8-(2-methylpyrimidin-5-yl)-9H-purin-6-yl)spiro[indoline-3,2'-pyrrolidin]-2-one;
1'-(cyclopropanecarbonyl)-1-ethyl-5-(9-ethyl-8-(2-methylpyrimidin-5-yl)-9H-purin-6-yl)spiro[indoline-3,2'-pyrrolidin]-2-one;
(R)-1'-(cyclopropanecarbonyl)-1-ethyl-5-(9-ethyl-8-(2-methylpyrimidin-5-yl)-9H-purin-6-yl)spiro[indoline-3,2'-pyrrolidin]-2-one;
(S)-1'-(cyclopropanecarbonyl)-1-ethyl-5-(9-ethyl-8-(2-methylpyrimidin-5-yl)-9H-purin-6-yl)spiro[indoline-3,2'-pyrrolidin]-2-one;
1'-(cyclopropanecarbonyl)-5-(9-ethyl-8-(2-methylpyrimidin-5-yl)-9H-purin-6-yl)-1-isopropylspiro[indoline-3,2'-pyrrolidin]-2-one;
(R)-1'-(cyclopropanecarbonyl)-5-(9-ethyl-8-(2-methylpyrimidin-5-yl)-9H-purin-6-yl)-1-isopropylspiro[indoline-3,2'-pyrrolidin]-2-one;
(S)-1'-(cyclopropanecarbonyl)-5-(9-ethyl-8-(2-methylpyrimidin-5-yl)-9H-purin-6-yl)-1-isopropylspiro[indoline-3,2'-pyrrolidin]-2-one;
5-(9-ethyl-8-(2-methylpyrimidin-5-yl)-9H-purin-6-yl)-1'-isopropylspiro[indoline-3,2'-pyrrolidin]-2-one;
(R)-5-(9-ethyl-8-(2-methylpyrimidin-5-yl)-9H-purin-6-yl)-1'-isopropylspiro[indoline-3,2'-pyrrolidin]-2-one;
(S)-5-(9-ethyl-8-(2-methylpyrimidin-5-yl)-9H-purin-6-yl)-1'-isopropylspiro[indoline-3,2'-pyrrolidin]-2-one;
1'-isopropyl-5-(9-methyl-8-(2-methylpyrimidin-5-yl)-9H-purin-6-yl)spiro[indoline-3,2'-pyrrolidin]-2-one;
(R)-1'-isopropyl-5-(9-methyl-8-(2-methylpyrimidin-5-yl)-9H-purin-6-yl)spiro[indoline-3,2'-pyrrolidin]-2-one;
(S)-1'-isopropyl-5-(9-methyl-8-(2-methylpyrimidin-5-yl)-9H-purin-6-yl)spiro[indoline-3,2'-pyrrolidin]-2-one;
1'-(cyclopropanecarbonyl)-5-(8-(difluoromethyl)-9-ethyl-9H-purin-6-yl)spiro[indoline-3,2'-pyrrolidin]-2-one;
(R)-1'-(cyclopropanecarbonyl)-5-(8-(difluoromethyl)-9-ethyl-9H-purin-6-yl)spiro[indoline-3,2'-pyrrolidin]-2-one;
(S)-1'-(cyclopropanecarbonyl)-5-(8-(difluoromethyl)-9-ethyl-9H-purin-6-yl)spiro[indoline-3,2'-pyrrolidin]-2-one;
1'-(cyclopropanecarbonyl)-5-(9-methyl-8-(2-methylpyrimidin-5-yl)-9H-purin-6-yl)-1-(2-morpholinoethyl)spiro[indoline-3,2'-pyrrolidin]-2-one;
(R)-1'-(cyclopropanecarbonyl)-5-(9-methyl-8-(2-methylpyrimidin-5-yl)-9H-purin-6-yl)-1-(2-morpholinoethyl)spiro[indoline-3,2'-pyrrolidin]-2-one;
(S)-1'-(cyclopropanecarbonyl)-5-(9-methyl-8-(2-methylpyrimidin-5-yl)-9H-purin-6-yl)-1-(2-morpholinoethyl)spiro[indoline-3,2'-pyrrolidin]-2-one;
1'-(cyclopropanecarbonyl)-1-(2-hydroxy-2-methylpropyl)-5-(9-methyl-8-(2-methylpyrimidin-5-yl)-9H-purin-6-yl)spiro[indoline-3,2'-pyrrolidin]-2-one;
(R)-1'-(cyclopropanecarbonyl)-1-(2-hydroxy-2-methylpropyl)-5-(9-methyl-8-(2-methylpyrimidin-5-yl)-9H-purin-6-yl)spiro[indoline-3,2'-pyrrolidin]-2-one;
(S)-1'-(cyclopropanecarbonyl)-1-(2-hydroxy-2-methylpropyl)-5-(9-methyl-8-(2-methylpyrimidin-5-yl)-9H-purin-6-yl)spiro[indoline-3,2'-pyrrolidin]-2-one;
1'-(cyclopropanecarbonyl)-1-(2-hydroxyethyl)-5-(9-methyl-8-(2-methylpyrimidin-5-yl)-9H-purin-6-yl)spiro[indoline-3,2'-pyrrolidin]-2-one;
(R)-1'-(cyclopropanecarbonyl)-1-(2-hydroxyethyl)-5-(9-methyl-8-(2-methylpyrimidin-5-yl)-9H-purin-6-yl)spiro[indoline-3,2'-pyrrolidin]-2-one;
(S)-1'-(cyclopropanecarbonyl)-1-(2-hydroxyethyl)-5-(9-methyl-8-(2-methylpyrimidin-5-yl)-9H-purin-6-yl)spiro[indoline-3,2'-pyrrolidin]-2-one;
5-(9-ethyl-8-(2-methylpyrimidin-5-yl)-9H-purin-6-yl)-1'-(methylsulfonyl)spiro[indoline-3,2'-pyrrolidin]-2-one;
(R)-5-(9-ethyl-8-(2-methylpyrimidin-5-yl)-9H-purin-6-yl)-1'-(methylsulfonyl)spiro[indoline-3,2'-pyrrolidin]-2-one;
(S)-5-(9-ethyl-8-(2-methylpyrimidin-5-yl)-9H-purin-6-yl)-1'-(methylsulfonyl)spiro[indoline-3,2'-pyrrolidin]-2-one;
5-(9-ethyl-8-(2-methylpyrimidin-5-yl)-9H-purin-6-yl)-1'-((trifluoromethyl)sulfonyl)spiro[indoline-3,2'-pyrrolidin]-2-one;
(R)-5-(9-ethyl-8-(2-methylpyrimidin-5-yl)-9H-purin-6-yl)-1'-((trifluoromethyl)sulfonyl)spiro[indoline-3,2'-pyrrolidin]-2-one;
(S)-5-(9-ethyl-8-(2-methylpyrimidin-5-yl)-9H-purin-6-yl)-1'-((trifluoromethyl)sulfonyl)spiro[indoline-3,2'-pyrrolidin]-2-one;
5-(9-ethyl-8-(2-methylpyrimidin-5-yl)-9H-purin-6-yl)-1-methyl-1'-(methylsulfonyl)spiro[indoline-3,2'-pyrrolidin]-2-one;
(R)-5-(9-ethyl-8-(2-methylpyrimidin-5-yl)-9H-purin-6-yl)-1-methyl-1'-(methyl sulfonyl)spiro[indoline-3,2'-pyrrolidin]-2-one;
(S)-5-(9-ethyl-8-(2-methylpyrimidin-5-yl)-9H-purin-6-yl)-1-methyl-1'-(methyl sulfonyl)spiro[indoline-3,2'-pyrrolidin]-2-one;
1'-(cyclopropanecarbonyl)-5-(9-methyl-8-(2-methylpyrimidin-5-yl)-9H-purin-6-yl)spiro[indoline-3,4'-piperidin]-2-one;
1'-ethyl-5-(9-ethyl-8-(2-methylpyrimidin-5-yl)-9H-purin-6-yl)spiro[indoline-3,2'-pyrrolidin]-2-one;

(R)-1'-ethyl-5-(9-ethyl-8-(2-methylpyrimidin-5-yl)-9H-purin-6-yl)spiro[indoline-3,2'-pyrrolidin]-2-one;
(S)-1'-ethyl-5-(9-ethyl-8-(2-methylpyrimidin-5-yl)-9H-purin-6-yl)spiro[indoline-3,2'-pyrrolidin]-2-one;
1'-ethyl-5-(9-methyl-8-(2-methylpyrimidin-5-yl)-9H-purin-6-yl)spiro[indoline-3,2'-pyrrolidin]-2-one;
(R)-1'-ethyl-5-(9-methyl-8-(2-methylpyrimidin-5-yl)-9H-purin-6-yl)spiro[indoline-3,2'-pyrrolidin]-2-one;
(S)-1'-ethyl-5-(9-methyl-8-(2-methylpyrimidin-5-yl)-9H-purin-6-yl)spiro[indoline-3,2'-pyrrolidin]-2-one;
5'-(9-ethyl-8-(2-methylpyrimidin-5-yl)-9H-purin-6-yl)-4,5-dihydro-3H-spiro[furan-2,3'-indolin]-2'-one;
(R)-5'-(9-ethyl-8-(2-methylpyrimidin-5-yl)-9H-purin-6-yl)-4,5-dihydro-3H-spiro[furan-2,3'-indolin]-2'-one;
(S)-5'-(9-ethyl-8-(2-methylpyrimidin-5-yl)-9H-purin-6-yl)-4,5-dihydro-3H-spiro[furan-2,3'-indolin]-2'-one;
5-(9-ethyl-8-(2-methylpyrimidin-5-yl)-9H-purin-6-yl)spiro[indoline-3,2'-pyrrolidin]-2-one;
(R)-5-(9-ethyl-8-(2-methylpyrimidin-5-yl)-9H-purin-6-yl)spiro[indoline-3,2'-pyrrolidin]-2-one;
(S)-5-(9-ethyl-8-(2-methylpyrimidin-5-yl)-9H-purin-6-yl)spiro[indoline-3,2'-pyrrolidin]-2-one;
5'-(9-ethyl-8-(2-methylpyrimidin-5-yl)-9H-purin-6-yl)spiro[cyclopentane-1,3'-indolin]-2'-one;
5-(9-ethyl-8-(2-methylpyrimidin-5-yl)-9H-purin-6-yl)-1'-isopropylspiro[indoline-3,3'-pyrrolidin]-2-one;
(R)-5-(9-ethyl-8-(2-methylpyrimidin-5-yl)-9H-purin-6-yl)-1'-isopropylspiro[indoline-3,3'-pyrrolidin]-2-one;
(S)-5-(9-ethyl-8-(2-methylpyrimidin-5-yl)-9H-purin-6-yl)-1'-isopropylspiro[indoline-3,3'-pyrrolidin]-2-one;
4-benzyl-6-[9-ethyl-8-(2-methylpyrimidin-5-yl)-9H-purin-6-yl]-1,4-dihydro-2H-3,1-benzoxazin-2-one;
(R)-4-benzyl-6-[9-ethyl-8-(2-methylpyrimidin-5-yl)-9H-purin-6-yl]-1,4-dihydro-2H-3,1-benzoxazin-2-one;
(S)-4-benzyl-6-[9-ethyl-8-(2-methylpyrimidin-5-yl)-9H-purin-6-yl]-1,4-dihydro-2H-3,1-benzoxazin-2-one;
6-[9-ethyl-8-(2-methylpyrimidin-5-yl)-9H-purin-6-yl]-4-methyl-4-(2-methylpropyl)-1,4-dihydro-2H-3,1-benzoxazin-2-one;
(R)-6-[9-ethyl-8-(2-methylpyrimidin-5-yl)-9H-purin-6-yl]-4-methyl-4-(2-methylpropyl)-1,4-dihydro-2H-3,1-benzoxazin-2-one;
(S)-6-[9-ethyl-8-(2-methylpyrimidin-5-yl)-9H-purin-6-yl]-4-methyl-4-(2-methylpropyl)-1,4-dihydro-2H-3,1-benzoxazin-2-one;
9-ethyl-6-[3-methyl-3-(2-methylpropyl)-1,1-dioxido-2,3-dihydro-1,2-benzisothiazol-5-yl]-8-(2-methylpyrimidin-5-yl)-9H-purine;
(R)-9-ethyl-6-[3-methyl-3-(2-methylpropyl)-1,1-dioxido-2,3-dihydro-1,2-benzisothiazol-5-yl]-8-(2-methylpyrimidin-5-yl)-9H-purine;
(S)-9-ethyl-6-[3-methyl-3-(2-methylpropyl)-1,1-dioxido-2,3-dihydro-1,2-benzisothiazol-5-yl]-8-(2-methylpyrimidin-5-yl)-9H-purine;
5-[9-ethyl-8-(2-methylpyrimidin-5-yl)-9H-purin-6-yl]-3-methyl-3-(2-methylpropyl)-2,3-dihydro-1H-isoindol-1-one;
(R)-5-[9-ethyl-8-(2-methylpyrimidin-5-yl)-9H-purin-6-yl]-3-methyl-3-(2-methylpropyl)-2,3-dihydro-1H-isoindol-1-one;
(S)-5-[9-ethyl-8-(2-methylpyrimidin-5-yl)-9H-purin-6-yl]-3-methyl-3-(2-methylpropyl)-2,3-dihydro-1H-isoindol-1-one;
3-benzyl-5-[9-ethyl-8-(2-methylpyrimidin-5-yl)-9H-purin-6-yl]-2,3-dihydro-1H-isoindol-1-one;
(R)-3-benzyl-5-[9-ethyl-8-(2-methylpyrimidin-5-yl)-9H-purin-6-yl]-2,3-dihydro-1H-isoindol-1-one;
(S)-3-benzyl-5-[9-ethyl-8-(2-methylpyrimidin-5-yl)-9H-purin-6-yl]-2,3-dihydro-1H-isoindol-1-one;
3-benzyl-5-[9-ethyl-8-(2-methylpyrimidin-5-yl)-9H-purin-6-yl]-3-methyl-2,3-dihydro-1H-isoindol-1-one;
(R)-3-benzyl-5-[9-ethyl-8-(2-methylpyrimidin-5-yl)-9H-purin-6-yl]-3-methyl-2,3-dihydro-1H-isoindol-1-one;
(S)-3-benzyl-5-[9-ethyl-8-(2-methylpyrimidin-5-yl)-9H-purin-6-yl]-3-methyl-2,3-dihydro-1H-isoindol-1-one;
3-benzyl-5-[9-ethyl-8-(2-methylpyrimidin-5-yl)-9H-purin-6-yl]-2,3-dimethyl-2,3-dihydro-1H-isoindol-1-one;
(R)-3-benzyl-5-[9-ethyl-8-(2-methylpyrimidin-5-yl)-9H-purin-6-yl]-2,3-dimethyl-2,3-dihydro-1H-isoindol-1-one;
(S)-3-benzyl-5-[9-ethyl-8-(2-methylpyrimidin-5-yl)-9H-purin-6-yl]-2,3-dimethyl-2,3-dihydro-1H-isoindol-1-one;
5-(9-ethyl-8-(2-methylpyrimidin-5-yl)-9H-purin-6-yl)-2,3-dihydrobenzo[d]isothiazole 1,1-dioxide;
5-(9-ethyl-8-(2-methylpyrimidin-5-yl)-9H-purin-6-yl)-2-methyl-2,3-dihydrobenzo[d]isothiazole 1,1-dioxide;
5-(9-ethyl-8-(2-methylpyrimidin-5-yl)-9H-purin-6-yl)isoindolin-1-one;
6-(9-ethyl-8-(2-methylpyrimidin-5-yl)-9H-purin-6-yl)-4-methyl-4-phenyl-1,4-dihydro-2H-benzo[d][1,3]oxazin-2-one;
5-[9-ethyl-8-(2-methylpyrimidin-5-yl)-9H-purin-6-yl]-3-(1-phenylethyl)-1,3-benzoxazol-2(3H)-one;
(R)-5-[9-ethyl-8-(2-methylpyrimidin-5-yl)-9H-purin-6-yl]-3-(1-phenylethyl)-1,3-benzoxazol-2(3H)-one;
(S)-5-[9-ethyl-8-(2-methylpyrimidin-5-yl)-9H-purin-6-yl]-3-(1-phenylethyl)-1,3-benzoxazol-2(3H)-one;
3-benzyl-5-[9-ethyl-8-(2-methylpyrimidin-5-yl)-9H-purin-6-yl]-1,3-benzoxazol-2(3H)-one;
5-[9-ethyl-8-(2-methylpyrimidin-5-yl)-9H-purin-6-yl]-3-(tetrahydro-2H-pyran-4-ylmethyl)-1,3-benzoxazol-2(3H)-one;
3-(1-cyclopropylethyl)-5-[9-ethyl-8-(2-methylpyrimidin-5-yl)-9H-purin-6-yl]-1,3-benzoxazol-2(3H)-one;
(R)-3-(1-cyclopropylethyl)-5-[9-ethyl-8-(2-methylpyrimidin-5-yl)-9H-purin-6-yl]-1,3-benzoxazol-2(3H)-one;
(S)-3-(1-cyclopropylethyl)-5-[9-ethyl-8-(2-methylpyrimidin-5-yl)-9H-purin-6-yl]-1,3-benzoxazol-2(3H)-one;
1-(1-cyclopropylethyl)-6-[9-ethyl-8-(2-methylpyrimidin-5-yl)-9H-purin-6-yl]-1,3-dihydro-2H-benzimidazol-2-one;
(R)-1-(1-cyclopropylethyl)-6-[9-ethyl-8-(2-methylpyrimidin-5-yl)-9H-purin-6-yl]-1,3-dihydro-2H-benzimidazol-2-one;
(S)-1-(1-cyclopropylethyl)-6-[9-ethyl-8-(2-methylpyrimidin-5-yl)-9H-purin-6-yl]-1,3-dihydro-2H-benzimidazol-2-one; and
5-(9-ethyl-8-(2-methylpyrimidin-5-yl)-9H-purin-6-yl)-3-(tetrahydro-2H-pyran-4-yl)benzo[d]oxazol-2(3H)-one.

15. The pharmaceutical composition comprising a compound of claim 1 or a pharmaceutically acceptable salt or stereoisomer thereof and a pharmaceutically acceptable carrier.

16. The pharmaceutical composition according to claim 15, further comprising one or more other therapeutic agents.

17. A method for the treatment of a PI3K-delta-mediated disease comprising administering to a patient in need thereof a therapeutically effective amount of a compound of claim 1 or a pharmaceutically acceptable salt or a stereoisomer thereof.

18. A method of treating a condition in a mammal that can be ameliorated by the selective inhibition of PI3K-delta which condition is selected from the group consisting of arthritis, asthma and obstructive airways diseases, autoimmune diseases or disorders, and cancer comprising administering to the mammal in need of such treatment, a therapeutically effective amount of a compound according to claim 1 or a pharmaceutically acceptable salt or a stereoisomer thereof.

19. The method according to claim 18, wherein said condition is arthritis.

20. The method according to claim 19, wherein said condition is selected from the group consisting of rheumatoid arthritis, juvenile arthritis, and psoriatic arthritis.

21. The method according to claim 18, wherein said condition is asthma or obstructive airways diseases.

22. The method according to claim 21, wherein said condition is selected from the group consisting of chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease (COPD), and emphysema.

23. A method of treating asthma in a mammal in need thereof, comprising administering a therapeutically effective amount of a compound according to claim 1 or a pharmaceutically acceptable salt thereof.

24. A method of treating arthritis in a mammal in need thereof, comprising administering a therapeutically effective amount of a compound according to claim 1 or a pharmaceutically acceptable salt thereof.

25. A method of treating cancer in a mammal in need thereof, comprising administering a therapeutically effective amount of a compound according to claim 1 or a pharmaceutically acceptable salt thereof.

* * * * *